US012576118B2

(12) United States Patent (10) Patent No.: US 12,576,118 B2
Hatfull et al. (45) Date of Patent: *Mar. 17, 2026

(54) BACTERIOPHAGES FOR THE TREATMENT OF TUBERCULOSIS

(71) Applicant: University of Pittsburgh—Of the Commonwealth System of Higher Education, Pittsburgh, PA (US)

(72) Inventors: Graham Hatfull, Pittsburgh, PA (US); Rebekah Dedrick, Glenshaw, PA (US); Carlos Guerrero, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1038 days.

This patent is subject to a terminal disclaimer.

(21) Appl. No.: 17/612,926

(22) PCT Filed: May 21, 2020

(86) PCT No.: PCT/US2020/033985
§ 371 (c)(1),
(2) Date: Nov. 19, 2021

(87) PCT Pub. No.: WO2020/237044
PCT Pub. Date: Nov. 26, 2020

(65) Prior Publication Data

US 2022/0233615 A1 Jul. 28, 2022

Related U.S. Application Data

(60) Provisional application No. 62/850,942, filed on May 21, 2019.

(51) Int. Cl.
| | |
|---|---|
| *A61K 35/76* | (2015.01) |
| *A61P 31/06* | (2006.01) |
| *C12N 7/00* | (2006.01) |
| *C12N 15/74* | (2006.01) |

(52) U.S. Cl.
CPC .............. *A61K 35/76* (2013.01); *A61P 31/06* (2018.01); *C12N 7/00* (2013.01); *C12N 15/74* (2013.01); *C12N 2795/10321* (2013.01); *C12N 2795/10332* (2013.01)

(58) Field of Classification Search
CPC ........... A61K 35/76; A61P 31/06; C12N 7/00; C12N 15/74; C12N 2795/10321; C12N 2795/10332
See application file for complete search history.

(56) References Cited

U.S. PATENT DOCUMENTS

| | | |
|---|---|---|
| 5,773,267 A | 6/1998 | Jacobs et al. |
| 2006/0292135 A1 | 12/2006 | Loomis et al. |
| 2015/0150919 A1 | 6/2015 | Alves Mendes et al. |
| 2017/0136102 A1 | 5/2017 | Sharma |
| 2019/0390175 A1 | 12/2019 | Decrulle et al. |

FOREIGN PATENT DOCUMENTS

| | | | | |
|---|---|---|---|---|
| EP | 2 332 562 A2 | 6/2011 | | |
| EP | 2332652 A2 | 6/2011 | | |
| WO | WO 2016066722 A2 * | 5/2016 | ............. | A61K 35/76 |
| WO | WO 2018/141907 A1 | 8/2018 | | |

OTHER PUBLICATIONS

Hatfull G.F., "Mycrobacteriophages", Microbiology Spectrum, 2018, vol. 6, No. 5, pp. 1-32. (Year: 2018).*
Alonzo et al., "Mycobacteriophage discover: potential applications for phage therapy of mycobacterial disease," 7th Annual SEA-PHAGES Symposium, Virginia, USA (Jun. 12, 2015).
Butela et al., "Complete Genome Sequences of Cluster A Mycobacteriophages BobSwaget, Fred313, KADY, Lokk, MyraDee, Stagni, and StephMih," *Genome Announcements*, 5(43): 1-3 (2017).
Da Silva et al., "Application of BRED technology to construct recombinant D29 reporter phage expressing EGFP," *FEMS Microbol Lett*, 344: 166-172 (2013).

(Continued)

*Primary Examiner* — Satyendra K Singh
(74) *Attorney, Agent, or Firm* — Leydig, Voit & Mayer, Ltd.

(57) ABSTRACT

The invention provides a composition (e.g., pharmaceutical composition) comprising a combination of two or more phages, wherein the phages are two or more of: (a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier. The invention provides a method of treating, reducing, or preventing a disease caused by *Mycobacterium tuberculosis* in a mammal comprising administering a pharmaceutical composition comprising a combination of two or more phages wherein the phages are two or more of: (a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier. The composition can be administered alone or in combination with one or more antibiotics, wherein the length of treatment is reduced as compared to the length of treatment with one or more antibiotics alone.

14 Claims, 39 Drawing Sheets

Specification includes a Sequence Listing.

(56) References Cited

OTHER PUBLICATIONS

Dedrick et al., "Expression and evolutionary patterns of mycobacteriophage D29 and its temperate close relatives," *BMC Microbiology*, 17(225): 1-15 (2017).

Dedrick et al., "Engineered bacteriophages for treatment of a patient with a disseminated drug-resistant *Mycobacterium abscessus*," *Nature Medicine*, 25:730-733 (2019).

Ford et al., "Genome Structure of Mycobacteriophage D29: Implications for Phage Evolution," *J. Mol. Biol.*, 279: 143-164 (1998).

Froman et al., "Bacteriophage Active Against Virulent *Mycobacterium tuberculosis*. I. Isolation and activity," *Am J Public Health*, 44: 1326-1333 (1954).

Gagneux "Ecology and evolution of *Mycobacterium tuberculosis*," *Nature Reviews Microbiology*, 16: 202-213 (2018).

Hatfull et al., "Advances in Virus Research Bacteriophages Part A," Academic Press, United States (2012).

Hatfull et al., "Comparative genomic analysis of sixty mycobacteriophage genomes: Genome clustering, gene acquisition and gene size," *J. Mol. Biol.*, 397: 119-143 (2010).

Jacobs-Sera et al., "On the nature of mycobacteriophage diversity and host preference," *Virology*, 434: 187-201 (2012).

Petrova et al., "Mycobacteriophage-repressor-mediated immunity as a selectable genetic marker: Adephagia and BPs repressor selection," *Microbiology*, 161: 1539-1551 (2015).

Pope et al., "Cluster K Mycobacteriophages: Insights into the Evolutionary Origins of Mycobacteriophage TM4," *PLoS One*, 6(10): 1-22 (2011).

Third Party Observation in International Patent Application No. PCT/US2020/033985, dated Sep. 21, 2021.

United States Patent and Trademark Office, International Search Report in International Patent Application No. PCT/US2020/033985, dated Sep. 11, 2020.

United States Patent and Trademark Office, Written Opinion in International Patent Application No. PCT/US2020/033985, dated Sep. 11, 2020.

"Gibson Assembly Cloning Guide: Restriction Digest-Free, Seamless Cloning." 2nd ed., Synthetic Genomics, Inc., http://sgidna.com/gibson-assembly (2017).

Lu et al. "Synthesis of Headful Packaging Phages Through Yeast Transformation-Associated Recombination." Viruses, 17(45), pp. 1-17. //doi.org/10.3390/v17010045 (2025).

* cited by examiner

FIG. 3C (Continued)

HRM-1
HRM-2
HRM-3
HRM-4
HRM-5
HRM-6

N0155

N1274

H37Rv

N1283

HRM-1
HRM-2
HRM-3
HRM-4
HRM-5
HRM-6

N0072

N0052

N0157

N0145

HRM-1
HRM-2
HRM-3
HRM-4
HRM-5
HRM-6

N0136

N0004

N0054

N0053

SEQUENCE LISTING

<160> NUMBER OF SEQ ID NOS: 5

<210> SEQ ID NO 1
<211> LENGTH: 49136
<212> TYPE: DNA
<213> ORGANISM: Bacteriophage

<400> SEQUENCE: 1

```
ggtcggttat gcggccgagc catcctgtac gggtttccaa gccgatcaga agcacgggcc      60
gacgctagag cgcctcgccc aggcgctgtg agccaccagg agccacgaac tcgcgaccca     120
cggggagtta taccccgga atcggctacg ggccatacag gcccggtatc tgtcaaggtg     180
atctacgcca ctccgtgggg tggctgtcaa acgcagactc cttccctatt aatgaggggc     240
tgaaggcccc tcctaagagc cgcttcaggc ggctcgctaa gagcgccttt cgggcgctcc     300
tgagtaataa ccggcccaac aagggccggg gaattgatcc ggcaaccgcc ggatctagcg     360
ccgcgcctga agcgcggctt attgaagggg tgacgcaacc gtgtacggca ctcgttcgag     420
tgcgtactgg agcactcaac cggggaagtt cgacgttctc aaccttcgga tgacgttccc     480
aagctcatcc gcgtacgaga tccccgatct gcggccgaca acctacgttc cggccaacct     540
cgcggcctgg aacatgccgc gacatcgcga atacgccgcc gtttcgggcg cgcactgca     600 cttcttcctt gacgactacc gattcgagac cgtctggtcg agcccggagc gccttctccc     660
```

-continued

```
ccgcgtgcaa gcggttggag ctgctctgac gcccgatttc agcctctggc gggacatgcc      720
acgggccgca gcggtctgga acgtctaccg cagccgctgg tgcggcgcgt actggcagtc      780
gcaagggatc gaggtgctcc caaccgcgtg ctgggcgacc ccagacacgt tcgacttctg      840
cttcgacggg atcccggagg gggccacggt cgcgatcagc tcgatgggca tccgctcctc      900
gaaggtcgac caggcgcttt tccgcgctgg cctccaggaa ctcctcgatc gcaagcaacc      960
gcgactgctg ctggcctacg gccggctgcg gtactgcgac gacatgaacc ttcccgaggt     1020
caaggagtac ccgacctact gggacagacg acgaaagcag gtatccgacg catgggcgga     1080
agaggatccg ccggtagcgg cggtgcccct ggaacccgag gacgcaacag cacccggcaa     1140
ggagccgggg caggcggcgt gggtggactt ggaggcggcg gtggagccgc cggaagcggc     1200
cggggcggtt taggcaccgg caacgcaggc accggtggtg tactcggtgg cggcggcagc     1260
ggagctggcg gcgggttcgg tggttcgacc ggcagccaga cgccagactg gacctacaac     1320
agcccgatgg accccgcgca gaagcgtgcg gcgttcaacg cgctggcggt cgccgcccgc     1380
gaccagcact caccgtcgga tgccaagcgc atagcgaaga gggaccagat gctcggatac     1440
gttcgagggc cgtgggagca gttggaggac gacgactcca cccgctacga caccctgaag     1500
caggcgatgg acgacgccat gtccaagatc ctgagccagg cgcaggtggt ccaccgcacg     1560
aagcacctgg acaagctcct ggactcgggc cggatctcct cgctgttcga ggtcggcttc     1620
tcggccggtg gcgacacccc cggtcagcgc gctctgtacg aggaggcgtg gttcggcaag     1680
ggccacgtcc cgccggtcta ctccgcgctg gagttcgacg gcgtcaagcc caagggcatg     1740
agcatgtacg gcagcaccaa gctctacctc aagcccgagg tgcgtgaccg ggtcactgtg     1800
accatcggcg actcgctgat gtcgagcgac agcgtgttcc ccggaaagcc gggtgacggc     1860
ctcggcctgc gggcgaatcc gaatgcgatc aagaacctcg tagacccgaa taagtctcgc     1920
gaagagaaca tgcaggcgat ctacgagagc ttcaagaaat acgccgaatc gaatttcatc     1980
gaatcgcaaa ttcacgacgg cgttattctc gaagacatcg agaaggttgt attcactcag     2040
ccgcccagct ctttcctgac tgataaactg gacaagctcg gaataccgtg ggaggtggaa     2100
tcgtaatggc gctgatgcaa gcgacacaca ccatcgaggg ctttctcgcg gtcgaaacgc     2160
acccgagggc gttcgtggcc gagaatggcc acgtgatcac ccgcctctcg gccaccaagt     2220 gggggtggctg ggagggcctg gagatccttg agtactcggg tgacggccag gtcgaggtca     2280
gcgacgagca gttggctgag gcggaacacg ccagccagat cgaagcacag atcatcgcgg     2340
aggcagccgc agagtgagtt gggccggctc gaagcgtcgg caagaactac cggaggactg     2400
ggagctgaat taccggctcc cggtcctttc tgctgccggg tggctgtgtg aggtcgacgg     2460
ccccggctgc gtccgggctg ccaccgacgt agaccacaag aagccaggga acgaccactc     2520
gcggtctaac ctgcaagcga tctgccgtgt ctgccacggc aagaagtcag ccgctgaggg     2580
cgtagcccga cggcgggaac tcaaggcccg gaggaagcga ccagaacaac gccaccctgg     2640
gcgtcgttaa gcgggccagg tgcctgctcc acccaggagg tgactgtggg cacacgtggc     2700
cccatcggaa agcgcgacga agaacgcgtt cgtcgcaaca ccccggagaa cccgaccgaa     2760
acgatctcga tgatcgggac ggtggagatc ccggaactcg cgacatgag ctacatgggc     2820 gagacccatc cgctcatcga agagatgtac gacgcgatca agcaatcggc agccgtgaag     2880
ttctacgaac cgaccgactg gcagttcgct cgcctcgctc tctacacact gaaccaagaa     2940
ctcatcgcgc ccaagcacca gggcaagccc atcggtgcga tgaagctgac cgcgatcaac     3000
cagatgctct ccgcactgct gctgaccgaa ggcgaccggc gacgggtccg cctggagatc     3060
```

```
gagcgggcac  ccgccgaccc  gaccggcggg  aaggtcgttg  acgtgaccga  cgtgctcaag    3120
cagcgcctcg  ccaaggcgag  cggcgggggg  tgatggtccc  cctggcgggg  ttctgagcgg    3180
ttgccgctac  cgactgctcc  cccgccgggg  gttgaccctc  cgaacttgaa  aggatccgca    3240
tggccgacct  cggcaacccg  ttcgacctgg  agatgctctg  cctggtcacc  ggccgcgact    3300
tccgctggtc  gatcccccac  ctcgacccgg  tcaccaagca  gcccaccccc  tggcctgcgg    3360
gcgacctgtt  cctcgaactg  gagaccggcg  gcgagcacaa  cgcgctgcac  caggtgtaca    3420
tcaccggggc  cacaggtggc  acgtacaccc  tgaacctcaa  cggcaccgac  accccggcca    3480
tcgactacaa  cgacgtgtcc  gagaacccgc  agggtctggc  cggtgacatc  caggacgcca    3540
tcgacgcggc  gctcgggggcc  ggtaacggcc  tggtgcatcc  ggtctcgctg  ttccccgcgt    3600
ggacgctgaa  cttcaacctg  aacgcccgca  agccgctgac  cgagcagttg  gtcaacacga    3660
tcaacaaggc  cacgaacgac  ttcttcgatg  cgttcgacca  gctcctcggg  gtcgacgtgg    3720
agatgacggt  caccgacacc  ctgaacttcc  agctcaaggt  gacctcgcgg  cgctcgttcg    3780
atgaggtcgg  cgtcgtcacc  ttcgcggtcg  gcgtgacctc  gacggcggtc  aagaacttct    3840
tcaacggctt  ctccgggctg  atcggcgcgg  tgaacaccgt  caacgtcgac  ttctactgga    3900
accggaccta  cgacatcgag  ttcgtcggcg  agctggccga  gacgccggta  cccgcctcca    3960
cggcgaacgc  ggccggtctc  acgggcacct  cgaaggccat  caccgtctcg  gtggtcgagc    4020
caggcaagga  ccgcctgacc  atctggccgt  tcacgatcga  cggcgtgacc  gcctcgatca    4080
aggtcgagtc  cgaagaggcc  gacaagatcc  cgaaccgctg  ccgctggcag  ttggttcatc    4140
tgccgaccgg  cgaagcggcc  ggcggtgacc  ccaaacaact  cggcgtcgtc  taccggcaac    4200
cccggtaggc  gcaccactga  cgtgtagctc  aatggcagag  catccggctg  ttaaccggac    4260
ggttgaaggt  tcgagtcctt  cctcgtcagc  caagcgggcg  gttccccaga  gcgtggggag    4320
cccccgcacc  aagtacacgt  agctcaattg  gtagagcagc  ggtctccaaa  gccgccggtt    4380
ccaggttcga  ctcctggcgt  gtatgccacc  acccttcccc  gttcgtctaa  tcggtaagac    4440
gcctggctct  ggaccaggta  attgaggttc  gagtccttgg  cggggagcac  ccacccagtt    4500
cccttgtggg  gctgggtctt  tcggtccctt  ggagtagcgg  ataactcacc  tggccctcac    4560
ccagaagatc  gcgggttcga  atcccgcagg  gactacaaac  gcgagatacc  caagcggcaa    4620
cgggatctga  ctgtaaatca  gacgcttcgg  cttcgcaggt  tcgagtcctg  ctctcgcgac    4680
ttgacagcca  ccacgaaagg  aacccatgac  gctcatagtc  acacgcgacc  acgcgcagtg    4740
ggtccacgac  atgtgccgcg  ctcgcgctgg  caacaggtac  ggctacggcg  gggcgttcac    4800
actcaacccc  cgagacacca  ccgactgctc  gggtctggtt  ctgcagacgg  cagcctggta    4860
cggcggtcga  aaggactgga  tcggaaaccg  gtacggctcg  actgagagct  tccggctcga    4920
ccacaagatc  gtctacgacc  tcgggttcag  gcgactccct  ccgggaggcg  ttgcggccct    4980
gggattcacc  ccggtcatgc  tcgtcgggct  ccagcacggc  ggcgggggcc  ggtactcgca    5040
caccgcttgc  acgctgatga  cgatggacat  ccccggtggc  ccggtgaagg  tctcgcaacg    5100
aggcgtcgac  tggagtcccc  gaggagaagt  caacggcgtg  ggggtgttcc  tctacgacgg    5160
cgcacgcgcc  tggaacgacc  cgctcttcca  cgacttctgg  tacctggacg  cgaagcttga    5220
agacggcccg  acgcagagtg  tcgacgctgc  cgaaatcctc  gctcgcgcaa  cgggtctcgc    5280
gtacaaccga  gcggtagcac  tgctgccggc  cgtgcgtgac  ggcctcatcc  aggccgactg    5340
caccaacccg  aatcgcatcg  cgatgtggct  cgcccagatc  ggccatgagt  cagacgattt    5400
```

-continued

```
caaggccact gcggagtacg ccagcgggga cgcctacgac acccgaaccg acctcggcaa    5460 cacccggag gtcgacggag acggtcggct ctacaagggc cggtcctgga tcatgatcac    5520
gggcaaggac aactaccggg acttctcccg gtgggctcac ggcaggggcc tggtccccac    5580
gcccgactac ttcgtggttc acccgctgga gctgtcggag ctgcgctggg caggcatcgg    5640
tgccgcctgg tactggaccg tcgagcgccc agacatcaac gcactcagcg accgccgcga    5700
cctcgaaacg gtcacgcgcc ggatcaacgg cgggctcacc aacctcgatg accgccgacg    5760
ccggtacaac ctggccctcg ctgtgggcga ccaactactg actctgatcg gagatgacga    5820
cgaattggct gatccaacga ttcagcggtt catccgcgag atccacgggg cgctgttcaa    5880
caccgtcgtg acgcagtccc cctacggcga cccgcagaac ccggacggct cggagccccg    5940
gagcaacctc tggcagctcc atgagctgat caagaacggc gacggcatgg ggcacgcccg    6000
ctacgtcgag gaatcggcgc gagccggtga cctccgcgag ctggagcgag ttgtccgcgc    6060
cgccaaggga cttggtaggg atcgctcccc cgagttcatc gcacgcgctc ggaacgtgct    6120
ggcccagatc gaggcagcca accccgagta cctacaggcg tacatcgcca ggaatggagc    6180
cctatgagcc ccaagatccg tgaaacgctc tactacgtcg gcactctcgt ccccggcatc    6240
ctgggcatcg ccctgatctg gggcgggatc gacgcgggcg cagccgcgaa catcggcgac    6300
atcgtcgctg gcgctctcaa cctggtcggc gcagccgcac cggccacggc cgctgtcaag    6360
gtcaaccagc agcgcaagga tggcacgctg accacctccc cggtggatca ggtcaccagg    6420
ggcgtcgagc aggtgctcgc ggccaagcag aacgctgagg ctgaggtcga gcgcgtcaag    6480
caggctctgg agtccgctgt caacggcgcg gtccccagc tcggcccgct ggccagccag    6540
atcctcaacg gcatccaacc ggcctacagc cagccgttcg acccgcacac gcagccctgg    6600
aaccgatgag caagccctgg ctgttcaccg ttcacggcac gggccagccc gatcccctcg    6660
ggcctggcct gcctgccgat acggcacgcg acgtacttga catctaccgg tggcagccca    6720
tcggcaacta ccccgctgcg gccttcccga tgtggccgtc ggtcgagaag ggtgtcgccg    6780
agctgatcct gcagatcgag ctgaagctgg acgcggaccc ctacgcggac ttcgcgatgg    6840
cgggttactc gcagggagcc atcgtggttg gccaggtgct caagcaccac atcctgcctc    6900
cgacgggcag gctccacagg ttcctgcacc ggctcaagaa ggtcatcttc tggggtaatc    6960
ccatgcggca gaagggcttt gcccactctg acgagtggat ccacccggtc gctgcccctg    7020
acaccctcgg aatcctcgag gaccggctcg aaaacctgga gcagtacggc ttcgaggtcc    7080
gcgactacgc ccacgacggt gacatgtacg cctccatcaa agaggacgac ctgcacgaat    7140
acgaggtcgc catcggccgg atcgtgatga aggccagcgg cttcatcggt ggccgggact    7200
ccgtggtagc ccagctcatc gagcttggcc agcgtccgat caccgaggga attgcgttgg    7260
cgggagccat catcgacgcc ctcacgttct tcgcccgctc tcgtatgggc gacaagtggc    7320
cgcacctcta caaccgctac ccggcggtcg agttcctacg acagatctga gaaaggaggc    7380
ggggtgagcc tcgacaatca ccacccggag cttgccccgt ctccgcctca cattatcggc    7440
ccgtcatggc agaagacggt cgacggagat tggcatctgc cggatcccaa gatgacccttt   7500 ggatggggc tcttgaaatg gctgtcggag tacgtcaata cccctggggg acatgacgat    7560
ccgaaccgcc tcaaggtttt gatctcgctg tccgaagcag gactgcttga gaacgagaac    7620
atgttcatcc ccaccgacga gcaggtacgc ctggtcctct ggtggtacgc cgtagacgag    7680
aagggccagt acgtctaccg cgaaggcgtg atccggcggc tcaagggatg gggcaaagac    7740
ccgttcaccg ccgcgctgtg tctcgccgaa ctctgtggcc cagtagcatt ctcacacttc    7800
```

-continued

```
gatgagaccg gtcaggcgat cggcaagccg cgccccgcag cgtggatcac cgtcgcggcc    7860
gtcagccagg accagacgaa gaacacgttc tcgctgttcc cggtgatgat cagcaagaag    7920
ctgaagaccg agtacggact cgatgtcaac cggttcatca tctactccgc ggccggtggc    7980
cgcatcgagg cagcaacctc ctcaccagca tcgatggagg gtaaccgccc gacgttcgtc    8040
gttcagaacg agacccagtg gtggggccag gggcctgacg gcaaggccaa cgaaggccac    8100
gcgatggcca aggtcatcga aggcaacatg accaaggtcg agggctctcg caccctgtcg    8160
atctgcaacg cccacatccc cggcaccgag acggtcgccg agaaggcgta cgtcgagtgg    8220
caggacgtgc agtccgggaa gtccgtcgac acaggcatga tgtacgacgc tctcgaagcg    8280
ccggccgaca ccccgatctc cgagatccct tctgagaagg agaatcccga cgggttccgg    8340
gagggcatcg agaagctccg cgaggggctg ttgatcgccc gaggcgactc cacgtggctg    8400
ccgattgacg acatcatcaa gtcgatcctg tcgaccaaga actcgatcac cgagtcacgg    8460
cgcaagttcc tcaaccaggt caacgcggcc gaggactcct ggctgtcacc gcaggagtgg    8520
aaccgctgct cgccgacccc ggacaagtac ctcgacaaga tgggcttcga gctggctccg    8580
ctggaccggg gccagaagat caccctcggg ttcgacgggt ccaagtccaa cgactggacg    8640
gctctggtcg gctgccgggt ctccgacggc ctgctgttcg tcatcgacat ctgggatccc    8700
cagaagtacg gcggcgaagt gccccgcgag ttcgtggacg ctgcagtgca ttccgcgttc    8760
tcccggtacg acgtggtcgc gttccgcgcc gacgtgaagg agttcgaggc atacgtcgac    8820 tcctgggggcc ggacctacaa gaagaagctc aaggtcaacg ccagcccgaa caacccggtg    8880
gcgttcgaca tgcgcggtca gcagaagcga ttcgcgttcg actgtgagcg cctggaggac    8940
gcggtcctcg aaggcgaggt ctggcacgac ggcaacccgg tgcttcggca gcacgtcctg    9000
aacgccaaac gacacccaac tacctacgac gccatcgcga ttcgcaaggt caccaaggac    9060
tccagcaaga agatcgacgc tgcagtctgc gctgtcctcg cgttcgggggc gagacaggac    9120 tacctcatga gcaagaaggc ccgcacgggc cgggtggtgg ccgtccgatg acagccccgc    9180
tccccggaca ggaggagatc gctgatccgg cgatcgcccg agacgagatg gtctcggcgt    9240
tcgaggacca gaaccagaac ctccgatcga acaccagcta ctacgaggct gagcgccgac    9300
cagaggccat cggcgtcacg gtgcccgtcc agatgcagtc actgctggct cacgtcggat    9360
acccccggct gtacgtcgac tcgatcgcag agcgacaggc tgtcgagggt ttccggctcg    9420
gggacgccga cgaggcggac gaagagctgt ggcagtggtg gcaggcgaac aacctcgaca    9480
tcgaggcccc gctgggctac accgacgctt acgtccacgg ccggtcgtac atcacgatca    9540
gccgccctga ccccagatc gaccttgggt gggatccgaa cgtcccgctg atccgggtgg    9600
agcccccgac gcgcatgtac gccgagatcg atcctcggat cggtcggccg gccaaggcaa    9660
ttcgtgtcgc gtacgacgca gagggcaacg agatccaggc tgccacgctc tacacccca    9720 acgagacgtt cggtggttc cgggccgaag gcgagtgggt ggagtggttt agcgacccc    9780 acgggctcgg cgcggtcccg gtggtcccgc ttccgaaccg gacccggctc tcggacctgt    9840
acggcacctc tgagatcacc ccggagcttc ggtcgatgac cgacgcggcg gctcgaatcc    9900
tgatgctgat gcaggcgact gcggagctga tgggcgtgcc ccagcgactg atcttcggca    9960
tcaagcccga agagatcggc gtagaccccg agaccggaca gacgctgttc gacgcgtacc    10020
tcgcccgcat cctggcgttc gaggacgccg aaggcaagat ccagcagttc tcggcagccg    10080
agctggccaa cttcaccaac gcactcgatc agatcgccaa acaggtcgct gcgtacacgg    10140
```

-continued

```
gactccctcc ccagtacctg agtaccgccg ctgacaatcc ggcctccgct gaggccatca   10200
gggccgcaga gagccgcctg atcaagaagg tcgagcggaa gaacgcgatc ttcggcggtg   10260
cgtgggaaga ggcgatgcgc ctggcctacc ggctgatgaa gggtggcgac gttcccccgg   10320
acatgctccg catggagacg gtctggcgtg acccgagcac cccgacgtac gccgcgaagg   10380
ctgacgccgc cacgaagctc tatggcaacg gccagggcgt gatcccgcgt gagcgggctc   10440
gcaaggacat gggctactcc atcgccgagc gcgaggagt cgccgctgg gacgaggaag    10500 aggccgcgat gggcctcggc ctgctgggca cgatggtcga cgccgacccg acggtcccag   10560
gctcccccaa ccccacgcca gctcccaagc cacaaccggc catcgaaggg ggtgattccg   10620
cctgacgcct gagcagtatg cagcggccca ggccgtgatc actgcggggc tcgccgggta   10680
cgtccagcgg ttcgccagtc tcttcatccg cccagctctc tccatcgcgg agtggctgcg   10740
gctactgcag gtgttgttcc cagaggtcca gcgtcggtat gcggaagctg ccgacctggg   10800
ccgggacttc tacgactccc agcgcagact ccaccacccg gagcttcccc gcaacgagag   10860
gttgcggagc gacctccagt gggagtggtt cgtcaggaac atggagcccg cacgaaaggg   10920
gttgtcgcag gccgactctc ctcaagctgc ggtcaccaag ctgaccttgg cgacagtgcg   10980
cgaagtggag atggcaggtc gccgacagat catcggcgct gtcaagaacg acccagctcc   11040
taagatcgtg aagggctggg cgagggtcgc caccgggcgc gaaacatgcg cctggtgtct   11100
gatgctgatt tcccgtggcc ccgagtacct ttcggcggat agcggggggtc ttcacctcga   11160 caccgagacc gtggtcgacc tctggaacga ggctggccgc gatctggaga agttccgcga   11220
agagaccaag ccccacatcg aggagtggca cgcaggtgc gactgcctgg tggtgcctgt    11280
cttcgacgtg gagaactggc ccggaaaggc cgcacaggaa cgcgctctgc agctctggat   11340
cgacgctggg aaagaagcca gccagctcat tgcatctggc aaggcccgct ccaaaaacga   11400
gaacaaggag acgatcaacg ctctccgtcg ccgcttgtat cgcggcgagt tcgcaatgtc   11460
cgactacgca ctcgctgcgt aatcccccga accccaggtg ggttcatcaa ccatgcccag   11520
gaggcgaaaa cacatgtccg acaccgcaac taccgaaggc actccggccg gcgacccgac   11580
cccggtggtc actgacaagc cgctggaacc gactccgaag acctacgacg aggcatacgt   11640
caaggagctt cgccaggagg ccgctgctgc tcgggttgcc aagaaagacg cagtcgaagc   11700
cgcagtcaag gcggcgaacg acgctcacac cgctgaactc gctgctcgcg acactcgaat   11760
caccgagctg gagaacgagc tgggacaggc ttggatccgg ctgcagaagc tggagacctc   11820
gcttgccgca aaggttccca gcgacaaagt gctcgcgttc gttgacatct tgcagggcga   11880
ggacgccgac tcgatcgccg agtccgcgaa gaagaacctc gaactgatcg gcggtttcga   11940
caagaagccg gtttccggtt tcgaccccac ccagggcttc ggtggtcggc aggaactgcc   12000
gctcaacggt gacccgatcc tcaacgccat gaagggcgtt ctcggcatca agtgatgtcg   12060
agctgaaacc cattcctaga caaggagatt agcagatggc cgcaggcact gctttcgcag   12120
ttgatcacgc tcagatcgcc cagaccggcg ataccatgtt caagggctac ctggagcccg   12180
agcaggcgaa ggactacttc gccgaggccg agaagacctc gatcgtccag cagttcgccc   12240
agaaggtgcc gatgggtacc acgggccaga agatcccgca ctgggtcggc gacgtgagtg   12300
cccagtggat cggtgagggt gacatgaagc ccatcaccaa gggcaacatg acttcgcaga   12360
ccatcgcgcc ccacaagatc gcgacgatct tcgtggcgtc tgcggagacc gtccgtgcca   12420
accccgccaa ctacctggga accatgcgta ccaaggtggc gaccgccttc gcgatggcgt   12480
tcgacggcgc ggcgatgcac ggcaccgaca gcccgttccc gacctacatc ggtcagacca   12540
```

-continued

```
ccaaggccat ctcgattgct gacaccaccg gtgccacgac cgtgtacgac caggtggccg   12600
tgaacggcct gagcctgctg gtgaacgacg gcaagaagtg gacccacacc cttctggacg   12660
acatcaccga gccgatcctg aacggcgcga aggaccagaa cggtcgcccg ctgttcatcg   12720
agtcgaccta cggtgaggcc gcgagcccgt tccgttcggg ccggatcgtc gcccgtccga   12780
ccatcctcag cgaccacgtc gtggagggca ccacggtcgg cttcatgggt gacttctccc   12840
agctcatctg gggccagatc ggcggtctgt ccttcgacgt gacggatcag gcgaccctga   12900
acctgggcac cgtcgagagc ccgaacttcg tctcgctgtg gcagcacaac ctcgtcgcag   12960
tccgtgtcga ggctgagtac gcgttccact gcaacgacgc cgaggcgttc gtcgctctga   13020
ccaacgtggt cagcggcggc ggcgagggct gagcctaact tgacatccac cgggagggg   13080 ccgttcacgc ggcccttcc tggggtgtct gagaggactt catgcggatc caatccaccg   13140
tcaacggtgg gttcgcggag gtctccgacg agtacgccca gcgcctgatc gcggctggcg   13200
gttggaagcg tcctcggaag cctcgcacca ccaaacccaa acccgctccg aagcaggagc   13260
ctgcgaccga ggagtaacac atggcctacg cgaccgctga cgacgttgtg acgttgtggg   13320
ccaaggagcc tgagccagaa gtcatggcgc tgatcgagcg ccgactcgaa caggtcgagc   13380
gcatgatccg gcgtcggatc ccagatctgg acgccagggt gtcttcggac atcttccggg   13440
ccgatctgat cgacatcgag gccgacgcgg tgctgcgtct ggtgcgtaac ccggagggct   13500
acctctcgga gaccgacggg gcgtacacct accagctcca ggctgatctg tctcagggca   13560
agctcgtcat ccttgacgaa gagtggacga ccttgggagt caaccgactc tcgcgcatgt   13620
ccaccctcgt cccgaacatc gtgatgccga catgagcgcc agcgacgttc agcgggctcc   13680
gatcaagtac ccgccggggt ttctcctggc ggtcacacct gaccaagtcg acgccgcgat   13740
gtgcgaccac gaagcggatc ctccggtctg ctactgcgtc cacgactggc gcatcgagtt   13800
cggcaacgtc tctcgccagc ccaagccgaa agcgacgtac atctgatgag cctcctcgat   13860
accggagccc ggtaccagcc ggtgctcgtc taccccgaag agctggtcat cgacgcggac   13920
gggaacaaga agacccagcc gtcgaagacc ccgatccaag cgatcgcacg cttccaggtc   13980
gccaaccagt ccggtacgtc ggcacgacgt gctgagcagg acaacggggg gttcacgacc   14040
gagaaggtct accggatgcg gttccctcgc tccttcacca aggagcacgg gatcctcggc   14100
gctcagaccc agatcgagtg gaagggccag cggtgggcgc tctttggaga cgccaccgag   14160
tacgactcat cgcccgcact ggcgcgggtc gactacacga tcaagaggtt ctgatggcga   14220
aggtctacgc gaacgcgaac aaggtcgcgg ccaggcacgt cgatgtccgc aagcgggtca   14280
aggaggagcg agacggcgtc acccgccgtg ctcgaaccaa cctggccaga gcgaacaaga   14340
cgacccgtat caccaaagag gggtacttcc cggcatcgat cgaagaggtc gacggcgatg   14400
tggacttcca cacggtcctg cacgcgccca acgcgttcgc ccttgagttc ggccacgccc   14460
cgtccgggtt cttcgcgggc accgacacga aaccgcctga ccccgaatac atcctgaccc   14520
gagccgccat cggcggcacc gtctcgtaag gaggacacat gggggcgatg ccccgagtac   14580
aaagtgtggt tgctccgatc ctccgagaag accctcgact cgccggggtc acgattgtga   14640
cctgggttcc cgacatcgac ttccgtgagt tcccgatgat caacatccgc cgcatcggcg   14700
ggatcaggaa cgccaacgcc ccgaagctgc actcgctgcc ggtggtcgag atgtcggcgt   14760
actccactga cgggctcatc gaatgcgagg agctgtacga gacagcactt gaggtgctgt   14820
acgacgcggt gaagaacgga acacaaactc ccgcagggta tttgagttcg atcttcgaaa   14880
```

-continued

```
cgatgggcgc cacccagttc agctccctct accaggactc ctggcgaatc cagggcctga   14940
tcaggctcgg cgtccgcaca ccgagatcca ccacctaacc gaaaggtagc cacatggcag   15000
aaaacgacga tgcagttttg actgctgcgg tcgggtatgt gtacgtcgcc gaagcaggca   15060
ccgctgcaca tacgccggcc gaactgaaga ccatcgacct gtccgacccg tcgacctgga   15120
ctggagccac cggctggtcg agcgtcggcc acaccagccg aggcacgctc cccgagttcg   15180
gcttcgaggg cggcgattcc gaggtcaagg gctcctggca gaagaagaag ctccgcgaga   15240
tcaccaccga ggatccgatc gactacgtcg tggtcctgct gcaccagttc gatgagcagt   15300
cgctcggcct gtactacggc ccgaacgcct ccacgacccc cggtgtgttc ggtgtgaaga   15360
ccggccagac caacgagaag gcggtcctgg tcgtgatcga agacggcgac atgcgccttg   15420
gccaccacgc ccacaaggcc ggtgtccgtc gcgacgacgc gatcgagctg ccgatcgatg   15480
accttgccgc actgccggtt cgcttcacct acctcgacca caaagacgag cttccgttct   15540
cgtggatcaa cgaggatctg ttcggcctct cgccgggcgg tggagcctga cccaaacttg   15600
acagccacca ggctgtctac cccggagggg gaggtttcct tggcgggcct tgcctccccc   15660
tcctcccgcc atctagcccg ccacacactc tgaaaggttc gccatgacaa acgtattcac   15720
gatcgacgca ttccgcgaag aagtcaagaa gaagtacgag cccgtcacga tcgggatctc   15780
cgaagatgtg accgtcgagc tgaagccgct gctgaagctg ggccagaagg cccgcgaagc   15840
cgtggtcgag gccgtcaagg aggtcgagga catccccgac attgacgagg acgacgagga   15900
ggccgaggag ctggtggacg agtactcgct ccgcatttgc gagatcgtcg ccaaggtctt   15960
ccggctgatc gccacgaagc ccaagaagct gatcgccgcg ctggacgagg aagaggatcc   16020
caggatccgg gccgagctgt acgcgaccgt actgcggacc tggatggtgg agacgcaact   16080
gggggaagcc gcgccctcgc cgagctgatc gacaagttcg gcggggcgat tctctccgac   16140
ttgtccgagt accacggggt cgacctgcgc gatctgttca gagatgaaga tccgctgtcc   16200
cccaggtacg tcctgaatct ggtgattcac ctcccgaaga caggcgcgtt ctacgcggag   16260
cgtcgaggtg gtcagcagta ccgaggttgg gatgaggacc ggtacgcgct cgcggacatc   16320
tacgacgcag tccaggcggg caaccacatc ctcctgatgg ccaaccggga tccgaagaag   16380
ccaaagccga aggcacccaa ggcatacccg cgtcccgacg actttgagaa gacaacgccg   16440
aagccaggtt cgttcgccgc gatggtagtg gccgcgaaga aggctgcgcg agagaagagg   16500
gaaagggagg aggcgaatgc cgaatagtgc tggcgtagag gtcgcacgga tctccgtcaa   16560
ggtcagcccc aacaccaaag agttccgtcg tgagctgaag accgatctgg agaagatcga   16620
gcgggagctg tcggccgacg ttccggtcaa cgccgacctg aacgcggccc aggccaaggc   16680
cgacttcaag cggctgatga tgcagctcaa gaccgaggct gcccgaggtg tcaacatccc   16740
cgtcgatgtc aacgtcgaca aggacaccaa gggcggcttc ctgagccgcc tgctcggcgg   16800
taagaaggga ctgagcagtc ttggtgatga cgccgcgaag gcgtcgtctc aggttcagca   16860
cctgggcaag tcgttcctgg atctgacccg cacagcgtgg atcggcgtcg ggatcgtcgc   16920
catcgccgcg ccgcttgtcg gcttggtggc tggcctactg gctggcctgc cgtcgctgct   16980
gtcagcgttc ggcgctggag ccggtgtggt cgcactcggc atggacggca tcaaggcggc   17040
agccgagacc atgatgcccg cgctggaagc ggccaagacc gccgtctcct cgacgttcca   17100
gactggcctc accccggtct tccagcagct cggtgggttg ctgacgaccc tcacccgaa   17160 cttgcagaac gtcgccaccg gcatagtgaa catcgccaag ggcttcaccg acgtggtgtc   17220
gcagggtccg gggctccagc agctccagaa catcctcgac cgcactggcg agttcttcac   17280
```

-continued

```
cgggctcggg ccggtcatct cgaccggcac gcaggcgttc ctgacgttgt ccaacgcagg   17340
agccaacgcg ttcggacatc tcctcgctcc tctgcaggag ttcgccaacg gtttcaacga   17400
catggtcaac cgcgtcacgt ccaacggcgt gttcgacggt gccatgcaag ggctttcgca   17460
gaccctaggc agcatcctga acctgttcaa ccggctcatg gagtccggtc tgcaggcgat   17520
gggtcagctc ggtggtccgc tgtcgacgct cgtcaacggg atcggtgatc tgttcatcgc   17580
gctgatgccc gcgctgactt cggtgtcgag cttgctcggc aacgtcctcg ggactctggg   17640
cactcagctc gctccgatca tcacggcgct gacgccagcg ttcaccacgc tggccgacac   17700
cctcggcacg atgctgacgg gcgctctgca ggctctgggg cctgtgctga ccgtggtcgc   17760
tgagaccctc ggcactgcgc ttaccactgc gctgcaggcg attcagccga tgctgcccac   17820
gctggtggac agcttcaagc agctctccga aacgctggtc acctcgctcg gcccgtacct   17880
gccccagatc ggggaagcgt tcggccagat cgtaggtgcg gtcattcagt tggccccgac   17940
gatcatctcg tcgctgatcc cagcgttcca gacgctgatc cccgcgatcg cacagctcgc   18000
tccgtcgctg gttcagatcg tccaggcgtt caccaagctg atgccggtca tcgtgccggt   18060
ggtccagatc gtcatcaacc tggctgcggc cgtggtgcag gctggcgcgt ccatcgcgtc   18120
gttcctgatc ggtggcatct cccggctggt tggcgtcctg gcagactgcg tcggcgcagt   18180
cgccgagtgg gtcggctcct ggtccagcgg tgtgcagcag gtctccgact tcgtcggaca   18240
gctccccggc aagatcaaga gctggttcga tgacgcaggc tcctggctga tcgaggcggg   18300
caagaacgtc gtccagggtc tgatcaacgg catcggttcg atgatcagct ctgcggtgag   18360
caaggccaag gaactggcca gcagcgtgaa gaacgctgtg accggcttcc tcgggatcca   18420
ctctccgtca agggtgttcg ctgagatcgg tcagttcacg gccgagggct tcggcaacgg   18480
cttcgaggaa gggttccagc ccgtcatcga gaaggccaag gccctggcgg ctgagctgtc   18540
tcaggcgatg gagtctggcg tggacccctc cgggatcctc gctggtatca gcaccaagga   18600
attgaagcag tactcggctg cgctggagca ggagcgcaag cggatccagg tcgagaagaa   18660
cgcaattccc aaggaggaca aggccggccg tgcggcgctg caggcgcagc tcgaccagat   18720
caaggcgcag aaggacatcc tcgcgtacca gagggaccgc atcaagaacg aggaggacta   18780
cgtcggcgca gcgggcgatg acccgctcgt gaaggcggct tccggcttga tgaacgcacc   18840
ggtcgacttc gcgaaagcga ctgggaagca gttccttacg gacctgggta tctccgggga   18900
cggtgcgatc tccaaggcca tcaccgaggg gattcagtac atcttccaga tcggctctgt   18960
cgatgaggcg ctgtcgatca aggaccgcga ggaatccaag aacgcgctgt cggtcgtggg   19020
ccgagcttga catccaccag gaggtaacca ttgatcaccg acaccatcgt tgaactcgaa   19080
ggtgtcaacg gtgagcgctt caacttgacg accggtgacc agggcgtgtt cctgccacca   19140
gacgtggagg gttgtttcta cgaccctccc gtcaaggtcg tctacgaaga gccggggaac   19200 tacccggtg ctcgctacct gggacaccga gttctgaagc gcgacatcgt cttcggggtt    19260
cagatcctca cgacgcgaa gcagggacca cggtcctggc tgtcgcgaga ctccgtgtgg     19320
cgtaaggcat gggcgttcaa ccgcgtctgc aagctctacg tcaccacccc ggactccggt    19380
acccggtacc tgtacctggc gctgttcgag tcccccaagg tcgagatgaa gaccgacccg     19440
cgtggcaaca ccatcaacct gacggtgatg tcgtgcatct cgtacgaccc gttctggtac    19500
gaggacgacc gagtgttctc ggtcaagacc aagaccgata ccaggttcga cccgaacttc    19560
tggacaccgc cgtggccgtg gggaggaactg cccaaggaga cgctgcggat caaggtcggc    19620
```

-continued

```
cgcgagcagg gcgggctcaa ccccaccgac cagtacatcg caccgaagtg gaccgttccc   19680
ggctccaccg agaagatccc tgacttcccc tggccgttcc cgccgggagt cgagatcccg   19740
tgggagaccg ctccgttcac gcagttcgtc atcccggact actcgttcga ggacgaggag   19800
ttcgccaacc gccggctcaa gacgccgggg ttgatctacg gcgagaactg catcatcgac   19860
accgaccgac gcgaggagca gatcagctcc gagtcgggct ccccggtgtg ggcgcggatg   19920
aacggtgtcc ggttccgcaa catgatcccc ccgtacacag aggagcgtga gttcgtcata   19980
gacgcatcgg gatgcgctcc gggacaagtg gttacccttc ggctcccgag gccgtggtcg   20040
cgctgctggg gtctcgaatg agtggcctga cgagcgttgc ccaggctgaa gatctctggc   20100
ggaagatcca actgcggcgc tgcaagcgcg agcaggagcg actgaagcca ccggacgtag   20160
agctgcgcga cggcgacttc cgtctgcgcg gcctcgtcgc gggtgagcga ctgctggagt   20220
gggagttcat cgagaacgag accggcgtag ccacgctgca gctctcgctg agccactacc   20280
tggccaagtg ggtgatgaac caccgggggtc gagcaaagcg caacgtcatc ctcaacgtcg   20340
agaagcaagg cgctcgatgg agcgggatga tggaccacta ccgggtggtc aaggaggact   20400
ccggggactg ctacctggag atcgtgtttt tgcacgactt cgagcagacc aagcacatcc   20460
gtgtctggtg caacccgttc ctgcgccctg agctgcagtt ccccaagatc tggatcatct   20520
tcgggccggc caagtggtgc ttgctggtca cgctgttcgt gaacctgctg cgactggaaa   20580
cgtccctgtg gacgatcccc gacgatccga cggacatctg ggagtggatg gggccgagct   20640
tcaaccccag caaatggcgg aacattgtca agccgttccc cttcctgctg gacaactcgc   20700
ccatcacgat ggtgttcagc cggttcggga cgttctacga cacggcgaag cagatccttg   20760
agaaccacca gctcacgctg acgtgtcgcc ggtacatcaa ggaccgcgac ccgcacccgt   20820
tcgatgacct gaagggtctg tggggcatcg accccgtcga aggtctgttg cagctcatcc   20880
cacttcggga tggctgcgtg gtctgggaca tcgaggacaa ctctggctgg ggcaccgaga   20940
ccgccttcgg cggctcctgg ctcaccgggt tcgtccgggc ggtcgtcaac ctggctggag   21000
acggccaggt cgaaggggtc gacgtattca cgggtgacta cacgttcccc ggcgagtact   21060 actcccgtg gttcctgggc accagcccga gggctccgca cgtcgtgttc gaagagggc   21120 cactgaccgg gatcaagtcg tcggagttct cgtactacga ggcaaccgac accagcttcc   21180
tggccggtgg acagtccgct ccgggcatca acgagggggat ctcggccctg gtgaacatcg   21240
gtggcgatct gctgacctcg ttcatcaaca gccagctcgc cgtgctcggc gcggtcggtg   21300
gcgcgatcga cctgcccccg ctgggcggtc tgatggatgc ggtcctgaac ccgctctact   21360
ccgacgtgtt cggcgcgttc atggaagtcc cgacgctgcg tgcgatgggt atctcgcttc   21420
ccattgcggg gcttgaggac atcgtcaccg gcctgggcga cttccactac tacgagaaca   21480
tggtggacag cccgatgaag gcgttcaccc tctcggcgtt cgcggccatc gcagcccaga   21540
tccacaagac ccgagcccga acggctcaca cgctcaaggt gtctgacgcg gcaccgtaca   21600
tcttcgcacc aaagccctac gggcactgct ggatcggaga tcgcgtcggc acatcggtgc   21660
tcggctaccc ggtcgagcat cagttgttcg tggagcggat ccgaaaggtc aagtaccgca   21720
tcgacaaaga cggcatgaag ccgttggaga tcgagatcgg ataccgcgaa ccgaagaacc   21780
cagctctgca catcctcgaa gagatcaagc gtttcaacgg cgctatggga caagcgggga   21840
ttctctaacc gaaaggcacg ccgcatgatt ccgtcacaag agactcacaa tccgaacgac   21900
ccgcgacagc acgtcgtctg ggcgctccgc aatctcccgt tgattgcagg cgtcggggcg   21960
atcacgcatc cggcgtacct ggcggattgg tcagagcact tgtgggaagtg cggctttcgg   22020
```

-continued

```
catgtcgact ggctccggga gctggctgat gaggacggca acatccacgt cagtcagctt   22080
cctgaccagc agatcaagtt ccagccggcc ttccgaggcc agcggcacga catgaacaac   22140
gcagcgaggt gggccgagaa ggacgctccc gacccagaac ccgtgcgtat cccagacatt   22200
cgcaagctca cagaccagga gaaccgagcg atgctcgcac agtacgaacg agacgggtgg   22260
atcaagaacg accgccccgg cccagcgatg gccgaggtcg tggagtgacg gagctattca   22320
accccgataa cccttgggag acagcacttt tgttcttcgc cgtgttctgt tcggtactgc   22380
ctgcgttgct tccgttctgg ttcaagatca agaagatcga cagccaggta tcgaactcgc   22440
acgacgagaa cctccgcgac gagatcaccc gagggttcaa agaggtccgc gaggacatcc   22500
gacttctaca tgaggcgctg aacatcgagc gccgcgaacg catcgctggt gacgaaaaga   22560
ggtgcgcttg acattcccaa ccaacccact cgaagcgatc ggagctgacg gcgcattcga   22620
gatcggcggc ggtgatttca gcttcggcca ggactacacc gagcagatca ttcggtcgct   22680
gttcacgatg ccgcctgtcc gactcgacaa cgcgatcacc ctcctccgcg agcacctgct   22740
gaagctgcct ctggaggcgc tgcagaggtt caaggagatg atcccggact gggccgaagg   22800
cgcgttcgac accgctaccg gtgctgtcga tgcgatcatg gacgcgctca gcgaaggtcc   22860
gctgttcctg aagctcgcag agttccaggt gttcctccag cggctgctga ccgaacccgg   22920
agaggtcatc ggggagatcc cccaggctct ggtcaacggt ctgacgagcg ccctggagac   22980
cgtgaacaac acgatccaga ccatcgtgga catgctgctg caggccctcg gcatcaaccc   23040
caagggcgac ctgcttgacc ggatcttcga cctcagcgac gagatcgagt ggctgcggga   23100
caccgcgagc caggtagcct ccgggctcca gcagacgtgg aaccacttct ggtcggccct   23160
gaccgggcgc agcccgggcg aggaccagac cgtcgttgag ccggccgagc agatcggtga   23220
gctggccggt acgactcagt cgaactcgtc tgccatcgcc gagctgcagg ctcgcctgga   23280
cgcacaggac cacaccggca tcgctggcgg ggatgacttc gagcgagtca acaccacggc   23340
ggtcggcccc ggctgggccg agttctatac cggcggcggc tacggatcgg gcagaggcta   23400
ctacgcgatc aaggacggcc atcaggccga gtggaccgac cagggagcca cacagaacac   23460
cgcacggttc gtccgtacgg acccggccga cgagaagacg gtcaccgact accagaagat   23520
gacgctcgtc gtcggcacca tccccggtga ggctgcaggc ctcttccggg gcggctcaca   23580
catccggttg tggctgcgcg tcaacgacaa cgcgcctacg gtcggcatca ccgacggggt   23640
ctatgtcgag gtcggtggcg cgaacctcgc gcagttgggc taccggcgta gaggctctga   23700
ccacttcgtc ggctcggcgt tcaactgctc ctggggagcc gggaccatct tcacgttggt   23760
cgctggcacg gtcgacggca tcgagaaggt cgagttctac aagaacggct ctcgactggc   23820
cctgtggtcc gacgacgggc tccggtcggc tatcggcgct ggcttccggc gctgggggctg   23880 ggaaggccag gcccgtaacc gcaacctcgg ccagggcacc ccgagttcgg tcacccgcgt   23940
cacgatcaac gacaacgacc ccagcggtct cggtggcggc tcggtccacc tcgaaaccgg   24000
cgtcgtcggc atcctgcaga tccccaacgg cggcacaggt gctaccagcg cggccgaagc   24060
ccgcgccaac ctcggtgccg aggcggctat cccggcaggg accgtcgcgc agtactggcg   24120
cggcgacaag acgtggcagc cgctgaataa ggtcgctgta gggctccacc tggtcgacaa   24180
cacgtcggat gcccagaaga tgtcggctcc cgccgtgctg acgaacaaga cgatctccgg   24240
ggctgacaac acgctcaccg acatcccagt ggcagcactg ggtctcggag ccgtgaacgc   24300
agtgcgggta atcgcgggcg ttccgatacc gaactctgtg acgatctgga tcgggactga   24360
```

-continued

```
ggcccagttc caagctctcc caacgaaaga cgccaacacc ctgtacttca ggacggcgta   24420
atggcgggga tctcgtcagg gctcgaaggc attcgggcca tctcgtggaa caccgtcccc   24480
atcctgaagg tcagcctcgg caacgaccag gtgtggccag cgttcgaccc ggtgctgact   24540
ccggtcacgg cggtcggcgc gtacacctac aacatcccgg cacaggccga gttcatcgac   24600
gtgattctcc tcggagctgg cggtggtgga caaggcatgg gctccgccac tgcgtggggc   24660
caaggcggct tcggcggttc ctgggtgacg gccacgctca ggcgtggcgt cgacatcccg   24720
tgggcggtca cacagatcac tggcgtcatc ggcgctggtg gtaccgcagg gcctggttac   24780
atcttcggac agaccggcgc gggcggcaaa gggggcgaca ccacagccac cttctcgggc   24840
ggtggcacgc tcatcgctgc cggtggtgct ggaggcaatt cgaggaaact ggacttcgga   24900
ggtaagtccc cgaatcctgc cgacatggtg taccgagacc ggacctacga cggcggcgct   24960
aggcagctca ccccaagtgg tatcgggtac gcacctggtg gcggcggcgc agccgcaacg   25020
gtcccagtgg gtatcaccgg tttggccggt ggtcccggtg cccgtggcca ggcgtggttc   25080
ctggcgtact aaggaggacg atggagtacg actacgccct ccggtacgag ggccaacaga   25140
cacccgatgg tccgtgggtg gaggtcatag ttcccgcagc cagcctcgca gaggctcggg   25200
ccgggtacga ggcgagcctg ccgacgatga tcgacaaccc cagcatccgc aatctgcaga   25260
tcgtctacac gcccaagatc caatggaccg tgtggactga gtgacaagaa acccccctct   25320
tgaggctgta tggccttggg aggggggctt tttgcgtttc aggggtaat ccctgccagc   25380 tccgacattc gcctcgctat ctcctcgtca cgggctgctg aggccatctg gtacttcatc   25440
gccatgcgcg gagtcgtgtg cccgaggcgc accatcagct ccttggtcgt cgcaccggcc   25500
tgagccgcca gcgtggctcc cacggcccgg aggtcgtgga tgcggaggtc cggtcgaccg   25560
atcttggcgt agcccttctt cagcgagcga gtgaacgcag acttcgacag ccgctgcccc   25620
cgcgtggtgg tcaccaggag agcttccggc cccttgttca tcttcgtccg gtcagccatg   25680
tgctcgcgga tcatcgccgc gacgtgaggc ggcacggtca ccggccgctt ggacctgacg   25740
gtcttggtgt tgccgacgac gatcttctcg ccgacgcggg ccgcgccccg cgcacgcgg   25800 agcttcatcg tctcgccgtc atccacgatg tccttgcggc ggatctcgat cagctcaccg   25860
aaccgcaggc tggtccacgc caggatgtag acggccacgc ggtagtgctc gaacacctcc   25920
ccggccacta cgtccagctc ctccggtgtg agggcttcca cgtcgcgctc agcgggtgcc   25980
ttctgctcga tccggcacgg gttctccgac accagcttgt cctctacagc ggtattcatg   26040
accgcccgga gtacgttgta ggcgtgccgc cgtgccgtcg ggtactgctt acccatcccg   26100
gcccaccacg cccggacaag ggcgggggtc atctcggcga ccggggtgtc gcccaacacc   26160
gggtagatcc gcttgcgagc gtgcgtgctg tagagatcct tggtgccgcc agcgaggtct   26220
cgctcggcga tccacttctt ggtgtactcc tcgaccgtga tggcactcgc cgcagccttc   26280
ttctcgcgct cggccggcgg ggtccactcc tcgttgtcga tcagccgctt ctcagacgcg   26340
agccacgctt cggcgtccat ccggttgtcg tagttcctcg gcccgaagta ccgctgcccg   26400
tcgatcgggc tgacgtacga cgcttgcact cgaccgctgc gctgggtccg cagcgatccc   26460
catcctctcc gtcttgctgc catgcgaaac aggctaccgg aatgcgacct tattgcgacc   26520
ttcagacgtc tttgcgtgtc cgtgaacagg cattttgtc cacttcaagg tcgcacaggg   26580
tcagagctaa aaacagggtc tgagctggga gaatgtgaca cgccgacccc cttacttcca   26640
aactagctac gcgggttcga ttcccgtcgc ccgctccaca ggtcagaggt ggttttagc   26700 ccgaggaccg gatccccgag aggggccgc gaccttagag cgacactaat gacctgcatt   26760
```

```
tatgctgccc ggatacagcg acacatctgc taccttcgac ctccgacaga cgaagaaagc   26820
cccccgcctg ctgcaacaga cgaggggcgg tacaccagat cggagctggt gcagtgaaga   26880
ttctctcacg tgacaaggtc gcacttaagg tcgcaacggc cggaaccgtc gccgtcggcg   26940
gtctggcctt cagcctcagt ttcaccgcgc tgagcgagct gtcagcggcc aacggagtgg   27000
ctcagtcgtg gatggtcccg ctcgttatcg acggaggcat cctcgtcgcg acgatggcga   27060
ccgtggccct gagccgacac ggttggtacg cctgggcgct gctgatcctc tcgtcgctga   27120
tgtcggtcgc gggcaacgtg gcccacgccc agcctcacgg gctcatcgcg atggtgatcg   27180
cggcgattcc gccgttgtgg ctcctcgcat cgacgcatct gacggtcctc ctctaccggg   27240
aggcccagga aagtggctca gaatcgatct cagagcctct tctgaccagg ggttttgccg   27300
aagcagcttg actgcgcccg accgggcata aagtacatag acagactatg tatttaggag   27360
gcacaaaaaa agggctccag aagggccagc acgaagccag cccctccaga gcccagaggg   27420
tgctaccggg tagctcactt accgatgggg cgcatcagcg cctcgacgga gtcacgttcg   27480
acgcggatca gcctggggcc gagccgcacg gccttgagcc ggccgtcggc gatgtagcgg   27540
cgcaccgtct tggtgctcac gccgaggaag tcggcggtct gttggatgga tgctctctgc   27600
ggcattcagc tctccttggg gtagacgacg cgctcgatcc cggatgcagc gatcaggttc   27660
gagcaggcgt agcagggctc tcgggtgacg tagagggtcg ctccgatgag gtcttcgcgg   27720
tcgcagtaga gcagtgcgtt tgcctcagcg tggacagcca cgcatcgagt tgctccgctg   27780
ctgtagtcac tgactccagg aaccgcccca gagagtcggc gagggcacgt actgcatcct   27840
gcagctcccg caggcgctcc gttgtagcca gttccgcgaa ctcgtcggtc cttgacgacg   27900
actgcaccaa ccttgctcct ttcacagtcc gatcgctggg ccgctgccgt ggcgatcccg   27960
aggaagtact cgtcccagtc cggtcgactc atcagaagaa gatcggcacg ttgacgccgc   28020 cccccggcggg cacgaagatc acgccgttcg ggccggtgta accgggtgcg gagccgccac   28080
cgtcacaggc cgtgaggccc agggcgaaag cgacgacgag cagcaggact gcgatggtct   28140
tcatgaggtc tccttgtcga gttgtcgttc cagttcgagg atttgggcct tgagcccttg   28200
gttctccagc agcgcctcgg cgagctggcc ttgtgcgatg tcgttggcct cgtccttgcg   28260
gacggcctcg tcggtagcgt cgtgcagtcg acggatcagg tccgggaggg ctccgtggag   28320
acccgcgacg aagtccgcgt cctgctcccg gtggaatgag ccgagccaca gcttgctgcc   28380
gtcggtctgg tcgacagcga agacctgcca ctgcaggtgc tcgtcaccgt cgaactcgac   28440
cacccagtag cgggatttgg cctccgtggt gtgcgaccac tgctggtaca gcacgtcgaa   28500
gaactcgtgg tcctcagcct cgtacatcga actccttcat gattcggtcg aacgctcgct   28560
gctgcacgcg catctccagg gcaaccgtcc gcttcagcca cgcccactcg ccgtcgtggt   28620
tgatctccca ctggctcttg aacgccacat cctcgacaag gaaatcgact gtcagcgtgt   28680
ggattccggt gttgctcacc tggaaggtga tgccctcctc ggcgatgtac cagggcagct   28740
cctggccgtc gaagaagacg gcccggtctg tcaccacgac atcaggaaaa tggtgcatcg   28800
ttgatgtacc cctccttggt gagggcctcg aacacctggt ccacgacctg gttgacgtgg   28860
cccccgaacc agaccggagc catgtgctcg aacgcagaga acgacttgtg ggtcagcacc   28920
ttgccgtcgg gagtccgaac acgaaactcg aactcccagt tgacctttac gtcgtcggcc   28980
atcagcgccg acccaggtac gggatgatgt tggcccggaa ctcgaagtag aagccgggag   29040
gccgaccttc ggggacatcg gcggtgtaga cgccgatctc gtctccctcg atcgtgccta   29100
```

-continued

```
gctggctgag cttgtggatc gccagaccca tcagctcctc ggtgagcttc ccgttcggtg    29160
cgggcagcac tacgttggct tgtgccatca gttcttctcc ttcagtagtt ctgcgattgc    29220
gatgagcgcg ttcaactgcg ccaccttcag ctcgaagtcc gcgtcgaagg tcatccgacg    29280
gcgacgagcc accctcttgg cttcttccag gtagttggtg tctgtcaagt tgccctcctc    29340
agtaatcagc gccgtagagc gagccccacg aacgctttcc aacttcgggg tcggtgccga    29400
tcagcaccgg acccatctcc tcggccatca gtcgagcgat ctcgcgagcg ccccagttgg    29460
ccttctcagc gggcagagac gcgacgatct cgtcgtggat gggcagacgt aggtacgggg    29520
tgaatccggc ttcgtggagg cgaatcagcg ccttgcaggt cacatcccga gacgtggact    29580
ggatctggta gttcagcgcc gagtacgtcc gagagcggtc caccggcagc cgccggccca    29640
tcgggttgat gatgtacccg ttgcgcttcg cctcgttggc gagcttgcgg ctgtaccgcg    29700
tcactccggg atacgccttg tcgaacccgt ccacgacctg cttcgcggtc tcgatcgaga    29760
tcccagtctg ctcggccacc gtgttggccc caccgccgta gacccggccg aagttcaccg    29820
tcttggcata cttccgctcc gggtcgtcct tggtgatgtg gtccccgaag gcagcgcgag    29880
ctgtcatcag gtggaggtcc gcaccgtcct tgaacgcctg gatcatcgtc cggtcgcccg    29940
agagcgcggc caggacgcga agctcctgcg cctggtagtc gatcgaggcc atgacgtgac    30000
cggggtcagc gaggaagcac cgacgcaccg tccagtcgga cgcgggcagc gtctgcgccg    30060
ggatgccagt gatcgacatg cgcgaggtcc gcgcctgcag cgggttgacg aacgtgtggc    30120
accggtcctc ggagtcccga gtgtccagga acgtctggac ccacgacgtg cgccacttcc    30180
cgagcttctt ggcctcctgg accatctcgg ccaggtgagc tttctcgcct cccgcagcga    30240
tcatgtccgc gtagaacccc ttgtccacct tccgcttacc ggagtcggtg aacgcggtga    30300
acttgtgtcc cagctcctcg aacgcctccg cgacatcctc ggtcgcgttg accttctcga    30360
tcccgtactc gttgaggagc acggcctccc agacctgctg ctcccccagc cacttgtcgg    30420
caagctgctg cgagtactcc acgtcgagca ggaacccgcg ccggtcgatg tagctgcaga    30480
tctcggagat cttgtgctcg tacggcacca acggccggct cacgtcgggc accagcggtg    30540
ccagcgcact gcagatccgg gccgtgaaga ccgtgtccat ccccgcgtac gtcaggtact    30600
ccgggtggta caggtcgatg gtcgaccaga tcttggcctt ggtcgtcttg tgctccttgg    30660
ccagcttggc catgagcccc ttgacgttct cagcctgctc cttcgagatg aactccgcga    30720
tcagctcctc cagcgagtgg ccgaacccac cggccccgaa aggccggggg tccaccagct    30780
tcgccaggat ctgcgtgtcc aggatcttag gccagagcga ctccatcttg atcccgaagc    30840
accggtcgag cacctggagg tcgtacgagg cgttctgcat cacgatcttg ttcagcacgt    30900
cgagcgcctc atgcacctcc tcccgcccca gcatctccag atcctcgatg ggcagcaccc    30960
aggattcggt ctgagtaccg aactggacta ggcggcaacg gaagtcggcg ctgtagatgt    31020
ccagcccggt ggtttcggtg tcgacggcga ggcagttctg atgagcccgg atgaagtcgc    31080
ggaagccgtc cagatcctct gggtgttcaa cgacgttgat ggtgacgagg tctccttgga    31140
cctcatgccg cagctcgatc atgcttctcc tagtacgggt tccgttcgac cgaggccgac    31200
gaatgaacgc gagtgactgt gtccctgtgg acgattgggc cgacgacctc cttcttggcc    31260
gtgccgtcag cgacgaaccg ggcagccagc aggttgtgct gccaggtcgt caggagtccg    31320
atctcgccac cgaagttgat cgtggcgttg tcggtgccgc ccgtgtaccg gacggtgttc    31380
tcttcgacat cggcgacctc cttcatcagg tcaatcgcca tgcgccgcag gccaacagcc    31440
tgcacatcga tcggtagcgc ctcatcacgc ggcagcgcga tcactacctg gatccgatcg    31500
```

-continued

```
gccatcagtg gtagatcccc cggacggtgc gcgagatggt ggcggggttc acgccgtagt   31560
tgtcggcgag atccttctgc ttcatgccac cccggtacgc ctcccggatg tcccggacct   31620
cacgctcggt gagcttctgg cggttcggcc ggttcgggcc gaccggagcc aagctgcctt   31680
tgacgaacgc ttcaccgaag gtccgcctcg cggtgtcgag ctgactccgc agatcggcgt   31740
tctccgaccg caggttctgg ttcacagcca cctggcggtt gaccgcagtg accaaccgac   31800
cgttcgcggc ggtcaggtct tcgttcttct ggatctcctg cgccagttca accttggcga   31860
ccccgaggtc tcgggcgagc ttggtgttcg cttctctcag gtgcttcttc cgcatcagcg   31920
gcctccctct cgacggaacc gctcggtctc ctcggcggtc atgtagtaga agtcgaggac   31980
gaagtcctag ttgatggttc gggacgtgcc gtcttcgaac gcgatgatca ggacaccctc   32040
ttgggtgtcg aggatcggct cgccgttgag caccttggta gcggccgttg gcgaggttga   32100
cgatggttgc tcgttgcgac atgctcagcc tccgtagctg tagggttcgg tggggatgtc   32160
ctggtaggtg ttgggagcga tctcccggag ctgccgaagc aattcccctg ccagttcccg   32220
gatttcggca tccgcggcct catgccagcg gttcttgatg acgtaccgcc acgcccggtg   32280
gttgcccgtg acgaccatcg gcgagttggt catgttcggc agaacggccc gagccgcttc   32340
acgcgccttc ttccggggga atccggcatc gctgaagatg tggacgaggt actcgtacgc   32400
ctcctgggcg aacgactgaa cgtccagcag gacttccttg gccttgtcgg cgtcggagcc   32460
cgacagctcc gtaaacgccg ggggcacatg gattcccagc tccgtgggat cgacgtaccg   32520
ctgcgacacc accgagaagc tcaggtgcct gtgacgctcc agttcggtca ggaccgaccg   32580
gctggcctcg atgtagaacg tcgcgctgga atgctccagc accgactcat ggcccacgtc   32640
gaggatgtgg ttgaggtagt cgacgttctc ccgcgtcttg gggttcggtc ggtcgaagct   32700
gaggtagcag ttccggccag cgaactccgc gagttcgtct gccgacgtga cggtttcgtc   32760
atcaccgacg tagtcggtgc ctgcccagct cgggtcttcg aggatcgtgg atgcgatcag   32820
ttggactttc atactctccg ctcagagttg tgaggggccc agtcgtcgtt gctggccccc   32880
ggtggctgtc aagcgtggat cagccgtttt tcttgctggg gtactgcgcg gggcactgct   32940
cgttgcgagg agcggtgcag gagaacagcg cgtaggtgtt ccccgccttg gagacaccgg   33000
acttgaactc catcttgccg tgcttgcaga accgctcttc gccgccaggg gcttcctgcg   33060
cctgctgcgg agcccgagac tggtgctgct ggccaccgcc gccgctaccg ccgccaccgg   33120
agttcggctt gctgccgcca cccaggttgg cgaagtgatc ggccatcttg gtcacccggt   33180
ccatcagggc gaaccacttc tggccctggc ccagcttggc aacctcgtcg ggatcaacgc   33240
ccaggtcgac cagagcctcc gtgacgctgg cgtacttcgg caccagccac ggcgcggagt   33300
agctgccgtc acccttgaac gtgatcgaca acgcgtcggc cggcgcaggc cgcacctcca   33360
cggtctgggt ctgctgggca gggggatccc agggcgactc agtcggcgtc tgctgctgcg   33420
cttcttcagc aggagcggtg tcgaccggcg cgctggcgaa cgggtcttcg taggacaatt   33480
ggtttcctct cacttaatgg ggcatgcgcc gttggcgcac tcttcatcga caccgtcagc   33540
gacggctttg atcgcagcag cctcgtactg ctgcttggtg attcgctcgt agggagcctg   33600
cgggaagctc tcctccggga agatcgtgga gcccttgatc agcccagaga acctctgcag   33660
atcggcggcg acatccacgc cctcgtaggc gtccgggtcg acgttggccg tgaagctcac   33720
agcgttgtcg gcccagcacg tctggtagag cgcctggaac gccaggagct ggtgcagcgt   33780
cagctcgttg gctgactcca cgatgtcctc ggcgtctcgg ccgaaccgtg cggccacggc   33840
```

-continued

```
ctcgaccaag gtgtccttcg tcgggatctc gaccacccag gtgttgcctg acttgtcgta   33900
ctggtccttc tcgacgtggt acccgtcagc cgcgtactgg gacgcggtga ggaactggtc   33960
gttgtccagc accgagaacc ggatgcgccg gatgaagtac cgggagaaga tcgggtggat   34020
accctcactg actccaggca tcttcgcgat ggtccctgtc ggggccaccg tgcgcttctt   34080
gaccggcacc gggatccgca actcatggct gaactcctcg gccgctctgt cgacctcagc   34140
ggccatctcc cgcaagaaag cggtgaaccg cttgtctccg ggtgcctgcg aataccttcg   34200
gcctgtcagg gccaaatagg aggccactcc gaggtgccca acaccgatgc gccggttgcg   34260
atccagaacc tctcggctct tcggatcagc gaccgctgag aacgtcgccc ggatcaggaa   34320
ccgcgtcatc agacggtggg ctcggatcag gtcgatgtag tcggtcttcc cggcgtcggt   34380
aacgaacgcc gcgaggttga tgtgccctag gttgcagggc tcccacggct ccagcgtgat   34440
ctctccacac gggttggtgc agacgacctc gttgggctca ccgacgttgg acaggctgct   34500
gtcccacatc cccggctcgc cgttgcgtac ggctccctcg gagagagcct tcagcacccg   34560
gtgtgccttc gtggagcgcg ggttgagcgg gtcgacagga gccttggcca ggctccagaa   34620
cgcatcgtcc acctcgacgg agatgttcgt ggtccagtga gatccgctgt cctgcttgat   34680
gttggtgaac gtctcgacct gccagtccgc ccagtgcatc atcgccatgc gagccgaccg   34740
gcgaacaccg cctgccacca cacactgcgc gatggcgtgg tcgatctcca tcgcatcgag   34800
accggtcagc gcaccgccgt cctcgaacct gtactgctcg ccttcgcggg cacaccggct   34860
caggatctcg gagacctcgg tcagcatctt cgccagaggc accggcccag aggccgtgcc   34920
gccgaacgtc ttcagcttgc gacccgccgc ccggacgcgg gacacgtcgt agacgcgctc   34980
cttgtgggcg acatcatccc ggtagtgggt gtcgatcagg tcgaccaagg cggctgccca   35040
gccctcgcgg gagtcctcga tcacgaacgc atcgacccag tcagagtcgt agcggctcga   35100
caactgaccc gcctcggcca ggtcagcgta gtcgtcgtgg tcctcgtcgc agacgatgtg   35160
gacttccagc tcctgcttca cgtgcgggta gtcagcgagg aatcggttcg agtagttcgc   35220
cccgacgcca ccgccctcca tgaggcgcat gaacgtgaat tcgaagtggt ccgagggctt   35280
ctcggtccac ccgctcaccc agcagttgaa caggtgctgg gcgttcttga cgcccgacgc   35340
ccacagatgt cgaccagcgg gcaggatctt gaactcccgc atgagtcgga gcagatcttc   35400
tcgctctcct gggagctgat accgactatc aacaagcgcg aggttcccag aaaccactcg   35460
ctccacagtt tccggccaag tttctcgcgt tccgtcaggc ttaaccctgg agtacgtccg   35520
attgtagaca agctctcctg ttggcccca agggatttca ccctctgtca ctacttcctc   35580
tcagtcagtt cgtatgcctt gaaataggcg tcagccgaat cgcccttgga gaacgagaca   35640
ccgtactcat cgccaccgat caggccggtg acaacgacgc ccttcttgcc ccggaaccag   35700
cgccatgtgc ctctggcggg gtacttggtc tcgtcgcgct ggacgatgac cttggtgccc   35760
ttcttcacgt cggcctccgc tggccgtagc caggggtgaa cacgccgccg acgtactgct   35820
ccaggtcgtc ctgcgaccag ttctccagga gcatcggctt ctggtgtggg aacagctccg   35880
ggaacacctc ggctcggtac atctccgagc caggcatccc gttgaacgtg ggatcaagca   35940
gattttgcat agcacctccc tcccaggaac tccgggatcg gcggctcgta gaggtactcg   36000
tcgcgcagcc cggggtgctc gaccagcatg atcgcgatgt tcgccgtcgg gtcagagtgg   36060 ccctcccccct gcacctttcg gatgtcaggg aagatggcgt gcttgctgcc agggccgtcc   36120
ttgacgatga ccttgccgtt gtcatctcgc tcaacaccag cggtgatcgc gatgatgttg   36180
acgtgctcgg tgagcgactt cacggctcgc ttcagcatcg cctcggcagc cgaacccctc   36240
```

```
tccgggacga cgccgtcgtc gtaccgaacc ctgatcgcct ctgcgtggcg ctcgttcttg   36300
gagcccagtt ccttcatcgc cagcggcagg atgtcgacca ggtaccgatt ggtcgactca   36360
ccccgcagcg cgtccttgac gttgtccgac gagtagtggc tgcgctcctg gaagagatcc   36420
ctggccttgg ccgagcccga caggatgttg tggacctgct tgcggacgta gatcacggcc   36480
tcaccgggcc gcagctcgcc gagcttcttc tggatgtacg gactttcgag gtaccagacc   36540
cacagctcct ggacgatctc gtccgctgtc aggttggtct cccagccgat catcgctttg   36600
cgggtggccc gcatgaagag cttgttgatg tcgcctgtca aggcatcacc ttccgtaggt   36660
actcctccct gtccagacga cggtcgaggt tgcgggtgat ctcctcggcg aagacctcac   36720
ggacctcgct ggagctgatc cgccgcgacc gtgcgttctt gtgcaggtac ggcagcttgg   36780
tggctgtcaa gtttcagacc tcccagacgt ggccgtcgac cgagaatcgg cctccgacga   36840
tcggaaccag ctcgggcttg acgtggttgc cgtcaaccgt caacagacca aacccgctct   36900
gccagttggc cgttgcaccc ttgaggtact gggccagttt catgttcatc aggttgccga   36960
cctccatcga ccacagcacc ttctggtggc ctccgtagcc ccaggtgtgg ggcttgatgc   37020
cttgccggtg ggtgtgaccg atgatcaccg acgtgccgaa ccgctgcatc gcgttgtacg   37080
cggtgtcagc cgacttctgc gtcacccgga cgccgccacg gtggccgtgc gtcgagatcc   37140
agcccggagc caccttgtag aactcaggca gcaccgtcac gccgaaaccg tcgaagtcca   37200
agaggttctc gaacttgaac tggtcggcgt actcgaccag agctggtgcg aacttgtgca   37260
gatagtcgaa cggccggcgg tcgtggttgc cttcgtggac gccgacaggg ccgtcgtaca   37320
cggcccgcag cggggccagg aacctcgtct tggcctgctc cgaatcgggc ttgatccgct   37380
gggcgaactc ctccgacgaa cccttggtcc accgagacgg gctcgggtag tccatcaggt   37440
cgccgatgtg gacgacctcg tcgggctggg tgtcgccgat gaacccgacc acagccttga   37500
gctgcttgcg gtcatcgaac gggatctgcg tgtcggagat gacgacgatg cgcttactca   37560
cccagtacct ccacgaacgg accctcggag atcttggcgt ggtcgagctt gaaaccgtcg   37620
cggtgccccc acaggcgctc gttgtagtcg gggtaccgcg accagaacgc gttgcccgcg   37680
ctccgcacgg tcttcacgtc cttcggtacg tcggccaagg tgtcccactg gcgaggttcg   37740
ccctcgacag gctcctcgta gatccgctcg acgcaaccgg cgtaaccggc catgtcggtg   37800
aacgaatcac ggtggtagcc ggtgcctttg accctggcga tcttcatcag gatcatcagg   37860
ttggccacgt cgatgtcgga gatctccttc tccaggtagc ccgagaacag cagggcgatg   37920
tccttgaagt tctctcgcgg gtggccgtag ttcttgttgc gctcaccgtg gatgaggcgc   37980
tgagcttcct cgaggatgga ttcactcaca gtccggtctc cgatgcggtg tagtagtcga   38040
tcaactcatc gaccttgtcg ggttgatagc cgatgatcgg ctcgaaatgg tcggtcacga   38100
tgaccggaac cgaggacgcc ttcagtacgt cctggacgta cgtcttggcc tcggcgttgc   38160
gcgtcaggtc gaccacgtcg tactcgaccc cagcgtcgtc caggaactgc tggatccggt   38220
ggcacgggcg gcaacccggc tgggtgtaga tcgtgatcgg tgtgaacatc gttcgcatca   38280
gatcctttcc agcagagcgt ctttgccctg cgatgtgact agtgagttga catcctcgcc   38340
ttctggcatg gggatgattc gtgcgttcgg cagcgtcttg gccaccgact cgcgaactc    38400 cataccgggc tcgtcgccgt cagccaggat gttcacgttg cgatacccga ggaacagctc   38460
gcggaagtgc ggcttccaca tctgagcccc tggaacgccg accgtcggga tcccgcacag   38520
ctcagcggta atcgcgtcga tctcaccttc ggtgatcgcc atgtcccgcg agtagcgggt   38580
```

-continued

```
cagtgcgacc gtgttgtaca gccggggctt atcccccggc atggtcatgt acttcggctt   38640
gccgtcgtcc agacggcgat accggatcgc tgcaaccgac cagttacgcc agggcgacca   38700
ccgcatgtac gggatcgcca ggcagcctcg gtacatctca tgaccaggga gtggatctcc   38760
cacgaatccc aggccgaacg gtagaacctg atgaacctga agaccgcgac tctccaaata   38820
ctcggcggct gggcttccgt gcaggcttcc tctgtactgg gatgttgcct cccacagata   38880
gtccctctgc gattcggaca gcctctgcaa aactcacctc ctcttcgtgt cggatgatcg   38940
agatcacgtc ccctcggact ccgcaggcca ggcagttgaa cccttggagg tcgtaactga   39000
ctgcggccga gggtgtttcg tccccgtgga aggggcacag gcacttgttc cactcgtagt   39060
gatccggtgg aggatcccag tccgggtagt accgctggat gacctccgcg atgccggtgg   39120
ctgtcaagtt tgactcctca gcttgtcggc ctcgatcggc gctatgcgct ccccgatgac   39180
ctggacggcc gggggcttac gcaggtagtc gatcgctcgc tggagcatct cgatgcaatc   39240
ccgcgcccag ccgaggatgt acttgttgca catcgtgcag agcagccctc gaacgatgcc   39300
cgtcttgtgg tcatggtcta ccgatagccg tttcctcttt ccgttcgccc gctggcagat   39360
gtagcagcgg ccaccctgga actcatagat ggcccagtac tcttcagcgg tgatgccgta   39420
ggtggccagg atccgggtct cccagctcgt tgagctgcga gcagccttga actcccggtg   39480
gtgcgtggcg caccgtgggc cgggatactt ggcgtcccgt gtgagcggca acccttgggc   39540
cacacagtct ttgcacggct tccgtttgtg cttacgattc tgcacccggt accccggagt   39600
cctcttcgcg gctctcccca tcgctcccct tcgggttgtc catcagcagg cagaagtacg   39660
acagcaccgc acacgcgatg atgtgtgcgt cgagcgcgaa cagcaccggg ttcatccggc   39720
acctgtgatg tatcgccgtg ggaacagatc cagcagagcc agcgcgatga gatcagccgc   39780
cagctccggg tcagccagca tccatgagtg gaagccgtcg actccgtaga aggaggcgtt   39840
ggtgatcttg gccgtgctca ggccggcctc gtacggaacg atctgatcat gcagcccgtg   39900
gagcacggcg gtcggtacgc cgtggcggta catcgcgtgc agcagcggtg tcgtgtcggc   39960
cttcatcagc gcgaacgcag cgcgaacgaa cctgagcccg gacaccgaat cccgcagcat   40020
tccaaggaag ctcagcttct cgccggtatc tcgcaggtgc atggcctcgt agccgtcgcc   40080
gacgatgtcg gtcacggcct ccccgagctt cttggcagct cggaacgcca gcgtggcgta   40140
gtggcccacc ttgatgttgt cgtggtgttc ctggccagca gccgcgtcca gcaggaccgc   40200
tgccgcgact ctgtgcgggt gacgcgccgc gatttcgacc accatgccgc cccccatcga   40260
gtggcccgcg aagatcgctc ggtggatgtc aagttcgtcc aacgtcttga gggtcacgcg   40320
ggtcatgtcc tcgaccgtgt ggccggtcgg cagtgagccg ctgcggccgt ggttggccgc   40380
gtcgagtgcg atgactcgga acccgtgctc ggcgagccgg gtcagcatct cctcgtacgc   40440
cttggcgctc accgagagcc cgtgcaggaa caccagcggg gcgccggtgc ctaccgttga   40500
gaccccgacg cggaaaccgt cagcgaggac gatggtttcg tgcttcatgg cttgtctccg   40560
aagttgatga caggaatgcc agccttctgg gcctcacgca tgcagtggcg cgtgccgact   40620
gacctaccga gagggaacgc caggcagaca tcagccccag ccctcaccat ctcgatgttg   40680
cggaggacgc cagccttctt gccgtgccac tcccagtccg cacggtgcag ctccggggtg   40740
acgttgaagc cttcctggcg catcccccaa gcccagcggt cagcgatgtc gtcagcgccg   40800
cgagcgccgc cgtgaaccac caccaggcca tacggggacc ggtgcagctc gtcagccagg   40860
gcgtcccaca ccgtggtgcg gtccttccag actcgcgagc cggtgatcag tacccgacgc   40920
atcagatctc cctccaatgc agcccgtcct cggactcgac caacttcgcg ccgtagacgc   40980
```

-continued

```
cgttgatgat cgccaggtac tcgatctgct gggcctgcag aatcccgaac gggcattcgt   41040
gaactccgct gcgcgggtag cggactccgt acttcacttg atccacctct tggccagtcg   41100
gtcgacgttc tcctccgaga cgttgcgggc caggccggtg acctcgcggc cgtggacctt   41160
ggtctcgatc acccgaggct tcttcggatc cgggctctcc gggtcgatcg ccttgtgcgt   41220
ccagacggtc ggacgcgtct tgatcagcgc gcccagcacc tgctggtgca gcgggttggc   41280
cttgcggggc atggcgttcg gagtggtcat ctgggtgttc ctttcggtgg ctgtcaaggg   41340
atggatgaaa agggttgggg cacatgaccg tttgtcgttt aagccagggc ggttcccgtg   41400
cgctcgcctt accgagcaga cgcgagagcc taggtcacgt acggtgacgc cctgcgcccc   41460 caacccccctt ggtcaacgaa gctcgatgtc cgggaggatg gactgcggct tgaagttgac   41520
ctggtagaag tcgtcggaga cgttcgcgcc ttcgatctgc tccacgaagt acgtgacgtt   41580
gtccgacagg cccaggaagt gcttcttgaa ctggccgttc tgcttgcagg tcacgtccag   41640
cttctgggct ccggtgtcgg gctcgatgga gcaccgaccc tggatctcca gcaggtactt   41700
atcggtgatc ccgttgaaga acacgatccg gcgcgggatc tcgaagttgt cagcggcctt   41760
gctcaggttc tctgaggcca cgtcggcgtc ggaggtacac ccgaccaagc ccagaccggc   41820
ggcgagggcg atggctgcgg tggcgatggc tttcttcatg tgcgctactt tctggttggt   41880
ggctgtcaag tcagtgatcg aagtcgttga tctgcatggt gtctccgatg aactccaagg   41940
cggcgtagtc attccccgac ggatcagact tgccaccccg gttcttgacc gtggagacgt   42000
tgagcgagtc cgggccgaag ccgtccgact cgcgatggag cgtgaggacc atctcgggca   42060
cacgcccgat ctgacccttg atccctccta gcgggatcgc tttgtcgccg tcgttgtacg   42120
ggccggtgac gtggtggagc ccgatcacgc aagagccagt ctccctggcc atttcgtgca   42180
ggtagtccat cagcgactcc aggccgctga acgggtcatc cccgtccccc gactcggtgc   42240
ggacgttggt gatgttgtcc acgacgatca gcgcagggaa gtcctcgtag agcgcgtcgt   42300
acgctgcgag ggcgttctcg atctcgtcca acgacggaga tgccttgtag ttgaaccgga   42360
tcgggatctc atcgaggtcg ttggcaatcg actcctcgat gctctgttcc cggactgccc   42420
gcgtcgatcg ctcgagcgac catccgctca ggatggagac tgaccgcgag atctgggtga   42480
acgcgtcgga gtccgccgag aagtacagcg tcggtacctt cgacttcagc gcgtaagcca   42540
ggacaaaagc cgatttacca gtgccaggac cggcgcatac aaggaccaac tgacctcgtc   42600
gtagacgagt ccccttctga tcaagtgcgt tccacaccgt tgggagtggg tcacccgcgt   42660
tccctcggat gtacaggctc tgcctcggtg tgtacagcgt cctcctcctt ttctcgttcg   42720
agcatctccc ggagcatcca accggggatg acgttgttga agctcacaga ccctcctcga   42780
tgtcgttgac catctcgcgg acctcgtcca tcggcaccag gtcgtgccag gcgtccagcc   42840
cgacgtggat ctgccgtggg ttggtcatgg tcgaccgaat gatccgggag tgcgtgtggc   42900
cgtgcagtag gatcaatcct tcatcccgca gccgccactg cgtgaagcgt tgctcggcgg   42960
tgtggtcgcc gacgtacggg aagtggctca gcagcacgtt ggtgtgaccg cctccgtcga   43020
gggggacgcg aagcctcgcg gccgtcgaca tgtaatcgag cacgttccag tacagccggg   43080
acagccgggg agcgtcccgg tacatcgggt gaggccgatc atggttgccc aggatcagcc   43140
gcttgcggcc tggccggttc agcagccagc ccagagcatc gagctgcgct cgggtgccgc   43200
ctgagctgat gtcccccagg atccagacca catcttcctt gccgacctgt tcgtcccaca   43260
gctccgcgag gtggaggtcg tggtccgggc cagcccagtc tcggtcctcc gctaccttgg   43320
```

-continued

```
cgtggccgat gtgtaggtcg gaggtgaacc agacgttgct cacgctggct ccctcacgtc   43380
gggccgaccg tgggtctgcc agatgaactc ttcgatctgg tcgaccgcga tgaagaggtc   43440
atccccgtcg atcttcgtcg ggagccccat caggatcgcc aggatcttgt ctcggatcac   43500
tgcttgacca cccccgcgtc atggatcggc cggccagctc ggtgcgccgc ctgctccgcg   43560
tccatcgctc gctggatctg gttcatcagt tgggtgcctc gaagcttcag cagcttcatg   43620
gtgtgagcac ccttgaatcc gacgcggtgc atccgcagga ccgccgccgt ctcatgcggc   43680
gcgtacggcg acttcagctt cgggtcgttg ggatcccaat ccttcttcat gccttctcct   43740
cttggtggct gtcaagttcg atgacgatgt tcacgcgacc cactccttgc cgttccaccg   43800
ccgaccatct gggtaggcga tgatgacttc ccggtcgggc cgctcctcgc tgtgagcgcg   43860
agcgaaccgg aacgccgctt ctggcgtcgg gaacggccag cgcgagggct gggccgactg   43920
gtgccacttc ggcatgtctg ggatcggacc cagctccacg taggtgtagc tcgtcccggt   43980
gctgagatcg agcgtcttcc ggtattcctt catgcctgcc ttaatgggga aggagtctgc   44040
gggtggctgt caagttgcga tcacttaaaa acggggcaac tgtaggacac atcacagaat   44100
ttgcatttgt ccggttccgg caacgggtcg aacatcgagg ctgcgatgcc ttcctcgacc   44160
ctgtggaact cctcggtgat ggcttcacgc gtccacttcg tcaggtcgta gggcttggtc   44220
ggcttcggtg ccttgccctt cttccccacc atgaagtagt cgccggtctt cggagcctcg   44280
acaccgtaag tcatcgcgac cgcgagcgcg tacacgccga gctggaagtc gtctcccggt   44340
tggttcccgg tcttgtagtc ccggactcga agctccccgt cgaccacgac gacggcgtcg   44400
atgtatccgc gaaccaggat cccgtcgagt tcgatttcga agtacagctc gatcgctggc   44460
gtaccgtccg gggtcaccca gatctcctgg ccgggagtcc cccgccacgc gaagaacttc   44520
tcgacctgct ccaggccgac ggtgtaccgg cgctcgatgt ctcgctggcc gttgtacgga   44580
cctgaccacg tccaccactc gaagttcggg gtctcctcgg tgaaggctcc aacgtcgttg   44640
gcgtagtgcc agcggaacat gtccttggcc tcgtcaagcg taagcggcat gccgtaggac   44700
tcccatacct cgaccgcctc ggcgacagcg tggaacgcgg tcccctgcgg cagccaggcc   44760
gctggccgct gccacacctt gtcgatccga gcgagcttgt acgccatcgg gcacttcgtg   44820
tactggttga tctggctcac cgagcgcagc ggaagcttga tctgcgtcac ggcgcggcca   44880
tttcgccgtt gccggtcaac gcggtctcca ccgtcgagcc cacgacctct cggatctcat   44940
ccagcgatgg gcacatcggg gactcaacga aactgtgtgg cctcagcctg gctaccaaga   45000
actctcctct cccgtgcatc atgttgtcgt catgccggaa gccacgtgcg agcacgtcaa   45060
cctggtcggc cttcagaatc tcctcggcga caggccgata catcggcttc gtgtctcggc   45120
acagcgggct ccggtacgcg agcagcaggg tgacaacctg ggaaggatcg tcctccatcc   45180
aagccttgca cttccatgct tccagccacc cgtgacgctc gaccagcttc tctggctgcg   45240
tgtaaacgac cccctcgaac tggcctacaa ggctagtgag cggcattgcg gttccttact   45300
gcgtgggctc cgctggctac ggagaacgca cgcgcgtcgt gttagttcag gagttcctcg   45360
atgtcgggtg gccagcacca gatcatctct ccctcgtctg tcaagttggt gtactcgttg   45420
acccggatca acaggtcgtc gtcctcgatg gttctcggga cgtacctgaa gcctccaccg   45480
gccatgccgg ggtagggctc aatgttgggg tcgaactcga ctaccacatc gttgtcgcgc   45540
agcatcttcc accacgacaa caggcgcttc cgcttgtcct ctgacatcgt cttgaagctg   45600
cccacgcgca tgtactcacc gtggtcacga agtctctggt aggccttgga cttcccctga   45660
aacttcgtcg tctgccacgg ccaggccagc gtggacgttc ttcttgcctt cacggcgcac   45720
```

-continued

```
acgctcacgg  ccggccggcc  tcaccacacc  tttcgcgtgg  gccagcagaa  cgtggccgct   45780
gcggtggatg  actcgaccct  tgaagtcgcc  ttccaaggct  tggacggagt  accacggctt   45840
gccctcacgg  tgcgtgaagt  gcaggttctt  gtagacgaag  acgcgaattg  gcttgggtt    45900 catgcgatcc  agtcatccag  gtagttgtct  ttgacgctga  agcgtcgggt  ccgactcaag   45960
acttcgatgg  ccgcgaggat  ctcgcggtcc  tcgccttcgc  gctccatcgc  ttcgtcttcg   46020
acgttgatca  cttcgatccc  ttcggcttgg  caggcggtgt  cttccagggg  ttcatgccca   46080
gccgccgagc  gcggcgcatg  gcaaccatga  tctcgacgtt  catgaggccg  aaacctccca   46140
cgtaccaacg  gcttcgccgc  gaaggtagat  gtgacctcca  tcgccgagct  ggtcgatgac   46200
caggccgttg  cgcgaagcgg  cagcttcgag  gtggtcgatg  aggatctggc  gatggctcgc   46260
cgataccttc  gtattcttgc  cgtcgcggtc  acgggtggca  gtcaaggtga  acacaggtca   46320
ggtacctctc  agtagtcgga  gtgctggagt  tcgaagcctt  cgaggtcacc  gacctcgtcg   46380
tcccacgcgg  acgggttgcc  gcgccagtcg  tcgcgaagcc  tctggccgct  ggcgttgtag   46440
caggcaccgc  agttgcgaca  gtccacgtcg  ctctggcctc  ggtacctctg  cgcctcatgg   46500
ccgcaccgtg  agcagtccca  cgcggcgtaa  tcgccgtcga  tgatgaaccc  ttcggcgtca   46560
cgcacagctt  cgacgtagcg  gtagttgttg  gccatgatca  gctccccagc  tcgttggcga   46620
tggcttggtg  ggcagcctca  cggaaggtca  gcccgtcgtc  gtacgcgtcg  tggtaggtcc   46680
agtccgcgat  gtctcgtcgg  ccgaccccga  acgtctcttg  catgtaggcg  tccaggttgg   46740
ccatccacag  gtggaagctc  acagctacct  cacttcttgg  tggtggagaa  cagaacgctc   46800
ttgcgtccgt  tgatgcacag  accgcaccta  gcgcaggccg  atcccttggc  gttgatcagg   46860
tcgaagtctc  ggttgttcag  ctccgggcag  cgcacggccg  tcgggaactg  tgccttgcct   46920
tcggcgaacg  tcgtgtcgac  gtaggcgatg  ttgatgccct  tgccttccag  gaaccgggcc   46980
acgtctacgt  tgtcgggatc  cgcgctgaag  tacagcgaca  ggttcgacag  cttctgtgcg   47040
tgcaggtaga  ccgctgcggt  ctgaaccctg  gtgtaggccc  agaactgcac  gtcgctgaag   47100
tctcggatga  cacgcgccca  cgctgcgacg  taggtcgggc  tgaagaagtc  gccatcccag   47160
tggatacgga  acagcttcgg  agccttcttc  ttgtcgcaat  ccttgacgaa  gtctgccatc   47220
atctcggaca  gcagggtcac  ggtgtctgtc  aagtcagcgt  cacgcaacag  ctcccagttg   47280
tgcagcagca  cactgctcac  ggctttgcgg  accttctcca  gcttgcccgc  gtagcacacc   47340
ttggcacaga  acgcggtcgc  gtccgggcag  gagaaccctt  gcccactggg  cagaccgatg   47400
ctgttcgcga  tgcctacggt  ggcgttgccg  cctttggtga  cgtggacgta  gttggtgact   47460
ttgcggtcgt  tcgatcgctt  cagcgatgcc  atgtctagaa  cccttcggtg  gctgtcaagt   47520
cagcggacgc  gaatgatgtt  ggtgcctcgg  cagacgtaga  tcttgccgtc  gatgtacacc   47580
ttgcgctcgg  aggacatagt  gaatcctttc  tcggtggctg  tcaagtctca  ggcccagcga   47640
cgtttcgtcg  gccgggggtg  gcgaaccttc  ggagcgttct  tacgcggtgc  cttgcggatg   47700
acggtgtcgc  cagtgatcgt  gatgtcttcg  accagggcag  cctcacgctc  tgcagcgatc   47760
tcggaggtcg  ggacgttgac  cacttccggc  ttgttgctga  agtcagtcca  ccccttggtg   47820
cccttctcca  gctcagcgtc  gacggtgcga  accgtcgaca  gctcaggtgc  gacgaacggt   47880
gtcttgatgg  actcgcgtgc  cgtgacgcga  acctcgcggt  gctcggtgaa  gacggacata   47940
gctcacccct  tccggtagct  gtcaagtcaa  gaatcaaagc  tcaggtagtg  ggtagccagg   48000
aatcgaacct  ggtagtcgtg  atgccgcgat  accaaagctc  aggtatccgc  cagaccatag   48060
```

```
ctcagcgatc attccatcgc gccagagcta cccggtagtc ttttgttctc cccgtgggtc   48120
aacagaatct atcggatcct cgccacaggt ctacattcag ttatccgcag tgtccgcact   48180
ttatcggcat cggacttccg cctcacccgc gaatgctgtc gaagccattc gcgaatgttg   48240
ggtcgggctg cggcccttcc cggtcttgcg tgattctcac tctaccggac tagtcggtgg   48300
ctgtcaagcg ggccgttttg gtatcggcat cgatgccctc gtttagcgcc gctggcataa   48360
ggcgctaccc gctcgactca ccggtccaag ttggtgatga cattcactct agcgtatcgc   48420
tcggtggctg tcaaccggag aatcacaccg gattttcacc ggatccggcg cgatcgtttc   48480
cgatccgcct atcgcgtcgt gcttgctgcg atgacacaag taaacaccac ggccgggtag   48540
ctgtcaagcc cgaattgcaa attggtgtgt gacgtgcggt tacgccgctg tccgggtggc   48600
tgtaaagggc acgtagggca cgtgtggcag gccagacgca acccactagc ggccggtagc   48660
cgcgtgcata ggctgctcgt tatgtgcccg gtatgggtgc tgtgagctgc acaatcgcgg   48720
gctgtcgggc tgtcgtcacg ctgtcgctgt cgtcgccggg tggctgtcca gtcgcccacc   48780
gaaataagcg aaataagcac cgtcgtcgca ggtccatagg ctgctcacta tcgcatcggt   48840
atgcccttgc acacgtgtgt gagctggtca cgtgctggtg tggtgtgccg tgtgcgctgg   48900
tgtgtatgcg ctggtcagcg tatgggcaca gtgtgcgtgt gagttagctg tgagctgagg   48960
ccggcattcg catcgtcgca ggtcagcacg cgtatgcgtg catgtgtcct cggttgctgg   49020
gcatcgtgtg cccctcgagg cacgcgtgcc gtgagcgttt gctgtgcatg ccatcgtcgc   49080
aggtcacggg gggtagggg  gttccccca ggggcgcctt cctgaccggt cggtta         49136
```

<210> SEQ ID NO 2
<211> LENGTH: 58212
<212> TYPE: DNA
<213> ORGANISM: Bacteriophage
<400> SEQUENCE: 2

```
aggcaccttt ctctccccag catttttttc caagccattt cagcgttttt ccacacccga     60
ccagcacagg agcaaccaat ggacatgacc gaatccgcac cgactgcgcg cgtgtgggcg    120
ttcgaggatc agcgcgaccg cgcggtgcgc gagcaatcaa tgcacatcgc gctgcgccag    180
gccgacagcg tgggtatcgg cgacttgacc gtgatcgagg cggccgacaa gatcgccgct    240
ttcatcctcg acggcaaggt cgaccggcgc cccgacgctg agcggagccc cgaatgatga    300
cgcccgccga gcgtctcgcc gcgcagcgcg aggccctcga caagcacgag tggaccgagg    360
tcgagggcga cctcacgccg atcacactgc actgcctggt cgccattggc gaggtgctcg    420
tcgagctgaa cgcccggcag gccgccagg aggccgcgac gatgggcgcc ccgtcgtgag    480
cgcggtcgtc ggcgtcgtgt cgcgcactct cgacagcgcg gccgggtcg cccgcgcgct    540 gaacgtggct cgcaccgttc caatgagcgt gccgtcgatc aagcaggggc acggccgcgg    600
gttcagtttc gacgccgtga tcgtcgacga cgaggtgatg ccgctcgatg actgtgtgct    660
cggcacgttg gccccggcga tgcacgctca cggcgcaaag atgtacgcgg ttcgggaggt    720
tgagctgtga ccccgactgt cggccgcatc gttcattacc agtcgtacgg cacgcccggc    780
ggcgagtacc tgcccgagcc gcgcgccgcg atcgtcacgc aagtgcacgc cgtcgagggg    840
gccgtcggcc tcgcggtact caacccgtcg ggcctgttct tcaacgagtt tgtggagcac    900
gccgaggacg acaagccgac tgcgggccgc tggaactggc cgccccgcaa ctgatccagc    960 gccgggggcct gttccgcgaa ccgcggtcct cccggcgcgc ctgggtgtgt agctcaatcg   1020
gtagagcagc ggtctccaaa gccgccggtt gcacgttcga gtcgtgccgc gcccgcttcc   1080
```

-continued

```
acaccggcta accgccggca atttgcattt ctgcacgtca atgccacgaa aggccgtttt   1140
gagctaacac ggcacctcac caaaccagga gatatgacca tgcgcgcacc cgctaccgcc   1200
gaggttcctt gcccggcctg cggcgagccg atcacgctcg cccttggctt tgagctggcc   1260
gagcccgagc ctggcgccac gacggcccca gtgttcgtgc ggcccctcga cgtgaccgag   1320
cgcgcgcagg agcacggcga ggtgtgtccg gtgtggtctg cgggcggtgg ccgtgatgag   1380
tgacgccaag ctcgaccggc tgaacgaatt gcgccggttg cacgagcgaa tctcgggcgc   1440
tgtgttcgat cctgagacac cgccgcgcga cctcgcctca ctgagtcgtc gactcatgga   1500
gatttccaag gaaattgagg cgatcgagct gcagcgcgct gagcagggcg cgggccaggc   1560
cgacgtcccg gccgatgagc cgttcgatgg ttcggacctg tgagccgcgg ctatccgagg   1620
ttgctcgcca cgtaatcaag cccgagggca tcacctcgac gtcgtggccg tccgttcgcc   1680
acgagtgcaa cgtcaacatg gggttgtatt tcgaccaatg gcaggacgac ctcggaaagc   1740
tggtatgcgc caagcgatcc gacggcctgt acgccgccga catgttcgca atgtcgatcc   1800
cgaggcagac aggcaagacc tactttctcg gcgcgatcgt gtttgccctc tgcaagatga   1860
ctcccggtac aacggtcatc tggacggcgc accgacacg tacggccgct gagacgttca   1920
agagtatgca ggcgctcgcc aagcgcgagc agatcgcccc gcacatcttg aacgtgcaca   1980
cgggcaacgg caaagaagcc gtgttgttca ccaacggcag ccgaatcctg ttcggcgctc   2040
gtgagaaagg tttcggccgc ggtttcgcca aggtcgacgt tctgatttttc gacgaggctc   2100 agatcctcag tgaaaacgca atggacgaca tggttccggc gaccaacgcc tcgcctaacg   2160
gtctgatcct gttcgcgggc accccgccga agccgacaga tcccggcgag gtgttcacca   2220
acctgcggct ggacgcgatc aacggtgaat ctgacgacgt tgcctacgtc gagatttcgg   2280
ccgacgagaa cgacgaccca gacgaagagt cgacgtggcg caagatgaat ccgagctacc   2340
cgcaccggac gtctgcccgc gctatccgcc gtatgcgtaa agcgttgtcc tgggacagtt   2400
tcaggcgcga ggcaatgggc atctgggaca agatcagcgt gcacgcgcag gtgatcaagc   2460
cgagcttgtg gcgcgacctg gccgacccgc tcggccccga gcccggcgcc aaaccggcgt   2520
cgctcggcgt ggacatgtca cacggcggcg ctatctcgat cggcggctgt tggctgatcg   2580
acgacgagct gaggcatgtc gagcaggttt gggcgggcac tgacaccgcg gcggccgtcg   2640
agttcatcgt cgagcgtgcc aggcgacgta tcccggtcgt gatcgacgac gcgagcccgg   2700
cgaaagcgct tgtgccagag ctgaaacgcc gccgggtcaa ggtccgcatt acctatgcgg   2760
gcgacatggc caaggcgtgc ggcctgttca agaacaacgc tgagggcgag accctcacgc   2820
atggcgatca gctcgacgtc accgaggcac tcaagggcgc caagcaaagg ccgatccgcg   2880
acgcgggcgg ctggggctgg gaccggcgag acccgacgtg cgtaatccat ccgctagttg   2940
ccgtgacgct ggccctgctt ggtgcgctcg acgccccgaa gcgcagcggc ggcgcgatgt   3000
tcgtatgaga gggggccgtg tgattcccgc tgcctatgac gaccgccagc tcgacgagcc   3060
cgacgacgac gaaatcgact ggcccgccga cgcgctcgac gccgaggcga tcggcgagct   3120
ggtgcagcgc atgtacgccc tgcacctcgc cgagcgtgac tcgttcgaca atatccacgc   3180
ctttaccaag ggcgagcgtg gcgtgccgag cgtgcccgac gaggcgagcg acgaggtgaa   3240
ggaactcgcc aagctgtcga taaagaatgt gctgcggttg atttgcaact cgttcgcgca   3300
gtcgctcagc gtggttggct accgctcgtt gacggcaccg gagaatgatc cggcttggcg   3360
tatctggcag gcgaacaaga tggacgcccg ccaggccgag gtgcatcgcc cggccgtcaa   3420
```

-continued

```
gtacggcgcc tcctacgctg tcgtgactcc cggcgtcgac ggccgcaagc ctgagattcg     3480
ttgccgctca ccgcggcagc tcatcgccgt gtacgacgac gcggtgctcg acgactggcc     3540
gcagtacgcg ctcgaaacgt gggtcaccac gaaggacgcg aagcctcggc gcaagggcgt     3600
gctgtatgac gagcggtaca tgtatcagct cgacctcggc gagctgccgc tgacgtcgac     3660
cgggcagccc gaggtggcga cgaagcccgt cacgctgcgc gacgtcgagg acatcatccc     3720
gcactacggc accgaggacg gtaagcccgt ctgcccggtt gtccggttcg tcaacgaccg     3780
cgacgccgac gacatgatcg tcggcgaggt cgagccgcac atcggtatgc aaaaggcaat     3840
caactgtgtg aatttcgacc ggctgatcgt gagccggttc ggcgccaatc cacagcgcgt     3900
gatcagcgga tggaccggca gcaaaaacga ggtgctcaag gcatcggcgt tgcgggtctg     3960
gacgtttgac gatcccgacg tcaaggcgca ggcattcccg ccagcctcgg tcgagccgta     4020
taacgccgtg ctcgacgaga tggtgcagca cgtcgtgatg gaagcgcaga ttaatccgtc     4080
acaggtcaag ctcgtgaaca tcagcgcgga cgccctggcg gcggccgagc accgcgagca     4140
gttgaagctc gccaccaagc gcgagagttt cggcgagtcc tgggagcagg tttttgcgcct     4200 ggccgtcgaa atggacagcg acgagacgac gaccccgac ctgaccgccg aggttatttg     4260
gcgtgacaca gaggcccgct cgttcggcgc cgtcgtcgac ggaatcgtga agctctcgca     4320
ggccggtgtg ccgatcgagt acctgctgcc gctcgtgccc ggcatgacgc agcaactcat     4380
tcaggcgatc aaggaagcca tgcgcggcgg cggcactcag gccctcgtcg acaagctgct     4440
cgccgccccc gagctgtcgc tgcccgacgc cccgccgatc gaccaggcgc tcgccagcgc     4500
cgacgacgac gaaggggggcg agggtgacgg agccgaaggc ggtaccggag tttcaggggg     4560
cgctcgcccg tctcagtaat gaggtgggcg gcgccgtcga ccggctgatg ccacgccttg     4620
gcggcctgac ccgatccgag ggcctcgctg tgatcagcga cgtgtacccg acgttgctcg     4680
acccgttcct gtcggcgtcg ggggagctga cggcacagtg gtaccgcgag caaacgccgg     4740
ccaaactggt tggcgcgcag gtcgcggggca caaaagccct cgcccggca aaggacttcc     4800 tgcctgagcc cgccgcgctg cccgatcgcc gccagctcgc ggcgtcgggc cgctgggcgc     4860
tgatgcaacg caaccctggc ctggcgctgc gcggcactgc cacccggtca gtgttcgact     4920
cgtctcgccg cacggtgcgc gacaacgcga tccgcgaggg cgtcaagtgg acgcgatacg     4980
cctcggcgaa cgcctgcggg ttctgccgga tgctcgccac ccgcgccctg acgaccgaac     5040
gccgcggcgc ccccggcctg tacaccagca aggcgacggc cgaacgcaac gcgcacaccg     5100
tcgatatccg cggccacgat cactgcaagt gcctggccgt gccggtgcgc agcggtggct     5160 acacccccacc cgaatacgtg aatgactggc tcgccgacta cgacgccgtg agcgtcggcc     5220
ccgacggtgc actccgcaac gagtggcaga tcgcccggct gatggaagcc cgcgccgacg     5280
agcgcctcgg caagcccaaa cgcaagacag gcaggccgcg caaggccgcg cagcccgtcg     5340
aggacgtgcg cagcacaccg cgcgaaacgg tgcgcgctac gcagcacctc gtcgacaccg     5400
gcaacgagcg cgctgcagcg tacggcgcaa tcgcgcacga gcacgtgctc actgcgcagc     5460
aggtcatcac ccgcaccgac gaggttgtga gcaccgcggc gcacatcacg cagcgcgtca     5520
agctcgtgac cgacgtcgcc gacaaggtgc tcggcggcgc cgttccggtc gtgcgcgacg     5580
tcaagcgcgt ggtcgacgcg gccgacaagg cactcggcag cgcatcgcag gtcacaggcg     5640
gtgcgcgtca ggccgcggac attgccgcac aggccatcga cagcacggtg caggttgcgc     5700
acggcgccaa gcagattgcc gacgaggtgc gcggcgtgct cgacgaggtg ggcctcgtcg     5760
ctgtcggtct gcgcacgctg ttcacggata cgcgcgtggc tgtgcacgac acggtgcgcg     5820
```

-continued

```
acgcacgcaa cgtgcgcagc ctgtcggacc tgtccgagca gatcggcgca gcgaccgaca      5880
ccgcgcggca catcgccgac gacggccgtg cactgatgga ccgcgccaag ggcgctgccg      5940
acgcaacgca gggcatcgct cagggcgtcc gcgagatacc ggaactgctg cggcagccga      6000
tcgccgacgc gcaagagctg gcgcaaacca tcgccggggc cgccggtgac gccggtcagg      6060
ttgtcgacga gctgcaggac gtcgcgcgtg cgatgggcaa gctgatcgac gcggtggccg      6120
gttccgccgg tgaggacgtt cgccaggctg cccgtcaggc tgccgacgac ctcggccgca      6180
ttatcggcga cctgttcaag gcacccgagg cgcctcgcgt gccggtgtcc gtcatgtcag      6240
aacgcctcga cgtgccgggc gctcgcgtgc tcggcggcag tcagccggtc ccggcaatcg      6300
ccgaacgggt cggcctcaag ccgattgacg cacccgaggc ccgccaggcg ctcgacggcc      6360
gcccgccgat gaaagcactt gaggcggcac ccgaacgccc gccggtcgcc ccggtggtcg      6420
acgacgtgct cgacgtcgag gtcgtcgagg ccccggcgcc tgccacgccg aagccgaagc      6480
ccgcaaagcg gacgctcgac gaggtagagg ccgagtttca ggcggccgtc gaggctggcg      6540
acgacgcagc gatcgacgcc ctggtcgccg aaatggagaa gctcgaagcg gccgaaaaga      6600
aggccgccga acgcgccgcg gcgaaagccg ctgcgaagca agcggaaacc gaggccaaga      6660
ccgaccgact gcttgagctg atcgagcaag gttgggatcc ggccgaggct gaatccgagg      6720
cgttcggcct gtccgtcgag ttcattcggc gccgcgactt catggctgag gctcgcgccg      6780
ccgggcacga gggccgatcg ttcgacgagc tgctcggctg ggtgttcgag gagcgcatca      6840
cagaggcgta tttcgccgcc gaggacgcga cacgcgggca gatgctcaag cggcgctacg      6900
gccccgacgg catgaacgtc gatccgcgaa agctgtggac tctcaacgag acaacggccc      6960
gcaagtacat gtccgaggag atggccgagt ggttcgacca gcacggccgc atcactcgcg      7020
ctgcactcaa ggaggcgatt ttggccggtc gcggcaattg gcgtagcgca acgaccgcgg      7080
actttctgca atgacccgcg acgagctggt cgccgcgtac caggccggtc gtgcggcggc      7140
cgtcggcgac accaacccgt acgacggcct cggcgccccg gctcgactgt ggcgccgagg      7200
ttaccgccag atgctcgccg cccggctcat gcaatcaccc gcactgcagg cgtatctcaa      7260
cgcccgcaag gactgagcac gacccctcac aactgaatag gagacacacg aaatgtccga      7320
aatcaccccg accgacggcg ccgacggcgg cgagggcacc gaggcccccg aaggcggcgc      7380
cccggccgcc accgacgccc ccaaggtcga caccccgaag gcgtacacgc aggccgaggt      7440
cgacgccatg ctcgccccgc tgcagaccgc cgccaacgag ctgcagacga tcaaggacgg      7500
cgaaaagacc gagctgcaaa aggccctcga ccgagccgcg gcggctgagg cccgcgccga      7560
gaccgtcgag tttgaacggc tgcgcgacaa ggtcgccaac cgcgagggca gcgcgcgtgcc      7620 ggtcgcctcg ctggtcggca agaccgaggc cgaactgatc gcctcggctg acgccctgat      7680
cgcctggcgc gacgagaacg cccccaagcc gcccgagcag cccaagcagc agaagcgcaa      7740
cccggctggt agcggcggcg ggttcaagag cggcgcaacc ggctccgacg gcggttcgac      7800
cgacccgaag gtgcgcgccg tagaagcgtt gcggcgcttg cgttctggca agtagtaccc      7860
acttcccaac acttccgcac gaggaccgac ctcggcggtt gatcacaact gaatagagag      7920
agaggccgct atggctgaca tttccgcgcg cgaggtcgac accctgatcg aagagggtta      7980
cagccactcg ctgctggccg ccgccaagca gggcagcacc gtgctgtcgg cattccagaa      8040
cgtcaacatg ggcaccaaga ccacgcacct gccggtcctg cgcaccctgc ccgaggccga      8100
ttgggtcggc gagtctgcca ccgaccccga gggcgtcatc aagacgagca aggtcacctg      8160
```

-continued

```
ggcgaaccgc acgctggtcg ccgaagaggt cgccgtgatc attccggtgc ccgaggccgt   8220
gatcgacgac gccactgtcg aactgctgac cgaggtcgcc gagcagggcg gccaggcgat   8280
cggcaagaag ctcgaccagg ccgtcatgtt cggcatcgac aagcccgcat cgtgggtctc   8340
cccggcgctg ctcaaggccg ccaccgacgc cgggcaggcc atcgcccacg tgtccggtgt   8400
cgccaacgag tacgacctcg tgggcgcctc caacaaggtt gccgagcagg tcgccctcgc   8460
cggttgggct cccgacaccc tgctgtcgag cctggcgctg cggtaccagg tcgccaacgt   8520
ccgcgacgcc gacggaaacc tcgcgttccg tgacggttcg ttcctgggct tcaataccca   8580
tttcaaccgc aacggcgcat ggtcgcccga gtccgcggtg gccttcatcg ccgactcctc   8640
gcgcgtcaag atcggtgtgc gccaggacat cacggttaag ttcctggatc aggcgaccct   8700
cggcaccggc gacaatcaga tcaacctcgc cgagcgcgac atggtggcgc tgcgcctcaa   8760
ggcacggttc gcgtacgtgc tgggtgtctc cgcaaccgcg atgggcgcca acaagactcc   8820
ggtcggcgtt gtcacccctg acgtgacccc gccgacttcg ggcgagtagt gcggtatcgc   8880
cacaccctga cggggcggt catcggggcg ccgaaaggca ccttgctggc cgccctcgtc   8940
gagggcaacc cgagctggat cgaacacgag ggggtggccg gtgctggcaa gtctggacga   9000
cgtaaaggca gctctgcggg caatgggaaa gcccgaactg gcggaagctc tcgcagccga   9060
ggacgtaacc gacctcctgc aggaggcgac cgacctagtg acggggcacc tgtggccggg   9120
ggaggtgccg agcccgacgc ccccgacgat caccaggggtg acggcctcgg tggcagcgac   9180
agcgctcacg aagccgaagg aactgctgcc ggaaacggag agcctgcaag ctgacgggtt   9240
cggcgtgaag ttcacacccg gcgcgggatc gccgggctgc tacctgacgg ccgcccaaaa   9300
gacacgcctg cggccctgga agcgcagcgc tgtctcggtt cccatgagca gcgagaggta   9360 cccgtgcacac tgccgacccc gtgggaagtg caacacacga cgtacgtcaa ggtcggcgaa   9420
agcgccgcgg gccaggccaa gaccgagccg cgcactcgac cccgcatggt gtcgagcttg   9480
cgaaagcggg tcaacgagcc tggcgccgcg gcgaccaact ccgatcaggt cgtcgtcgag   9540
tacacgatgg cgactcccga aagcgattgg gcgcacggcg atctggtcaa ggactggcgc   9600
ggccgtgagt tcaaggtgca cggcgacgtc gacgactaca acagcggccc gttcgggttc   9660
cggcccggct acctcgtgac gctgcgaaag gtggagaaac gtgccatacc gaccgcttga   9720
tctgccgttc tctgagcacc gcaagatccg caacctgccc gacctcacca aggcgtgcga   9780
gaagctcggc gacaagctgc gcgacaaggc ggcggccaaa gccaacgccc acacacccgg   9840
cgccggtgac gattacgtga ccgagaccgt gcacggccgc gaccgtgtgc gcgtctacgt   9900
gcgcgctgag ggcgcagcga tcggcgtcga gaacgacata gcaccgctga tgcaggtgtc   9960
tgcggaatcg gggccgcggt gacggtactc gttccgccgg tcggcccgct gacggccgca   10020
cgccggtacc tgctcgacga gctggctgcc cgcggtaacc cgctgatcgt cgagcagcag   10080
acggtacccg agggctcgcc gacgtcgtac gcaatcctgt cgcgcccggg cacgagcacc   10140
gaggtgttcc tgcagcacag cctcattcgg gtgcgggtgt acgacaacga cctcgtgcgt   10200
ttggagcgca acgccgatct gctgcaccgg ctgctgctgc acgcggtgca ccgcaaggtc   10260
gtcgtgcccg acgagggcga ggtgtggatc accggcgcca cgcacgaata cgggcctgcc   10320
gagttcgacg accggcgcgt accgctgccc ggctatcagt cggcagtgtt ctggacgatc   10380
ggtctgcgcc ccgagcgcag ctaagtcgcc ggccgatgcc ggccgacctc gagaaccgcg   10440
cttgacgtgc ggcgatgcgc gctgcccgca ttcggcagca aacacaactg aataggagac   10500
aacatgacgc agcccactcc gccctcggcg ctgggcgacg ccaccaaggt gttcgcagcg   10560
```

-continued

```
tcgccgtcgg acctggaaac cgttggtggc ctttggttcg caccgttcgg caccaagctg   10620
ccgaccgacg tcgacgagcc cctcgaagcg gcattcaaga acctgggttt cgtgtcggct   10680
gacggcgtaa ccgtcaagat cgacagccag accacaccca ttgaggtgtg gggcggcgac   10740
gaaatcgggg cgctgcgaga caagttcagc atcgagtaca gcatgagcct gtttcaggtg   10800
ctgtcgcccg aggtcaacgc ggccattttc ggcgcgggca acgtctcgac tgcggcggct   10860
accgaggcgc acggcgcccg catgaaagtg ctgatcaact ccaagctgcc caagcggtgc   10920
agcctggtgc tcgattcggt gtacgaggac aagatcattc ggcaggtggc gcagatcgcg   10980
cagctttcgg gcctggccga catcaagctc gtgcacaacg ccccgatggc gttcgagccg   11040
acgttcaagg tgctcaaggg caccgacggc aatcacgtca tccagtacag cgacgacggt   11100
cagatcgtgg ccgcctagtc gctcgatagg ccagcacccc gcgcgttttc ctggtggcgc   11160
gcggggtgct ctctcgttct accaaaacac caggggcaca ccaggaaaca caccagagag   11220
gcagtaccag catggcaaaa gagaccaaga ccaacgagac cgacgtcgac gacgccgccg   11280
aggctgtcgt ggctaccgag gatgagcagg ccagcatcgc cgaggagtgg gccgacgact   11340
acgacgaggg caccgagctg ttcgtcggca agttcgacgc tgacgacttc gacaccgact   11400
acggcgtggc cgacttcccc gacggcgcaa cgatcgccgt caagcgctgc ctgcgcaagc   11460
ccccgccggg atggattcgc cagcacgcgc acctgtccga ccttgagcgc acgttcgctc   11520
taatcgaaat gcacgccagc gaccgggctc tcgaaatcct cgacagcctg cagcagaagc   11580
cgtgggacga cttcgtggag cgctgggggcc gcgacggcgg gctgatcgag ggaaaatcgc   11640
gcaggtctgc gcggcggcgc gccaggtaga ggacgcaata cggcgtgacc tgatcgtcgc   11700
cgggcgcgag ttcgacgacg gcacaatgtc gtgggacgac ctgtacgcat tcatttttgc   11760
ctcgccgcca acgtcggcaa tcttccacgc ctttgaaaag ggctggaata caaccgatta   11820
cctgctcgcg cacgtcattg acgcgctgcg ggtgggcctg tggcagcgca ccgaggatgc   11880
aaccaaaccg aatccgcggc atgtgcccga gctgttcccg cggcccggcg acgacgaaaa   11940
ggccaccgac ggcggcgagt acgtccaagt tggctcgact gtggcgacca agacaacggt   12000
cggcaagttc ctagaaatgc gcgccgaacg cgaaaagcgt tggcgtgaac ggaaaaaggg   12060
caagagcaag ggggcgtaat gtccgcaacg tactacctca cagttctgcc tgagacgagc   12120
aagctcgttc ccggaatccg aacggcaatg aagggcgccg aaaaggattt aaccctgcag   12180
cccaaactcg acacccgcgg cgccgctgag gcgggccgcc gtgccgggcg cgaaatgcag   12240
gacggtatcg agcagtcggc ccgcggttct ggcattggcc ggttcctgcg ggccgacggc   12300
gctcgttcgg tagggcagca agcaggcagc gagattaacg cggggctgca gtcggccgac   12360
gtcggccgcg gcctcgggtc gcagctcgca tcgaacctga cgagcggcgc aatgaacctg   12420
ggccgcaacg tcggcagcat gattgcgact ggcctcaagg cgacagcggt tgtcggcggc   12480
acggtcgccg ccgcgggtat cgctggcgcg ttgcacgccg gtatgagccg gttgacggcg   12540
atcgacgatg ccaagttcaa gcttcagggc ctcggcaacg acacgcaaaa agtccagaac   12600
attatggaca acgccctggc cgcggttgat aagacggcgt tcgggctcga cgaggccgcc   12660
accactgcag cgtccgcggt ggccgccggt atcgagccgg cgagcggct gaccggctac   12720 ctgaaaagcg tcgccgacac cgcagctatc gcgggcacgt caatggccga tatgggcgca   12780
atcttcaaca aggtgcagac ctccggcaag gcgttcactg gcgatctcaa catgctttct   12840
gaccgcggcc tgccgatatt cacttggctg caagaggaat acggcgtaac cggcgaggcg   12900
```

-continued

```
ctctcgaaga tggtcagcga gggcaaggtc gacgccgcga cattccagaa ggttgttgcc   12960
gagcgtatcg gcggtgctgc tcaggaaatg ggcggcagta ccgcggcca gctcgccaac   13020 ctcaaggcgt cctactcgcg tttcggcgct gagctggccg ggccgatctt tgcggccgtg   13080
tcgccattaa ccactgcttt cacaggcgct ttcaacaaga tcacggcggc gatcaagccg   13140
tacaccgcgc agttgactgc gatcattggg ccttgggcaa ctgacctcgg caacaagatc   13200
acggcgtggc tcgacaacgg cggcattcag aacgcaatcg actggatggg ccgcttggtc   13260
gaccgcgtgc aggcgttgcg cacgggcgag ggtcgaggcg atgcgctgca gtcgatttcg   13320
gattctgtcg gcaagctcgg cccggcgctg caacaggctg gcccggcgct gcaaggcgtc   13380
ggatcggcat tcgcgcagtt cggccggacg atcgccgaga ttggaccggc gacgcttagc   13440
ggtgtcctca ctcccgcgct gaacctgctc gccggtgcgc tgaaattcgt tgcagataac   13500
gcctcgtggg cggttccggt catcggtggt ctcgcggtgg cattcctggc ggtgcgcgct   13560
gcgactgcgg cggctgcacc gttcatgcag gcgtacacgg cgacgttcaa cctgattcgt   13620
agcccggtca ttctcctgca ggcgcaagcg cagcggcagc tcgccgccgc gatgacgcag   13680
cacacggccg ccctggtggc gaacactggt gctcagggca caaacacggt cgcgcagaac   13740
accaacgccg cgacctcggt tcgctcgcgt gtcgcagcga tggcctcggc cgtcgccagt   13800
cgcgcagccg cagccgcgca atggctttgg aatgctgccc tgactgcaaa cccgatcggc   13860
ctcgtgatcg ccgcggtggt cgctatcggc gtcgcattgt gggcgttctt caccaagacg   13920
gagaccggcc gcaagctctg ggacaagatt tggaccggga ttaagacgac ggcggtcgta   13980
gtttgggact ggctcaaggt cgcgttcgac tggctcggcg aaaagctcac gtggctatgg   14040
cagaacgtcg cggtgcccgc atttgagggc atcaagggcg ccgtcgaaac attctggaag   14100
ggcgcaaaag tcgtctggga tgcgttcaca acggtgctcg acacgatcgg caccaaggta   14160
ggcgcgttca aggacggcat cgtgaccgcg ttcaacgccg tgaaagacgt tgttacgtcg   14220
gtgtggtcgg ccattggcgg catctgggac aagatcgtgg gcggtatcgg cactgtcgcg   14280
gacgcactca agggtgcggg cggcacagtg ctgcgggcgt tcggcctggg cggcgctgcc   14340
cgcggtggct acatcgaggg cggaatggca cggtacgcca acggcggcca gatcaacggc   14400
cccggtaccg gcacgagcga cagcattctc gggttcccgg cgatggtccg cgtggctaac   14460
ggcgagttcg tcaccaacgc ccgcacgacc gctcagtacc tcccgctgct gcaggcgctc   14520
aacgccggta tgccgctgag tgacgtactg ggcaagctgc tgccgcggtt cgccgacggc   14580
ggcctcgtgt cggccgacga gctggtcgac ttcgcgcgtg gcgtcgaggg caagccgtac   14640
gtgtggggcg gcaccaactg gggcgactgc tccggtgctg tctcggcgat cgccaactac   14700
gcgaccggcc gatcgccgtt cggatctcgt tttgcgacgg cgaccgaggg cgacgagctt   14760
gcggcacgtg ggtttaagcc tggcctcggc ccgacgggct cgctgcaaat cggttggtac   14820
aacggcggtc ctggcggcgg gcacactgcg gcaacgctgc cggatggcac gaactttgaa   14880
atgggcgggg cacgcggcaa cggcagtttg ggtggctcgg ctgcgggcgc ggctgattct   14940
gagttcacca accgtatgca cctgccaccc gaggcgttta cgggcctcga cggcggggcg   15000
ccgacggtcg ggtcgagcac ctcggcccgc ggtgccggta cgtacacccc ggcgacaagc   15060
tcgcagttga gcgcgtcgtc gcgcaaggtc gacactgccc gcacgtctgc caagaacgcc   15120
gaccaggccg tcgacgaccg cacctacgcc cgcgacaagg cacagcagcg gctcgacgag   15180
gccaaggcca agggtaaggg cgtcgacgat gctcagcacc ggctcgacgt cgccaaccgc   15240
gagctggccg acgccaagga gcggcaggcc aaggcgcacg acaaggtgac cgacgcgatg   15300
```

-continued

```
agcgccgacg aggaactgcg caccaagggc aagttcaaag agggctcgtc gtcgtcgtcg   15360
agtggcgacg gcctgtctgg cgctgatttc ggcaagacgt tcgtatcggg ggcgcttgag   15420
tcgatcggcc tcgacgggtc gctgttcagc aatccgcttg agtggccgac ggttaagtcg   15480
ctcatggctg gcgtgaacta cgcgggcggc ctgctcgcca acggcaccgg cgccgcaaca   15540
agccctggtg gcttcgctga cggcgtgggc caggcggtcg ggctcgatgg cctcatggca   15600
gcgcttccgg gcgctgtggg cgatcctgcg gccggttgga cacctcagag cggcagcccc   15660
gcgctggcgc ccggtcagtt caacccggcg attgcaggcg cggcccctc gatcgccgag   15720 ggcgtcgcca acgccatgag tgcgttcgca ccggacacca cgcagcacgg gcagggcggg   15780
ggagctgaac ccggcccggc gggagacgtg aatttcaacg gccccgtggg catggacccg   15840
caagcgctgc gaaccgagtt ccgcaccgag ctgaacgcgc gttcgcgcta cagcggcagc   15900
tctaacacga agtaagcagc taacggccgg cgagtcgccg atctggtctc tgacctgcgg   15960
cggctcgtcg cgccagctat cgaactttca caactgaata acggggtgag tgagccgtga   16020
cgcttggcgg catccatgac gatttctatc tcgatccgcc gcggtacaca gatgacgcct   16080
acgggcgacc gctgtacggc cccgagaatc cggcgcaccc gagctggcgg cgcatgtcgc   16140
actggggcga cctcggccgt aacggcgagt acctgcggtc aacgcagacg aagtgggtct   16200
atatccaccc gagcaacaac aaggtgtggc acctcgccgg gcctatgcgc ggccgtgagg   16260
gcgtcgtgct ggccaaggaa cttgagggcg tcatgcagcc cgagtttgaa attctctaca   16320
gcgagggcgc ctatacgatc ggcgccaaac ccgagcggat caactacaag aaacgcacga   16380
tcagcctcgg cgtagtcatc cagcccaacg gcaacgccga gcgggtcgag gagcctaacc   16440
cgttctcgta ccggctgatt gaggactcgt ggtggtcgtc gctgtcggag acgcagcccg   16500
gtttcctggg ctcgttcacc cgcacgcacg gctggcggtg gctggctgtg atcctggccg   16560
aggcgtcgaa aacctccctc aagatcgacc cgacggcgca cgacaacaac tctcagcagt   16620
acaacatcgt gctgcacgcc ccctggccgt tctacgccaa gcgcacgctg agcaaggcgt   16680
ggctttccga cctcgagaat gtcgtggcga acgacggtgt ggcgcaaggg attatccagt   16740
gcccgaaccg cggcacctgg gagtcgtggc cgaagtacct cgttaagggg cacgggcagg   16800
cgtggattca ggacggcaac gacgggcaga tgatcaagct gcccaagttc tacgagacgg   16860
acggcgagta catgctcgtc gacaccgatc cgactaagcg cacgatcaca accgagaaag   16920
acccggttga cgggcagctc tacaagtatc tgcgcgggtc gcagttgctt gagctgctgc   16980
tgcacgacgt gacggccgcg cgcctcccgg cgcagcgccg catccccggc ggcatcgggt   17040
tcgacggcaa gattccgccg cgcacggtcg ccaatatcaa agtgcggcat gacaacccgt   17100
acgggtcgat tacgtcgtc atgccgcagc actaccggat ggcgtggtca tagatgtatg   17160
tacagaatgg ccgcaagctg tgggtgccac cagcgtgcgg cgctaacggc gttcccgatc   17220
ccgtcaagaa tccgatcgag gcgtttcggt acctcgacct caagcgcgag ctgatcgacg   17280
ccgaggcccg cgagaagcca ctcattcggc tgtgggacaa ggcgtttaag tacatcggca   17340
ccgtggcggc cgagaagtcg gtcgacgccg aggaaatgct gcacgacacc gggcagggcg   17400
acattgtgct gcgcggcgac gactggctcg tcgagttcat cgtaccgac gtgcgccgcg   17460 aggaggatct gcacgtcacg atcgacccgt acccgcaccg gcgcaactgg cggcggcggt   17520
ggcacgccaa ggtcaccaac gtgcgggttg cccgcaacga gaacggtcag cgcacagtca   17580
cattggagtg cgcgcacaac cgcgagcact ggaaacacct gctgttcggg gcgacgcctt   17640
```

-continued

```
tcagcctgcc cgaggtgcag cctatgcgcg cctggctgct gccgggcaac acgcgaacga   17700
tcgtgagcac aacgggtttc atcaacctgg cgcgcaacta ctggcccttg ctggcgctgc   17760
cttcgcaggt gatgaatccc ggcgcgtgga tcgggcaggc gtccaacctc gccaacctca   17820
acccgttgaa ctggccggtt caaatgcagt tcgtcaaccc actattcgat cggtcgcgca   17880
cgagcgtgct catgtcgagg tggtcgaacg cgcacgacgt gtgcgacgcg ctgctcaagt   17940
acgccgggtg tcacgttcgc gcgtactgct ggctggaaga ggacgaggac agcccgcacc   18000
ccgagctggc ggcgatcgtc ggcgagaagc tcgccaggcc gacgcgcaac tgcatcgtgc   18060
tggcagtcga ggacatgagt ggcacgaccg gggtcaccgg cacggcgatc gacggcgtgc   18120
tcgacctcat tgcagtgtcg gccgacaaca ttctcagcac cctggtgcac gtcgaccgtg   18180
acggcgacgg cgtggacgat ccgtttatcc gcaagctgct gggcgtcgcc ccggcgccgc   18240
cggatattac atttcgggat cacgaatatt cgtcgattat ctcgtctgag cacagcatgt   18300
ttcgtgcaaa ggcgcagaaa attctcacgg gcggccgtag tcctggctgg gtaaatcaag   18360
ttcagacatt cgccattaag tacgcgctct ctcaaatttc cgcaattatc caagctggcc   18420
cggctggtgc atatcagcaa cccggcagct cgggtttgga ggaaatttat cagggccagg   18480
ctgacaatat tttgctggcc tatattcagg taaccgaccc ggtgcgcgca atgcgctccg   18540
gaccctacgg ttacctggaa catttcgagc aaggctcggg ttcagcatac acggtcagct   18600
cggcaatgac attagctgag gggcatcaca agacgcgggc atatcaggcg ttcaaggtgt   18660
ccgtacgtaa tggcgggcaa ttccagctgt attacgattt cgatctcggt tggcgcgcga   18720
actttgaaat tgatcgcatt ttccacaccg accaggtgtc agctattcgg ctgcactaca   18780
acgagacgac accgaaaact ttcgacctgt ctatcggtag tgactcggaa tcggaaagcc   18840
cgctagcgca ggtggctcga tcggccgcag cgttctggaa tgccattggc atgttgttcg   18900
gatcaggaga tatgttctag tggaaattcc cacactgccg ccgctgcccg acgtgccaga   18960
acacgtgccg ggcgccaatt cgacggttga cgcgatgtat gacattgccg aggccctcac   19020
atatccggtc gacagccgcg gtcgacggta cgacgtgcga tttctcttgc cggtgattgc   19080
gtatcacctg gcgcgcgctg gttgtgtcgt cgacccggct cgggccgtga tcaagaagcg   19140
gcgcctgccg ccgacgggcg gcgtcgtcga ggatgcggtc gactgggtgc cgctcgacgc   19200
ccccgactcg atcgaggacg agctagacgg cgcgaccctc gacgacctcc cgcacctgtc   19260
cgcggcggcc caagccgaat ttcgacgccg ggcgctcggc gagcccccgg cgccgacggc   19320
cgtcgacgac cagggcgtcg acctcgacga gcgcgccccg tggcacgtcg aaacgtcgat   19380
cacattcgac gactgagcaa ccgccggcaa aacgtcggat tcataccctg acctgcggcg   19440
gagcctcggg tcggcaaaca actgaataag gagcaccata tggccgagct gcgcccccgg   19500
ctgacgggcg atgcggtcgc gctatttcag accctcctgt ctgccacgtg gtacggcatc   19560
gtcggcgacg gaaacacacc cggcggcatg tcggcaacgc tggaaatgat cgacggcgag   19620
gccgtgatca ctaccgacgt tctgatcgga cccaagggcg acaagggcga cccggccccg   19680
ctggttgatc tgcaatggcc cgcactggaa tccccgactg aactggtcga gctgcaagac   19740
gagctaggcg aggacgacaa gggcaagggc tggtggatcg gcacggttgt ctacgtctgg   19800
accggcaacc aattccagat ggtgcggccc ggcccggcgg ggcctcccgg cgccacgcct   19860
caaatctcgt ttgagttcga gacgatcccg atgtcggagc gcggccccgg cgtcaaggac   19920
gaggtaatcc gttccggcac ttcgcttaac ccgcacatca aggtgcgggc gctgtcgccg   19980
caggggcctg tcggcccgtc gacgaacatc accggcgcac cggactacga caacagcgag   20040
```

-continued

```
ccgccgacca acgggcagac gctcgtgtgg aactcggtaa aagccaagtg ggagccgtcc   20100
gacttcactg ccaagcaccc gcggctgtac tcggttcccg aggcagcgtt tacgccgttc   20160
accggcccgg cgcagcggca gccgatcctg cagtaccagg tcgagccgca ggacttcgcg   20220
tggaccccgt acgtcaccgg acacatcaag gcgtttggcc ttgagctgga cgccgacccg   20280
ctgacgatcg gcgtcgaggt gcgcctcggc gacccgctga caggcgagct gatcggccgc   20340
gggttcggca actcgtcgat gtggtcgacg attgcgccgc actggtcgac ctcgggcgac   20400
cccgcgaccg cggtggcccc cgacaacggc gtcgctaccg tcgccgccgg gcaggccgcg   20460
cagatcaacg taaaccttta caacgatggc ctgttcggcg tctacgtgtt caacggcaaa   20520
ggcgcgcagc tcgccattct cgttgtgccg caagggggat agctgcacat gccatacacc   20580
aagaattacc gcacggtcgt gccgcttgag ccgggcgtcg acctcgaact cgcgcggtgg   20640
ctggctcgtg agtcgttcga gcgtgcagcg gaaaacatgg gcctgacgat cgtcgagtac   20700
ggcgagcgtg aggtgccgtg gaccgagctg ccgccgaagg cggccgagca cctggcgctg   20760
cccgctgatg aatacacgtg gttcgagttc accggcgtag gtgcggtttc cgaggttcag   20820
atcgagtggc tgactgcaga gtcggcctgg cgcaaaacgc aggcgggagg tcggtaaatg   20880
cctcccgtct ttgatcgccg ctccctcgtc atcgaccgca acccgctcgt tggtctgacg   20940
cccgaccccg gcaccctgcc caagctcgac ccggcgatgc tgtggaaaca gtggattgac   21000
ggtttcaaga cactgaccgg cattgaccta tcgtcaccgg ccgcgctcgt cgccagcctc   21060
ggcgacctga tcggcagcgc cctcgatcct gcaaagctga tcgaggcgct gacaaaggtt   21120
ttcgggtacg tcggcccgcc gctggcctca cttgaggcgc tggcggcatg ggtcaacagt   21180
cagattttcg gcctgatcga cccgcggcgg ctggcacaga tcccgctcgg ctcgatcgtg   21240
caggagtcgc caaacctgtt gaccaacggc tcgtttaccg acgcaatcgc catcgacgac   21300
gagacgggcc gctgggtccg cgacaccgcg acgtacaagt cggcgccagc gtcggcgcgc   21360
acgaccgccg acggcacgat cgccgaactg ctgagcattg atctgatccc ggtcaagccg   21420
aaacagaagc tcgacattgc gggattcgtc cgctgggcgg gcctggtggc gtctgacggg   21480
tcgatcggta tcgggctgat ggagtacggc gacgctggcg agcagcgggt gctgatcaag   21540
gcgctagacg gcgccagcgg cacgcaactg acgtggcaga aggtcggcgg ccagtacgtc   21600
gtgcccgaca ccggcgtcga cggtgtgcgc gttcggctgg tcgtcaacga cggcgcaacc   21660
gcgggcaacg tgtggtacga cgagctgaac gcgagcctgg gcgcaaacct gctgcccaag   21720
accgccgttg agggcctggt cgccgagctg aaagcagcgt ttgactcggc cgaggccgcg   21780
gctaagcagt cctcgactt cctccaaaac caatggcagg cgatgctcaa cggcatcaag   21840
ggcggcgtcg tgtggagcaat cgaggacttg tggaatcggt tgctgcactt gacacctgac   21900
ggccttttcg acgcctcgca gctcgtcaac gtcgacaaca tgccgcagct tcccccggcg   21960
gtcgtcgcag gtatcgaggg aatcgagaat atcggcgaca cgattcagca ggcgatcgac   22020
tacctgtggt cgggcttccg tcgtcaaacc gggcaaggca aatcgttctc gtcgctggca   22080
caagccgcgc aggaaacatc gaacgacatt cagacggccg tgcatctggc gacgatgcac   22140
gcgggcattc tcagcgagcg gcgcaacaag cccgcacact ggggcctcgc cgataccgtc   22200
gaggtgtcgt tcccgttgac cgatattgcc tacggcacaa cggcgccgac aattccggtc   22260
acagcgacaa atgcccggct ggcgttcatc cgctgcggcg aagcgtccac aaagggattc   22320
gtgcagtggc tcggctacgg cacccctgac gccttctacg tgaacgtgta caagatggac   22380
```

-continued

```
gccgagggca acctcgttca cctgcacacc tcgccgaata tcagcaacca actacagacc   22440
acgatcggct gggagatgta cgttttcgcg ggcgccgatc agaccgacgt cgagccgggc   22500
gacgtgctgg cggtcgagtt cgtcgtcgag ggatcgacgg catacaacat cgccgggtgc   22560
gtcaactcgt gggttccggt gcacccgtcg gcgaacacca aacaccttgg tgcggtgcgc   22620
ggctcggcgc ttggcgggcg gtcaccggcg acaattccgg ctgagcttgt ctcctggacg   22680
ggcgtagtcc cgtgggtgtc gctcggcatt agcaacgtgc cgccgagcta tcggcccccg   22740
acagcgaccg agttcacgga gactgggcag cagacctacg agattccact gtgggccaac   22800
tacattgacg tgatcgcctg cggtggcggt ggcggcggcg gtagctcggc gaacttcctc   22860
acagggcagg gcggcgagtg tgggcactgg atcgcggtaa cgctggtgcg cggcgtcgac   22920
ttcgcagagg acgcaacgac gatcaccgtc aacattgggc ctggcggcgt tggcggcccc   22980
ctcaacgcca accccggcgg caggggatcg ccaacggtcc tcacatggcg caagccagac   23040
gggtctatcg gaatggctac cgcacccggc ggcgagtacg gcggccccgg ccccgtgcac   23100
aacggcaaca accccaacac ggcatctgct ggcatgggcg cgccgaactt ccagtaccgc   23160
ggcgcaacgt atttcggcgg ccccgatgcg tcctacgcgc cgggcagcgt gcccggcggc   23220
ggcggtgctg gcgggttctc gtactcgtct ggctgggcgg gcggccgagg ttcggcgtgg   23280
ctggtcgccc ggcaatccga ggacgactga gaggggcgc tatggcggga tggggtaccg   23340
acccgcagcc gtcagcgcgt gccggtagcg gctgggcaac gtcgcccgcc gcaccggcgc   23400
ctccgcggcc cggctcggta tggcggccga tcgtgcacga gctggcggcg gccctgagcg   23460
tctcgaccac cgaggcggcc ctcgctatcc gcgcaacggc cgcagcgctg agcgtttcac   23520
acggagacgc tgcggccctg ctgcgcatga cggccccggc cgccagcacg agcggatcgt   23580
cagcgtcggc acgagagcac tatttcaccg cggcccccgc ggacagcacg agcacgaccg   23640
gggcgtcggc ggtcgtcaag gcggtggctg cagcactgaa cgtcagctcg acgtcagccg   23700
ccgcggtgct gcgggccgtg gcgcccgcgg cgtcaacgag cggcacgtcg gcctcggcag   23760
cgttcccggc aatggcgccg gtttcgcagc ggttcgccac tgtcggcgag ttcgagtttc   23820
tgatcccgta ctggtgccgg tacgtcgacg tgatcctcgt cggcgcgggc gcaggcggca   23880
acggcgggtc tgcagcactg gccgccgggc atggtggcga gggtggcaag tgggccgcgg   23940
tcacgttgga gcgtggcgtg catatcccgc tgaccctcgc ctcgatcgtg tgcaccgtgc   24000
gtgcgggtgg cacgccgggc ggcggcgccg tcgtcggcgg tatcgccacg gacggcaacc   24060
ccaccacggc gcaggcggcg ggctgggcag ggctgagtgc tgcgggcggt gtgcaccgcg   24120
agcggatcgg gctgctgcat cagccgggcg acggccccgg cgatttcact ttcaagggcg   24180
tgctgtacgt cggcggcgcg ccgaccaata gcggcaacgg cacagcgggc aactcgcctg   24240
gcggtgctgg ccgcggcggc gacggcggcg cgttcgtcgg ttctcccggc ggtgtcggcg   24300
cacccggagc ggcgtggttc cgcgcatacc agtagcaacc gccggccaaa tgccggactc   24360
atagcttgac ctgcggcgct gcctcgggtc ggcaaacaca actgaatagg agcgttctgt   24420
ggcttccgca gatcagttca agctcgacac cctcgctgca atcctcgcgc agggcaacct   24480
gctgagcctg cacagtggcg accccggcaa gacgggcgcc agcgagatta ccggcggcgg   24540
gtacggccgc aagacgttcg cgtggggcgc cccggcgatc gtgtcgggcg gcgccgacga   24600
cggcaaggcc aaggcgaccg gcgccactca gcagatgaac gtcgctgcgg gcgtggcggt   24660
tacgcactac ggcgtacgca aggccgacgg cacatttctg tacggcaagg ccctgagccc   24720
cggcgcgact ctcaacgcga acggcgtcat tgacgtgacc ccgacgcaca cgtacgacgg   24780
```

```
cccggtttag aacggagaca accgaatatg gaaaaggtac tgccctacga tcgggtgatc   24840
gtcccacagg aaacgggcta ctggtgcggc ccggccgcaa cgcagatcgt gctcaattcc   24900
cgcggcctgg tcgtgcccga ggcgaccctc gcccgcgaga ttggcaccac ggtgcgcggc   24960
accgactacg tgggtctgat tgagcggatt ctcgacctgc gggtgcctga tgcccggtac   25020
acgtcggtgt acatcgagaa cgacccgccg accgctgtcc agcgggagac gttgtggcgc   25080
aacctcaagc ggtcgatcga cgccggttac ggcgtggtga tgaactgggt tgccccgccg   25140
agcaactacc cgcgcggcgt caagggcagc gtgagccccc ggtatggcgg cggcaccgtg   25200
taccactacg tcgcggcgat gggctacgac gacaacccgg ccgcgcgtgc ggtgtggatc   25260
gctgacagtg gctttcagcc gcaaggctat tggatctcgt tcgaccagtg cgcgtcgctg   25320
atcccgccga agggctacgc attcgccgac gtcgatcacc ccgacggccc cgaggcgccg   25380
gtcgacgccg acgcgcaggc ggccgacgcg ctgctgcggc tgatgggcgg ctcgctgccg   25440
ttcgctcggt atcaggcgct actgcccgcg gtgcgccagt gcctcaatga gtgcgagtgc   25500
acgaccgagc cccgcatcgc tatgtggggc gcgcaggttg ggcacgagtc ggtgggcctc   25560
aaattcatga gcgagctgtg ggggccgacg gccgcgcagc agggctatga aggccgcgca   25620
gacctcggca acacgcagcc cggcgacggg taccggttcc gcggcgccgg gcctatccag   25680
gtcaccggac ggcataactt cacggtgctg tcgcagtggg cctacggcaa gggcctcgtg   25740
ccgacaccga cctatttcgt cgacaacccc gacgaattgc gcggcgaccg ttacggattc   25800
gtcggcgtcg tctggtactg gacgacgcaa cgcccgatga acgacgcggc agacgcccgc   25860
gatctggtgc gcgcaacgca gtacgtcaac ggcggtcaga acggaatcga cgaccgccgc   25920
acccgataca acggcgccct ggcgatgggt gccgacctac tcaagatcgt taacggaggc   25980
gatgatttca tgtctgcact gaccgctgcc gagcagcgcg aaatgctcga tctgctgcgc   26040
tggttggcag caccggaaac cggcgagctg cgcaagaagt tcccgagccg cagccagttg   26100
cgcgccgtcg gcgagggcct ggtcgacacg tgggcgggta tggacctcaa ccaggacgcc   26160
aacattcacc tggtcgccga gtacgtgctc gccggtatcg gcgatcccga cgcaatcgcc   26220
cggctgcgca agctggccgc gacgaccgac gccacccgtc gggggagcgc ggcgctcgcg   26280
cagcgcatcc tcgaccacta cgaccaggcg cacgaggccc ccgccgaggt cgacccggcc   26340
ccggcgcgca aggtggcgtg tgcgcagggc ggtggcggct gtgtcctcgt cgccaacggc   26400
ggtgacggca cctgcggcct cgctggcagc gagtgcgtgc tgcgcaaggg cggtgccctg   26460
tgagcaagcc aatgctgctg accgccgcgg gcaccaaggc cgacgagtgg accggctacc   26520
cggccgacct cgcgcggcgc atggaggatc tgtactactt ccagccagtg cggtacggcc   26580
ccaacggaat cccggcaatg tggccgatgg gtgcctcggc taagaccggc atcgacgagg   26640
gtgtgcgcct ggtgctcgaa gccgaggcgc ggccatcgcg ggaggtgccc gacgggtacg   26700
ccgtgtgtgg atactcgcaa ggcggctggg tcgtgtccga gctgctcgac gagttccgca   26760
ccggccgact caagcacctg cgcggcaagt tgatggccgg tgcgacattc ggcaacccgt   26820
accgcgagct ggacagcgac ggcggccgag gaatctccga caagcggatc gtcaacacgc   26880
ccgatttctg ggtcgacgag ttcgaccgcg gcgacatcta cgcgaacgtg ccgaacaacg   26940
acgttggcga ggacatgacc gcgattttca agctggtgcg gttcaacggc attggtgacg   27000
tgatcgacct cggcagcgcg atcgacctcg gcagtatcgc gggcggcctg gtgccggggc   27060
gcggccacct cggcggcatt ctcggcggcc tcggcggggct gctgggtggc ggcgcgcggc   27120
```

-continued

```
agcaagacaa catcgtcgag cagatcgtcg aaatgctcag gagtccgctg cgcgagttcc   27180
cggccgcggt gtcggcgatc ctcaagggcc tggtgttcgt cggccagaag cccgcgaccg   27240
cgccacacat cgagtaccac ctgcgcgagc ggtcgccggg tgtcacctac tacgagcacg   27300
ccgtcgccca catgcgcgcg atggcggcat aaggggggcga gaatggcaaa ggtcgtcgag   27360
acaatcctcg gcatgttagt gcaggtgtgg acaggtgtgc ggcaattcgc cgccgagtgt   27420
ctcggcatcc gcacgtggga ggatttgcgt ctgcagattc acgtgctgtc gccgtacgca   27480
gttacggcaa tggtcacgtg gaacatcgcc agcgaggaca aggccaagct gattgttggc   27540
ctcgtgctcg ccgttgcgag cccggcgctc gcgttcttca acacacgtga cgggttccgg   27600
cgtttggtgt acggactgct gccgccgttg caggcgttca ttgtcggttt cggttgggcg   27660
caggattcga ccctgacgcc tctcatggcg gcgatcgtcg cgctgctcgg cggcgcaatg   27720
gctgccgcta acacgccgtc gagccgcggg ccgaaagaca cgcggacggc ggcagtgccg   27780
tgagcatgtc tgacctgatg accggcgaga cagtcggaat gatcgccggg tcgtcggtcc   27840
tgtctggcgc cgtcggggca ctactgtccc ggcggcgcga caacttcaag acgctgactg   27900
atgcactgat caagcgcgtt accgaccttg aggggcgcgt cgatacggtc gagtcgaaac   27960
tcgacgccga gcagaccgcg cacgagcaca cacgcaggct gctcgtgcag tccgaggcac   28020
tgctcgccgc ggcccgtgcg ttcatccgca ctgtgatgcg ttggagcgca ggcgatcgtg   28080
ccgagccgat gccaacgcca cccgacgagg tgatggccga atgagcctcg ccgaacgtct   28140
cggcgacccg cagcccgcac cgtcgagcga gtgcgccgtg tgccgctggc tcgaccaggc   28200
cgacgagacc gatcgtgcag cgttcgacaa ctggctcgct tccggcgggt cgctgtcggc   28260
gctgtggcgg gcctgcgcca acgatccgag taacccgctg gcgatcaagc gcccgcggtt   28320
ctctgagctg atcaacgacc atcaccgagg aggcgcacgt gtcgctgtct gacaggctcg   28380
ccacaccggc ggtcacaaac gagaaatacc ggcccacggt cgagttcgac aaccgcggcg   28440
ccacgatcga cacgggcacc gtgtaccagg agccgggcca gccacccgag tacgcggaaa   28500
ttctgcgcca ggtcgggcgc gaccccgaac ggttccggct cgtcgagatt ctgagcgaga   28560
agcattggca ggtgccgtat cggccgtacg tccgcgacga cgacggtcag ccgatctttc   28620
acgagttcgg caagccacgc cttgaggagc aagagtttcg gtgggcggcg tcctacaagc   28680
tgcgcgtcga gccgatcgac cgcggcgccc cgagcgacct tgaggcgctg atcgccgacg   28740
cccgcaaggt gccgacgatc gccccggcga cgacctcgcc gtactggtac gtgtttcagg   28800
cgggcgacct gcagctcggc aagcggtcac gcgacgggtc taccgagcag atcgtcgagc   28860
ggttcgtgca gtcgcttgag gccgccggtc ggcagtaccg cgagctggcg gcgtccgtcg   28920
ggatcgccgg tgtgcaaatc tcgatgccgg gcgactgtat cgagggcgtc gtgtcgcaga   28980
agggcgcgaa tagctggctg acacaggaga cgatcgccga gcagttccgg ctgctgcggc   29040
ggctgatggt tgaggccgtc gacacgttcc gcgcggcccc ggccgtgtac ctcgacgtcg   29100
tgaacggcaa ccacgaccag gccaatcggc agtggaacac caaccccgga gacgggtggg   29160
cgaccgaggc agccatcgcg gtgcgcgacg cgatggtgct caaccgcgac gtgtacggac   29220
acgtcgaggt gcgggtgcct gaaccgtggt cgggcagcat gacggtgccc gtcggcgaca   29280
ccgtggtcac tgtgatgcac ggacaccagt cgcccaaggg caaggccctc gactggctcg   29340
ccaagcaggc ggtgcacaac cagcccgcgg gggcctgcca ggtgttgcaa cacggacact   29400
ggcacgtcgg cgccgtcgaa atgcacgcca caaagacgat cgtgtgctcg ccgacattcg   29460
actgcggcag cgattggttc cgcgagcgcc aggggcggcga gtcccgccgc ggcgctctca   29520
```

-continued

```
cctacctgct gcgcagcggc gaggtgtcga acctgggcgt gctgtagcaa ccgccggcaa   29580
aaacctcgag cgcctgccgt gacctgcgcc gatcaatcga aacgccgatt tccggcaaac   29640
attgcgaacg cccctcgtcg atccgtcggc gggggcgtt tcgtcgtatt gttgacctgc    29700
atacaggtgg cccgtattgt tggcatggca acaacggcac aacgggatag gagcccgaaa   29760
tgagcacgga cgtaatgaca gtgcgcaagc tgtccgaaca ggaggccgcc gctatggcac   29820
gaggcaagtt ggtcagtgtg ggaggcaccc gccgaacgat cccggcggcg aacgtgccgc   29880
ggtacgagga gcaggtcgcg gcgattgagg ccgagtggcc cggcgccgac gaggcgcaca   29940
ttcggcgcgc ggcgattgag gccgtcggcc ggtacctgtg cgacgaggcc gacctgcccg   30000
agacgatcgg cgaggagctg gccgaggcga aagagcagta cgaggccgcg acgtcggcgg   30060
cccgcatggt cgtgcgcctg gcggtcgagg acaacgccag cgagctgagc ctcgcgcagc   30120
gtatgggtat caaccggctg actgtgcgca agtaccgcgg caaggtcgat cgccgttggc   30180
agcgcccgtg agcgccgcgc cggtcgggtc tgaggtgtgg gtactcgatc tgacgatcga   30240
aggccccgag ggcggcgact atgacgggtg gcagtcggtg cacgcgagcc gcgagggcgc   30300
actcggggcg atgctcgaca agctcggcga gcatggcgtg agcctcggcg ccgacgtcga   30360
cacgatcgcc agcgcggcgg ccgacaatgg cagcctggcg ggcgattttg cgatcgacga   30420
gctggctgtg agctacggcg tgcacctgat gccggtcgag ccctaaccca cgtgttgaca   30480
tgcatacagt tcgcgggtta ctgtatgcat accaacaacg cacacgggat aggagcccac   30540
gatgagcgag tacaccaagg ccgaggccaa ggcagccgat gcgatcctcg ccaagctgac   30600
cgatgagttt ttcgaggcgt atgccgcctg ggagcgggcc gccgaccggc tgcacggcgc   30660
cgcgggcgac gacaagaccc gatacggctg gaagatgagc cacgacgagg ccctcgccaa   30720
ggcgaccgag cgcgcggccg acgagcggat cgtcaaattc aaccgcgacg ggtacgcccg   30780
cgccgtcgag gcgtacccccg cggcagtggc cgccaagagc gccgccgaca aggcgatcga   30840
cgaccacgag gccgccaact acaagggatg gctgcggttc ttcctggtgc cgggtgggca   30900
cattcaccgc tcgcgcggct gcgcgtcgct gcggatcaca accaagatcg gttggctgcc   30960
caacctgtcg ggcgagaccg aggccgaggc cgtcgcggag cacggcgcca tgctgtgcac   31020
aaagtgcttt ccgtcggcgc cggtcgagtg gacgatcggc aagcccgccg accccgacgc   31080
ctgccctggt agcggcgagc gcccggtcga gggcacgatc gtgcgtcggt accgcagcgc   31140
ttacgccgag tgcaccggct gcggcgtgcg gcacgtctac accatgtcgg gcgtgatcaa   31200
gaagcacaag cgcccaagg tcaagtagcc ccggcccggc gaggcccccg tcgacacggc    31260 ggggggcctcc ttggtgttga catacataca ctcgacgggt tactgtatgt acatcaacaa  31320
cgcacacggg ataggagccc acaatgtcga tcaacaccgc taccccttc acctgcaacc    31380 ctggcacgat caacggccgc gaggttgccc gcggctacat ggccgaggcc gacgacgcac   31440
gcgagctggc ggcgttcgac gaccgtctca ctgaggcgca gtaccgcacc ctgcaggctg   31500
cgatcaacag cggcctgccg gtcgtgctga cgatccgtga gcaaggcgag cgcccggccg   31560
cccgcaaggt gacggcgatc gtcgagtacg caacgatttt cccgcgcaag gccgacgacc   31620
ccaccgcggg ctcgggcaac ctgattcgcg cgcgctactg gggattcggt cacaacgtct   31680
ggctgcagga cattatcgac ctcgacaccc ccgaggttga gttcatcgac ctgcccgagt   31740
agctcggcct gagcacctcg acgacgacgc ccccggcggg attacctgcc gggggcgttt   31800
tcgtgtctat gcgggctact cggcggtgtc tgggcacagc tcacgctgcg cgctgtacgc   31860
```

-continued

```
gatcccgtcg gcatggtcgc gtgtcatgtc gagcaccttc aagaacatgc gatcggcgac    31920
gacctcgcgg ggcttgcccg tccgcagctc gtcgcacacg gcgtaaccga gcgcgagcgc    31980
ctctcgctcg tcgagtatgt cgagcccgta gtcgacactg atcctcgcca ggtatccggc    32040
ctcaccggcg tgtgcggcgc cgggcgccag gacgacagag gcggccccga tcgtggccgc    32100
gacgagtatt cgtttcaccc ggctaagcct agttggcggg gcctggtctg tggcggcacg    32160
ccgcggtacc gtctgccgta tgcgtcagtt tcccggcaca ccggcgagcg gcgtttgctg    32220
gcgcggcaaa cgaacggggg gcgtggatgg ggcgtggatg gcatccacac agcccgcgtt    32280
gccctgcgga ttgccccgtg ttttcgcgta ctctcgcgtg tcagttagcg gcgtttccgc    32340
aggtcagagc ccctagaggg gctcggttca attcccggca gctccacccg taaacgccct    32400
ggtcagagcc aaaaatctga ccggggcgtt ttttacatcc acacccacat ccacaaatgt    32460
gtacgatctg cggctatggc atcccgcggc tgagcgcaac acgcacgagc cccgaagctg    32520
aacgcctcgg ggctcgtttg ctgtatctgg ggcctactgc aggtcagcgg gcaattcgag    32580
tgctttgccg gcggtagcta ggcggcctcc cgctcgatgt cggggcgcag acgtcggcga    32640
tgcgcctcgg cggtgtcatc gcgcagtgca cggcgactgg tgcgggtcgc ccgaatcagc    32700
ccgcgatacg gccgaatctt cgtccaccac gaccaggcca ggcacgccga cagcatgacc    32760
gtggtcacgt atccacagac cgagatcatt gccgtaatgg cgtgctgggt ggccatgaag    32820
gcgctcgcca cggcgagggc gcagcacgcg atgcagaacg ccaggcgac gatccagacc     32880 accgcaatac ggccctggtg ctcgtcgtgg gcgatgtgcc agaggcaggc gacggccacc    32940
gcgagcaggt gcatggtcgc gtagtagtgc agcgccgtcg ccccgacgat gccaatgtca    33000
gtggcgggca tgtcgagcat gttgtggtgc acggcgggct cgcgcagcgc cgggctgctc    33060
acctgcagcc ccagcgtcac aaccggcgtg aggtagagcc acggtgcgac ccaacgtgcg    33120
aagaacacgc gcacctcgtc gtcgtcgcac acgcggtgca acatgctgac ggcgatagcc    33180
ccggcgctga acaggtagag cgtgcggccg agccagtcct caagatgcca gacgccaatt    33240
gcttggtaga tggtgcggcc gagcgtcatt gacgccacgg tgccgcacag cgccgcacca    33300
agaagctgca gcagcagggc cgaggtcagc agtccctcgt gcaggatgcg aaagctacgc    33360
cagcgcaaca gaactgccgc aagagctacc acacaaacaa tccagcgcag cacgataaat    33420
gcgacagcta ttgacatagc cactctctca gggaaggcgg gcggcggccc gacgatcaaa    33480
ctgccgccac tgtaaaccac gcctcagagt ggtgagaaat tacacatcaa agactctcag    33540
gcatggctcg tgattcctgt ctgttgttcg agctgttcat tccctcggcg tgtcacttta    33600
gttcagtttt cgggactgaa caactctctt accagcgttt atgcacttct tatgcagtcg    33660
ttagcgtccc gaaacaacgc agatgttcct gatttcggga cttttggtgc tactgtctca    33720
caccgtgcag acaaccactc atcagttgcg ttggcggcgc gacaacgtgg caaagaggat    33780
gcgccgcaac aacattcaag atcgtgcaac tttggcaaaa aggatcaacg tcgggcgaac    33840
cacgatttac tccaccttcc gcgcggactg gtcaggtgtg gcaacgcaca cggtgctggc    33900
gcagatcgtc ggagaactgg ggggctcgct atctgaactc gtgtcagttg aggcccgcgc    33960
atgacggccc ccgcgctgac ccgtccgctt gctgaggtcg cggcactgat tccgtgctca    34020
gagcgatggc tgaccgagca ggttcgagcc gggcgcgttc ccggccgcaa gatcggccgc    34080
cactggcgca tgacgcaggc cgacgtcgac gccgcccttg agtccttccg agtcagcccc    34140
gagtcgggcc gcaagtcggt cgcacctccc gccgaccggc cgatcgcact tacccccacc    34200
tcacgccgtc ggactaggag ccgctgacat gacgatgacc acccgcaccc gcaacctcgc    34260
```

-continued

```
cgccgcggcc cggctgcgca tcgaactgaa cgaggcccta cgcgagcgca accaggcccg   34320
cagcgagcgc gacgccgggc gccaggtaat cgccgaccag gccgccgcgc tgcacagcct   34380
cggcgatcag aacgcctacc tgctgcagga gcgcgacgag ctggacacgg cgcaccgcgc   34440
ggcgctggcc gacctcggcg aggcgcatcg ccagctcgct gagcgcgaca acctcgacaa   34500
cctgatgcaa ctcgccactg cgaccgtcgc ggccccggcg ccactgcacg acgagccgga   34560
tatggagcgg ttcggctgag cttggaggtg gggcgtcaaa cgggtttctt tcgctgtttt   34620 cttccccgc aagcgtggcc cacgacccgc tgactacttc cggcgaggtc actgctgcgc   34680
cccacctccc cacaaacgac gcagccccgc actaggcggg gctggccgac acaaccaagg   34740
gataggagcc acttgttatg tcgagcaaaa tcctagcgca caagcgccag gcggcgcggg   34800
atcaacggca cggcgagcgc ctcggcgcga tcgtcggcgt gttcctgctc cacgccacga   34860
tgggcgccgt tggcggcctt gtcggggcgg catgggtcgg cctctacctg ggggcgccct   34920
ggtgatcacg ctcaaccacg acgaaatgca ggccgctgcc cgcgccatcg acgccaacca   34980
ggccgagggc gtgactaccc tcggcgcact ggccgccgcg gtggccgctg tcaacaagct   35040
gcgcagcccc ggccggtcgt ccgactgcac cgactgccag cggtgtgacg ccacctgccc   35100
cggtcacgtc aaggcgcagg cggtgtcacg gtgacggccg cgcagctcgg cgagggcgag   35160
gccgctgtgc gccttgggat tacgcgcaat gcactgcgct ggcgccgccg cagcggcacg   35220
gcacccgagc accagctcgt cggccgcaaa atcatgtacg acgttgcggc acttgacgag   35280
tacgcgaccg cggtcgacaa cacgcacgtg ctcgacatgt tcacgccgcg ggttggcgac   35340
acggcgaccg ctgacgaggt gtgccggttg ctgcggattg accaaagcga cgtactgggc   35400
aaggttttga agcgtcacgg tgacgaattg gctgctcacg gctgggatcg tgaaagtggc   35460
acgttcaccc gccgggcgat cattcaggtt gcgttgctgg tgcgttcgtc gacctcggcg   35520
cgtgcaggtc gcatcgccaa ggccgccaag gcaggcagtc ggccgatcag tttcgaccac   35580
agcccgcggt cgcagcagtg cactcacatg cttgagcgcg cattcgatct ggcgaccgag   35640
gtacacgacg acgaccccgg cgaggtgtgg gcacggctgc gcaagctcga ccgtcacgca   35700
ctgaccggcg tcgctgtcgc cctggccgcg atggtcgacg ttgagggcac cggcgccacg   35760
aagtacctgc gccacctgtc ccgcggcggc ctggcggccg agggcctgca gcggttagtg   35820
ccgactcgtg agacgaccga cggcgtgccg ctgtcagtgc tcgaccagat cgaggccgac   35880
gacgaggccg accagcaaga cgagggcgag gtggatcagt gagcgacgca gagcatttcg   35940
acgacgaccc cgaggcttgg cgggataacg ccgtatcgc gcagaccgac cccgaaatct   36000
tctttccaga gcagggcggc agcacccgcg aggccaagcg catttgcggc ggctgccagg   36060
tggccgacga gtgcctcgcg tgggcgctga gtcagccagt caacccaacg ggcatttggg   36120
gcggcacaac cgaacgagca cggcgacgaa tcaagcgcgg acttaaaggg gttgcagcat   36180
gagcgattac aacgacgcga ccggcgcccg gtgcgatgtg tgcggcaagt acgaggcgcg   36240
ggtgttcgac ccgtgcgggg cgatgtggtg ccgggtgtgc gacctgatgg gcctcggcgc   36300
cctggcggtg agcgagcagc tcgccgaggt cgccgagttc gtcggcaaga cgttcgacga   36360
gacgccgctg ttcggcatgg acaccgacag ctcggcgacc gaggcgggcg accccgaggc   36420
atgggccgac ccgacgttca tccttcccga gccggtgcag cagatcgccg acctggccca   36480
ccagttcgcc gccggtgacg acggcgtgag ggcgcaagcg caggtgtggc tcgacgaggc   36540
gctgccgcaa gtgctcggcg agagcaaggt cgacagcctc gacgacgccg accccggcgca  36600
```

-continued

```
cgtgtggcag gacgcgctcg gcgcgcactg gggctggctg catggcagcg gttgggttgc   36660
atggaatagc ggcgtctacg tgcatggccg cggcgcggtt ggcccgttca aggtcgcata   36720
tcggcggccg gtcggcgagt tcaccccgat gctgctcgaa ctcggcggcg gcctcgcgtt   36780
cggctgcgac atggcccacg gccctagcaa cgacaccggc gtcacggaaa actccacgac   36840
cagcgcagac agcttggccg gcgagcctgc cgagcaaacg cccgacatgg tggcgcaccc   36900
gtcgcactac acgtccagcc ccgccaagtg ccgggcgtgt ggtcacccaa tcgagtgcat   36960
cgacatcacc gagcacatgg ggttttgcct cggcaacgcc accaaatacg tctggcgctg   37020
cgacctcaag cacgacgcaa tcgaggactt acgcaaggca attcagtaca tcgagtttga   37080
aatcgcccgg cgcgaagcgc tgagcacaac cgagggatag gagcccacaa catgattcgc   37140
aagattgccg tcgtcgccac cgcggcactg atcgcagcag gcgccaccgc gtgcgagggc   37200
ggcgcagatg gcggcggcgg gcagcaggat agcgggccta gcggcgtgat cttcatgccg   37260
atgccgggcg ttcccggcgc cggtatgccg atcttcttct gaccaacgac caaccaccaa   37320
aggggcacaa ccaatgtcaa tgatcaaccg tattgccgtc ggcatgaccg tcggcgcgat   37380
cggcgccgcc gcggtgctgt cgggctgcgc cacgtccaac caggaatggc acacgggttg   37440
caccgtcaag gccaaggaca ttgtttacg cggcagcgac ggaaacacca cgcgcacaaa   37500
gcgcgtcacc acgtcgtgcg gatcgttcaa cgtcgaggac gcgatcgagg tcgggcactt   37560
caactcgtgg gacgtctggg agtccgtcga ggtcggcaag acgtacgaca tgttcaccgg   37620
cggcccgcgg atcggctggc tgtcgacgtt cccggttctg ctggaagtca agccagcaca   37680
gtgaccgtca gcaaccggcc gtggtgggcc gaccgtgagg tcgtcgagga tctggtcgag   37740
cagaagcgtt tcgacgcgac gctcgcctac ctcggcggcc tcgccgacgc catcgagcac   37800
cggatcgcct acgcgtcga cgatcccgcg atggccgcca gctcggcgct gcgaaacctg   37860
cgcgagattc accgctggcc ggttgagttc gcggtcacgt ggggcggcga cacgctcacg   37920
cggccgatgc tcgtcacccc gttggagcga caacgcgaac tgaccagcgg cctagacgac   37980
gtgccgagcg tgcgcgacct gggcgacaag atcgaccgcc gcgactttct gcgccgcagg   38040
cggcaactga aaagggatag gtaagtggat atttcagcgg taaagggtca cgtcgacctg   38100
ctcgcgcacg cgcggatcga gaaaaagaag tgggaggaaa tcgagaagaa cgccaaggcg   38160
gcgatcgacg aggcgctcgg cggtgacgac gagggcacgg tcggcggcga ggttgtcgtc   38220
aagcgttcgc gcaccaaggt gacccggctc agcggcaagt tggtgcaatc gctgcacccc   38280
gaggtttacg ccgagtgcct cgacaccaac gagcagactc gcctatcggt ggtgggcaag   38340
tgaaggtttc agagacgcac cacaccacga tcacggtcga gccgggcgac aaggtgcgcg   38400
acctgtgcgc ggtgctcgac gaaatgccga acggcgccga aatcagcgtg tacgcaccgc   38460
ttccgatgtt caacaccgac ccgaccgtca accagtacgc cggggtgatc agcgtcgatc   38520
acctctcaat cgagggatag gagcccaag catggcaagg caattgatcg tggtcgacct   38580
ggaaacgacc agcctcgact acgacaccgc ggccccgttg gaggtcgcac tgctcaacgt   38640
cgacaccggc gagtcgctgc ggttcgtgcc gcacgtgacg tgcgagcagc tcggcgcggc   38700
cgacccgaag gcgatggaaa tcaacgggta ctacgagcgc ggcgtgtggc gtgaggcgct   38760
gaccgagcag cagaccgccg tcgcgtggtc cgaggtgaag gattggctgc gcggcaacac   38820
gtttgcgggc agtaacccgg cgttcgactc ggcgatcgtc gcccggcagg ccgccggtgg   38880
catgttcccg gcgccgatcg gccgcgtgtg gcatcaccgg ctcgctgacc tggcggcgta   38940
ctccgcgggc aagctcgacc gcgatccaac cgagctggcg ggcctcgacg acgtggccga   39000
```

-continued

```
gcgcctgggc gtgcaggtgg cgcagcggca caccgcaatt ggcgacgcgg cagcgacggg   39060
gctgtgcttc gacctgctgc gcaacaccaa ggcggcggca ctctgatggc gttcaactgg   39120
gcagggcagc ggatcgagcc gggcgcgacc gtgtggcgcg gcggccgtga cggaaacaca   39180
agcagtttca aggtcggtcg cgtcgaggcc gtcgacagga cggcgcgcgt ccggtgggtc   39240
gctgagatgg attggcgcgg caacgtgcgt ctgctcggcg agaagtcggt cgggcggccg   39300
aacgtcgaca gcctggcgtt gatcaacccg gcgacattga gcgacagggt gcgggaggca   39360
ttgcagcagt gagtaacaac aatttcgtgc acgtcggcaa ggtgacggtc ccggtgggta   39420
agggctcgat cggcaagccg cgggtgcccg tcgtcgagga cgtcgagatt gtcgtcggcg   39480
tgcgcgccga cctcggcgag gtggtcgtcg cgatcgacgg tcagcgcaac ggcgccctgc   39540
catcgctgac cggaccgcaa gcgtctgcgc tggcggagct gctcgacctg gccgcgggtt   39600
ccgccgcctc gctgtccgag gcataccaga cctatcaggc gacgctgcag cgggccgagg   39660
ctgacctaga gcaggcgttc gcgcaggggg cgagcgcatg agggtgagtt ttgctctgac   39720
cgtgctcggt tgccacctgg gcacgctcga cgtcgaggtc gacggcgacg acgagaccac   39780
ggcccccgcg gcgccagtga aggcggcaac gaagccggtc aagtgggcga gtcgcctgtg   39840
ggttaagggg atgatggcgt gagcaccaat gcagcgtttt tcgggctgac cgacgacgcc   39900
cccgagcggg atcggccgcc gaccgacgag cagcagttca acgccgatct gctgccgac    39960 ctcaagggcg tgtttaaacg cgcctgggcg cagcatggcc ggtcactgca gcgcgctctc   40020
gggccgtctg agattgggca cccgtgcccg cggcggctgg cgtcgtcgat gcttgagctg   40080
cctcggatta accccgaggg cgacccgctg cccgcgtggc tcggcactgc cgggcacacg   40140
aagttcgagg atgcggtcaa cctcgacaac gagcggatta tcgaccagtg gctcaaggac   40200
cgcgagcagc gttgcacggt cctgcgcggc gtcactggcg gcgatgaccc gcagtatgtc   40260
ggccggtggt tcactgagcg gcgggttacg gtgcgcggcg gcctgtctgg cacgtgcgac   40320
ctgtacgaca cgtggactga caccgtgatt gacctcaagt ttcctggggc gtcgcggttc   40380
gccgagtaca agaaagaagg cccggcgccc gagtacaagg tgcaggcgca cgcctacggc   40440
cgcgggtacc gaaatgaggg gttccccgtc aagcgggtgg cgaactggta tatcccgcgc   40500
ggcgggtcgc tggcgtcgtc gttcgtgtgg tccgaggcgt acagcgacga gattgtcgac   40560
gagacgctcg gcaagctcga caacattctc gtggcgctcg acgagctgca ggtcgaccag   40620 cacccgaac ggatcgccat gctgccgaag gtgcctagca gttgcatgtt ctgcccgttc   40680
ttctcaccgg acggtaggcg ccccgagccg cacgcctgca cgggcggtgc gcagtgaagc   40740
cccccgcgcc ctggcgtatc cgccagctcg tcgagcaggt gcccgtcggc gacttcgata   40800
gcaccgcgac gcggcagacg gtcgtcgtcg ggtgggtcgt cgagcagttg accctgtaca   40860
cgttcacgcc cggctcggtt gagggcgagt acgtcactgt cgactacttc ccgaacggcc   40920
cggccgcgat cgacgcattt gccggatacg gcagtttggc gatctgacat gcacggatgc   40980
aattttgccg gcggtagctg gcaggggata ggagcccaca ccatgagcgg cgaggcaggt   41040
cagtgagcgc gggcctgcgg tcgacgttca ccgcgaagta tttcggccgg tgcggcggct   41100
gcccgagcca gatccgacct ggcgaggagg tggcgtttat ggctgatggc ggccttatac   41160
atgttgattg cgaggacaac tcgcatgagc ccgtaaacgc ccgcaagcgg ccgacatgtc   41220
cgcactgctg gcttgagcac gcaggagatt gcccgtaatg agttcgcacc gttgcgtagg   41280
tgacgactgc gggatctgtg cgcaacggat cgaacaggcc gagtatgacc gcgactgccc   41340
```

-continued

```
ggccgacgac tatcccgact actacgacgg aacatagcca cccgccgcgc ctggcgggcc   41400
gagagggaaa cgggcgcaac gcaataacgg aacaactgaa caaaggaaca actgaacaat   41460
gagcaacgac tcgtacgact tcctcggcgg cggcggcgtc ccatctggca agttcggcag   41520
ccccggcgac gtcgtgggcg gcgtaatcgc catcgagccc gagcaacggc agatgaccga   41580
ctacaagacc ggcgacctgc tgacctggaa ggacggcagc ccgcgtatgc agctcgtcgt   41640
caccctgcag accgatctgc gcgaccccga ggtcgaggac gacgacggca agcgtcgcct   41700
attcgtgaag ggcgaaatgc gcaaggccgt tcagaaggcc gtcatttcgg ccggtgcccg   41760
cggcctggac gtcggcggcg agctgcacgt cacctacacc ggcgacggcg acaagaaggg   41820
caacctggac ccgccgaagc tgtacagcgc cacctacaag aagcccgcac cgggcgcagc   41880
cgcggcagcc cccgcgcagg ccgacccgac ggcgggcatg acgccgagg cgctggccgc   41940 actcgctgca ctgctgccac agaagtaagc gcacaacgcg ctgcgagccg gtgacgttcc   42000 gcaacgggc gttaccggct cgctctgtct aacaagccat ttcgacgagg ataggagcc   42060 caccgaaaaa tgctgacgat ctacaccaca ggccccgagt gctacaagtg caacctgaca   42120
aaggacaggt tcgacaaggc gggcgttgcc tacaccgagg tgcgcctcga ccaggccgac   42180
gaggctgtca ctgcgaagtt cgtcgccgcc gggcacgctc acgccccggt cgtcgtcgac   42240
gagctgacca atgtcatgtg gtcggacttc cggcacgaca tgatcaaggc cgcgatcaag   42300
gcccgcgcat gaagccccgc aatcgccgcc gcgcgtacgc cctgttcact gtcctggcgc   42360
cgtcggcgtt catcctcgcc atgatgctga ccggctgctc tggcaccgat caagagaccg   42420
gcaacgacat tccgagctgg atcgccccgc atacggtcaa cctgcccgac ggccgaaagg   42480
tcttgtgcgt gtgggagaaa gacgggtacg gcggcggcct gtcctgcgat tggagccggg   42540
cacagtgaac ggcgcagaac tgttcgaccg catcgccctg acccgagccg acggccgctg   42600
cgagtgcgaa ggcgcttgcg gcagtagcca tcggtgcgcc ggtcacaccc gctgcgccaa   42660
cgtgcacggc cgcccggcga ttcacggcgc cgacaaggtg gtcagcctca ccgtggtgcc   42720
acgcaacggc gacggccgga atctcgccga cggcaacctg attgcgttct gtcaggcgtg   42780
ccttaagcgg caccgcgcca agctcaaggc tgccgcggac aaggatgcag cccgagcggc   42840
ggccgaggct gccgacggcg ggctgttcga cgtgcccgac gtcccggtcg ctacaggcaa   42900
cggcgtcacg ctgtgaacgc gcgagcagcc ttgccccaca actgaataga ggaatgagtg   42960
aacggcctaa ctgatctgct cgaactgctc ggctacgccg acggcgagca cgtgagcctc   43020
aactaccagg cgcccggcgg cccgttctcg tcgacggtcg tcgagtacca agaggacagc   43080
gacagcctgc agggcctcgc aatgtcgctc gccaacggcc gcaactgctg gtttggtgtc   43140
aacccgacgc taccgcggcc ggtcgacgct gacggcaagc agaagggccg cggcggtgcc   43200
gacgacgtga cccggctcgc tgcgatctgg tgcgacctcg acgtcaagcc gggcgcctgc   43260
cgcgacattg agcacgccca ccaggtgatc gacgagctga gcgcaattct cggcacccgg   43320
ccgagcgcag tcgtgtacag cggcaacggc ctgcagccgt attggccgat cgacgacggc   43380
acgatcgccc cggccgagcc ggtcggcgac ctcgacgagc agacgatcgc cgcgagcgct   43440
gagctgcgcg ccgacgccgc ggccctactc aagcggtggg gccgcctggc gtgcatcgtc   43500
gccgacggcc tgggcgccaa gatcgaccga ggcgtctacg acctcgcccg cgtgctgcgc   43560
gtgcccggct cacacaacct caaggacacc gacaacccga gcccgtcac gatcgacggc   43620 gacaccggcg ccccgctggg cctcgacgag ctgcgcgagc gcctcgacga gcacggcgtc   43680
gccgagtacg agggcgaccg acgcacctcg cacgaggtga tcagcaagcc cgacggctgg   43740
```

```
acgttcgcgc cgagcacctg cgactatttc gcgccgacga tcagggcgtg gcgcgaggag  43800
ccgatcaccg aacggcaccc gtggctggtc aaggtcaccg tgcggctgat ggcagcggtt  43860
cgcaacaagt gcctgacggc cgacgagtac gccgaggccc gcaagatgat cgtcgacaag  43920
ttcatggccg agtgcgcggc gactggccgc gacgtgccga gtttcgagat tccgaacgca  43980
ttttcgtggg ccgagcacca cgtcgccacc aagacagacg ccgagctggc gaccgagttc  44040
ggctcgcacc tgcacctgtg gcagcgggcc gagccccggc agatcgagct tgcgcctatg  44100
cccggcgtcg acgaccggca gcaaaccgcc ggcattggtg ccgagggtgt tagctcagag  44160
ggatcattag ccccggtcgt ggacattaac gcccggcgca atccggttgc cccggcggtc  44220
acgctgaccg acaccggcaa cgccgatctg ctcgtcgagg cgtggggcgc ccggctgcgg  44280
tactgccccg acacgggtaa gtggctgagc tggaagggca cccgctggga gcacggcacc  44340
gaccagggcg aggcgatcgt cgccgcgcgc caggtggtcg aggcgatcaa gctcgacgac  44400
gacagcccga aagacgttat ccagcaccgt atgcgcagcc tgtcgcgcaa gggacttgag  44460
aacatggtcg cgctcgccaa gtgctcgccc gacatgcgcg tgcgcctggc cgacctcgac  44520
gccgagccgt acgagctgaa cacgccgagc ggcgtcgtcg acctgcgcac cgggcacctg  44580
ctgccacaca gccccgacgg gtggcatacg aagatcaccg cgccgggta caaccctgcc  44640 gcggtggccc cggcctggca gaagttcctt gctggcacgt tcggcgacga cgtggaactg  44700
atcgggtatg tgcagcgcct cgccgggctc gccgcgatcg gcaaggtgac gcaccacgtg  44760
ctgccgttcc tgttcggcgg cgggtcgaac ggtaaaagcg tgctcatgga cgtgctcgca  44820
aacgtgttgg gcgactatgc gattacagcc ccggccaact tcctgctggc gggccgcgat  44880
cggcacgaga cggagatcgc ccggctgcac ggcgcccgca tggtcgtgtg ctcggaaatc  44940
aacgctgaga gcaagttcga cgaggccaag gtcaaggtgc tgacgggtgg cgacattctg  45000
tctggccggt acatgaggca ggactatttc gacttcaccc cgtcgcacac gctgtttctg  45060
atgggaaacc atcaacccca agtcagcgcg ggcggtacat cgttctggcg gcggctgcgc  45120
ctgttgccgt tcctgcatac ggtcccgccg gagcagcgta accccaacct cgccgctgag  45180
ctgatccgcg acgagggcgc cgccatcctg gcttgggtcg tggcggggc gcgtcaaatc  45240 gccgctgacg gcctccgcga gcctggctcg gtcttggcag ccaccaagga gtacagcgag  45300
caggaggacg ctctggggcg gtttatctcg gagtgctgcg agctgacgcc gggcgccagc  45360
ggcggggcta aacggccct ggtgttgaag gcgtatcagc gctgggccat gtccaacggc  45420
gaggacgcga tggtgtctca gatcaagctc gggcgtgagc tgtcggctcg gttcggggtg  45480
cgcagcgtgg cgactcacgg gcagcgggtc tatgcgggcc ttgccctgca agcttcctgg  45540
gacttgtcgc acgagctggc gggcgggttc cgctgatgct gcggtggccc tcgcaatcga  45600
cggcggcagc taacggcacg gattcacgcc aaaacccgtg cccggcggca cagatggcac  45660
agattggcac agattcaaaa aacgaacttg tgcccgcgtt gccgcaggta aataccccta  45720
acggggcttt gggcacagat ggcacagatt tttacgggtt gacttcacgt gtagagattc  45780
ggggcgtttt ccctggtcga gtcgcgccga gtgcgtggtg tgaggctcat atgcaaaaaa  45840
gtgtgccatc tgtgcccgac ccgtgccgag caaactccga gacgcgcccc gccgtagcgg  45900
gggcctggcg gggcgctgac aggcgtcgtt gacggtttct gccgccagaa tgctgctcga  45960
ccacaactga atatggagaa acgagtgact gaccacactc tcgacctcgg gcttgccgcc  46020
gaccaggtgg ccgccgccga ggctgccgag cgggccgagc tgcacgccaa ggctgaggct  46080
```

-continued

```
gccgagctgg tgctcgacat gctgcccgcc gagtcgcacg aggccctgta tgcggccctg   46140
agtgcccgtg tgacgcacga gcgcaacggc ggcaggcagt tgcgcctgtt cgtgccgggc   46200
aagcctgcgc cgcagggatc gaaggacttc aaggggtttg cgaagccgaa gccgggcgag   46260
acgcgcggta aggcgatcct cgtcgagtcg agcgccgcgg ttgggccgtg gcgcgaacgt   46320
atcgccctgg ctgcggccga cgcgatgctc gccgccgggc tgccggtgct cggcaagaaa   46380
ttcccgtgca cggcgtcgct gacgttcgtc atgcctcgcc cgtcgggcac gcccaagagc   46440
tacacgcccg cggctgtgaa gcgccccgac ctcgacaagc tggcccgcgc cgtgttggac   46500
ggcctgactg atgttgcctg gcttgacgat tcgcaggtcg atgacatgca ttgccgcaag   46560
gtgctggctg cgatcgctca gcagccgggt gtgcatatcc gcctcgcgtc gccgggctgg   46620
ggcgatgagg ctatcgccga gtggatggct gcgaacgctg cgggtggtgt cacgcatgtc   46680
tgatctgatc gagttgtcgg tcgccgaggt cgacaagatg gccgaggttg tcgctgcgcg   46740
tatcgcgcac ccgtcgcata cgcctgctcg ggcgatccgc gcggggctgt cggcggtgaa   46800
cgcgatgcgc ctcgatggtg cgcaggtgcc gcgggtggga ttggtgcagg agcgccgcgc   46860
gcctggcacg atgccgcgcc cgatcgaggc acgtcgcccg ttggcgccgg tgcccgccgg   46920
taagcgccgc gtgtcgcatc tggggatggc tgagcgcggc agcgtgtggg aggacgccga   46980
cggcgatcaa tggcgctggt gcttcatgca atcggtgtgg cagtacaagc agttcgacga   47040
tccgaacggc ccgcagtggg tgaactgccc gagtaattac gccgaccagg cgccgaatcc   47100
gaactatgga ccgttcacgg aggttggccg cgcatgagtt tgccggattc tccgagtttc   47160
ggcgatccgc gcaggtcacc gggcacgccg acgatttcgc cggccgttag ccacggcctg   47220
agttattacg ggtcgccgcg gccgtctgga ccgtctgagt tggacgtggc gactgcgccg   47280
tcggtgcctg agccgctggg gcgttgcttg cattgttcgg cgcctgcgca gacgtttctg   47340
tgctggtcgt gtgtgggcat gttgcgccgc cagctcgtcg aggtgccttg gctgttgcgt   47400
cgtctgcagg agtcggcgta cggcgaggcg aaggtcgccc gtaagggtgg gcctcgggtg   47460
tcgacggggg agcggctgcc gtcgttgccg ttgaacactc gcgcggccga catgctgcgc   47520
gacgctgcgc gtctggtgtc gtggtgggag caggtgggtg cgtcgacca gggcggcccg   47580 catgatgctg cgcgcgtcga gtccgcggcc cgctggctgg ccgccgagcc gggcgcgatg   47640
atggcgcacc cgtgggcacc tgacgcgctg ggttgggtgt tgcagtggcg ccaggacgct   47700
gagcgtgtga tcgacttgcc gccggatacg cagtacgccg ggccgtgcca gaacgtcgtg   47760
cagccgccga gtgcatccga cgccggtacg ccgctgccgc ctcgtgagtg cggcacgccg   47820
ctgtatgtcg acgccgaggc cctggtcgcc gagtgctacc gctgcggctg ctcgtggcgg   47880
gtcgaggatt tgcagcggca ggccctcgat cgcatcgacg aggccgcgcc ccgcacggcc   47940
gccgatatgt ggcggctgct caagttcgcg ggccgcgacg ttaagcggtc gacgttttac   48000
aagctgatga cgaccgttga ggcgcacagc tatgacgctg acgggtcgcc ggtgtacatg   48060
taccgcaagg tggttgacgc gctcgatgct gccgatcgga aggccgccga gcgccaagct   48120
gccgctgcag cccggcaggc cgccgtgctc gatgcccacg attcaggtat ggcgccgtcg   48180
acgatcgccc gcacattgcg catgggacac gctgcagtga aacgcatttt gatcagtgcg   48240
ggtgttgacg cgcatacaga atgtgttgac gtgcagacag ccgaggcgtt accgtctgcg   48300
ccgaagcaag tcacgggata ggagcccctg cagatgtaca cagaaacgtg gtactcaccg   48360
gctggtacgc cggtgacgcc gaaggttcgc aacgaggtcg acgagccaca gctcgccgcg   48420
ttgtacgagg ctgaggtgtc gcccgaggtt gggcggttca acgagctgta caacgccgcc   48480
```

-continued

```
agcacggcga cgcgctacgc ctggcagtac gggtatcgca acccgcgggt gccgggccgt   48540
gtcgccgaat gcgaggcgct ggtatgaagc gcaccaagac agttcggccg tcgccggtcg   48600
ccccgcagcc cgacgttgtg gtgcatggcc gcacgttgga gccgggcacc gaggtgtcga   48660
tccgcggcga gcgtggccgg ttccggttcc gcagtgcgtc gttgacgagc gcgggcagga   48720
tcgtgtgcga cttcatcggc ggccctgctg gtcacgagac ctggcggtcg ttctatcccg   48780
accgtatccg cacggtgcac cgtttgaacc gcacccgcgc gaacgctgcc gcatagtcac   48840
gtgttgacat gcatacagcg tgaggggtac tgtatgcatg tcaacacaca ccgggatagg   48900
agcccacagt gacgatttcg accgcgaccc gcaacatgac gcagatggaa gctcaccaga   48960
tcgccgttgg cctgatccgc gagcatggtc tgatcggctg gactgtgagc tgggacaacg   49020
cccgtcgtcg cgccggtcag tgccgctaca cgtcgcgcac gatcagcttg tcaaagccgc   49080
tgctgcgcca gcgttcctac gacgacacga tgatgaccat tacgcacgag attgcgcacg   49140
ccctggtcgg cccgaagcac gggcatgacg ccgtgtgggc ggccaagcac cgacagctcg   49200
gcggcaacgg tcagcgctgc tttgagcacc tcgacgagtc ggcgccgtgg atgggcacgt   49260
gcgaccacgg taagaagttc gcgcggtacc gggcaccgaa gcgcctcgac gggtggcgct   49320
gcaagtgcac ggccgccggt agcccgtgg tgtgggtcaa ccagcgatag cgtcgacgcc    49380
cccaatcttc cgaggttggg ggcgtttcg tctctcatgt tgacatgcat acagcccacg    49440
ggttactgta tgcataccaa caacgcactg accacctacc gataggagcc cacaatgtcg   49500
aacatcgtcg ccgccgcccc cgccgccggt cgtttcaacg ccgctgccgc gctgaacatg   49560
attctcggta tcaacctgtc ggacgggcag aagcgtgcgc gcctgctcgc gctggcggtg   49620
tcgaatgacg ctgcctctga gttcaacttg cgcgccgctc gcaaggcgct ggccgccggt   49680
cgcctggccg aggctgatcg ttgcgtcgac gctgcggagt tctacaacaa ccgcgccaag   49740
cgcctgcgcg acgaggcccg cgctatctag cgcgcccggc gcgtcgccgc gcaaaggtca   49800
ccctggcgcc cggtgcgccc ccagaatcgc cgatcgaggg ataggagccc acgaacgtga   49860
atcgccacct gtacacgcaa cccgagctgt tcgacgccga cgacgcccgc cagttcgacg   49920
tctacgagcg ccccgacggc tcgcgctacc gcgttgagcg ccccgctgcg gcggtggccc   49980
tgtgagcgcc gccctgacgc cgcgagagtc ggcgcaaagg tatttccgcg gctggcttgc   50040
cgccggtgtc gtgacgtcga ttctgggcaa cgctgcgcac gctgtgctcg accctgacgc   50100
cgggtctgtg gtgatcgcgg tcgcggtggc cgtcctgctg ccgctgggca tcctcgggtc   50160
gacgcacggg gtgcacaagc tcgtcgccgc cgggatcgtc ggccgcgcat acacggcggc   50220
gctgagcatt tcggtgaccg tcgtcgctgc ggcgttcctg ctgtcgttcg cggcgctcgc   50280
cgagctggcg gtcgactggg cgggtatctc gatctggttg tgctggctgg tgccggtgtt   50340
cattgatctg agcatcgccg ggtgcaccgt tgcactgttc gcgctgtcgg gtgcggagcg   50400
cggcgaggtg ctcgacgctg cggtgcacgt cgctgcgcag gtggtgcacc ctgctgcgca   50460
gtctgtgcac gccgttgcgc agcccgctga cctgcatgtt cctttgccgg ccgaattgca   50520
gcccgatacg cacctcgtgg cgcgtgaggc tgacggcctg gtgcacgtgt tcgaggagtc   50580
ggtgcacgat ccggtgcccg gcggtgtcag tgtcgccgat ctgatcgccc gcgaggctgc   50640
gaccagcgac gcgctggctg cgcacttgcc cgcggccgag gcgatcctcg ccgccggtgt   50700
gacgcgcatt gatcgcgtca aggtcgccga ggtgctcgcc gagcatgagg ccgacgtcaa   50760
gccgagcatg atcgcgcgca agctgggcgt cgggtacagc accgtggtgc gcattctcga   50820
```

-continued

```
ccatcacact gcgcaggacg atgcacaggc cgaggtgctc gacgcggagg tgctcgcgtc   50880
gtgagcatcg cagcgcagta cccggcgcgc actgacacgc tcggccgcac gtggtggcgc   50940
ccggtgcgcc cggcgggcac tgatctgtcg cagtggggtt ggacgtcgga cccggcgcag   51000
gcgcaccccg actatgacgc gctgaacacg tgcacgtgcc cgtacgtcga cccgtcgctg   51060
tggacgacgc attacggcgc cgtggagccc ggcagcgcgc aggagcataa cccgctgtgt   51120
ccggtgcacc cggcgacgct cgtcgacctc atggtcgccc gtgaggcccc ggtggtcgcc   51180
gccgcggctg agcgtgccga ggtgttcggc gatgcgtggg cgcaggtgtt cgagctggcg   51240
ggcggtggcc gtgcgatcgt gccgcgcgac ccgctgccgg ttgaggcgct cggcgagctt   51300
ggcgacgagt gggtgcagct tggctatgtg gatgagacgc aaggggcttt gtggtgagta   51360
tcgaggtgta tcgagtcgcg ccgttcccgc actatcacgc ccgccgggct gctcgggtgc   51420
tcggcgtcgg cctggctgtc gtcgaggcga tggccgccgc gggcaaggtc cgcgctgtgc   51480
gtgtgcagaa cggtgccggt ggttcggtgt gggcgctcga cgcgctgcgc gtcgacgagc   51540
tggtcgccgc caacgagaac acggggctgc accctgagtg ggcgtgtggc cgcgactgca   51600
gcggttgcgt cggcgagggt gaggggccgt gatgggcgac tgtctcgtcg acccgctgcc   51660
gcgccgtgtg tcgacgacga tgcgcattga ctcgacgggc acgcactact ggcggcgcga   51720
cgccgacggc aacctgagcg tgataaaccccg cgacgagtgg cgacgtctga cgttctggcc   51780
gtcgacgccg atctacgacc aggtgctcga cgacctcggc gcgtgcctca actgccggtg   51840
tgctgactgc ggctgctgct acggctgcgg gcagcccgac gctgacctgt tcggctcgca   51900
tgggtacggc gccgagtatg gcgggtgcgt gtaatgctca gcgtctcacc gggtatggac   51960
gtggcccggc agcgccgcaa gttcattggc cgaatactcg ccgaggacga cgaccacgct   52020
gccgcgtatc tggtctggct gctgagcctg ttcgatgccg cggtggccgc cggtacgccg   52080
aggcccgcga gcgagtttct gccgatgttc caagaggagt ttgaccgatg accgaaaccg   52140
aaaagctcgc cctgatcgag gcgtggatgc accccggcct gtggtcggcc ctcgacggcc   52200
gacgcaacgc aatcctgcgg attctcaagg gcgagagtgt gaccccgccg gattgggcgg   52260
taaccaaccc gctgccctga ccggcgcgac acgccgacac gacgcccccg ctgaaaggtc   52320
aagcggggcc gtcgttgtgt gtttggctca atgtgtctga ccaacaacta aatagcggga   52380
taggagaacg tgtgtcacct acacgtgtca atgagcgcct gatcaacttt gcgagcgagg   52440
tcgacgacca gaccctcgcg caggcgcagc agatcgccga tctgcctttc gtttatccac   52500
atgtggcgct gatgcccgat gcgcatttcg gtaagggcag cagtgtcggc acggtgatcc   52560
cgaccgaggg cgctgtgatc ccggcggctg tcggcgtcga tattggctgc ggcatgatcg   52620
cagcccgcac cacgtacacg gcgaacgatc ttgagggcct caagctgtcg gatctgcggg   52680
agtcgatcga gtcggctatc ccgatgagcg ccgggggata caacaagagc ctgaaccgtt   52740
ttgagttcac cggcgcccgg ttggactggc tgcagctcgt cgctacccgg ttcgacgtcg   52800
acctgtctca ctccccgaag tggcgggagc agctcggcac gttgggcggc ggcaatcact   52860
tcatcgagct gtgcctcgac cacctcgacc gcgtgtggtt gttcctgcac tccggttcgc   52920
gtggtgtcgg taacaagatc gcgcagaagc acattcaggc cgcgcagggc tattgccagg   52980
ccaacgggct gcacgtgccg cacaaggatc tggcgtacct cgtcgagggc acggtcgagt   53040
tcgaccgcta cctcgttgaa ttgcgttggg cgcagcggtt tgcgtactac aaccgcgccg   53100
aaatgatgga ccgatttata caggcgttcg cgcattggat tccggacaat caccagagtc   53160
acggcgattt cgtcgtcgag accatcaacg cgcaccacaa ctacacgcag aaggagcggc   53220
```

-continued

```
acggcgaccg tgacgtgtgg ctgacccgta agggtgcgat cgacgcgaac gagggtgtgc    53280
ggggcctgat tccgggctcg atgggcacct gttcgtatgt cgtgaccggc aagggcaatc    53340
ccgaggcgtt gtgctcggcg ccgcacggtg cgggccgccg gttctcacgc acgaaggcgc    53400
gcaagctgtt cacggtcgac gacctcgagg cgcgtatggc gggcatcgag taccgcaagg    53460
gcgaggcgtg ggtcgacgag attcccgacg catacaagcc gatcgacgtt gtgatgcacg    53520
acgccgaaac gctggtgtcg gtggatgctg agctgcggca gctcttgaac gtcaaggggc    53580
agtgatgttg gacgatcgca acgcgcacag cttgctgttg tcgtcacgct ggcggcaggg    53640
cggcaagacc acggcactgc tcgacgtcgc gctcgccaac gctcgccgcg ggcttgaggt    53700
ggtgttctgg tcgggctcgg cccgccagtg cactgaggcg tttcggatgg gtcggtcgct    53760
cgctgagcgt gaccgggtgc cgttctcgtg gtcgcccgcc aatggcaatg agtggattcg    53820
ctacgacggc ggcggccgtg tgcggttcat ctgggggcac cagggcagcc gggtcgacgc    53880
tcacgtcgac atggcaattc aagacagcaa cgggctcacg ggcctgatcg agcggcgcag    53940
cgagcgccga ggaatgggcg tgatctgatg gccgactact catacgcgcc aggcggccgg    54000
ttcgaggtct cacctgtccc gatcgccgag ggggaggacg aggcgctgca cccgtggcag    54060
gcgcagacgg ttcgcacgct gcaggagcgt cgagaggtgt cgttctcgct gcagttcccg    54120
cggcagccgc agacgggtat gccgttgtgg ctggcgcagt tgttcggcgt ggtcgtgacc    54180
ccggcgccgc cgacggtgcg cgaggccgcg gtcgacgtat gggacgcgct gcgcgtgctg    54240
ctgcgcgtcg tgtgggtggc tgtgcggggc gctgtgacag cggcggccga tcgtgtgggc    54300
gattggtggt ttgacgtcgt ttacggcgct ttcgaccgct gggacgtgct gcgcgggtgg    54360
ggttggcgtc gccagctcgt cggcccgaca gtgacgctgt ggagcgcctc gtttatctac    54420
cagtacacgg tgcctcgtcg gcgtgagacg gggcgcgagt ggctgcggcg gcaggctggt    54480
ctgccgttgg cggtgtggcg tgggtagctc gccggtgatg ttcctcgacg gcccgctcgc    54540
cgggactacg cgcgaggtgc agacgtggcc gaatggcgaa ctcgcgccgt acttcaatgt    54600
ggcgacgccg ccgaagttcg acccgtccga aatgcgcgag ccgccgcgga cgctgctgcc    54660
tgagacgcac acgtatcgga tcaagtgcaa tcggctgagc tacggcccgc agtgggtcgg    54720
ggcgatcggc gataaggtcg gcgagcagat cgtcacggtg ctgccgtacg acgagcgagc    54780
ccgccagagc gtcggcgtcg acgagttcga ggagtacatc acccgcaacg cctaccagag    54840
cgcgcagcgg cacgcgggcg gcgagggcct ggtcgccgtt gaggtgcacg aggtttggcg    54900
tggcacgcaa gccgaggccc gcgagcagat ggtgcgcgag ggtaagccgg tgaagggcgc    54960
cccggcgttc ctcgccgccg acggcccggt gttcctcgac tcgaccgtgt cgtcgtgca     55020 tgaggccgtg gctgtcccga aagatcaggc gcgggaggtg attctgtgac tgacaccggc    55080
accccgctgg acgacttgac gcccgagcag gccgagcgtc tcacgcggtc gctgcggcgg    55140
ttcaacgagg cgatgggctg gcagctcgac cacgcccggc aagagttgga ccgtgaccgg    55200
ctgcggcggc tgttcggcac cagctaacgc cggcaaaggt cgccggcctg gctgtcgccg    55260
caggtagttg cggtgcgggt ctggaagttg gcaaacgccc ctcgggtaat cctcgggggg    55320
cgttctgctt tccgtgttga cgcacataca accaatgtgt ttgcatatca acacacacca    55380
cgggatagga gcccctgaa tgttcaagat gattgtgcaa ctgcatggcc gccaagaggt     55440
tacggagcac gacacgatcg acgaggcccg caagcgcctg gtcgatattg ctgtcgcaag    55500
caactgccgg gttgagggcg acaacgccac gggcgtgttc atcgcgctga cccgcgaggg    55560
```

-continued

```
tcgggacaat ccgctggtgg actggaccta tggcgcgtac cgcatcacgg aggagcccgc   55620 cggggggcgtc gaccaggcgc tcgccgccgc tactgcgcgg tacatgatcg acagagaacct  55680 cgacgccgac acggtgcaga tgatccgcaa cagcgaccgc gacgggcgcg acctgctggc   55740
cgcgatcgtg gccgagtggc tcaagctgca ccctgagctg tccgaccggg atcggcacgc   55800
tgtggctgcg gcggccaatg gctggcagcg tttcgactac gccctcgtgc cgtcgcaggt   55860
gcgttacgtc cgtgatggcg gcgagctggc gatcgtcgag tacgacgacg agcgcgcggc   55920
ccgcagcgcc gagctgtacg tgcacggcgt gtgcgacgcg gcgctgatgc agtgctgcga   55980
cctcggcgac gtcgacaggt ggctcgtagc ggccctgtg ccgctctgag agcttcaaac    56040
agatgaggga aagggataac atggcaacca tgacaattac gaggtacacg gcggttgtga   56100 cgccccggcga gcagtacacg ctgattcacg tgcctgagat cgaccagtgg acgcaagccc   56160
gtagcgagga tgaaatcgag ccgatggcgc gggatctgat tgcgacgtgg ctcgacgtgc   56220
cggtcgagtc ggtcgaggtc gaggtgcagc gcggctgacg tcacagcgac aagagcgccc   56280
ctgagtcaat gcaactcggg ggcgctttgt tgttgacatg catacagcgc gggtgttact   56340
gtatgcatgt caacaactca acagggatag gagcccacaa tgccgaagcg caacgaggta   56400
atcaccaaga tccgcaaggc ggccaaggcc aaggggctga aattcaagtc ggttcgcaag   56460
ggtgcgaatc acgagatttt cgacctcgac ggcgtaatgg ttccgatcgg gaatcactcg   56520
atcttggacg gttacctggt actcaagatt tacaaagagt gcgagccgaa gctaggcaaa   56580
ggctggtggc gataaccaca gcggcgacgc cctcgaccac atggtcgggg gcgttttcgt   56640
ttctgtgttg acatgcatac agccacgggc tattgtatgt atatcaacag cgcgagcggt   56700
tgagattgac aactcaagag tgacagtgga taggagccca cgatgaacga tttctacatt   56760
ccgcgtttcc tctcgccgag ctgctcgttt acctacgacg aactcggtaa ggccctcgca   56820
aagctgcagc cgcgcctgaa caaagcgact gaggcatggc tcgccgccaa gcgcgaccac   56880
ggcagcgaga gcccccgagga acacgccctc tggcccgagc tcgaccggct ggaagtggct   56940
aaggcccgca tcctgcgcga ggctaatcgc ctcgacaaga tcaacggcct ggccgccgcg   57000
atgcccctct aaccgactac gccccgccgg gccgaccaca ccggcggggc gttttcgttt   57060
tcgtcgatgc ccgccgacgc ccgccgacgc ccgccgaagc ccgccgacgt tcgcatacgt   57120
ggcgtgattg gcgcgcgtcg ctttttagact gccgatcgca acagcacagc tgtacccaaa   57180
acggcccggg cgctccgaaa tggagtgttg gggccgttcc cattccaggc gtcgaccagc   57240
gttgcgcggc ctcctatccc cgcgccctgg tcgacgtcta agcccgtcgc cgtgatcccg   57300
acactggcgc tacgcgcgcc tcggcgcgat ccgctgcagc ccctcgccgc gttggctggt   57360
caccacgcga gcaccggcgc agcgcagcgc tacagaggtc gacgcgatcc ggcggcgggc   57420
acttacttca cgagaggaaa cgccatgtcc gacaccgcac ctgacgccgc caccgaggcc   57480
cccgcacagg aggcccccgc aatggcccct actgcccgcg ctgaggcact ggcggccaat   57540 gccagggggta aggggaaagg gcggcaggct acggcgtacg tggccctcga cccggccgag   57600
gccaaccgta gggccaggcg gcggcccgct gccgaggcgc gcaagcctgt ggcacacgag   57660
ccgtacgaat ggtgaggctc tcaccacggc gcgctgagag ctggttctgt accaccagca   57720
tgaagctggg cgagctggtc gaggcgctgg acctacgcaa gcggtacgcc gagcgacacg   57780
gtgaacgcgc tcgcctgttc gtgttctcgg tcggcaagct gctgatcgtt tgggaccgag   57840
acagcaagcc atgagcgagg gccgcaacac tgcacgcgcg aacaggttcc ggcgctactg   57900
gctgcggcgg cgcgaggact gcgcagtgtg cggcgagccg atcgactacg aggcgcatca   57960
```

-continued

```
cctgcaccct gactcgtttc aggttgacca catcacgcca ctggacgcag gcggctcgga    58020
cacgctcgac aacacgcaac cgacgcaccg caagtgcaac cgcgacaaga gcaacaagct    58080
gcccgacagc ggcggcccgg cgcctgcctc ggtgggcgtc acgttcgtga ccgaacggca    58140
ctggcgaccc tgacctcagc aaaggggtgg gggagtactc cccgacccct ccccggtgca    58200
cctcgtaggc at                                                        58212
```

```
<210> SEQ ID NO 3
<211> LENGTH: 57722
<212> TYPE: DNA
<213> ORGANISM: Bacteriophage

<400> SEQUENCE: 3
```

```
aggcggtttt ctaccccta gcttttttc gcagctcaag tgggtcgcgg gcgtgtagcc      60
acgcctacac cggcgcgtct gctgtaggcg cgtctacacc aggaggatca ccaggaatgg    120
atgcgttcga gaaagcgcgt gtgctgatcg acgtgctggc gctcgcggag cgtgcggtcg    180
agcagggcac gcacgacggc acgatcgtcg aggccgcgtc ggacttcgcc gacttcatcg    240
aggggcggct gtgatcgcgg tgatcgcggc gacgaagccg cgcgccgagc agctcgcccg    300
cgagctgaac attgcccgct cgctgccgat cggggcgcgc accgtcaaca cggctgtgcg    360
cggtttccag ctcgacgccg tggtgtcgga ggtgccgctg tcggcggccg acctcgacgt    420
tgtgtacccg gcgctgctgg cgaccggcgg gcaggtctac cggatcgggc gggtgtcgtg    480
agggcggcgc ggaagctggc cgccgtggcc ggcgcgctgg tcctggcgct cgggctgtcg    540
gcgtgcgacg gctccaccgg cggcagctcg acgaacgacg gcccgaacgg cgtgatcttc    600
attccggtgc agggcaaccc ggtcggaatc ccggtgttct tctgatggcg actctcgtta    660
ggttcatcga cccggccgcg cctgagaccg agtacaggct cgacgtaggc aacttcgacg    720
tgacgaccga ggaagggctg caggcgctgc gcgacgcaat ggccgagctg tgctccgatc    780
catcggttgt cgctgtcgag gaaggcatga acggcaatct gtggatgggt gagtcgctgt    840
acttctacgc gaagctgacg acctacccga cgctgcagga ctacgtcgac tcgttgagcg    900
gcggttcggt atgagctacg cgacgccaga gtcggcggtc gaaatcgcca accgcttcac    960
gtaccacccg gccaacaccg tggcccggca gaacgcacac gagggtgtgc gcaccgcgtg    1020
ccgcgagctg gcgcgctacc tcgacgagca tctgccaccg gggcggcata aggcgctggc    1080
gctcacgtcg cttgaggaag cgatgcactg ggcgaacgcg gcgatcgcct gccaggacgg    1140
caacccggtc cagccgaaac caaccgagga acaactgcag cggccgctgc ggccgggcca    1200
gccgatcacg ctcgctgaga ttcaggcacg cgcccgccag cgccgcgccg agaaaggcga    1260
ccagcagggc tgatggacgt gatctacccg gtgcggccgg gcgacaagaa cgacgagctg    1320
cgttacagct tgcgcagcct cgcagagaac tttccgcacg accgggtcgt gatcgtcggc    1380
tacatgccgc actgggtgcg caacgtcgag cacatcgagg gcaacaaagg cccgagcacg    1440
cacgcgaacg tctacaacaa cattcggctc gccgtcgagc gtgacgacct gagcgatcgc    1500
gtcgtgatct tcaacgacga cttttttcgtg accgagccgg tcgacgccgc gccggccgcg    1560
ttccgctgct cgctcgacga ccacattcgg ttgccgcgcg tgcagcgcaa cggcggctgg    1620
tggcttgagt cgctgacgct gacgcgaacc tgtcttcagg cgcacggcat cgagaaaccg    1680
atcagctacg agctgcatat cccgatcgag gtcgaccgtc gccgcatggc cgaggtgctc    1740
gaactgttcc agtatgtgca gccggccaac ccgccgcagt ggcgctcgct gtacggcaac    1800
```

-continued

```
ctggccgacc acggcggcga gcagctcaag gacgtgaagt gtttcgacgc cagcgcgttg    1860
cgtcggccgt tccactccac cgaggaccgc agctttccgc gcttccaccg cgagctgcac    1920
aagctgttcc ccgagccttc cccgtacgaa gcggcctgat ccaccacacc accaggaggc    1980
ccgcatgaaa ccacccgcga ctacgcacgt gcagtgcccc ggctgcgcag cacctgtcac    2040
ctgtgacacg aggactgtcg tcgccgacaa gggccgcaac gtgttcgtga ccgtggacgc    2100
cgccgaggct gtcgccgagc acatgtcgac cgcgtgcctg cgcccggtgg cgcggctgtg    2160
ggacaaggac atgaactacc tcgggcagct gccggccgac gtgaaggtgg tttcggcccg    2220
gtgagcaagc aggacaaccg cccaaccaaa tcggtcgctc aggcgtgcgc tgacggcgat    2280
ctgcgcggca tgttggttgc cgcgcaggcg atcgtggcgc gcaagctcga cgaccccgac    2340
acgagggccg ctgacgtggc cgcgctgacg aagcggctgc gcgagattac cgacgagatc    2400
gccgaaatcg acgccgcagc cgacaccgac cccgacagcg tggccgctgc ggcagcgaca    2460
cccgatgagc aattcgacgg caactcttac tgatgttgca cgtcacgtag ttgcgccgac    2520
aggcattgtc tcgacaggct tctcggcggt tcgcgcgacg tgccgccaca tgggcctggg    2580
tttcgaccgc tggcaggacg acctcggcaa gctgatctgc gcgaagcgtc ccgatgggct    2640
gtacgccgcc gacatgttcg gcatgtcgat tccgcgccag accggcaaga cgtacctgct    2700
gggcgcgatc gtgttcgcgc tgtgcgtggc ggccgtcgac cggccgctga ccgtgatctg    2760
gacggcgcac cgcacccgca cggccgccga gacgttcaag tcgatgcagg gcttcgccaa    2820
gatgccgcgc atcgagccgt acatcgagaa ggtgtcgctg gcgcgcggtg aggaagccgt    2880
gatcttcacc aacggctccc gaatcctgtt cggcgcgcgt gaacgcggtt tcggtcgtgg    2940
tttcgccggt gtcgacgtgc tgatcttcga cgaggcgcag attctcaccg agaacgcgat    3000
ggacgacatg gtgcccgcga cgaacgcggc acctaacccg ctcatcatcc tggccgggac    3060
gccgccgaag ccgaccgatc ccggcgaagt gttcacgatg ctgcggcacg acgccatcac    3120
cggcgaggcc gacgacgtgg gtttcgtcga aatctcggcc gaccgggacg ccgacctcga    3180
tgaccgcagc cagtggcgca agatgaaccc gagctacccg caccgcacga gcgcccgcgc    3240
gatcctgcgt atgcggaaag cactgtcgga tgacagcttt cgccgcgagg cgatgggcat    3300
ttgggacgag tacgcggttc accagccgat cgtcaagccg acgatttggc ggtcgctggc    3360
cgacctcggc cccgagctgg acgcccggcc cgacgcgctc ggcgtcgaca tgtcgcacgg    3420
ccgcgacatt tcggtcggcg cagcgtggcg catgatcgac gaggacggca acgacgacgg    3480
ccaccacatc gaggaagtgt ggcgcggcgc tgatccggcc gccgcgattg agtggatcgt    3540
cgagcactcc ggccgccgca tcccggtgct gatcgactcg gcttccccgg cggccgcgct    3600
ggcaccggac ttgaaggcgc gccgcgtcaa ggtgcgcatc acgacggcca acgatatggc    3660
gaaggcgtgc ggcctgtttg aggacagcat caaggccgag acgctgacgc acggcgacca    3720
ggacgccgtc accgacgccg ttcaaggcgc acgcaagaga ccaatcaggg acgcggtgg    3780 ttggggatac gaccgccgcg acccgaccgc atccatctat ccgctagtcg ctgtgaccct    3840
ggcgctgctc ggcgcggctg agacccgccg cccggcggcc cgcaagggcg cggcgcaat    3900 gttcgtgtga gagggggctc gatgacgacc gcaatcccgg ccctgtggc ctacgagccg    3960 atcgacaccg tcgacgacga cctcgacgat ttcgagtggc ccgacgacgc tttggacgag    4020
agccaggtcg gcaagctcgt cgccgatctg tggcagttgc agctcaccga gctggcgtgg    4080
ctcgaccgca tctacgagta cacgaaggggg ctgcgcggca tccccgaggt gcccgagggc    4140
gcgagcgacg aggtcaagga gctggcgcgc ctgtcggtca agaacgtgct ggcgttggtg    4200
```

-continued

```
cgggattcgt tcgcgcagaa cctgtctgtg gtcggctacc gcacggtagg cgcgacggac    4260
aatcacccgg cttgggagat ttggcagcgc aaccgcatgg acgcgcgcca ggccgaggtg    4320
taccgcccgg cgctgaccta cggcgcggcc tacgtgacgg tgctgcccgg cgacgacggc    4380
ccggtgctgc gcaccgttc gccgcgtcaa ctgctcgcgg tgtacgacga cccggtgctc    4440
gacgcctggc cgcagtacgc cgtcgagacg tgggtgacgc agaaggatgc gaagccgcac    4500
cggctgggcc agctctacga cgacaagtac gtctacgaac tcgacttcgg cgcgctgacc    4560
aagtccgaga ttgagggcgg caagacgcgg ccgctgcggc tgcgcaaggt gctgtccgtg    4620
acgccgcatc atgcggtgtt cgagggcgaa cctgtctgcc ctgtggtgcg tttcgtcaac    4680
gcgcgcgacg ccgacgacat gatcgtcggc gagattgcgc cgctgatcct gttgcagcag    4740
gcgatcaact ctgtgaactt tgaccggctg atcgtgtgcc ggttcggcgc gaacccgcag    4800
cgcgttatca gcggctggac gggctcgaaa gacaaggtgc tgaaggcgtc tgcgctgcgc    4860
gtgtggacgt ttgaagaccc cgaggtgaag gcgcaggcgt tcccgccggc gagcgtcgag    4920
ccgtacaacg cggtgctcga cgagatgctg cagcacgtgg cgatggtcgc tcagatcagc    4980
ccgtcgcagg tcaccggcaa gatgattaac gtcagcgccg aggcgctggc cgccgccgag    5040
gccaaccagc agcgcaagct ggccgccaag cgcgagagct cggcgagtc ctgggagcag    5100 gcgctgcgcc tcgcggtggc gatgcgccgc gcaacccgcg acgacgagga cgacctcgac    5160
gacgacgagc tggccgacct cgacggcaac ggcattcccg atgacgttga ggccgaggtt    5220
atctggcgtg acaccgaggc ccgctcgttc ggcgctgtcg tcgacggcgt cacgaagctg    5280
gccgggcagg gtgtgccgat cgagtacctg ctgccgctgg tgcccggcat gacgcagcag    5340
cagatcaccg ccattaagca ggccattcgc ggcggcaacg tcaagtcgct ggtggatcgg    5400
ctgttgcagc agccgccccc gccgcccgcc gaggcaccgc cgctgaacga ggttcggcag    5460
accgtcgacg agtcaccggc tgatagcgat gacgcaggcc gttcctgagt ttcagggcgc    5520
gctgcagcag ttggcgatcg aggccggtaa cgctggccgc cgactggtgt cgcgcatggg    5580
tgagctgagc accgccgagg ggctgcagct cgtcaccgac gcctatcccg agctgatcga    5640
gccgttcgtc gtcgcgtcgg gcgagatgac ggcgcagtgg tacggcgaga acatggttcg    5700
gccggtgcgc cggatcgcca gcgagcgcct gttcctgccc gagccggccg agctgccgtc    5760
gcggcagcgc ctggcgaagt ccggtcgttg ggctgtgctg cagcgcgatc ccggcacggc    5820
gatcgtcggc tcgtcgacgc gctgggtgtt cgacgagtcc cggcgcacgg tcaacgacaa    5880
cgccgagcgt gagggcgtgc gctggacccg gtacgcatcg gcgaatgcgt gcggattctg    5940
ccgcatgttg gcgacccgcg tgctgaccgt gggggagcgc ggcgcgcctg gcctgtaccg    6000
aaccaaggcg gccgccgagg cttcgccgca cacacctgat gtgcgcggcc acgatcactg    6060
caagtgcatc gcggtgccgg tgcgcgacgg ctacacgccg ccgggctacg tctacgactg    6120
gctcgacgac tacaacgcgg tgtcccgcga cgacgacggc tatctgctgc ccgagtggaa    6180
gatcgccgac cggatggagc gccgcgccga ggaacggctc ggacgcaagc gccgcccgcg    6240
tggccggcca cgcgccgagg gcagcactcc cggcggcggc caggcccggc gcagccagcc    6300
gcgcgagaag gtcgcggccg aggacacggc gacggcgttt cgccgcgacg acgcggggcg    6360
gttcatcggc gagcgcaggc tgtttcagcg caaccacgag caggcggcgc agattgcccg    6420
cgcggcccgc gatcgtgtcg cgtcggcgca gcgcatcgtg tcccgcgccg acagctacgt    6480
cggcaccgcc gcgcggatca ctggacacgt caagacggtc acggacgcgg ccgcgaagta    6540
```

-continued

```
tgcgggcggc gcgtacccgg tgctgcgtga tgtgaaggtc gtcgtcgacg ccgccgacaa    6600
ggcgctcggc agcgcgtccc gcgtcaccgg cggcgcgaat cgggcgctga cgctggtcga    6660
caagacgatc aaggacaccg aggcgatcgc gcacgcgacg aagcagctcg ccgacgaggc    6720
ccgctcggtc atcgacgacg tgacgttcgt tgcggtcggc gcgcgccagc tcgtcgtcga    6780 cgccgggggag gcggcccgcg ccacggccgc gaacgcgcgc gaggtgcgcg acctggcttc    6840
gcttcggtcg agggcggccg agaccgccgc cacggtggac cgtctgcagg agcaggggct    6900
cgatttggcc gaccgtgcgc gtagcgcgct ggccacgctg cagagtctgc cgctggacgc    6960
ggccgagctg cctgaccggc tgcgcgcccc gttgaacgac attcggaagc tgctgcgctc    7020
gctgcgctcg acggccgacg acgcgcgcct ggccgtcgac gacgccgccg ggctggcccg    7080
cgcggtgcgc agcctcgtcg aggctgtcgc cgagtaccgg cggtacggct tcaccgacag    7140
ctacagccgc acagcggttt acgcctacag cacgcgcgtg gtcgacgagc tgggcaacgt    7200
gatcggcggt gtgctgcccg cgccgaagac gccgggcatg gtgcggccgc cgacgtgggt    7260
gctcgccgag cgcatcgacc tgccgcccgc accccggcgg cccgagctgc ccgccggatc    7320
gagcaccggc gcggccgagg tgcccgaagt cgctgaggcg atcggtgtgc gggagctgcc    7380
gtcgacgccg acgctgcgcg cgttggaggc ggcaccggac ccggccgagg tgatcgacgg    7440
cgaggtgctg tcggtggtgc gggagctgcc gccgacgccg acgctgcgcg cgttggaggc    7500
cgcaccggag cggcccgacg tggccgacgt ggccggtgtg cgggagctgc cgccgagccc    7560
gacgctgcgg gcgctggaac gggcaccgga gcccgagccc gagctgccac ccgcgccgcg    7620
cactctcgac gttgtcgagg ccgagctgaa cgcggcgatc gaggtcggcg acgaggaact    7680
gatcgaccgg ctggtcgccg agatggacgc gctcgaagaa gccgagcggc aggccgccgc    7740
caaagctgct gagcgtgaac gccggaaggc cgagcgccag gccgccaagg ctgcgcagaa    7800
agaggccgag gaccgtgccc gctgggaccg catcggcgag ctgatcgagc agggctatga    7860
cccgatcgac gcggaggccg aggtgctcgg cgtcgacccc gagaagctgc gccgccgcga    7920
cttcatggcg caggcccgcg ccgagggcca caagggcaag ggtttcgacg agctgctgtc    7980
gagcgtgttc accgagaagg ccgccgagca gtattggcag gccgagcagg cgaccaacgg    8040
ctacatgctg aaacgcaagt acgagggcaa ggttgacccg accgacattt ggcacgtcaa    8100
cgagcgcacc gcgcgtgcgt ggatgagcga cgagctggcc gcgtggttcg acgagaacgg    8160
tcgtctgaca aagcaactgc tgcgcgagtc gatcctgtct ggccgcgcga attggcgtaa    8220
cccgctgcaa gaggacttcc tgcaatgacg aggcgagacg acattgtggc ggcccgccag    8280
gccggccgca ccgcgacgcc gggcgacggc aatccctatg ccgggcaggg cgttctggcc    8340
gacatgtggc ggctcggcta caagcagatg ctgctcgacc ggctgaaccg ctcaccggcg    8400
cgccaggcgt tcctggcggc cgacgacgac ggcgacgagt agccgcaccc ctgagtttcc    8460
cctaccgcgc gacgcggccg gggcgctgcc tgcgcgacgc aggcgatcca acacaccaaa    8520
aggagatggc gcgatgcctg acgacaacct gacccctgaa gctggcggcg acaacaccga    8580
caccgccggg gctgacaacg agaacaccgg cggcgcaacc gatgccggta agaacgacga    8640
cgccctgggc gagggcggcg agaaggcact gaaagcggag cgcgaggccc gcaagaaggc    8700
cgagcgtgac ctcgctgctg cacgggccga gctgcagaag atcgaggacg ccaagaagtc    8760
cgagctgcag aaggcgctcg aacgggctca ggaggccgaa aaacgcgccg agcaagcgga    8820 attggcggc cttcgccaga agatcgccaa ccgcgaaggc aaaaaggtgc ctgtctcggc    8880
actgaccggg accaccgagg aagaactcac tgctcaggct gacgcgctga tcgagtggcg    8940
```

-continued

```
cgaccagaac ggcaagtcgg ccgagaagca gaccgaaaag aagcgcacgc caccacctcc    9000
cggcggcggc tcgctcaagt ccggtgccag cggcaacggc aacaccaact ccgatccgaa    9060
ggctcgcgct gctgaggcgc tcaagcgtct gcggcagtcg ggctaactcc ccaacttccg    9120
cgcgaggaaa cggcctcggc gggatcacat gaaaggagcc gaatatggct gacatttcgc    9180
gcgccgaggt cgcaaccctc atcgaggaag cgtacgcaga tacgctgctc gcggccgcca    9240
agcagggcag caccgtgctg tcggcgttcc agaacgtgcc gatgggcacc aagaccacgc    9300
acctgccggt gctggcgact ctgcccgagg ccgggtgggt ctccgagtcg cgaccgagc     9360 ccgagggcgt gaagccgcag agcaaggtca cctgggccga ccgcaccctc gtcgccgagg    9420
aaatcgcggt catcatcccg gttcacgaga acgtcatcga cgacgcgacc gtggccgtgc    9480
tgaccgaggt cgccgagctg ggcggccagg cgatcggcaa gaagctcgac gaggccgtgc    9540
tgttcggtct ggacaagccc gcttcgtggg tctccccggc gctgctgccg ccgccgtgg     9600 gtgccgggca ggcgatcgag gtcgtcgacg gccaggccaa cgagtccgac ctcgtgggtg    9660
ccaccaacca ggccgccgag ctggtcgcgc tcgccgggta cgcgcccgac acgctggtgt    9720
cgagcctgtc gctgcgcttc cgtgtggcga acctgcgtga cgccaacggg cagctcgtct    9780
tccgcgacga gtcgttcaac gggttcacga cccacttcaa ccgcaacggt gcgtgggtgc    9840
ccggttcggc gagcgcgctg atcgtcgaca gctctcgcgt caagatcggc gtgcgccagg    9900
acatctcggt gaagttcctc gaccaggcca cgctgggcac tggcgagaac cagatcaacc    9960
tggccgagcg cgacatggtc gctctgcggc tgaaggcgcg ctacgcctac gtcctgggca   10020
acggcgctac ctcgatgggt gccagcaaga cgcccgtcgc ggccgtcacc cccgacgccg   10080
gttcgggctc gtaatccgct gtggttacgc gctacaagca cgtcctgacg ggggcggtca   10140
cagcagctcg tgagggctcg ctgctggccg ccctcgtcgc gggcgatccg aactggcagc   10200
cggtaacggg caaggcgaaa gggggccgcg acagtggcag cgttggcgac agcgcaggac   10260
gtgacgacgg ctctcggccg ggagctaacc ggcgcagagt ccgcagccgt ggagggtctg   10320
ctgctggaag caacggacct cgtcgtcggc tatctgcatc ccagctcggt gccgacaccg   10380
acaccggacc cgatcacgcg ggtagtggcg tcgatggtgg cggcggtgct gacgagaccg   10440
aagtcgattc cgcataacgc gactcaactc acggccgacg tgttcagcgc gtcgttcgag   10500
tcgggcacga cttcgcccgg cccgtacctg accggggcga tgaagctgcg gctgaatccg   10560
ttccgtgacg gcatggtgtc gcaggaactt cgagcgaac ggttctgacc gtgttcccga    10620
cgccagagaa caacacgatc aagcacatca cgcgggagaa gatcggcgag aacgcgctcg   10680
gccaaccgat ttacgccgag cagccgacga tccgcgaacg cgcggtgtac gggtggcggc   10740
cgaagctggc gcgcgacggc gcgacggcgg cgctcgacgg ccgcaccatc accgagctgt   10800
atctgcttat gcccgaaggc gattacgccg atggcgacgt gatcgagctg cctgacggca   10860
agcagtacac ggtgcagggc gacgtggagg acttcaacca cggcccgttc ggttgggagc   10920
cgggctaccg gctgacgatg cggagggttc atgatgggca agcttgacat tccgatcagt   10980
gagcaccgca agattcggcg cagccccgag gtgcaggcgc ggctgcgttc gatcgcgtcc   11040
gacgtggccc ggcgggccgg ttccgcggcc ggcgaccccg cgggctacgg caccgacctg   11100
accgtcgagt ctgaccgcgc ccgcgcccac gtgtggcccg agagcggcaa ggcgatccgc   11160
gccgaggtga agaacgctca cctcatggga attgcggcgg ctgagggaca atgagcgccc   11220
cgatcctgct gccgcccgtt gggccgctcg tcgccagcaa cgcatacctg caagccgagc   11280
```

-continued

```
tggccgaccg ctccaacccg ctgccggtgg gcatcacacc acccggcggc accccgacct  11340
cgtacgcgct gctgtcgctg gtcaacacga acacgcgcgc ctacctggcc gactacctga  11400
tccgtgttcg cgtattcgac ggcgacgctg tgcgtttgga gaacaacgcg aacctgctgc  11460
accggctcat gctgcacgcc gtgcgccgca agatcgacac cgccgagggc agtgtgcgga  11520
tcaacggcac caagcatcac tacggcccgg ccgacctcga cgaccccgac gttccgctgt  11580
tcggcagaga gctgtcggtg ttctggacga tcggcctgca ggccgaatcc cgctaaccac  11640
caccaggact cgaacgtcca ccgcgccaac cgggcgggtg gcttagttgc cctttcgggc  11700
aagttaggag agcgaaatga ctcagcccga tgtttcgtgg ggcgacccga ctcaactgtt  11760
cgcagcctcg ccgtccgacc tcgtgaccgt gggcggcctg tggtacgcac catacggcac  11820
gccgctgccc gaggacgtgg acgagccgct cgatccggcg ttcaagaacc tgggctacat  11880
cggcgtcgac ggcgtgacgg tgacgatcaa cgacgagacc gtgccgatcg aggtgtgggg  11940
cggcgacgag gtcggacagc tccgcgcacag cttctcgatc gagtacgagg tgccgctgtt  12000
ccaggtgctg tcgccgatcg tcaacgcggc gatcttcggt gaggacgccg tctcgaccac  12060
gccggccaac gcgcagcacg gcaaccgcat gagggtgctc atcaacaaca agctgcccaa  12120
gcggtgctcg ctggtgctcg attccgtgta cgaggacaag atgattcgcc aggtcgctgc  12180
catcgcgcag aagtcgggca tcggcgaaat caacctcgtg cataacgagc cgatgacgtt  12240
cacgccgacg ttcaaggtgc tgaagaacac cgacggcaac cacgtcgtgc agtacagcga  12300
cgacggccag ctcgtcggca gcgtctaagc gccgcaaccc gagactgccg ccccgcgcac  12360
tttcctggtg ggtgcgcggg gcggcctaca cccattcgca caccagggac caaccaccag  12420
gaggtatctc gtggagctga atagcacccc ggcggctgac gacggccagg agcgcgtcga  12480
caccgagcag cccgtcgtcg ccgaggctca gcccgaccag tcggccagcg tggccgccga  12540
gtgggctgac gagtacgagg aaggcgcgga gctgttctgc gccgtgttcg acgccgacga  12600
cttcgacacc gagtacggga aggcgtaccc gagtggcacc acgctcgcag tgaagcggtg  12660
cctgcggaag ccgccgcccg gctggattcg ccagcacgcg cacctgtccg acctcgaacg  12720
cactttcgcg ctcgtcgaga agcactgcag cgacaaggct ctcgacattc tcgacagcct  12780
caccgagaag gcgtggaacg acttcgtcga ggcgtggggc aaggacggtg gcctcatcga  12840
gggaaaatcc accaaatctg cgcggcggtt aggcaggtag aggacgcgat tcgccgcgac  12900
ctcatcgtcg ccggtcgtga gttcgacgac ggcacgctga gctgggacga cctttacgca  12960
ttcatcttcg ctgcaccgcc gaataccgct gtgttccatg cctacgaaaa gggctggatc  13020
acaacggact acctgctggc tcatgtgatt gaccggctgg atatcaacaa ctggcagcgc  13080
accgaggacg cgcacaagaa gcctccccgc aatgtgccga agccgttccc acggccggcc  13140
gacgacagcc cgcagggcaa gcagcgccag cagcagcagg cgctcgacga caggttcgtt  13200
cacgtcggca acggcgtgat ggcgaccaag acgacggtcg ccgagtttct cgaaatgcgc  13260
gccgagcgcg aaaggcgttg gcgcgaaaag catgggaaga agggagggta gccgtggcag  13320
gaacgtacta cctgacgatc ctccccgaaa ccagcaagct cgcgccgggc atccgcaagg  13380
ctgccgagca ggccgagcgt ggcctcaagg ttgcgcccga aatcgacacc agcggagcgc  13440
aggccgttgg caagaaggcg ggccgggagc tggcgcgcgg catcgagtcc aacggtgccg  13500
aagtcggccg gatgatccgc accgatggtg cgcggtcggc cgggcagacc gccggtaagg  13560
aggtcaacgc cgggctgcag gcggccgaca ttggtcgtgg tgtctcggcg cagctcgaat  13620
cgaacctgtc gcgtgatgcg cgcggcatcg gctctcgtgt cggatcggcg atcggtcgcg  13680
```

-continued

```
gtctcaagac ggccgcgacc gtcgccgggg ccgggctgac cgctgtcgtc ggcggcgcgc   13740
tggcgtccgg tatgcgccgg ttgaccgcga tcgacgacgc gcgctcgaaa ctgatcggcc   13800
tgggcaacga cacgcagaag gtcgaggcga tcctgtcgaa cgcgaaggac gccgtgctgg   13860
gcaccgcgtt cggcctcgac gaggcggcca cctcggcggc gtcggccgtc gcggcgggca   13920
tcaagccggg caccgagctg accgagtacc tgaagttggc gggcgacacg gcggcgatcg   13980
ccggcacgaa cctcgccgac atgggcgcga tcttcaacaa ggtccaaacg tcgggcaagg   14040
cgttcaccga cgacctgaac atgctgtcgg atcgcggcct gccgatcttc cagtggctgc   14100
aggacgaata ccgcgtcagc gccgaggaac tcggcaagat gattaaggac ggcaaggtcg   14160
acgccgtcac gttccgcaag gtcatcgccg agaacatcgg cggcgctgcg caggagatgg   14220
gcagcagcgt tcgcggcacc ctgtcgaacc tcaaggcggc ctattcgcgg ttcggtgccg   14280
agctgtcggg gccgatcttc gcaatggtga tcccgttcgc caccgcgttc acgaaggtgt   14340
tcgactctct cacaacgcag ctcaagccgg tgctcgaaca gatcacggct caggtgcagc   14400
cgtgggccga gcgcaccagc gcctcgatcc aagcgtggtt cgagggcggc gggctgcagc   14460
gcgtcatcga ctggttcgtg cgcctcaagg acacgatcgc cgggttcgtg agcgcagacg   14520
gcggcggcga cacgatgcag aacctcgcgg ccggcgcgtc cagcctcggc gaggccgcca   14580
agaacgctgg cccggcgctg caggcgatcg gctcgtctct cggcgcgttc ggccaggcgc   14640
tcgtgcaggt cgggccggaa gcgttgcagc agatcatggt tccggcgatg aacctgctcg   14700
ccagcgcgct gcggttcctg gccgacaacg cgagctgggc cgtgccgacg atcattgcac   14760
tcggcggcgc gttcctcggg ctgcgcgcgg tcggtagcac gctgacgccg atcatcaacc   14820
tgtggaacag cttcttccag gttgtccgca ctccgctgat cctggcgcag acggccgcta   14880
ttcggcagca gtcggctgcc atgacgcaac tgtcgaccgc gttgggcacc aacacggttc   14940
agcagaacct caacgcgcag gcgcaggccc gcaacacggc ggcgacgagc gccggggcgg   15000
cggcgcagac tcgcggccgt atcgccaccg tggcgtcgac cgtcgccgag aaggcgaagg   15060
ccgttgcgct gcgcgcgtc acggccgcgc agtgggcttt caacgcggcg ctgcgcgcta   15120
acccgatcgg gctcatcgtc acggccgtcg tggcgctggg caccgcgctg tgggctttct   15180
tcaccaagac cgagaccggc cggaagctgt gggacaaaat ttggaacggt atcaaagccg   15240
ttgcgacgcc ggtcattgac tggctcaaga acacgctgag caccgcgtgg caggcgatcc   15300
agcctggcct gcagaagatc ggcgaaatcg ccaagactgc gttcggtgcg ctcggcaacg   15360
cgatcaagac agtttggggc ttcattcagc ccgcgatcgg ggcgttcggc cgtttctacg   15420
ctgccctcgt caagtggcag ttcaacaacg tcatcaacgc tctgaaactc gttggcagca   15480
cgatctcgtg gttgtggcgc aacgtcgccg tgccggcgtt ccagggcatc ggcctggtca   15540
tcaaaacgtg gtgggccggt gtgcaggtcg tgtggaacgc gctcaagact gcgatccagt   15600
tcgtcggcga caagatgctg tggctctggc acaacgtgtt caccccggcg tgggagggca   15660
tcaagaccgg catcggcgcg gcctgggact tcatcaaggg cgtattcgac aagatcaaaa   15720
ccggattcga cacgctcaag aacgcgctcg tcgcggtggc cggcgcgatc aaggacggca   15780
tcaccaaggc gttcagcggc ctggccgaca tcatcaaggc accgctgcgc gcgctcggct   15840
cgttcctggc cggtgtgccc gactctgtgt tcggcgtgag cattcccggc gcgggccaga   15900
tcaagagctg gggccagtcg ctgcaggggc tcgccaccgg cggcgtcgtg cgcgggccgg   15960
gcaccggccg cagcgattcg ctgctcggct acccggcgat ggtgcgcgtc tccaatggcg   16020
```

-continued

```
agttcgtcgt gaacgcggcc gcgacgcgga agttcctgcc gctgctgcag gcgatcaaca   16080
gcggctcgct gtccggtctg ctgccgggct tcgccgatgg cggcctggtg tcggccgacg   16140
acctcgtgcg gttcgccaag ggcgtcgagg gccagccgta caagtggggc ggcaccaatt   16200
ggggcgactg ctccggtgcg gtgtcggcga tcgccaacta cgccaccggg cgcgccccgt   16260
tcagctcgcg gttcgccacg cgcaccgagg gggcggagct gcgcaagcgt ggcttcaagg   16320
acggtctcgg cccgcccggc tcgctcaaca tcggctggta caacggcggc ccggcgggcg   16380
gccacacggc cgcgacgctg cccaacggtg tgaatttcga gatgggcggc gcgcgcggca   16440
acggacagta cggcggccag gcggccgcg cggacgatcc gcagttcacg caccacatgc   16500
acctgccgcc cgagcatttc accgggttgg acgggctgac cggatcgacg tacggcggcg   16560
gcagctcggc gagcgcgatc ggcggcagca cgagcgccgg tggggcggc ggttcgtacc   16620 gcccggcgac cgacaaagag ctgtcggcgt cgtcgaaccg cgtctacaac gcgcagaaca   16680
gtgtgcgcca ggccgagcag tccgtcgacg atcgccagta cgcggtcgac aaggcgcaga   16740
agcgtctcga cgagctgcgc gcggcgggca aggacacggc cgacgccgag cacagcctgt   16800
cggtgaagca gcgcgagctg gccgacgcga acgagcgtct gcgccgggcg cgggagaagg   16860
ccgccgaggt cgaggcggct gactccgagc tgcgctccaa gggcaagttc gtgcccggca   16920
agggcggcag cagcagcggc tccggtggcc tcgacggcaa ggacttcggc aagacgttcg   16980
tcgagggcat cctcgaaacg atcggcctcg acggcagcct gttctccaac ccgttcgagt   17040
ggccgaccgt caagtcggcg atggccgggc tcaacttcct gggcggcctg ttcaaggggcg   17100 ctggcgacca ggcggccgac gagctgggcg cggccaccgc tcccggcggc ttcgcggccg   17160
gcgcggctga cgcggtcggg ctgggcgaga tgttgtcgcc gctgtcgtcg gaggttcccg   17220
aggacttcca cagcggcaca ccgcagctcg caccgggcca gtacaacccg cgcgacggctg   17280 gcgtcaactc tgtggctggc gcggcaggcc cggccgatgt gctgtcggcg ttcgcgccga   17340
ccggcccgct gcccggcccg gcgactcagc agccgcagac gatcgacaac tcgatcaaca   17400
ttcagcaagc cggtatggac ccggcctcgc tgcgcaacga aatccgcgct gagcagacac   17460
agcgcacccg caccacagtg aggcgataaa tgacgactcc cggttggatg cacgacgatt   17520
tctacctcga cccgatccgc tatccgaatg atgcgtacgg gaatccgcgc tacccgcaga   17580
tgaatccgac tcatccgcat tggcagcgca tggggaactg gcacgacctc ggcaggcatg   17640
gcgagtacct gcgttcgacg aaaacgaagt gggtctacat ccacccgtcg aacaacaagg   17700
tgtggcacct gtcggggccg ggccggggcc gcgaggcgt catgctgtct aaagagttag   17760
acggcgtgct cgatcccgag ttcgagcacc gctacagcga gggtccgtac gtcgtcggct   17820
cgatccgcga gcgcaccgac tacaagcgcc gcacgatcaa cctcggcgtc gtgatcgcac   17880
ccaacgggaa cgcggagcgg ctcgacgagc caaacacgtt ctcggcgtgg cgcattttcg   17940
actcgtggtg ctcgtcgtgg tcggagaccg agcgggcta cctcggttcg ttcacccgca   18000
cgcacggctg gcgctggctg caggtcatcc tcggcaagcc gtccaagacg acgctgtcgg   18060
tcgacccggc cgagtctgac ggctcgttcg agatgaacat gtcgatcgac gcgccgtacc   18120
cgttcttcgc caagcgggcg ctgtcggcga catgggaagc gtcgcaggac gacatcgacg   18180
agcacggcgt cgcgcacggc acgatccgca ttgccaatcg cggcacctgg cgctcgtacc   18240
cgaagttctt ggtgaagggc gcgggcgagg tgacgattca ggacggcgtc gagggccgca   18300
tgatcccgct gccgaagctg tacgcagagg acggcgcgta catgatggtc gacaccgacc   18360
cgacgcggaa aaccattgtc accgagaaag acccggtgga cagccaggtc tataagtacc   18420
```

-continued

```
tgcgcaacag ccagcttctg aacatcttcc tgcacgacac gctggcgaag cgtctgccgg   18480
cgcagcgccg catccccggc ggcatcggct tcgataaccc gatcccgccg cgcaccgtgg   18540
cgcacatcaa ggtgacgcac agcaacccca acggttcggt cacgtgcatc atgccgcagc   18600
actacaagat ggcgtggtcg tgatggcggc aacgattttg aagccaccga cgatcggcgt   18660
cgacggcgca cccgacccgg tgaaagcgcc gctgtcggcg taccgctacc tcgacgcgcg   18720
ccgcgacgtg atcgacgagg aagccaaggc tcgaccgctg atccggttgt gggacaagaa   18780
catgcagtac atcggcaccg tggcggccga gaagtcggtc gacgccgagg aaatgctgca   18840
cgacaccggc cagggcgaca ttgtgctgcg cggcgacgac tggctcgtcg agttcctgcg   18900
caccgacgtg cgcaaagacg aggacttgca catcacgatc gacccgtatc cgaaccgccg   18960 caactggcg tggcggtggg gcgcgaaggt cgtcaacgtg cgggtgaagc gcgacgagaa   19020
cggcacgcgc actgtggtgt tcgagtgcgc acataaccgt gagcactgga agcacctgta   19080
tttcggtgcg acaccgttca tggacccggc cgtgcagccg atcaaggcgt ggctgctgcc   19140
cggcaacacg cgcacgatca tcacgacgac cgggttcatc aacctggcgc gcaactactg   19200
gcctctgctg gcgctgccga cgaacgcgct caacccgttc gcgtgggtgg gggaggcgag   19260
caacgtgctc aacctcaacc cgctgaactg gccggtgcaa atgcagttcg tcaatccgtt   19320
gttcgaccag tcgcggtttt ccgtcatcat gtcgcgctgg tcggatgcgc acagcgtcac   19380
cgaggcgatg ctgaaggacg ctggttgcca tctgcgcgcc tacacgtggc tcgaagagga   19440
cgaggacagc ccgcaccccg agctggccgc gatcgtcggc gagaagctgg cgcggccgac   19500
acgtaactgc atcgtgctcg cggtcgagga caagtcgcag cgcaccggct ggaccggcac   19560
cgcgttcgac ggcgtttga atctcattgg cgctgttggc gataacttcg tcaccgagac   19620
gatctaccag gtcatcggaa cgaacaaggt catcgacccg cgcaccaaca gtcccgcgcc   19680
gccgatcatt tcgagcattc tcggcaccgc gccggcgctg cccaagatca cgttccgcga   19740
gcacgagcac tcggcgatca tcagcagcga acactcgatg ttccggtcga aagcgcagaa   19800
gattctcacc ggcggcaaat cgccgggctg ggtgaaccaa acgcagacgt tcctcatcaa   19860
atacgcgctg tcgcaattga gttacgtcat ccagaccgcg atcggccccg aggtcaccgg   19920
cgtgcagaat cccggcacac cgggcttgga ggaaatctat cagggccagg ccgacaacgt   19980
gttgctcgcg ttcatccagg tcacagaccc ggtgcgcgcg ttcgcatctg ggccgtacgg   20040
gtacctcgaa cacttcgagc agggcggcgg caccgcctac accgtgtcgt cgggattgac   20100
tctgcgcgaa gggcattaca agacgcggcc gtaccaagcg ttcaaggtgt ctgtgcgtaa   20160
cggccgcccg cacacgctgt actacgactt cgacctcggc gacccggccc tgttcgagat   20220
tgacggcgtt ctctacaacg accaagtcag cgccgtgcgg ctccactacg acgagaccac   20280
gccgaagaca ttcgacctgt ccatcggcga cgactccgaa tcggaaagcc cgatcgctca   20340
agtaacccgc accgctcaag cgttctggtc ggcgctggcg atgctgttcg gatcaggaga   20400
catgttctaa atgaccgaca ccacaccagg aatcccaact ctgccgcccc ctccgaagat   20460
caaggaaccg gcgcgcaatc agctctccga cgcgatgtac gcgatcgccg aggcgctgca   20520
gtacccgacc gaccatcgag gccgccggta cgacgtgcgc tacctgatcc cggtgctgtc   20580
gtaccacctg gcgcgcgccg ggttcggccc cgtcgagggc caggccgtca tcaagccgcg   20640
caaggtgcca ccgccaccgg agtacgacgg caccaagtgg ggcgagggct gggacgccgt   20700
cgagtgggtg cccctcgacg ctcccgagtc catcgacgac gagctggccg gggcgacgat   20760
```

-continued

```
cgacgacctc gatcggctct ccccggcggc ccgcgccgag ctgattcgcc gcctcggcgg   20820
cactccggcc gagggcgcgg ccccggcacc gaccgacctc gacgagcgca cgccgtggca   20880
cgtcgagacc tccattcaat tcgacgacga cgaggacgtg aaaccatgac tcagccattg   20940
caaaccggcg acgccgtcgc gctgttccag acgctgctgt cggcgacgtg gtacggaatc   21000
gtcgccgaca aggacacgcc gggcgggttc gcggcgacgc tcgaaatggt cgacggcgag   21060
gccgtcatca cgaccgacgt gctggtcggc ccgaagggtg aaccgggcga accggccccg   21120
atcgtcgacc tgcagtggcc accgctcgat tcggcgtcag aactgatccc gattaaggac   21180
acgctcgacg agtccgacaa gggcaaggcg tggtggatcg gcactctcgt ctacgtgtgg   21240
acgggcagcg acttcgtcgc ggtgcagccc ggcccggccg ggcctcccgg caagacaccg   21300
aacatcacca tcacggccga gaccatcccg atggaggaac gcggccccgg cgtcactgac   21360
gaggtgatcc cgtccggtac gtcgctcaat ccgcacttcc atctgcgcct gctggcaccg   21420
cagggtccgg tcggcccgtc gacgaacatc accggcgcac ccgactacga cagcagcctc   21480
gtgccgcagg acgccaggc gctcgtgtgg aacgaggcgc tgcagaagtg gcagccgtcc   21540
gacttcgtgg cgaagcaccc gcgtttctac agcgtgcccg aggccgcgtt ctccaacttc   21600
acgggcctgc cgcagcggca gccgatcctg tcgtatgtcg ttccggcgca ggacttcgcg   21660
tggaccccgt acgttaccgg gcacctcaag gcgttcggcg tcgagctgga caacgacccg   21720
ctgacgatcg gctgcgaggt tcgtctcggc gacgccatga gcggcgagct gatcgggcgt   21780
ggcttcggca acatctcgtc gtggacgacg attcagccgc atttctcgtc cagctcggac   21840
ccgaataacg ctgtcgcgcc ggataacggc gtggcgctgg tgcccgccgg tgagcccgcg   21900
cagatcaacg tcaacctcta caacgacggt ctgctcggcg cgtacatctt caaccgcacc   21960
ggcgcgcagc tcggcattct cgttgtgccg caggtgtca gcgtcccggt cgagagcgcg   22020
taggagcaac cccggtggcg tacagcaaga cataccgcac catcgtcccg gttgagcccg   22080
gcactgattt cgacctgctg ctgtggctga cgcgggaatc gttcgagcgc aaggccgaga   22140
gcgacgcgct gacgatcgtc gagttcgagc accgcacggt atcgcccggc gacctgccgc   22200
cgaaagcggc gaagcagctc ggccggccgc tgaccgattt cgagtggttc gagttcacag   22260
gagtggcccg ccgtgcctag acagtacgat ctgcgcccgg tcccgatcga ccgcaacccg   22320
ctgtggtcgc tgtacgagcc gggcatcccg aagctgcccg agttgaagct cgaccccgag   22380
gccatgtggc aggcgttcat caacggcgtg aagctgacga ccgggctcga tctttcgtcc   22440
ccggcgaagt tcgtcgagag cctgggctcg ctgatcctca ccggcggcgg cctgatcgac   22500
ccgtcgcggc tgccgctgat cccgttggcg aacatcggcc gcatcatcgc cagcctgctg   22560
ccgacagggc acttctctga cccgtctgcg gtcgaggacg acgacgagcg gtggacggtc   22620
gtcgaggacg gcggcccgtc cggtaccggc gcggtgaagt tcaccgctga cggcacgatc   22680
gccgacctgt attcgaccga cctcgttccg gtcgtgcagg gcgagacgat caacgtcgtc   22740
gggaagctgt tctacgagaa cctcgtcgcc agcggcgacc cgatcgtgct cgggttgacc   22800
acctacgccg acaggttcgg ccgcacggtc gtctcgcatg tcgacttgat cgtgcccgag   22860
gtgacgagca gcaccctcga cgactgggtc gagctgacgg gcacctacac cgtgccgtcc   22920
ggtgtgcagt cgctgcgcgt gcgcatgacg gtcggcgctg acgccacgtc cggcgacgtg   22980
tatttcgccg aggtcgacgc caataagggt gacgagctgc tgccgatgga gttcgtttcg   23040
ggcctgctcg gcgagctggc cgcgcgcctg ggcctcgacg tgtggcagga cttcctcgac   23100
gcggccgccg ggcatgtcgg cggcacgatc caccacatca tcgaccggat tgtgaacctc   23160
```

```
gatctgttcg gccggttcga cgcttcgcag ttgaccaaca tcgtgaacat tcccacggtg   23220
cccggtacca acgtcggcgg cgtcggcggc gtcggctcga tcgtgtcgca tctgcagcag   23280
acgtggaaca acttctgggg cgcgctcgtc ggacgccaga cagacgacga cgtgagcctg   23340
gctgatccga ccgagcagat cgccgagctg gcgtcgacca cggccgcgca ctcgtcggcg   23400
atcgcgcagc tcatggcgaa ccaggacggc aacaccaacc agggtgtcgt cggcggcgac   23460
gacttcgagc gcgtctcggt cggcagcctc ggcggcggct gggccgagtt ctattcgctg   23520
ggctctggta acggctacta cgacacgtcc aacgggcacg acgccgtgtg gcacgacgag   23580
ggcgcgtcta ccaacaccgg cacgttcgtg cgcaccgacc cggccgacga gcgaaccgaa   23640
accgactttc agcgcgtcac tttcgttgtc ggcaccgtcg caggtgaggc acctctgccg   23700
ttcatcctga ccggcggcca gcacatcagg ctgtgggtgc gcgtcaacga cgacgccgac   23760
accgccggga tcaccgatgg cgtgttcatc gaggttggcg gcgcgagcct ggcgcagttc   23820
ggctaccgca agaacggcac cacaacgatg gtcggcagca cggtgagctg cacgtggggc   23880
gtcggtacgc ggttcacgat tgacgccggc acggccgatg gtgtcgagac gttccggttc   23940
tacaagaacg gttctccgat gctgacgtgg gaggacagca gcggcgtcac ctcttacggt   24000
gaggacttcc ggcgctgggg ctgggaaggc caggcgcgcg ctcgcggcct gggccagggc   24060
accccgtcgt cgtgtgcgcg catcacgatc gccgacaacg cgccaacggc cgtgtacggc   24120
acgacaatgc gggtgttccg caccaacacc agcggtgtgt ccatgccggt ggtgaacaac   24180
actgtcggat cgccgttgcc tgcgaacgtg ttcgactcga tcgcctacaa gtcggccgac   24240
ctcgactgga acccggcaac caacaccgtc acgttcctca ccgataggcc cgcaacctat   24300
ttcgtgcagt gccgtatcga gaccagcaac gcgctcggca acggcgcgta cctgttggtg   24360
ctctacaaga acggcgttgt ctacgcctat aacagggcca cccagttccc attcaacgtc   24420
aatctggtga gcgatccggt cacaaccatc attggcgact tcgtggttta cgccgagccc   24480
ggtgactcga ttcagatgta ccggatcaac accgacgcgc aaaacgtcgt cggtggcttc   24540
ggcggggcgg tgacgttctt gaacgtcgcc aagatggggt gaccaatgcc gtggagcccg   24600
aatccaattc agctcacacg gcagtcggtc ggctggacca ccagcccggc cccagtggcg   24660
gtcggtaacg cggctggctg gcgggctggt atccgtgagc tggcgcgcgc ctacagcctg   24720
agcgaggcgc aggcgattct cgtcgtcaag acggtggccg ccgggctggg catcagcgac   24780
gctgaggcgc tggcgctggt gacgttgaat gccccggcgg cgagcgtcag ctcgccgagt   24840
gctggcgctg tcgagcacgt gctcggccgtg gctggcgtcg ccagctcgac ctcgtcggcg   24900
tcggtgctcg tcgcggcgca gctcgtcgcg gcggcgaccg gcgcgactgt ggcggccgcg   24960
accctgctca tgcggatggt ggcggcgtcg ctgtcggcca gctcggcgtc ggccggggcg   25020
gcgttcccgg cgcagtcacc cgcgccgact cagtacgaca gccccggcac ctacaactat   25080
tcaatcccgt actggtgccg gtacgtcgac gtggtgctcg tcggcggcgg ggcgggcggc   25140
aacggcggca gcgccgcagc ggcgactggt cacggcggct tcgctggttc gtgggccgcg   25200
atcactcttg agcgcggcgt tcacatctcc tggactgtgg cggttctcgt cgtcgtcgtg   25260
ggtgttggcg gcacggccgg agcgggtggc gtcgttggcg cgctgggcgg caccggcggc   25320
acctcgtcgg cgtcggcgac cgggtgggcc ggtatttccg ctgcgggcgg caccgcgcgt   25380
ccgctggttg gtctgctgca ccgtcccggc gacggccccg cgactacac gcacaacggc   25440 atcacctacg tcggcggtgc ggagtcgctg aacggcgcga acggcaaccc gccgggcggc   25500
```

-continued

```
gcgggcagcg gcggcgcggg tggcgtgttc tccggtgcca acggcggtgc gggagcgccc    25560
ggccgtgcgt ggcttcgtgc ctatcagtga cagacaagta aggagcatca aatggcagga    25620
gcggcagacg ctttcaaaat cgcggccgtc gaggcgatcg gcgctctcgg cgggctcatc    25680
agcctgcata gcgtgcgatcc tggcaccacc ggggcgaacg agatcagcgg cggcggctac    25740
tcgcggctga cgaccacgtg gggctcgggc gcgatcgtgt ctggcggccc caacaacggc    25800
aaggcacgca tcgtcggcag cacgttgcag ttcagcgtgc ccggcggcac ctcgatttcc    25860
tactacagcg tgcgcgcctc gaacggcacc ttcctgtacg cgcggccgct gacgccgggt    25920
gtgaccctca acgccaatgg cgtggtcgac gtgactcccg agcatgtcta cgacctcgaa    25980
acctcttaat tcccaacgat tgaagcgagg ggcttaacct tgtctgtctt acgcgcgaat    26040
gtcgaggccg cgaaatcgtt catccgcaac cggctgggca atgcctacgt gtacggcggg    26100
gcgctgtcgg ccagcaaccc acggcagggc accgactgct ccgaggtgtg gcagaccgtg    26160
ctcgaaatgg tgcatggccg ctacgtgcaa ggtcgccagg ccgagggcgc gacgaccgag    26220
agctaccgct acatcgaggt gggccaggtc ggcccgttcg gcaccatcag agtggcgcgg    26280
ccgcaggaca ttccggctaa cgcggtggcg aagctggcgt ttcaccacga gggcagcggc    26340
ggccgctcgt cgcacatgtg gggcgagctg gacggcatga ggatcgagtc ggccagcggc    26400
aaggggcttg tgacccaacc ggcggcgtgg ccgattgacc acagctacgc gaacgcttgg    26460
gcctacttgc ccggcccgat cgtcgaggac ggtacgccga tcgtcacacc ggagccgcgc    26520
gacaccctgt acgccgacgt gtccgagtgg caggttcccg tcgacgacag ctatccgcac    26580
cgcgtgctgt gcatccggtc gaacgacggc acctaccgcg acaagaagtg gcacatcaac    26640
tacccgtggt gcaagcgcgc tgtcgacgac ggccgcctgg cattcttcat cgtttacttc    26700
gtgtggcggc cgaattggcg cgacgccgtc gccacgctga aatcgcaagt gggcgagcct    26760
catccaaaga tggccgtgat gatcgacgtt gagagctggg gcggccagat cggcggcaac    26820
cagtcgtcgg ggatcaacgc ggcctacgac gagattgccg cgtggctggg cgatcgccgc    26880
cgggtgatcg gctacggcaa cgtcggcgac ctcgaccggc tgtggccgca gaagccgccg    26940
ggcatccggc ttgtcgtcgc cgggtacggg cggctgccga gctaccccgg catgatcgcg    27000
caccaataca cggacggcag cggctacggc ggcggcctgc ccgaaggtgc accaccgttc    27060
ggcaactgcg acatgaacgc tgccaacggt ttgaccgcaa cacaattcgc tgccgagctg    27120
ggcatcgaag catcacacgg agaggacggt ctgttgtctg cattgacccc tgacgaacag    27180
cgcgaggctc tgttcctgct gcgcatcctg gccgacaagc ggttcgtgag ccgcagcccg    27240
ttccggcatc tcggcgagaa ggagaccgag acagtcgccg ggttcggcct caacaccgat    27300
ggcctgacgc acgcgcagta cacgatcgag gctgcgcggc tgggcgatcc gacgcatatc    27360
gcgctgctgc gcgaggtcgc cagcgccgag ggcgacgacc gctaccccga tcggcagtgg    27420
gacgcgcagt ttgcgcggcg cgtgctcgac cggctcgaca ttcccgtcga ccccgacgcc    27480
aagcccgccg cgccggccgc ggtggagacg ccgagccagt ccgatcagtg cgcgctcggc    27540
ccgacctgca agctcaacgg cagcagctcg gcgtgcgcga tcggcggcga ctcatgcgcg    27600
ctgaccgcca accccaaggc cggtgactga tgccgcaccc gctcaacccg acgaacaagc    27660
cggtgctgct gacgctttcg ggaaccgggc agaacatgtg gaccgggtat gccatcgacg    27720
tggcgcaccg cgtcgaggac gtgtggttcg ttcagcccgt cagctacggc cccggcggcg    27780
tcccggcggt gtggccgatg ggccgcagcg ccaagagcgg cgtcgacgag ggtgtgcgcc    27840
tggtcctgca ggagcactcc gacgcgcccg gttactcgat cagcggctac agccagggcg    27900
```

-continued

```
gcggcgcggc cgcgatgctg ctcgacgagt tccggcacgg ccgcctcgcg tcgttcggcg   27960
atcggctgct cggcggcgtc acgttcggta gcccgttccg cgagaagggc tcgtacgccg   28020
gggcgattga ccccggcggc cgtgggatcg ccgatacccg cacggtcgac accccggccg   28080
gttgggccga ctatgtcgac cccggcgaca tttacgccaa cgtgcccgac aacgcggtcg   28140
gcgacgacat gacgttgatc taccggctgg tgtggctcga cgacgcggga gacgtgctgg   28200
ccctggtcgc caagctgatg cggctgctcg tcagcccgtt gcgtgagttt ccgtccgtcg   28260
tcgaggcgct ggtgcgcgga atcatgttct acggcagcaa gcctcgttgc gcggcgcacg   28320
tcgagtacca cctacgtgag tgccccggca ccggcatgac ttacgtcgag cacgctgccc   28380
ggcatctgcg tcaactcggc cagcaggccg cagccgccta gttcccttat ccctcgaaac   28440
ctgaaggacg acaaagctat gcgtaagttt tgggatcgcg tgcgcgctgt gctggcgcaa   28500
cggttcggca tcgaaacgtg ggccgacgta cgcaatgtca ttcacctggc cacgccgagc   28560
atcgccggcg cgctggtgtc gtggaatctg atggaagccg acaaggcgaa gctgatcggc   28620
gcgctgatcg cggcgctggc gtcgccgctg ctggcggtgc cgtacagcaa ggacgtgtgg   28680
cgctcgtaca tctacggtgt gctggccgcc gggcaggctg tgctgatcgg cgtgctcggc   28740
atgactgagt ctcaggtggc cccgatcatc ggcgcggtgc tcgcgcttgt cggcggcgca   28800
ctggcgtcga cgaacacgcc gacgagccac gccgggctga agacaagac ggcatgagca   28860 ccgaggtgat cgccgctctg tgcagcttgg tcggcgtcgt cgtgacggcg atcctggcgc   28920
accgggccgg cgggcgtgcg gcgctgcggg gcgcggagac ggccgactgg aaggcgttca   28980
ccgacagcct ttccgatcgg ctgctgcggg tagaggaacg gctcgccaaa gccgaggaac   29040
gcaccgcgaa agccgaggac cgcgcaaacc gggccgagtc cctgtaccgc attgccatca   29100
cgtacctgcg gcaggtcgtg cagtggtgcg gtgagcggca cggcgagaag ctgcccgagg   29160
ttccggccga gctggcgggt gatctatgag cttggccgac gacgtagcgg cggggaacgt   29220
cgcaccggca ggtatcggcc cgtcgtcgcg gtgcagtgtg tgccgctggt atgagcgcct   29280
cgaccagcgc gaccgcgatg cgttcgacca gtggctcgac gacgtggccg ccggcgtgga   29340
gggccgcacc gtgtcggggc tgtggtggct gtgccgggcc aacgggttgc gggccagcag   29400
gcgctggttc gccgagcatg tgaacgtgtg ccatgtcgct ggctgacgac gcggccgcct   29460 accggcggc agggagtaag gactaccggc cgagcatcga gttcgacggc cggacagcga   29520
cgatcgacac cggcaccatc gaggccgagc ccggtcaacc accggagtac gccgagctgc   29580
tgcgccaggt gggccgcgat ccggcccgct ggcggctggt gtcgatcgac cgcgagaagc   29640
actggcaggt gccgtatcgg ccgatcgagg gctacgacga gcgcggcaag ccgatctacg   29700
gcgagctgac cgagaagtgg ctggcctcgt acgcgatgcg gtgcgagttg atcgacgacg   29760
gcgcgccggc cgacctcgac gcgctgatcc tggccgcgaa gtcgcgccgc gacgacgcga   29820
gccggggcgg gccgtactgg ttcgtgttcc aggctggcga cttgcagctc ggcaagatca   29880
gccgggacgg gtcgacaccg gagattgtcg agcggttcgc gcagtcggtg gaggccgcga   29940
aggccgagct gcgggccgct cgccggttcg gtatcggcgg tgtgcagatc agcctgccgg   30000
gtgactgcat cgagggcggc cagtcgcagg cggccgcaa catggcgttt atgacggcgc   30060
agaccgtgcc cgagcaggcg cggatactgc gccgcttgat gctgtacgcg atcgacgagc   30120
tggccgacgt tccgcacgtc tacctcgacg tggtgaacgg caaccatgac gagaacgagc   30180
gccgctggaa tgagcggccc ggcgacgggt gggccaccga gaccgcgacg acggtgcatg   30240
```

-continued

```
acgccctggc cctcaacccg gcggcctacg ggcacgtcga ggtgcgggtg cccgaggttt   30300
ggtctggtca catgacggtg ccggtcggtg acaccacggt gacggtcgtt cacgggcacc   30360
agtggcggca gcggcagaag gcgatggact ggctcgccaa gcaggccgtc cacaagcagc   30420
caccgggcgc ggccgatctg gtgcagcacg gccactacca cacgctgctg atcgagcagc   30480
acaaaacccg cacgatcatc gggtcgccga cgttcgactg tggcagcgac tactaccgcg   30540
agcggcacgg cgcggagtcg cggcgcggcg ctgtcgtgta cctgctgcgc ggcggcgagt   30600
tcagcaggtt ggccgtggtg tgacgatgag accggctgat tgtgcatggc tgggcctggt   30660
ggctggtgtt gtcgcctacg aggtgctcgc gccgcgcggc gagctgctca gtgaggggat   30720
ggaccgctac ctggccgggc ggtgggcctg gccgacgcgg gcggctgttg tggtgacggc   30780
cgcgcacctg ttgaacgtgc tgcccgaccg ggttgacccg atccaccgtc taggaaagtt   30840
gatggtgccc cgccggagtt tcgatctccg tacccgccgg ttaaaagccg gctgctcttc   30900
cgattgagct agcggggcga gacacactat agcgacgccg ctctccggtg cctaatcagc   30960 gccgggggggc ggcgtttctg tgttgagtgg tctacacgct cgtgtatcgt gtgggttgac   31020
ctacacgggt acgtgagaag ttaggagcca caaaccatgt cgccaacacc aacgggtcgg   31080
ctgtcgcagg acacgttgac catgattcgg gacgcctacc ccggccccga gaataaggcc   31140
gagcgggacc gggcgatcga gctggcgcgg ctgtacgcga ctggctcgat cacggtcgag   31200
accgtcgccg agacgctggc gcaggcgcgg gagcaactgc ggttggagat ggcggcggcg   31260
cgaggtgtcg cgctcgcggc gatcgcggcc ggggagttcg agaagaccgt cgccgagaag   31320
ctcggcatcg accggatgac gctgcgcgac tggcagggca agcggcgcac acgcagtagc   31380
tgacaaccac gagacaggga ataggagccc ctctatgtcg acaacatcgt tcaaggaagc   31440
gcggcagcgg gtgctgtcgg ccgcggccgg cgcagcgtgc gagctgtgcg gcgaggtgcg   31500
cgttcacggc aaagtgctga cgccgggcac cgaggtgtcg gttcgcggcg agcgtggtcg   31560
gttccggttc gtgaaggcgt cgaccacgtc gacgggacgc caggtgctcg acttcatcgg   31620
cggcccggcc gggcatgagc agtggcgctc gttctacccc gagcggatca agacggtgca   31680
tcggatcgcg cgcacgaggc agaacgtcgc atgaacgtcg gggagctgaa acgggcgatc   31740
gccgagctgc ccgacgacat gccggtgctg atcgcggggg agaccggggc gagcgaccac   31800
ccgaacctgt acgtcgtccc ggcgacgatc aagcacttca ctcacggcaa ctgggtgatg   31860
gagggccacg cccggctgtc gccgacgagc tgccgcgact tggagcacac gacggcgctg   31920
ctgctgtccg agtgggggaa cgacgacggc gaggacatta cgccgagtca cgactggccg   31980
accgtgatcg agggagaatt ggccgatgga taacccgagc tgccagcatc accggatcga   32040
caacgagacg tggaagtgtg tcgagtgcgg cgagcggatg atcgcgcagt cggtcgacgc   32100
cgacacggtg ctgtccgcgc cgaatgccgc cgggtgcagc aacccggcgt gccgggcggc   32160
gctgactgac ggcacctacg acgagaacaa cccgcccgcc ggatgcacca acccgcacgg   32220
cgtctacgtg gccgacacga tcgccagcg cgaggtcacg gtcggctacc gggtgactta   32280
tgagtgcgag cggtgcgcca acgacggcac gatctacacc tcggacggcg tcacgtggga   32340
gtgcggccgc tggcaccggg gcgactacg gcgggcgcgg gagacggcgt cgtgagcgcg   32400
cagcggctct cggatcgttc ccggcggcgc attgagcggt cgaccgggct ggcgatcgtg   32460
cgggcctggg cgcacggcgg ctacgtgttc gacttcgtga cggtcgacca ccagcacggc   32520
tcgtgggata agcgcaccgg cgagtggcag ctcgacgacg acccgacgca ctactcgtcg   32580
tgcgccgagc tgttctctga gtcgaactgt gtcgaccacc cgacgctgcg cgggctcgtc   32640
```

-continued

```
gaggcgcgcg aggctccggt cgtcgcggcg gccgccgaga gtgcggcgcg gttcggcgcg    32700
gcgttgcagc aggcgatgca gctcgcggtc ggcgaccagg ccgtcgaggt tgcgtggcgc    32760
gatccggccg ggccggaaga tcgggctgcg gtggtgtcca ctgtcatgca gtcctccgag    32820
tgagccaccc ttaccggccg tcgaccgcag cgttcacagg ataaaggaaa ccgcccacct    32880 atcccctcg gctaggtggg cggtttcgtc tatgcgggtg gctacagcgc caggcgcgcg     32940
ccaccggaga acggcgagtc gtgcagccgc agctcggcgg gctgggtgcc cggcggcacg    33000
tcgaacgcga cgcgggcctc gatctggttg ccggggttta tgtcgccggt gccggggttc    33060
atccacatgt cggcttcgct gttggcgtcg tactcgcggc cgtcgcggtc gagcagggtt    33120
tggttggtgc ccgagaacga gcgggcctcg tcgccgatgt tcttgacggt gagcgtgacg    33180
acgatgaact caccttgcgc ctcgacggtc atgaacgggt tgccggtcgg gtcggtgacg    33240
gactttgcgc gctcgacgct gacgacggtg aactcgaatt tgccgtcgcg caccgagctg    33300
cccgctggcg cggccgtgtc gctgcctgct gctgcggcgg cctcggtggg ctccgatccg    33360
gccgtcgtag acggcgcgca cgccgacagg ccgatcgctg ccattgcggc gacggcggct    33420
gaaagcgcgg tgagggactt catcgctggc tccaatcctt tgctcgttgg gtgcaggccg    33480
gcactgtacc cgagattgag gcgtttttgg gtacatgttt gggtacaccg ctacgagcac    33540
ggtgcttctg acctgcggtt ttacggtgga ttgcaccgga atcggctgat taaaagttcg    33600
tcgcctcggc gtgtcgacca ggcataacac caggtcacgc taccccgtag tgctgtgtag    33660
tgcttggtag gagtaccggc ttgggtacac ctgtgggtac agtcgcgggc atggcaacga    33720
agcgacgcgc gcccggcgag ggcggtctgt tcaagcgcgc cgatggcatg tgggtcggac    33780
gtgtagacgt tcctacagcc gatggtcggc gacgacggcg agtggtctac agccgcgata    33840
aggcggtggc cgccgagaag ctgcgcaagc tccgcaatga cgttgctgag ggccgcgtca    33900
gctcgtcgcc gacgatgacg ctcggcgcgt ggctcgatca gtggctcgac attcacgggc    33960
cgcacgtgcg ccccaccacc cggcggcacc acgagcagag catccggctc tacatcaagc    34020
cgcacatcgg cgatcggcgg ctcgacaagc tcaccctcga cgacgtggag aagatgctgc    34080
gcgccgtggc ggccaggtcg acgaagtcgg cgcagaaggc gcaccagacg ctgtcgcagg    34140
cgctgaaaga ggccgagcgc cggggcttgg tctaccgcaa cgtcgcggcg atcgtgcgga    34200
agcctcggca cacgccgcgc cagcgtgagg cgctgactgt cgaccaggcg cggcacatca    34260
tcagcacggc gatcgacctc gagccggccg ccgggccgca cctggcgacg cggtgggcgg    34320
cggcgtttct gaccggggcg cggcaggccg agctgctcgg cctcacgtgg gaccgggtcg    34380
acctcgacgc cgggacgatc gacctcgcgt ggcagttgca gcagttgcag cacgtgcatg    34440
gctgcggtga gcccgacgac gacggcgagt ggccgtgcgg ccgcgtgcgg ccgggctggt    34500
gcccgtcgcg gcggtgggag ctgcccgccg gtttcgagca caaggtcgtg catcgctcgc    34560
tggcgttcac ccggccgaag actcgcgccg gcactcggat cgttccgctg gctgagccgt    34620
tgcggctgat gctcgtcgag cacgcgaagc ggtcggggcc gaatccgcac aacctcgtgt    34680
ggcactaccc cgatggccgc ccgatcgggc cgcgtgacga tctgcacgcc tggcgggttc    34740
tgctcgcggc ggccggtgtc gacccggtgc cgctgcactc ggcgcggcac acgacggcga    34800
cgctgctgct ggccgctggc gtcgacgcgc atgtggtgtc ggcgatcttg ggccacagcg    34860
acgtgatcgt gacgcgcggc tatcagcatg tggacctgac gttggcgcgc caggccgccg    34920
ggcagctcac tcggctgctg agttagcagt cggtggccgg tcgtcgccgc gttcgcgtcg    34980
```

```
gcgcggctgc ttcggctggt ggtggatggc gttccacagc ttcgtgaacg agcgggtttt   35040
ctgctgccag ctccgcaccg ccgagatgac gagcagcacg gcgctgatgc cggtgagcgt   35100
ccagatgatt ggcgcttgcg gcagcgcctc ctgcagcgcc cgcacgttgg agcggatcgg   35160
cacccacacg ttcgcggccg acaggacgta cacggctact agctgccagg ttgccgttga   35220
gcgcgaacgc gggtcttggt cccgcacgat tcgcaggcac cgaatgatgt acgccagcag   35280
gtagccgagc gtggtcgcgc cgatgagcca gtaggcggtg agccagaagt cggctggcac   35340
gttgaacatg atgcagcagt attcgtcgac ggcgtcgctg agcacgaggc acgcgaacag   35400
gagcgcaatc gccggtggcg caacagtttc gacgtgtcgc ttcatgcggt cctgtaggcc   35460
gcgcgtgctg gtcacgcggc tcatcacgtt cgccagcatg gcgacggctg cgctgatgta   35520
gagaacatgc ccgaggtaca cgtcgaggta gccgacgccg gtgaagtgtt tcagcattcg   35580
accgatggcc ggcccggtcg gcgcgatgag cacgatcgcc aggcactgaa acaccagcgt   35640
gagtgattgc ccgcgttccc agtagctgcc ccaacctaag cgccgtaccc acagcgccag   35700
tagggtgaat gtgacaaccg tggacacgaa cgtagacagc atcatcggcg tagttcccta   35760
accatctaag gaattgagcc gcaacctttt tcgggttgtc gaccgtatgg ggggctatgt   35820
gtgccgctgc tacacaacat agtccagatt tatggacaaa gcaactcgat tgacgtgcag   35880
attctccaga tcatcgggca acacgctgtc aagatatccg taatgatgtc cacaaacctg   35940
gacacagtgt tgtaccttcg taggcatgcc agccctcag acctacgaac tccgatggaa   36000
tccggaagca atcgcaaaac tgctgcgccg caaaaagatt cacgatcgag ccgagctggc   36060
cgaggcaatc ggaatcagcc gcgcaaccgc ctacaacctg ttcggcgctg actggtcggg   36120
caaagcgacg accgttgtct tggcccaact cgtcgggtgc ctcggagcca acccagcaac   36180
catcgtcgaa accgtcaagg tgtcgaaatg accgccgatc agattctcgt gacccgcgac   36240
gaggccgctc gaatgctgtc gctgtcggtc gccgaaatcg acaacgagcg ccgagccggg   36300
cggctaatcg gccgaaagca cgggcgcaag gtgctgatcc cggtcgacga gcttcgccgc   36360
tgggccgggg agctgcccgc cgacgaggcc cggtgacccc atgcccggcg cgacgagct   36420 ggcgagcctt cggctgcagc tcgaagaagc gaaccgagcc ctcgacgccg cgcacgccga   36480
tgcccgcaag ttccgcgaag agcgcgacgc cgcagtcgcc gagcgcaacc gggtgctcga   36540
cgagcgcgat cgcctgatcg ccgagctggt ctcgctgcgt gactgccgcg acgccgcgat   36600
cgcggccctg aacaaccagg cgctcgtcgc ctggtggaaa gagaaccggc ccccgctgtg   36660
aacgagggtc ggtcgacaca tcgagatgga taggagcccc tcgaatgtca ccgagaagta   36720
tacggccgac gctcagcccg gccccgtact gcgtcggctg cgccacgcac cacacgcgcc   36780
gctgcgatca gcagcgccgg atcaaccgcg ccaaaaccgc tttcggcctc gtgtgcctgc   36840
tggccgccga cgtgctgatc ggcgttgcga tcggagtgca actgtgagcc ggatcgttct   36900
gtcacatgac gaattgaacg cgggtgctcg ggcgctcgac gcgcacctgg ccgagggcat   36960
cacggcgtac ggcgcgctgg tcgccgccgt ggcggccgtc aaccgggtgc gcagcgaggt   37020
cgccgacccc gccgagggcg agctgcgcat gtcgccgatg ggcacgtggg cgcagcgcca   37080
gggcggccgc tgggtgctga tgttccccag cagcaacgag aaggtctacg gctgcgacga   37140
gcaggttcgg agctggccgg tcgtcggcaa cgcgaacgcg ggtgagcagc agtgacattg   37200
gcgtgcgacc tgattgtgca tcccgtcaac aacaacgagg gactgcactt tcgaggcccc   37260
ggcatcgacg acgagctgta cgccggtggc cggtcgacgt tcgaggtaac caccacgatg   37320
gggcggcggc tggcgttcac gttcgagccc gaccgcccga tctggatgca caacgccgag   37380
```

-continued

```
aacgtcgctg gcgtctggtc ctgcagctac taccgcccaa acggaaagaa cacccccacc   37440
atgcttgccc ggctgctgcc gggtgagcgg atcgaatcag taaggaacac aacacatgtc   37500
taagaacacc acccgtcgct tgttggcgct tgccggtctc ggcggcctgg tcgccggtgc   37560
cgcgatctac ggcgcgagcc cgtcgtcggc caccacgatg gacgacctttt tcatcgcggc   37620 gctgaacaag gaaggcgtgc cgtacaacaa caaccccgcc ggcgcgatcg acctggcgca   37680
caccgtgtgc cacgcgctcg acatgggcgt cggtctcggc accgtgatgc tgacgatcgt   37740
ccaggccggt gacggctact ggaccgtcga gcaggcaggt tcgttcgtcg gcgcgagcat   37800
cggcgcgtac tgcatcgagc acgccccggc cgggacggag gtcgcgtgat ggaggccaac   37860
gtgacccgcc tcgacgaagc gaacaccctc gtcgagcccg ccgagccgca gcacgtcatg   37920
tacgagaagc ccgcccgcac gcccggcggc ttcgagctgg ccgtgctcgg cggcctgcag   37980
aacctgtcgc acatctacgc gggcaccgtg ccggcggccg agaagcagcg ccgccgcgca   38040
cgcaaccgcg ccgcccggcg ctcccgcaag atcaacagga ggaaatgagt cttgttgcgc   38100
gacaagtaca agaccgagac gcggcccgcg cagcagaagc ggcagcgccg caacgtgatg   38160
gcccgcaaca ccgaggttct cgacgacttc ggcatcacga cgcagatcgt caccaccgac   38220
gagctgtgct cggtgctgcg gatcgtgccg caggcgctgc gcaacattct gcgcacgcac   38280
cgccaggagc tgctcgacgc cgggtacgac ccgactggcg aaggctactt cacccgcgag   38340
gctgttatgc gggtggcgct gctgctgcgg ccgacgacga gcgcagtcgc cggacagatc   38400
gccgaggccg ccgggatgcg ctacacgcgg atcacgttcg gcggcggcgg cgctcatgcg   38460
tcgcgctgct cggcgatcat cgaccaggcc gccgacgtgg cgcagcgcgt gcatgaggaa   38520
tgcccggccg agctgtggca cgacctcacc aagatgaacc gctacgagct gcaggcgctc   38580
gctgtggcgc tcgcggcgat ggttcccgtt gatacggcga gcaagaacga attgctcggc   38640
tgggtagccg gtttggccga caacaacgat caccgcgcca agggcggcat ccccgccgga   38700
atggcgcaac tcatccccac caaggcgacc gctgacggcg tgccgccgac caagctcgac   38760
gactttctag gaggcgcagc gtgaccgagg caggagaccc gacgatgtgg cgggacgacg   38820
attcaaaggc ggcgcagttg ctcggcgacg cgggcgatct gtcgatgacg ttcaatcggt   38880
ggctgccggg cgacccggtg ctggtgcccg ttcccgagaa cgtgttgcag gaggcgcagc   38940
ggctgatctt cggcgaccgc gagcagcagt acggcaaccc gagcgaatcg ttcgaccgga   39000
tcgccgcgct gtggtcggcc tacatcggca ccgagctgaa cgggctcgac gtggcgaatc   39060
taatgatctt gctcaaggtt tcgcgcacga agggcaccta tcaccgcgac agctacgtcg   39120
acattgccgg gtacgccggc ctcggcgagc ggctgcacga ggcggcgcag cggtgaaccg   39180
gcatatcgac ttcgccgccg agctggccga gatgtacacg atggcgaacc tcaactatct   39240
gcggatcgag cagaccgccg accgcgcgca ggccgccggg aaggcgatcg acgagctgaa   39300
ccgcgcggtg cagccgctga ccgggttcgc actggctcac gttgtgcagc aggccattac   39360
cggcgcggcg gtggcccggt gaagcggagc caggtgctcg ccaagatcgg caaggccgcc   39420
aaggccgccg gggcgtcgtt cgagctggaa cgggagggca gcaaccatgc cctctaccgg   39480
ctcgacggcg tcctggtgcc gatcggccga caccccaccg gagacctgcc cggcggcatc   39540
gtgcgccgga ttttcaagca gtgcgagccg actctcggca aggactggtg gcgagcctag   39600
cgacccgccg acaactacat attggggttc ccggcgactg gggacacaac atgtagtgtt   39660
tcccacctga cagagatagg agacctacgg caatgactga cctctctcat gtgcggcagc   39720
```

-continued

```
acgtcgaact gctgcgccac gtcaaggccg aaaaagcgaa gctctcagag atcgagaagg   39780
ccgcccgcgc ggtcgtcgag gaagctctcg gcgacgccga ggaaggcacg attgacggcc   39840
agcccgtcgt gcgcaacaag ttcgtgaagt cgaaccggct ggatcagaag ctgctcgcca   39900
gcctgcaccc cgaggtgctg gccgagtgca agaccgtgat cgagtcgcgc cggttcgagg   39960
tgctctgatg atcgcccgcc tggccgtgat ctggctgttc gtgctcgcgg ccgttctgtt   40020
ctcgctcggc gtcatggagg cttaccagtg agcaggcaac tgatcgtcgt cgactgcgag   40080
acaacgggat tgcacgacga cgccgcgatc ctcgaaatcg ctgcggtcaa cgtcgagacc   40140
ggcgacgagc tggctttcgt tccgtacgtg agcggcgagc agctcgccaa ggcgcaaccg   40200
gacgcgctgc ggatcaaccg ctactacgag cgcgccgtgt accgcgagat gctgagcccg   40260
gccgacaccg ccgacgcttt cgacgagctg gcgacgatgc tcaagggcaa cacgttcggc   40320
ggcagcaatc cggcgttcga ctcgaacctc gttgcccaag cgcgggttac accgcccgcc   40380
tacgcatcgg tcggttccca gcccgtcgtc ggccgggtgt ggcatcaccg cctggccgac   40440
ctggccgcct acgcggccgg cgtgctcggc ctcaacccga ccgagctgcc cggcctcgac   40500
gccgtgatcg aaaaggtcga cttcatggtg ccgatcggcg aggtcgacaa ctacgagcgg   40560
cacaccgcgc tcggcgacgc ccgtatcacg gcgtcgtgct tccggcggtt gaccctgtgg   40620
gccgaacaga acaggagccg ctgatgaacg tcacgatccg actcaacgtg ctcggcgtcg   40680
agctggcggc gatcaacgtc gacctcgacc tgctcgacga ccccgcctcg gtggccgccg   40740
tcgagaaggc cgccaaacgg ccggtgaagt ggatcagccg cctgtgggtc aaggggatga   40800
cggcgtgagc acgccgcag catttttcgc cgacgacatg gtcgacgagc cgcccaggt   40860 ggccgccgac aaggcgctgc tggccgacct gaaaagccgtt atccggtatc actacgtcaa   40920
cacgccacgc aacatgcaga aggcgctcgg cccgtccgag gtcgggcacc agtgcgcccg   40980
gcggctcgcg gccggtctgc tcgaactcga ccggatcaac ccagagggcg acccgctgcc   41040
gagctggctc ggcaccgccg ggcactcccg attcgagcag gcgatcgagc tggacaacct   41100
gcggatcatc cgcgaggccg ccgaggacgc ggccgccaac ggcgagcacg ccacgaagcg   41160
atgcacgttc cacaacggcc agccgatcgg ccgctggttc tccgagcgcc aggtgacggt   41220
gcgcggcggc ctgtcgggta cgtgcgacct gttcgacacg tggacgaaca cggttatcga   41280
cttgaagttc cccggctcga cgaagtgcgc cgagtacaag aagcacggcc cgtccgtgca   41340
gtaccgggca caagctcacc tgtacgggcg cggctaccgc aacgaaggat ttcccgttga   41400
gcgcgtggcg atctggttca tccccgcgcgg cggtttcctg tcgaactcgt tcgtgtggtc   41460
cgagccgtac agcgacgcga cggtcgacga gattctggcc aagctcgaca acatcatcct   41520
gttgctgaac gacctcgacc tcgaccagca ccccgagcga atcgcgctca tccccaagac   41580
caccgggaac tgcgaatact gcccttactg gtcgccgcgt cccgatccgt tgatgcggcc   41640
gcacgcctgt gcgggaggtg ccgagtgatg aagcctcgtt accggatcag gaagcgcaac   41700
ggccgctggc aggtgcagag tcgcggcgcg acaggcattc gctaccgcac ggtggccgcg   41760
ttcatcaccg gggccgaagc cctggccgcg ttcgcaggag ccgacagatg aactacagca   41820
agccattccg agccaagtac cccggcaagt gtgagacgtg cggggaggcg ttcgacgagg   41880
gcgacctcat ccggctgacc gacgaccggg cgacggttca cgccgtggcc ggtgactgcc   41940
tcggcgaccc ggccgtcgac gtgaactgga cgaacgtgcc ggtttgcacg ctgtgctgga   42000
cccagcaccg aggtgagtgc gcatgaggat cgtcggaccc gcaaagcccg ccgagccgag   42060
cggttttcac ccggtcggca cggtcgccgg tgacggcccg cagctcaccc gccccggcgg   42120
```

-continued

```
cgatgtgccg gcgtggggga agcaggtcgt gcgggcgcag gaacgccgtc aaatgaagtt  42180
ccgtatcaag ctcgactcgt tcccgcccga gatggtggcc gcgatgttcg gcgagcgggc  42240
cgcgctggcg atgcagttcg ccaacctgta ccggccgctg tggttcctcg gcggtgacgc  42300
atgagccgcc actactgccc cggcgaggac tgcgcgtact gccagcgccg gatcgaggcc  42360
atcgagtacg agcgtgactg tcccgagccc gtcgacgact actacgacgg cacctagacc  42420
ccaccggccc ggcggtggtg aaacaaccgg gcacgcaatg taaatcgagt gaatcaggag  42480
aatcgagatg agcgatctcg ccggtttctt cggcagtgga gtcccgtcag cgaagttcaa  42540
cgccattggc gacacggtcg gcggcaagat cgtcgccgag ccgacgatcg agcagcagcg  42600
tgactacgac actggtgcgc cgctggtcta cgacgacggc aacccgcgta tgcagatggt  42660
cattacggtg cagaccgatc tgcgcgacc cgaggtgcct gacgacgacg gccagcgccg  42720
cctgttcgtc aagggcgcga tgaagtacgc catcggccag gcgctcaaag ccgccgggaa  42780
gcagcagccc gaggtcggcg gcgagctgta cgtgacctac acgcacgacg gggagcagaa  42840
gaacccgcgc ctgaacccgc cgaagcagtt cgcggctcgc tacaccccgc ccgccccggc  42900
ggcgcagttc ttcaacgggg cgcaggcgca gcccgctgcg gtgactcagg ctgtcgcggc  42960
ggccccggcc gctgtggccc cggctcccgc cccggccgct gctgctgtgg ctcccgcgcc  43020
ggccgcggtg gctccggcac aggctgcagc gcccgccccg gcggccgcac cggctgctgg  43080
tgttccggcc gggttggaga acctgccgcc cgaggctctg gaagccctca agcagttgca  43140
gggcggccag cagtagcgag tctccccggc gagcggcgtc gacaggttgg cagccagcgc  43200
gccgccgccg ccggggggctc accctcacc cagccagata accgaataag gagtgaacac  43260
agcatgacag cggcggccgt gaccgtctac accactggac cgcagtgcca gaagtgcaac  43320
ctgaccaagc ggttcctcaa caagcgcggc atcccgttca aggaggtgcg cctcgacaac  43380
gaccccgaca cgttagacca gctcaaggcc aacggctttg gcattgcgcc ggtcgtcgag  43440
gcccgcatcc ctgacggcag cgtggaccgc tggtgcgact tccggctcga ccgtctggaa  43500
gccctggcga aggcgatggc agcgtgaccg tctactacgc cgacagccgc atgacgctgt  43560
accacggcga cgcctacacg gtggccgatg gactggcgag cggcagcgtc gacagcatcg  43620
tcacgtcgcc gccgtacttc ggtctgcgca actacgggca gcccggccag tacggcatcg  43680
aggcgacccc ggccgagtac gtcgagaagc tgcggaagct gtttggcgag ctgcgccgcg  43740
tcctggccga cgacggcacc ctgtggctga acctcggcga cacctacaag ggcaagaacc  43800
tgctcggtat gccgtggcgc gtggcgctgg cgctgcagga cgacggctgg attctgcgca  43860
acgacgttgt gtggcagaag cccaacgcga tcccgcagtc gagccgcgac cggctcaccg  43920
gccgctacga gcacgtgttc ctgttcgtca agcagtcgag ctactggttc gacctcgacc  43980
cgatccgcgt caagtacgac ggcgaccggg ccgccagccg ccgggcacgc agcggccggg  44040
tcaacaaggc gaacagtgtt gcgtccgagt ggaaaccgga cgacagcaag ggccgcaacc  44100
ccggcgacgt gtggacgatc ccgacgacac cgttccccgg ctcgcacttc gccacgttcc  44160
cgcaggagct gccgcgccgc tgcatcttgg ccggatgcaa gcccggcggc gtcgtgctcg  44220
acccgttcca cggttccggc acaacgggtc tggtggcgct cggcctcggc cgccgctacg  44280
tcggcatcga gctgaacgcc gcctacctcg atctgtcact cactcacccg aagcgcctgg  44340
cgcagatcac gacggaggtt gcgagctgat gggacaccgg cagaagggca agggctgcaa  44400
gcgcaagcgt tcgtggcacc ggctcggtaa ccaggaccgc ctgtaccgcc gggcgatcga  44460
```

-continued

```
ggcgctcgac gccgcccagc agcgcgcgat cgagtacgcc gaggtcgacg accgggaggt   44520
ggtgcgccgt ggcgcgtaag tccgacatgc ggctgctggc gctgcaggag tggatcatcg   44580
agacccgcgc cggcgggcgc tgcgagtgcg acggcctgtg cggcaagcgg caccggcgct   44640
acggcatcga cgacgatccg cgctgcccca acaagcacgg ctatgacgcg atcgacggcc   44700
gcaaggtcat ggtgtcgctc atcgtcgacc gggtcgacga gatgcagggc gacaccgacg   44760
tgaatctcat cgcgctgtgc cagagctgct cgcggcggca ccgggacaac ctcagcaagg   44820
ccgcagccga gcgcgcggag cgtgaagccg ttgaggcgca gcacgatccg ctgttcgacg   44880
tggacctgtt cggagccgca gcgcaatgac cggcgggcgg tgggcaggtg cggctcgtgt   44940
cctcctatcc gcgagcccct gcccgccgct cgtcccacac gacgacgtga ggacagacga   45000
gtgaatttct cagacctgtt ggaagccctc aactttgggg gaggtgagta cgtcagcctg   45060
ttgaccgtcg accgggacgg caacgcacag tcgagcgtcg tcggcgctga ccacgccgcg   45120
cgcgttgctg acgcactctg ccggatgagc gaccgcaatg tgtacttcgg cgtcaacccg   45180
acccggcggc gcgaggaagg cgagaagggg cgcggcaacg cggccgacgt gacgcggctc   45240
gcggcgctgt tcgtcgacct ggacgtgaag cccggcgggt gcgacagcta cgagaccgcg   45300
cgggcgatca tcaccgacct gtcggcaatg ctcggcaccg caccatcggc gatcgtgcgc   45360
accgggcacg gcctgcaacc gtattggccg atcgaagacg gccagctcgg ccccgagcaa   45420
gggcacgtca aagcggccgc gctgctgcgc cgctggcgtc ggctggtcga ccgggtggcc   45480
gaggcgcacg gcgcgaaggc cgacaacgtt cacgagctgg cccgccagct ccgcgtgccg   45540
ggcagcttca acgtcaaggg tgagccgatc ccggtcgtcg ccgaggtatc gccgggcggc   45600
ccgctgaccg tggcgcagat cgacgaggtg ctgaccgatc agggcatcgt cgagaccgag   45660
ggcgacctgc tcgaccggag ccgcgacgcc gagctggtgt cgacgccgcg cgactggcgc   45720
tactccgaca caccgtgccg gtacgccgtc gaggcgatca agtcgtggag gaccgacgtg   45780
ccgccgaagg gtcggcacca gtggatgctg gcgcagctca cccgcctggc cgcgttccac   45840
cggcgcggct gcctgaccga ggaactgcac cgcgagggcc gccgggtgat cgagctgcgg   45900
ttcaccgagc tgtgcgagca gggcatcggc ggcgacccgc gcccggtgaa gcaccgcgag   45960
gtcgacgagg ctgtgcccga gagcgttcgg tgggcggcct cgatgaccga ggcgcacctc   46020
gtgtccgagg tcggcggcca catgcacttg cgcgacagtg acccgactgc tgcgccggcc   46080
gcggccggct cgagcggcga gcccgtgacc agcgcaaaca cggctggccc ggctgatatg   46140
ccgcccggcg gcccgagccc ggccgacacc gcgccgcagc ccggcagccc ggcagcccgg   46200
caggacgaca gcggcccgac cgtgttgacg ccgtggcaga tgaccgacgc tggtaacgcc   46260
gatcggctcg tcgctcggca cgccgatcgt gtccgctact gccccgacat gggccgttgg   46320
ttggcttggg acggcgcgcg gtgggagctg tgccccgagg acagcccggc ctatcaggcg   46380
gcgcgggaga ccgtcgagag catccggccg ggtgacagcg aggctgtggc taagtggaag   46440
ctcaagagct tggcgcaggc gcggctgcag gcgatggtgt cgctcgctaa gcgtgacccc   46500
gagctgcagg tgcgtgtcga cgacctcgac ggcgacccgt acaagctgaa cacaccggac   46560
ggtgttgtcg acctccgcag cggcgagctg ctcggccccg atcccggcgg ctggcacacg   46620
aaggtgaccg gagtcggcta cgcgccggga caggttgcgc cgcgctggtc gcggttcctg   46680
caggacacgt tcggcgacgg caacgtgtcg ctgaccgcgt atgtgcagga gttggccggg   46740
ctggccgcga tcggcgaggt gcgcgagcac gtgctgccgt tcctgttcgg ttcgggcgcg   46800
aacggcaaga gcgtcatgtt ggacgtgttc gccgaggtgc tcggcgacta cgcgatcacg   46860
```

-continued

```
gcaccggcga cgttcctgct tgccgggcgg gctgagaagc atgagacgga gattgcgcgg   46920
ctgcgtggcg ctcggttggt cgtgtgctcg gagattaacg ctgacagcac gttcgacgag   46980
gcgcgcatga agatgctcac cggcggcgac aagctcaccg gccggttcat gcggcaggac   47040
catttcgatt tccggccgtc gcatctgttg atgctcgcgg gcaactatca gcccgaggtg   47100
gcgtcgggtg gcgattcgtt ctggcgtcgt atgcggctgg tgccgttcac gcgcacggtg   47160
cccgctgacc gccgggtgga ggggctggcg cagcagctcg tggatcagga aggcccggcg   47220
atcttggcgt ggatcgtggc cggcgcggtg cgtgtgctgg cgcaggggct gtctgatccc   47280
gatgaggtga ccgaggcgac gagcgagtac gccgagcagg aggatgcgct ggcgcggttc   47340
ctcgatgagt gctgcgagcg gctgtcgctg cccgccggga ggaataccac cggggaggta   47400
gccaacgctt acgcgatgtg ggcgcgccgc aatggcgagc ctgagctgag cggccgccag   47460
ctcggcaagc agctcaaggc gcggttcggt atcgccagct cgaagtacaa cggcgatcgc   47520
gtctatcgga tgctgcggct caaggaggag tggctgccgt attcgttcaa ccggcacgcc   47580
gctcagcaaa cagggtcgtt tgtccctggg ggtgcccagt gattagggcg gtatcgggac   47640
atgtgaggga cgtttctaga gacgtcaaaa acatgcctct acctgcgaaa gggacatgta   47700
gggacatttt ttgcacacat atctcacact gctctgtttt ggcgctgttg tcccaggtcg   47760
ttgcttcttt cggagcgatt tctggggat atgcaaacca atgtcccta tgtccctgct     47820 ttgtccctcg gcaaatgtgg gcggtggttg tcggtgggta agcgggtgga gcgtcgggtg   47880
ttgacttccg acgactttct gatcgacacg cagatgaagc cgagccgctg ccggaagtgc   47940
ggcggcgcgg tgctcgcggg ctacgtcacc gggacgatga cgctgctcga cccggcgcac   48000
ttgtctttgc tgggggagac gatcgcgctg ctggctggtc tgccgacgta ttcgattgat   48060
gagtcgtcaa cccggcggcc ggcgcgggcg catcggcggt ggacggtgca tatccgcaag   48120
gggctgcccg aggaccggca cctgttcacg gtgcatcgct gcggctttgt gtggccgccc   48180
gcgcttctgg atgaccgggg cgatttgcgc gcccggctgt acccgccaac accggatgag   48240
tgcccgttct gagggaggtc gacgtggctg aggttgtgtg taaggactgc atcgccgagg   48300
ggatcacgac ggtgcgtaaa ccggcgctgg acgccgaggg gaatccggtg ccggggaagc   48360
ggtgtgtgac gcattggcgc gcggtgagga aggcccggcg gcagcgtgcg cacgagcgcc   48420
atgttgagcg gcagttctcg ctgtcaccgg agcagtacca ggcgctgtat gaggcgcagg   48480
gtggccgctg cttcatctgc cagcacgcga cgggcaagag caagaagctc gcggtcgacc   48540
acgagcacaa ccggccgggt tgcgatcacg cgcccgaggt cggttgtccc gagtgtgtgc   48600
gctgcctggc ttgcacgacg tgcaaccgca tcgtgttggg ccggtacagc gtccaagccc   48660
tagcgcgggc gatcgtcgcg ctagtcaatc cgccggcgcg ccgtgtgctg cgcaacacc    48720 aggaggtagt gcaggatga ccgacgagtt gacgctcacg gatgacgagc gggaggccgc    48780
cgaggccgct gtcgacaagg tgctcgacaa ggtcgtcgtg tcggccgacg ttgtgctcga   48840
cgcggcgctc gacgcgatca atgcccggcg gcgctcggag accgatcagc cggtcgggac   48900
gatcgtgcgg cacaagaaga ctgggcagct cgccgaggtc gtcgaggacc agggcgtgcg   48960
ccggttccgg ccgttgcagc gcgcgccgct cggcgtgggc gtgacggtcg acgacagcag   49020
cgactggcag acggtgttta agccgggtca cgaaacgctg ctgctcaagt cgccgtgttt   49080
tcctggcccg ctgatggcgt tcggcggtgc gccggtgaag ttcttcggcg cgggcggccg   49140
gggtgctgct gggccggtcg tctcgcccgg cggcggtggc cgtgcgggtt tcaagcctga   49200
```

-continued

```
cgtggcgcag ctcgacgacg acggggacca ggacgacgac gaggccgggg agtacgtcga   49260
gggcacggtt gtcgacgcgg tcggtttcgt gggcattccg cgcgctgccgc tggatggtgt   49320 gccgggcacg ttccgcgatc gggacggcga cttgtaccgg catcgcaatg gtgtgtggca   49380
gttcgccgat cgtggcgcgc ggctgtgggc cgagctgggt gatgtggaca tgctgcgcaa   49440
tttcgggccg taccgccggg tgcagctcgt caagtagggg atcgggagag gggagcgccg   49500
gatggcgacg gagtgcagga gctgcggcgg ccgcgccgag ctggtcgtgt gctggaagtg   49560
cgcgaagcgg ctgcgccggt tgctggttgg gcaggatgac gagccgggtt tggactggtt   49620
cgcgcagcgc ctggctgagc aggcttacgg gcaggcgaag atgggccggc ctggccgctc   49680
ggcgtcgggt ggcccggcac cgttgccgtt gaatcagcgc gcggctgagt tgctggctga   49740
ggtgaccagg gcgacggcgt cgtgggccgg tgaggtgctc ggtgtggatg gccgggcacc   49800 gttctcccccg gcggcttact gtcatgcgat cgcgcgggac gtggccgggt tgatggctgt   49860
cgacggcgcg gcgcggatga tcgctgatgc ggacaggttc aacaggcagg cgtcgcgggt   49920
gattaatcgg ccgcccgatt tgtactgcgg cccttgcccg aatgagctgg acgacggcga   49980
gcggtgcggc atggatttgc gcgcggaggc tgacgagcgg atggtgcagt gccgccgttg   50040
ccgcgcggtg tttgatgtgg agctgctgcg cgagcggcta ctgcagcacg tcgacgacga   50100
gcccaagagc gcggctgatc tgttgcggct gttccgctgg ctgggtgtga acgtgccgcg   50160
ttcgacgttc tactatcgcg tgaatcgggt gccgccgcgc atgttcctgc ataaggacgg   50220
gacgcggaat ctgcgccgcc aggagggctc gacgccgctg tatgcgtaca gcgatgtgcg   50280
ggcggcgatc gcgtgcgata acgacgagga ccaggccgac gctgatcggc cgcgtaagcg   50340
ccggcgtgcc cggcggcaac accaggaggt agcggggtga cggagcagct cgtggatgag   50400
gcgcagaagg cttatgcgcg tgagttgttc gagcgtgcgg tgaggaacag gaaggctgtt   50460
gcgtggtggc gtggcgcgcc gattacggat ggggaggcgg ccgctcaggt tgtgaccgag   50520
gtcgtggccg agcggcggcg tgcgttggcg ttggcgttgc ccgaggggaa ggtgctgcgg   50580
tgacgttgat tcggtttctc gacgggccgc tggccggtga ggtgcgcgac atgcccgcgc   50640
cggttggcgg ttgggctcgg gtgcagcaga ttacgtctga tccgcgtgac ttgttgggtg   50700
agggcgcgga gctgcaaacg cggctggtcg agtatgtggt gaagcgcaac ccgtatggcg   50760
agccgggtgt gccgcatgtg ggtgcggtcg gcgagaaggt cggcgagaag gtgcgtgtgg   50820
tgctgacgac ggctaaggag gcgctcgctc acttcggccg ggacacgatc gagcatcacg   50880
cgatgacgga gttcgcgcgg gcgtgcggtg agttcgggtt ggtgccgtcg tgtgtgcgga   50940
aggtgttcga gggcaccagg cgggacgcga tgagcacgga gtgggagttg gtggttccgc   51000
gcgatttcgg ttacgactcg gtggtttttc atgtgtggga ggctgtcgcg gccgcgccgg   51060
atggttggcg gccggatgcg tagcaccgtg tgttgacagc cctacacgtt tgtgtagagt   51120
gccctacatg accgacacgc acatgactca agccgaggcc cgccgtatcg ctaccgagct   51180
gatccgcaag cacggtctga ccgggtggac ggtgacgttt gacaatgcgc gacgccgcgc   51240
cgggcagtgc cgctacacga cgcgaacaat cagcctgtcg aaaccgctga tggcgcagcg   51300
cacctacgcc gagacgatga acaccatcac gcacagctg gcgcacgcgc tggtcggccc   51360
cgaccacggg catgatgccg tgtgggcgcg caagcaccgc gagctgggcg gcgatgggaa   51420
gcgttgcttt gagcacttcg accacaccgc gccgtgggtg ggtacgtgcg ggcacggcaa   51480
gcagttcgcg cgctaccggc agccgaagaa tctgcacgtg tggcgttgcc gctgcaccaa   51540
ggctggcagc ccgatcacgt gggcgcgcaa cgctgcccgc ccggcggccc ggcccgcgcc   51600
```

-continued

```
gacgccgagg ccggttgccc gcccggcggc tgtggcggcg cagcggtcga cgatcgactg   51660
gtcgcggccg atgccgagag gccagcagct cggtctgttc tgaccgccag gagcgccccg   51720
tcatcacggc ggggcgcttc tgtgttgaca cgtctacacg tacgtgtaga ctgccctaca   51780
taccgaccac caccgagagg caggagccag gaatgtacga ccacaaggag cttgagcaga   51840
tgcttttcgc cgaggaagcc gagcgccgcc gcgtcgagta cacccagggc cacgccgagc   51900
aggccgcccg tctgtccaag taatccgacc accgagggat aggagccccg ccatgaaccg   51960
cacgcccgag cagctcgccg cgatcaaccg cgagaccgcg atgctgaacc gcattctcgg   52020
tctcgaccgc acggccgacg agcgcgaggc cgacctgatc cgcaccgcga acaaagccga   52080
ggcggccgtc gaccggctgc tggccgaggc ccgcgccgcg ctcgacgctg gcgacccggt   52140
cgaggccgag gcgctgacca accgcgccga ggcgatgaac cgcacggccg ccatgtaccg   52200
ccgccaggca gccaacgtct gaggggatag gagaccaccg tgaccgatac gtctgctgtc   52260
aacgcgctgc tgagcgcgaa gctgaggccg cagagcaccg ccgagctggc cccgttcggc   52320
gtctacgcgc acggcggcgg ccgtggcaat ccggtcgtcg tgacggccgt ctacagcacg   52380
ccggcacgcg cgttcgcgcg gctggctgac gctgcgctgc tgctgtcggc cgccgggtac   52440
gtcgtcgagg acacgcgcgg cccgagcgtg ctggtgacgt ggccgcagga cgcggccgac   52500
gagctggccg agaagcgcct cgaatcgttc taccgctggc aggcgctgca gatgcgcgcc   52560
gacgaggccc gcgccgagta cgagcgcctg gacgcgctgc gggagggttt ggcatgaccg   52620
ggccgtacac gctgcgggtg accggccgca ccgctgctga tgtgccgtgg cttgtcgagg   52680
ccgatcgggc tggcgcgcgg ctgatgttcg gccgctggcg cgttgaggcc ggtttcctgc   52740
ccggtggccg gcggttgtcc atcaccgagg ctgagcccgc gtgagctgcg ccccgtcgat   52800
accggcgggg cgttttccgt gttgacatgt ctacacgctc gtgtagagtg ctctacagat   52860
cgaccgcaac gaggaaggag ccccgaatga tcgtccacta cgcgcccgag gtgcaggacc   52920
gccgcgagct ggacagcttc gtgcgcaagg tctacgacga gcacagcgcc gccggtgatc   52980
gcctgtcgcg cagcaactac gaggcccttg tgcaggcggg cgcgaacgct gtgcaccgtt   53040
tcggcgagac gttcgtgccg cgcacccgcg acggtgaggt gcatgtgatc gccaccaagg   53100
ccagccagtt cgcccgctga tccgatcgac acgagatagg agcccgcgat gaccgaagag   53160
accacctacc gcgccgctcg gctcgacgcc gagacgatcg acgacctggc cgcgctgccg   53220
tcgtcgagca tcacctacga cgatccgcag gccgacaaca acacgcgcgc ggcgttcgcc   53280
gccgaggcgc tcgtcgcgta cgtgcgccgg gttggcgacc ccggcgagct ggaaacggcc   53340
gttacggact tgctcggcga cctgcgccac ctgtgcgacg cgctgggcct cgacttcgag   53400
gacgcggcag aaatgtcgtt ctgccactac gacgccgaga ttcgcggcga gctgtgaaag   53460
gagctggacc gatggaattg atcgagtgca tggaaatcag cccgcgcggg ttcgcctgca   53520
cgcgaccggc cgaccacggc ggcgcgttcc atgtggcgca cactgacgag gtgcgcgacg   53580
gccgccgggt cgtcgtcgac cgctggcaga tcgacgggga ggcgtgaccg tggcgaagtg   53640
caagaagtgc ggccgcgacg ggctggaatg gctgcagaac aaggccgggc gctactacct   53700
ggctgatcgg ttctacggtg cgcgcggcag ctcgtggacg atgccgcact tcaagcagtg   53760
ccgaccgccc gagcccgagc ccgagccgcg ccaggtggtt ctgacgatca ccccggcggc   53820
cggcggcgat ccggtcgtgg tgtccgctca cggtgacggt ttcgaggccg ttcacgcgct   53880
gtgggtgttc gccgaggatc gcgggttgaa gatcggccgat cgctgggagc tgttcgggcc   53940
```

-continued

```
ggatggcgcg atcgcgtacg aggtcacgat caagtagccg agctgcacca cggagcgccc   54000
cgagccgaca tggccggggc gtttccgtgt tgacttccct acacgatcgt gtagagtgcc   54060
ctacatgacc gagaccgcag ccaccgaaac cgccctcgtg ttcaccaagg acaccagcag   54120
caagaccggc gtgaccatct accgcgcgac cggcgcggcc tacagcttcc ggctgttcca   54180
gctcgacggc gtctggtacc tcaaggcgac gccgctgggc cagattctcg gcgtcgagct   54240
gcgtttcgac acgatgcgcg acgcgcgcct ggccgctgcc cgcatcgacg acgccgaggt   54300
cgtcgaggac caggacgacg acgagccggt cgtcgcggcc gccgccgagg tcgtcgagac   54360
cccggtcgtg gccccggccg ctgccgagca gctcgccctc gacctcgatc cggccgcccc   54420
ggccgaggtg accgtgatcg cttgcgcggc cgccaagctc gacgagcccg tcccggcggc   54480
cgagctgtac acgagcgcca atttccggct gatgctgcgc gcggctcgcg ctcaggctgg   54540
ccccggcggc cgggtgctga tcctgtcggc gctgcacggt ctgctcgacc tcgacacggt   54600
cgtcgcgccg tacaacgtga agatgggcga cgcgggttgc atcggcgcgg ccgcgctggc   54660
cgctcagttg cgcgctcgcg gcctggacgt gcccggcgcg cgcatcacca ccctgttgcc   54720
gcgtgcgtac gctcagcggc tcgctgaggc tgtcgcgctg gccggtgagg ccgagcaggt   54780
cgacctgttc gccgacgcgc cggggatcgg ctaccagcgc gctgttgcgt cgcgcctgct   54840
ggctgaggcg tgttgacacg tctacacgtg cgtgtagact gccctacata ccgaccacca   54900
ctgagggata ggagcccacg atgaccgaga ccgccacctg gaccaaggac gaggccaagg   54960
ccgccgacgc caagctcgcc gagctgaccg aggccagcta caaggcaggc gctcgctacg   55020
atcgcgcgct cgacgcgatg caccacaagg ctggcgacaa gaagcgctgg ctgagccgca   55080
gcgtgtcggt ttgggggatg agcaccgacg aggcgcgcga gaaggcgctc gacgtggccg   55140
ccggatcgga ggacaagccg tggctgcgcg aaccggcccg caaggctgtc gaggcgttcg   55200
accaggcggc cgccgagctg cgcgccgcgc aggatgcgat caacgagcac gaggccgcca   55260
actacaaggg ctggccgcga ttcttcctcg tgcccgatgg ccacattcac cgctggaccg   55320
gctgcagctc gctgcgcccg acgacgcgga tcggctggct gcccgagctg tcgggtgaga   55380
ccgaggccga ggctgtcgag gcgcacggcg cgatgctctg cacgaagtgc ttcccgagcg   55440
ccccggtcga gtggacgcgc ggcaaggccc cggcggccga ccagtgcccc ggcagcggca   55500
cgtgggacta cccgcgcgag accgcccgca tgggctacgc cgcaggcaat tacgcgtgt   55560 gctcgcactg cggtgagcgc atcacgatca ccagcaccgg caagatgcgg aagcacaaga   55620
cgaagtgagc cgccccgcga gcgccccgtc gacaccggcg gggcgtttcc gtttccgtgt   55680
tgacagccct acacgcctgt gtagactgcc ctacatgagc aacaccacga tcacctacca   55740
gggccgcaag ttcgagctgt cgacctacgt cgacccgtac cccggcaaga acggccggga   55800
tcgcatctac tacaacgacg tgtgctgccg ctgcggcggt tccggcgtct accgctggtg   55860
gacctcgctc ggccaggccg ccggcacctg cttcaactgc ctcggcgcgg gcaaggtcga   55920
gcgcagcaac gcggtgtcga cgctgcgccg ccaggccaaa gaggacgcgc tgtggcgcga   55980
gtacggcgac cagctccgcg ccgagatgca ggccgccgcc gaggccgccg agaaggcgcg   56040
cctggccgag gaatgggcgc aggcgtggga cgaggcccac cgcgagcagg cccgccgcgc   56100
cgccctcaac aacgaggtcg tcggcgaggt cggcgagcgc gtgcgcaacg tcgaggccac   56160
ggtgcaggtc tcgacctcgt tcgagcgcgc cagcttcacc ggctacggca ccgacctcgt   56220
gaagctggtc atcttcaagc tcgacgacg ccgcgtcatc aagagcaccg gcaccggcct   56280
gaacctgtac gggctcgatc gcggcgaccg cgtcaagctg accggcaccg tgaagggcta   56340
```

-continued

```
tggcgagtac aagggccagc gacagaccat cctgcagcgc gtcaaggtcg aggtcgtcga    56400
ggctgccaat cccggcgact gaggccgcca ggccgccgcg agcgccccgc cgagctggcg    56460
gggcgttttg cgttcggcgt cgctgtaggt tcgcgctgtt agactcgtcg acgcagtagc    56520
acaactgtgc ccaaaagcgc cccgagccac ccagccgggg cgttttgcgt atcccgacca    56580
ggaggcccga cgatgagcgc cagcgcgttc gacccggcgg ccgacgacga ggaccgggtc    56640
gacggcgagc tcgacgaggc accggccgat cgcagccccg ccgaaaaccc gcccagcagc    56700
catgtagaca gccctacacg gccgcccgag ctgttcatac cggcgaagcc attcgagccg    56760
cccacagggc acgtacgcac caaatacgag ccgttccgct ggtgaaccat ggccggccgc    56820
aacacaaccc gccgcgaccg gcaccgcagg atcatcgcca gcggcaatca tccgaacttc    56880
cccgagcctg aaccgccctg ccacgtctgc ggattgccga tcgactacac agcgcaccac    56940
ctggacccgc tcgcgttcac gatcgaccac atcaccccgc tggcgctcgg cggcgaggac    57000 acgtcgaca acctcggccc ggcccaccgc aaatgcaacc gggccaagtc agacaagccg    57060
cccacgtggc ggcccggcgt cacgttcgtg actgagagac ggtggagcgc gtagtgatcg    57120
aggtcgacgg catcaagacg ttcagcaaca aggcggcgct cgacgcgctc gccgagctgg    57180
ccgctgccgt gccagccgac caggcgatcg tcgaggtcgg cgtctatcgc ggcggctcgc    57240
tgcgcacgat cgcacagcac gccagcgcgc acgtctacgg cgtcgacaca tggggacttg    57300
aaggcgcgta cgccagcggc tccgagcccg ccacgaacta cggcatcgac aacatgacga    57360
tcgctcagcg cgccgtcgcc gagctgccgc acgtgacgct cgtgcgggcg ttcagcgccg    57420
acgccgccca cgactacgac ggcccggcga tcgggctgct gtacgtcgac ggggagcaca    57480
cctacgacgc cgtgctgacc gacttccact cgtggcggcc gtacctcacg cccgaggccg    57540
tcgtcgcgtt cgacgactac cgcgccagcc accggccgt cgtcgacgca gtgcggcggc    57600
tcgtccgcga cgggcacctc gccgcgccga gcgtggccgg cggccgcctg ccgtttgcc    57660 agcgcgacca gcgcgaccct ggggactagc ccccccggcg cgcgccgcc tctcgcggcc    57720 at                                                                  57722

<210> SEQ ID NO 4
<211> LENGTH: 47148
<212> TYPE: DNA
<213> ORGANISM: Bacteriophage

<400> SEQUENCE: 4
tgcgttcggc tgatcatgta cgggtttcca ggttttggtc accccagcac cagcagtcac     60
aggggataaa agcccaggtc acgctcgagg acaggtgagc tgcctcacaa gggagaactg    120
ccactgaaac tttctggcga agtttcaccc attatcgggt gaggggtaa agaggggaa    180 ccattaaagg aggggtgcc agaggcgctg cggccagcgc cgaccagccc gctgcggaca    240
gcgggccacc ctccaataga ccgccgtttt cggcggcggt cttacttgac atatgacaga    300
ggcaccgcct cagagcggtg ccctcaggag aggtcgaaga cctcactcac tgtcgttcgg    360
tcttctctgt cggcagccgc cgaccacagg cggctgcctc tataaggggg tgtccatgag    420
ttggaactcc tcagaccgca gcagtcggct tccggccgac tgggaggaga actaccggca    480
gcccgttctg cgggcagccg gataccggtg tcagattcgc agacccggtt gcctcgggaa    540
ggcaaccgat gtggatcaca tccgcagagg agacgatcac cgtctcagca acctgcaggc    600
agcgtgcagc cgctgccacg ggaagaagtc atccgctgag ggccatgccc gcaagcgaga    660
```

-continued

```
gttacgagcc aggaggaagc gaccgaccga acgccatccc ggctcccgtt gatcagcggg     720
ccgggagccc gcttctcacc caggaggtgt caagtgggcg agcgaggccc agttcgcaag     780
aggtcggatc agcgcatccg acgcaacaag gacgcggtac ccaccgagaa ggtggttgcc     840
atcgggaccg tcgaggtccc ggaactcggg ttcgaggacc cgcatcccat cgttcgtgat     900
ctgtatgaag ctctgaagga ctccgcgcag tcgcgctact acgagccaag cgactggcag     960
tacgcgaggc tggcgctcca cttcatcgac gggttactga agagcccgaa ggtgaacggc    1020
caggtgctcg ccaccgccaa ccagatgctc agcagtctgc tcgtcagcga gggcgaccgc    1080
cgccgcgtgc agctcgaagt cgagcggcag caggcagagg gcgtcgttgt cgacgtagcg    1140
gagatgttcg ccaagcagct cggcgcacag cgcaagggct gatcccgcag accctcccgg    1200 aggggggttga gcgcgttttc ctctcggcgc agctcccccct tccgggactg gaaccgacta    1260
cctgaaagga acaagaccca tgtccgtgat cggaccccag ctcgaagccg acacgctcgt    1320
cctgacgcgg ggccgcgact tcaagtggtc gttcgagaac ctcgatgcgt ccggacagcc    1380
cgtggacttc cccgaggggc agctcttctt cgagttcgat acgagcccga agacgctctg    1440
ggacttcgtc atcgacggtt ccctcgcgac gatcaaggtc gaatccgagg acgcagacct    1500
gatccccgcc cgcacgaagt ggcaactggt cttcctgcca gacggagagg ctggcggcgg    1560
cgaccccatc gcactgggct cggtccaggt ccaggggtga tccgatgagg ctgcgaggat    1620
tcccgactga cggtcggccg gcggtctcct acgtcggcac tcccaccggt tccatcgtcg    1680
gcagcctgca gcagtccttc ggccgcatcc gcgtccgcac gcagccccgt ggcgggctgg    1740
tgtcagtccc caccgagacg ccgcgaggca tcgtcggcct gtcgcggcag ccgtcgcgac    1800
tgttcgcact tcccggtcag gtcggcccgc aggggcctcc cggcccggag ggcgcaggcc    1860
tggtgatcga cggccaggtg gacagctacg acgacctccc cgagaccgca gtggacgggc    1920
aggtctggat cgcaggcggg ctgctgtacc gctacgacgg cggttggccc gacgaggcat    1980
ccggagcgcc cgtagagggc gtcccaggcc cgcaggggcc acaaggtccc atcggccac     2040 aaggtctgca gggaccccga ggattcaccg gagagcaagg cccacaaggc atccagggac    2100
cgatcggacc ccaaggccca caaggcgaga cgggtccgga aggtcctcag ggtccaaccg    2160
gcccgcaagg gccgaagggc gacaccgggt cacaaggccc tcagggtgag caaggtccac    2220
agggcatcca aggcccccag gggccacaag gcccgcaggg tgagaccgga ccccaggatc    2280
cacaaggtcc gcaaggcatc ccgggtcccc ctggtccgca gggtgaggaa ggaccggctg    2340
gtccgtccgc gtacttcgtc gcggcgctca acgggttcat cggcaccgaa gcggaatggc    2400
tggagtccct cgtcggcccg gaagggccgg aaggtcccga aggacccgaa ggcccccaag    2460
gaccgcaagg tccccaaggt cctgcgggac cgaagggtga cacgggcgcg cagggacctc    2520
agggcctgca gggtccaaag ggtgacaagg cgacaaagg cgacaagggt gacaccggag    2580
cccaaggacc acagggcatc cagggaccgc agggtccctc tggtaccccg tcctcgaacg    2640
gcacggtgct cgacttcgtc aagatcaccc aagccgccta cgacgcacta gcccgaagg     2700 tagcgacgac gttctacgtg atcgtggggt gacacatggc gattcgactc ggcagcgtta    2760
atccgaatgc gttccgcgtc ggcacccaga ccccgagccg gatttcctc ggcaacgacc     2820 aggtctggcc cgagttcact gaagtcaggc agcagttctc cacggcaggc gcttacacgt    2880
tcaacatccc agcgggctgc ctctacatcg acgtgattct ccttggaggc ggcggtggtg    2940
ggcgcagtat gccgctggca ggtgtggggg gcgaggtgg ccgcgcaggg acctggtcga    3000
cctacacgtt gcgtcgtggt gttgacatcc cttggagcac agcccagatc accggcacgg    3060
```

-continued

```
ttggtgctgg aggtgcgggc ggcgccgcag cagtcggcgc gaacccggc aaaccaggtg      3120 gcgcgaccac ggcaaccgcg accggagtcg gcactctctc ggcggcaggc ggcgcgggcg      3180
gtggaaacgc ctttgacccg aacggccaag gtgcgggcag tcgaacggtc aacggcgtgc      3240
tctaccaggg cggtgcagaa agagcctcgg tgggtacggg cctagcgggc aacccaccgg      3300
gcggcggtgg taccgcatcg caggtctcgc tcttcatcat cggcaccgca ggcggcaatg      3360
gcgcaccagg cagcgcgtgg ttccgtgcat acgtctaatc ggcgggcttc gcccgcccct      3420
tgatctgtag ctcaaccggc agagcacccg gctgttaacc gggccgttgg aggttcgagt      3480
cctcccagat cagcacccac cccgtcctct cgtcagggcg gggtctttta ggcgcgtagc      3540
tcaattggta gagcagcggt ctccaaagcc gcgtgctgca ggttcgagtc ctgccgcgtc      3600
tgctatttga catcgcacat agagaggaag acatgggaat cctgaagacc atcgggaacg      3660
agatcgccaa gacgctggtc ccccgcgtgg tggacaccgt ggcgaccgag atcgagaagc      3720
acatccccgc gctgaccgag gccctggtga ctgcggtcac ggaggcaatc gaacagcgtg      3780
ccgacgacgt aaccgacgcg atcccaggcg atctggacga ccggatcatc gaccccatcg      3840
tcaagcgcgc cctggacatc ttccgaggga ggagtcgatg acggaacggg tactcccta      3900 cgaccgcaac atcgtcccgc aggagaccgg ctggtggtgt ggccctgcgg ccacccaggt      3960
cgtgctcaac tcgcggggca tcatcatccc cgaggccacg ctcgccaacg agatcgagca      4020
gatcgagaac cccggccggg gcgacgaccg ggacggtacc gactacgtcg gcctgatcga      4080
gcgggtcctg gaccgtcggg tcccgcaggc tggctacacg tcggtctaca tgccgaacga      4140
cccaccgact gccgcacagc gagaggcgct gtggcagaac atcgttcgtt cgatcaacgc      4200
cggatacggc gtgatcatga actgggtcgc tcccccgagc aacaagccgc gaggcgtgaa      4260
gggctctccg aatccgcgct actcgggcgg caccacgtac cactacgtcg cgtgcatggg      4320
ctacgacgac accccggcg ctcgggcgct gtggatcgct gactcgggct tccagccgtt      4380
caactactgg atcagcttcg accaggctgc caccctgatc ccgccgaagg gctacgcata      4440
cgcggccacc accgcgacgg ccccggcccc cgcaccggct ccggtcgacg ccgcgccgat      4500
cctggcgcgt gcggcgggca tctccgaggc caaggcccgc gagattctgc cgacgttccg      4560
cgacggcctg cggctggccg agtgcaacaa cgtcccccgg atcgcgatgg cgattgccca      4620
gtggggccat gagtcggaca acttcaacgc gacccaggag tacgaccacg gccggaacca      4680
cggtgacccc aatgaggtca ctgaccggtg gaagtacaag ggacgcacct ggattcagat      4740
cacctggcga ggcaactacg aacggttctc gcgctggtgc ttcgaccgca agctggtccc      4800
gacgccgacg tacttcgtgg acaacccgcg tgctctggct gacgttcgct gggccggcat      4860
cggtgccgcc tggtactgga cggtcgaacg cccgtcgatc aaccggctct gcgacgaacg      4920
caacctcacc gaggtcaccc gcctgatcaa cggcgggacg agctgggaag cgccgacgtg      4980
gatgaagcac cgcaaggagc ggtacgaccg cgccctggcg gtcggtgacg acctgctgaa      5040
actactgcac ggagaggagg agggcttctt gagtgccctg accccgaagg aacagcgcga      5100
gctgtacgac gagatcatga agcgcgggcc gagccgctcg ttcctggccg acgacggccg      5160
tcagttggaa accctgctgg gcttcatcta caacatcgac ggcaacgcct ggaacatcct      5220
gaacgtcatc ggattcctgc tcggcgtccc ctacgccgtt gagcatgtgc gccgggtggc      5280
tgagcacggt gtggcaccgg gctcctacgc cgcccagaac gagttcgtgc gcgagtacgg      5340
ccaggagttc tgcaaggcgc tgctcccgct ggagggaaag ctgcgcgacc tgctgaacgc      5400
```

```
ccaggagttc aaggtgaccc acaaccgggt catcgagcag tgagcgaccg ctggctgttc   5460
acggtccacg gcaccggcca gcccgacccg ctcgggcctg gcctgcccgc cgacacggcg   5520
cgacaggtgc tcgacctgta ccgctggcag cccatcggca actaccccgc atcggcgttc   5580
ccgatgtggc gctcggtgat ggacggcgtc cgcgagctgc gtgtgcagct tcgccgggtg   5640
cgtccggagg acgaggtcaa cctggccggg tactcccagg gcgcgatggt cgtggcctac   5700
gtcctgaagt acgacatcat gaacccggca ggcgagttcc actacctgct gtatcaggtt   5760
cgcaaggtcg tcttctgggg taatcctatg cgtcagcagg gaattgccca cgatgaccgg   5820
tggattcacc ggatcgccgc accggacacc cacggcatca tggaggaccg tctggagggt   5880
ctggagcacg ccccgttcga ggtgcgtgac tacgcccacg acgaggacat gtacacctcc   5940
atccgcgacg acgacatgca cgaataccag atcgccatct gcaagatcgt gatgcgagcg   6000
acggactggt tcatcgggga gaactcgatc atgcaccagc tcatcgaact cggtcagcgg   6060
ccgatctggg aaggcatcgc cgccgtcaac gccgccatcg acgcgctcaa gttcgccggg   6120
agcaccgcgc acggctacaa catcggcccc gcagtcgagt ttctacgcga cttgacatga   6180
cacacggaag gaggagcggt gagcctgaac aactaccatc cagcgccgct cctcccgcag   6240
ccaccgcaca agatcggccc gatctgggcc gtgcgggagg acggctcctg gtacctgcct   6300
gagaagaccc tcggctggga gattctgaac tggctggcgc agtacgtccg gtcgcccgca   6360
ggcggcgggc cgttcctgcc gacgctggag caggcccggt tcatcctgtg gtggtacgcg   6420
gtcgatgacc aaggccggta cgtctaccgc gagggcaccc tgcgccggat gaagggctgg   6480
ggcaaggacc cgctgtgcgc ggccatcgcg ctcgcggaac tctgcggccc cgtagcgttc   6540
tcgcacttcg acgccgacgg caacccggtc ggcaagccgc gccacgccgc gtggatcacg   6600
attgccgctg tctcccagga tcagacgaag aacacgttct cgatgttccc ggtcatgatc   6660
tccaaggagc tgaaggccga gtacggcctg gacgtgaaca agttcgtgat ctacagcgag   6720
gtcggtggcc ggatcgaggc cgcgacttcg tccccggcgt cgatggaggg taaccgcccg   6780
acgctggtga tcgagaacga gacccagtgg tggggcgttg gtccggacgg caacgtcaac   6840 gacgcgtcg acatggacga cgtgatcgag ggcaacgtcg cgaagattcc gagcgcacgc   6900
aagctcgcga tctgcaacgc gcacattccc ggcaacgaca ccgtggccga gaaggcatac   6960
gaccactacc aggacatcca gtccgggaag gccgtcgaca caggcgttct ctacgacgcg   7020
ctggaagcgc cggccgatac cccggtctcg gagattccct cacagaagga ggacccggaa   7080
gggtacgagc ggggcatcga caagctgatg gcgggcctgg aggtcgcccg aggcgactcg   7140
tactggctcc ccctggaaga gattctgggc tcggtgctga acaccaagaa ccccgtgtcg   7200
gagtcccgac gcaagttctt gaatcaggtg aacgcacacg aggattcgtg gatcgccccg   7260
aacgagtggg accggctggc gctgaccgac aagatgttcg cgctgaagcc gaatgaccgg   7320
atcacgctcg ggttcgacgg gtcgaagtcc aacgactgga ccgcccttgt ggcgtgccgg   7380
gtcgaggacg cgatgttgtt cgtgctccgg gtgtggaacc ccgaggactt ccctgggdac   7440
gaggtccccc gagaggacgt ggatgcggta gtccgctcgg cgttccagcg gtatgacgtg   7500
gtcgccttcc gtgccgacgt gaaggagttc gaggcatacg tcgaccagtg gagcaaggac   7560
ttcaagcgga aggtcaaggt caacgcgacc cccggacatc ccatcgcatt cgacatgcgc   7620
ggccagacaa agcgattcgc tctcgactgt gagcggttcg tggatgccgt gctcgaacgg   7680
gagctgtatc acgacggcaa tcccgttctg cgccaacacg ttctgaacgc ccgccgcacc   7740
ccaacgacat tcgacgcgat ttccatccgc aaagagagca aggacagcag caagaagatc   7800
```

-continued

```
gacgcggctg tctgcgcggt cttggcgttt ggcgcgagac aggactacct gatgagtaag      7860
aagcatcgca gcggtcgagc ggtggtgatt cgctgatggc aacaaagagt ccgctgcaac      7920
agcagcaggc gtccatcgac gtgaatctcc gtcgcgagca actgctgaac gagttccaag      7980
agaagacaac cgatctcgaa gacaacaccg cgtactacga gtcggagcgg cgtccggacg      8040
ccatcggcat ctcggtcccg cctgagatgc aggacctgct ggcccatgtc ggctatcccc      8100
gcctctacat caacgccctg gccgaccggc tgaagatgga gggcttccgg atgggcggcg      8160
ctgaggaggc cgacgagaag ctgtgggact ggtggcaggc caaccagctc gacgtggaat      8220
cgacgctggg ccatgtggat gcactggtgc atggccggtc ttatgtgacc gtctcggcac      8280
ctgacccgca gttcgacttc ggcgtggacc cgaaggtccc gatcatccgc gtggagccgc      8340
cgacgaacct gtacgccaag atcgacccga agagccgcct ggtcaccgag gcgatccgag      8400
cgatctacga cgagaacggc aacgaggtca cctcggccac cctgtacctg ctcgaccaga      8460
ccgtctactt cgacaaggtc gagagcgagt gggtccagac ccgagccgtc cagcacaaca      8520
tgggcatcgt cccggtcatc ccgctggcga accggacccg gctgtccgat ctgtatggca      8580
ccacggagat cacgcccgag cttcggtctg tgaccgacgc agcggcccgg acgttgatgc      8640
tgatgcagtc gacggccgag ctgatgggtg tacctctccg actgctgttc ggcgtcaccc      8700
gacgcgagct gggcatcccg gacgacgacg aggcggtcac accgcgtcag gcgttcgagg      8760
cgtactacgc ccgcatcctg ggcttcgagg ccccggaggg caaggcgtac cagttcgacg      8820
ccgccgagct tcgcaacttc gtggactccc tggacgccct cgacaagaag gcagcggcct      8880
acaccggcct cccgcccag tacctgtcgt tctcctcgga caacccggcc tcggctgagg      8940
ccatccggtc gtctgagtcc cggctggtga tgaacgcgga gcgcaaggcg ctgatcttcg      9000
gtggggcctg ggaacaggtc atgcgcgtgg cgcacaaggt catgaatccc ggctctgaga      9060
ttcccccggc catgtaccgg ctggaggcca tctgggctga cccgagcacc ccgacgtatg      9120
ccgccaaggc cgatgccgcg agcaagctct acaaccaggg caacggcatc atcccgaagg      9180
aacaggcccg gatcgacatg ggctactcgg tcgagacgcg ccggaagatg aaggagtggg      9240
acaaggagga gaacccggtg ggtcagctcg ccggcctcta cgctccgcgc cccggacagc      9300
ctcagcagcc tgagaagcca gctccgaatg agccccccgc caaggaggtt ccgcaggagt      9360
gaacgctgac gagtacgccg cccagcaagc ggtgatctcg gcagcaatcg cccgctacgt      9420
ccttcagcac gcgaagttcc tccggacccc gtcactgacc gtgacggact gggtcaactt      9480
cctggagctg atcttcccgg aggtctaccg acgccggttg gaagccgccg agctagctcg      9540
ccagttctac gacagcgagc gccaaaagca cggcaggcca ccacatcccc ggtacttggt      9600
cgagtacgac ttcgaggagt tcctggacga catggagccc ctccgcacgc ggttctcgcg      9660
tgctgacgcc cctgactccg ctccgggcga actcgctctc cggatcgtcc ggtcagtcga      9720
aatggctggc cggaaacaga tcatccgtgc cgtggagaac gatccacagt ccggagtggt      9780
caagggctgg gcgcgggtcg cgactggccg agagacctgt tactggtgcc tgatgctgat      9840
cagccgagga cccgtctacc tcggggctga cacagcaggc ttagacctcg atgacacgac      9900
ggcagccgaa atgatcgctg ccggtgagga tgtcagcgag tacatgcggc agtggcatga      9960
cgggtgcgac tgcaaggtgg tgccggtcta cgaccgacgc aactggcccg gttacgacgc     10020
atggaagcga gccgagcagt gtgtggatcga ggccggtcga gaggccgacc ggctcatcga     10080
gtccgggaag gcacgcacca ccaacgtgaa caaggagacg cagaacgcgc tccgtcgtcg     10140
```

-continued

```
tcttgagaga ggcgacattt ccatgtccga gttcgctgct ctcgcagcgt aattcaccaa    10200
ccaaggcccc caggtggggc tgtcactacg cccaggaggc aaacaccaat gtctgacacc    10260
cagacgacca gcaccgagac cccgagcacg ccagacaacg gccaggagcc gaaggtcgaa    10320
tcgttcagcc gggagtacgt cgaaggactc cgtcaggagg ccgcgaagta ccggaacgag    10380
aagaaggacg ccgtcgaggt cgccaagacc gagacccgag ccgaagtggt tcgtgagtac    10440
gaagcgacgg tcgccgcgaa ggacaccgag atcaccgatc tcaagtccca gctcgattcc    10500
accacgctgg agctgaccaa gctgaaagcc gttgtggaag cgaagattcc ggtcgaagac    10560
atcctcgatg tcgtgaccct ggttcagggc accgacgagg aatccgtctc ggagagtgtc    10620
aatcgggtca agacgctact gaacaaggcc cccgcgagcc accccgccta cgaccacacc    10680
cagggcgctg gcggcggtac tcccccgctc aacggagacc cggttctgaa gattctcgaa    10740
caggcagtcg gcgctaagtc acgccgccgc tgagcgagac aaccccacca acgaaggaga    10800
taacactatg gcagtcaacg gagtgcaggt ccctacggac caggtcgccc tcactggcga    10860
cttctccgcg ttcctgaagc cggaacaggc tcaggactac ttcaaggaga tcgagaagac    10920
ctcggtcgtc cagcggatcg cccggaagat tccgatgggt ccgactggca tcgccatccc    10980
ccactggacc ggtgcggtca gcgcgtcgtg gaccggtgag gccgagcgca agccgctgac    11040
caagggcagc ttcgggcaga aggaactgaa gccggtgaag atcaccacga tcttcgctga    11100
gtcggctgaa gtcgtgcgtc tcaacccgct gggctacctg gagaccatgc ggaccaagat    11160
cgccgaagcc atcgcgctga agttcgacgc cgctgcgatc cacggcatcg ccaagccgag    11220
cgagttcgag ggctacctgg ccgagaccac caacgaggtg tcgctggtgg atgtcgacca    11280
ggccacggcc aacgcccagg gcaacgccta cctggcggtc aacaacgcgc tgtcgctcct    11340
ggtcgacaac ggcaagcggt ggaccggcac gctgctcgac aacgtgaccg agcccatcct    11400
gaacaccgcc gttgacgcca acggtcgtcc gctgttcgtg gagagcacct acaccgagca    11460
ggtcggtgcc atccgcgagg gccgcatcct gggtcgtccg acctacgtcg cggacaacgt    11520
cgtggacggc gaggccggcg agcgcgtggt cggcatcatg ggcgacttct cgcaggtcgt    11580
ctggggccag atcggcggtc tgtccttcga cgtgaccgac caggccaccc tcgacttcgg    11640
tgaggtccag ggcggcgtct gggtgccgaa gctgatctcg ctgtggcagc acaacatggt    11700
cgctgtccgt tgcgaagctg agttcgcgtt catggtcaac gacaaggacg ccttcgtcaa    11760
gctgaccgac aaggtcgaca ccgaggtcga caccgagggc tgagcctgac ttgacatcgc    11820
acaccgggag gccggggctt cggccccggt cccctggtga gcgagaaagg accacatgag    11880
gattcgacac aagatcaacg gtggtcacgc agtcgtgagc gacgaggtgg gtgaacgtct    11940
cgtcgctggg aacgtctggg agcgcgctga cgctccgaag ccacaaacgc cgaagcgccg    12000
caggcgcagg gcatctgaga agccagcaga ggtcgtcaac gacggagagt gaggtaagac    12060
atggcgattg cgactgcaac tgacgtagag aatcgctggg tccgagaact ctccgaggaa    12120
gagaccaggc tcgtcaacac gcggctggcc gatgccgagc ggatgatccg tcgccggatc    12180
aaggacctgg acgacaagat cgacgccggg gacatcgatc ccgaggacgt gaaacaggtt    12240
gaggccgaca tggtcctgcg gctgctccgc aacccggagg ggttcacgca ggagacggac    12300
ggcaactaca cgtacatgct gcatcagcag ctcgcctcgg ggaagctcga agtcactgac    12360
gacgagtggg agacgctggg catccgcagg cgcgggatgt cgtcctgta cccgcagatc    12420 gtgaggccga catgacgcaa ccgcagtacg gccccgacaa cgtcgatgtc acgaaatgcc    12480
atgacaacga cgagaatccc gagcaccact gcgtccacga ttggcgcatc cattgggggca    12540
```

-continued

```
acgtcgaccg gaggcagttc cgatgagcct cctcgaccgt tgcaatcagg acgtgatcgt  12600
gtacccgcag gaggtcacga cggacgcgga cggtaacacg agaacccgtc ccgccgccga  12660
agggattccg accaaggcga ggattcaggt cctcggccag tctggcactt cgtcccgtcg  12720
acaggagcag gacaacgagg gtttcgagtc ggagcgggtc taccagattc acttcacccg  12780
gaagttcgac cgcgagaacg gtcctctcgg gatgcagtcg cagatcgagt ggatgggtgt  12840
ccggtgggct ctcttcggag aaccggccta ctacaccggc tctcgtcgta ccgagcacat  12900
cggttacacg atgaagaggt actgatggcg aagctggtcc gaaagtccgt cttacatcac  12960
atcgtttctc atctcgatgg cgtgaaggcc gcagtccggg atgccaccga cgagggccac  13020
gacaagtcgc aggctcggtt ggaggcagct cgggcgtcga cccagtggca caagatatac  13080
ggccctgacc acctgaccca ggtgaccaag acctacggcg acgtggacgg cttcatcaac  13140
ctcgaagcgc ccaacgcgat ggcaatcgag ttcggccacc agccgtctgg tgtgttcgag  13200
ggcaccgaca cgaaatcccc tgagggcctt tacatcatca cgaagggctc cggggccgtg  13260
tcctaaggaa ggagggttca tggcagagat gccccgcatc caggccgtgg tcatccccct  13320
cctgcgggat gccctagtgc ccgagaaagc cgccaaggtc ggatcgtggg tggagaacat  13380
caactaccgc gagttcccac tgatcaacgt ccggcgaatc ggcggtactc ggcacgaaac  13440
ccggccgaac caactgtcca agccggtcat cgaattgacc gcctatcacc aagctgggct  13500
catcgagtgt gaagagctgt acgaggacgc cctcgaagtg ctctacgacg cggtgaagaa  13560
ccagacgcaa accgaggcag gctacctcca ctccatcaag gagacgatgg gagccaccca  13620
gttcagctca ccgttcatgg actcctggag ggtccaaggg ctgatcgcac ttggcctcag  13680 accccccacgc aagtaaggag atacaccaca tggcactcaa cgacaatgcg gtgttgaccg  13740
ctgcagtcgg ctacgtgtac accgccccgg tgggcaccgc tgcgccggcc gcttcggctc  13800
tcgacaccct cgacctgtcc aacacggcag actggggcgc tggcctcacc gtctgggaca  13860
gcgtcggcca caccagccgt ggcgacatgc ccgagttcgg cttcgacggc ggtgacacgg  13920
aagtccgtgg cacctggcag aagaagaagc tgcgcgaggt cacgaccgaa gacccggtcg  13980
actacctgct catctacctg caccagttcg atgaggacgc cctggcgctc tactacggcc  14040
cgaacgcctc cagcaccgct ggtgagttcg cggtctcggg tagcgccgat cccacggaga  14100
aggcgttctt cgtcgtgatc gaggatggcg atgtccgcat cggcttccac gccgccaagg  14160
cgtcggtgcg ccgggacgac gcgatccagc tcccggtcga tgagttcgct tcgctgccgg  14220
tgcgcgccac cttcctcaac cacaacagcg agccgctgtt caagtggatc aacgaggacc  14280
tgttcccgaa cgccggttcg ggcggggggcg gcgaaggctg acccatactt gacatcgcac  14340
acgcgatgtc gcagtgaccg aggggggaggg gtttccttgg cgggccttcc cctcccccctc  14400 ttactactgg cccgcctcat caacatctac gaaaggtccg ctatgtcaaa gattttcacc  14460
ctcgactcgt tccgcgaaga ggtcgagaag gagttcgctc cggtcaagat cgaggtcgac  14520
gccgacaaca gcgtcgtgct ccgcaacctg ctgcgtatcc cgaagggcgc acgcgaggag  14580
attttcggtc tgctccgaacg catggacaag atgtccgagg gcaagtcgga agacgagatg  14640
accgtcgagg agcttgaggc cactgctggc atcgccctcc ggatgatcga actcgtcgcc  14700 gacacccccgg ccgggggccg gattctggtc gagtcgttgg aggacgatct ggcgttgacc  14760
ctcaaggtgt tcgaggcatg gatggaggcc acgaatccgg gggaagcgcc gcgctcgcac  14820
gactgattga cgactacggc gatgccgtcg ccgctgacct gatggagaca tacggtgtgg  14880
```

-continued

```
acctccggga cctcttcgtc ccggagtccc gcctgactcc gaagtgggtc ctcgtcctga   14940
tcaaggagct gccggtgggc tcccgcttct actcagagaa gcgtggtggc ccccagttcc   15000
gtggttggga tgagtcgagg tacaccctcg cggcaatcgt caacgcggtg cgggctcttc   15060
agcacacgta cctggcggcg cacatgaagt cgacgccaaa gcccccgag ccgtatccga   15120 ctcctgatcg gaacaccagg aagaagaaca acaacaagcc caactcgttc gcgtccattg   15180
cggcgcagat gatcgcggcg aagcgagcga agaaagcaag gaaggcggca caggagtaaa   15240
tggcaggagg cggcgcaggc ggtaccgaag tcggtcggat ttcgatccga gtcgtcccca   15300
atctggacaa cttctaccgc gaactgaaga ccaagctcga agcgattgag aagcagcttc   15360
gaggcaacgt cccaatcgac atcgacctga atgccaaggg cactcgggcc aagatggcgg   15420
ctctcatggc cggtctcaag gcccaggcag cccaggcgt ggatgtcccc gtcgatgtca   15480
acaacaaggg cctcggggct gcatggcgcg agttccgcgc cggtctggcc gacttcggtc   15540
ggctgggcaa gcaagcggcc cagggtgtca agtcataccg cgacgaagtc aaccggctga   15600
cgctggaaca gcagcgccag cgccctctcc tgaaccacac gtatgcgtgg tggcgctcga   15660
acaacatcat ggcccgtcga ggggccacga tccttcggga cttcaccgac gcactccgga   15720
cccagcagca gtggctgcgc cagcaggacc gcaccctgac ggccaaccag gcccgatgga   15780
agtcctgggc gatggcgatc cgggacgcga acgtgaacgc caccaacggc ttccggcgct   15840
tccgggcctc cctgcaggcg ctgcgaggcg gcggtggtgg tgatgacgga gacgggttct   15900
ctcgcatctt cggctcgctc ggccggttcg gtaatgaggc cgagaaggct ggcagccagg   15960
tcgagcacgt cggcaagaag ttccttggcc tgacccggat gggctggctg gtcacaggcg   16020
tgttcctggc ggctgccccg gccatcgccc tggtgtctgg cctcctggcc ggtctgcctt   16080
cactgatcgg tgcgttcggt gccggtatcg gcgctgtggc gctgggcatg gacgggatca   16140
aggcagcagc cgaggtcctg atgcccgcct tcgagcagat gaagacggcg gtctccagca   16200
ccttccagca ggctctggtc ccccagttcc agcaactgct ggggctcatg ccgatgatcc   16260
agaccgggat gcagggtgtg gcccaaggca tgtcgagcat gttccagggg gtcaccgacg   16320
cgctgtcgaa gggcgcaggc cccgctcaga tcgagaacct gctggcgaac acgaagacgt   16380
tcttcgagca gttgcagcct gcagccaacc agttcaccca gtcgttcctg acgctggcta   16440
gctcgggctc cgacgcattc ggctacctgt ccgggtcgct gaacacgttc tcgactcagt   16500
tcaacgacat ggtgaaccgg gtctcgcaga acggcgtcat ggacggcgcg atgaagggtc   16560
tctcgcagac cctcgacggt gtcaccaacc tgttcacccg actcatggag tcgggcctgc   16620
aggcgatgag ccagctcggt ggaccgatga acaccttcct cacggggatc ggtgatctgg   16680
cggtcgcact gatgcccgcg ctgacctcgc tgtcgggtct gttcggcaac gtggctggga   16740
ctctcggtac ggctctcgca ccgattgtca cggcgctgac gccggcattc acgacgctcg   16800
cggacacgct gggctcgctg ctggtgccca acatccagac gctcgggaac atcctgacgc   16860
ccgtcgcgac gatgatcggc acgacgctga ccacggcgct gcagcagatt cagccgatga   16920
tccccggcct ggtggagtca ttcgctcagc tcggctcgac gctggtttcc caactggcac   16980
cgcatatccc ggctctcgcc acggcgatgg gccagatggt ggagcggtg atcaagctcg   17040 ctccgatgct gatcagtcag ttggtcccgg cgttcatcga cctgatcccg tcgatcacgc   17100
agctactgcc tcacgtcgtg tcgctggctg agtcgttcgc ccggatgatg ccgaccatcg   17160
tcccgctggt gtcgatcatc ttcagcctga tcgccgcctt cgcacaggcg ctgcgacca   17220 tcggtggcgt tgtcctgggg gcgatctcgt ccctgatcgg ggttatctcc gaggtcgtcg   17280
```

-continued

```
cgaagatcag cgaatgggtg tctagcttcg cgcagggcgt gtcggacatc gctgccaagg   17340
cagctgagct acccggcatg gttaagtccg ctctgggcga tctgggctcg ttcctggtgt   17400
cgtccggtaa ggctctggtg cagggcttca tcaacggcat caagtcgatg gtgggtgctg   17460
tggctgacgc cgcacgaagc gtcgtgcagg cggcgcgaga cttcttcccg ttctccccgg   17520
cgaagaaggg tccgttctcg ggctctggct gggtggacgc ctcgggtcag tctgtgggcg   17580
aagcgttcgc agacggcctg gccgggacgc agggcaagat tgtcgagacc gctcgggcca   17640
tcatgcaggc cgcgaaggac gtgttcggtg acgctgccaa catcgccttc aacttcaact   17700
tcggccagat gcagagccag atggcgtccg tcgcgtcgag cgcgggtgat ctgcagcgca   17760
gcatgtcccg caccgtgtcc cagtcgactg ggtccgggaa gattgacgac gagactcgcc   17820
agatgctcga ccagatcagc atccgcaagg acgagctgga gctggaacgg cagaggctgc   17880
aggccgagaa gaatgccctc gacaccaagg acaaggccgg tagggctgcg ctccagcagc   17940
gcatcgacga gctgaacatc cagaaggatc agctcgaact gcagcgtgag cagttgtcgt   18000
accagagcaa gtacaccgac tcggtggccc agacgggcgc tcagtacgac gagatgttca   18060
acaagctgac caggatgccc tacgacttcg ccacggcgaa tgccaaccag ttcctctcgg   18120
acatcggcat ttccggcgat ggggctctgt cccaggcgct caaggagggc ctgaagttcg   18180
gcgagcagtt catcttcaac gtcggctcga tggacgaggc cgtgcagggc cagcagacca   18240
tccagaacaa gaagtcgttg caattcgata ggaggtaacc cgtggacacc ctcgtagaac   18300 tggaggggg caacggcgaa tggttcaccc tggccggtcc cggagaaggg gaccgggggg   18360
tgtacctggg tactgacgtg aagggtctct acgacccgcc cgtcaaggtg gtgtacgagg   18420
agccgggcaa ctaccccggc tcccgctacc tcaaccaccg gattctgaag cgtgacatcg   18480
tgtttggcgt cgagattccc aacgacgctg ccatcggtcc taattcgtgg ctgtctcggg   18540
aatcggagtg gcgcaaggcg tgggcgttcg accgcgactg caagctctac atcacgaccc   18600
cggaatccgg taccaggtac ctgaagctcc gtctcgcgga gtcgcccgag gtctcatggt   18660
tcaccgatcc acgcggtaac aagatcaacc gcacggtcat ggtgtgtgtt gctggtgacc   18720
cgttctggta ccaggacgat gtcgtgtaca ccgctgtgac gcaggaagat acgacgttcg   18780
acccgaaccc gctgccgtgg ccttggccga aggaggagct gcccaccgag accctgacca   18840
tcacggtcga cccgtctgac ggcaagggcg gtctgaatcc gaccgaccag ccgatctggc   18900
tgaagtggat tctgcctggc tccaccgagg agccggccga gccgtacatc cccggtatcc   18960
cctggctggg tgccccgaac tcccctgccg tcatctggac ggtcccggac tactcgttca   19020
ccgaggcaga tcaggccaac cggcgcatcc ggatgcccgg tctgatcggt ggcctgcgga   19080
cgtgcgaggt ccaacagatc agcctgatcg gtaaccccac aggcggctcg ttcgtgcttg   19140
agttcaaggg agacttgaca tcgcccatag cgcgtaacgc gacggcggca acggtcaagg   19200
cgcgtctgga ggccctgccg agcatcggct cgggcaacct gaccgtggcc ggtggtccga   19260
cgctgctgag cccgcaccag ccgtggcgcg tgtcgttcac tggcccggac ttcgcgggtg   19320
aaccgcagcc gatgatcacc gtcgacagcc acacgctgac cgacagcgac ggcgattcca   19380
acacggtccc gaacgtgcgg gtcgaccgca cgaccgaggc tctacacggcc ccggccgaga   19440 acgccgtggt ggacacggac ccgcgtgttg agcaggtctc gtcggagaac ggcagccagc   19500
tctgggcacg catgaacggc gtccggttcc acaacccggt gccgccctac acgaagtcga   19560
agacattcga gatcactgtg agcggagcgg ttccggggca gatggtcgtg ctccgcattc   19620
```

-continued

```
cacgggcatg gactaggccc tgggggctcg aatgagcaac cacgccacca tctccaccct  19680
ggaggacgct aaccgcgtct ggaacaccgt catggcccgc agggcatggc gtgaggcaga  19740
gcggctgaag ccgcctctga tccggctctg ggacggcgac atgaccctcc ggggtgtcgt  19800
cgccggggag cgtggcggcg acttcgagtt catcgagaac gacacgggca cagcgtcgat  19860
ccagctttcc ctggatcacc acatggcgaa gtgggtgatg aacttcaagg gccgcgccaa  19920
gcggaacgtc atcatcacca tcgacaagca gggtgctcgg tggtcgggct tcatggacca  19980
ctaccgggtg gtgcgtgagg agaacgggga ctgctacctc gatgtcgtgt tcaagcacga  20040
ctacgagcac gccaagcaca tcctcgtctg gtgcaacccc ttcctgaggc ccgagctgca  20100
gttccccaag ctgtggatca tcttcggccc tgcgaagtgg tgcctgctgc tcacgctgtt  20160
cgtgaacatc ctgcgactcg aaacgtcgct gtggacgctc ccggataacc cgctcgatcc  20220
gtccgaatgg atgccgctga gcttcaacat cagcaactgg aggaacatcg tcaagccgtt  20280
cccgctcatc ggggacaact ccaacctgac gattgtcttc tcccgcttcc agtcgttcca  20340
cgacgtggcg aagaagacgc tggaggacgc tcagctcacc atcgtttgcc ggcgctacct  20400
caagggcgaa gacccgcacc cgttcgagaa ccttcgcggc gagctgaaca tcggcccgct  20460
cgaagacctg ttgtcgctca tcccgattcg gcatggctgc ctggtctggg acatcatcga  20520
caactcgggc tggggcacgg agaccgcctt cggcggctcc tggctgacgg gcttcatccg  20580
ggcggtggtc aacatcgcct cggacggtat gaccgagggc gtggacgtgt tcacggggga  20640
cccgacgttc cccggcgagt actacacgcc gtggttcctg gggacctccc cacaggcccc  20700
ctggatcgtg ttcgaggaag gcccctacac cggtatcaag tcctcggagt tcaagtacta  20760
cgaggccact gacacgtcct tcgtggctgg cggtgagtcg atgcccggtg tgaacgaggc  20820
gatctcggct gccgtgaaca tgggtggcga cttcttgaca tcgctcatca acagcgccct  20880
ggcgagcctc ggtgcggtgg gtggtgccat cgacctgccg ccgttgggcg gcatgatgga  20940
cgcagtcgcg aagccgttgt acgagaacgt gttcctggcc ttccaggagt acccgacgct  21000
ccgggcggtc ggcacaccgc tgccgatccc actgctggag tccagcgaga cgggcctggg  21060
tgacttccac tactacgagg gctgggtcga gaacgccacc aaggcgttca cgctgtcggc  21120
gttcctggcg accagggcca aaatctggga gaccagggcg cacacggccc acaccatcaa  21180
ggtgtcggac gcggctccgt actacatcgg tgaacccggc tacggccact tctggctcgg  21240
atcgcgggtc gggacaacgg ttctcggctt ccccatcccg gacaccgtgt tcgtggagcg  21300
ggtctcgaag atcagctaca agtggggcaa ggacggcccg aagggctggg agctggagat  21360
cggctaccgc gaacctcagg accccgtcct gaagctgttc gagctgatcc agcggttcaa  21420
cggcgcgatg ggccagctag ggattctgta actacgacgg gacggcgcac ctcttcgggg  21480
gtgcgcctcc cactgaaagg cacgccaatg atcaagccgc aggaggaggt cgactggaag  21540
aagcccgagg agcacttcgc ctgggctctc cggaacatgc cgaccttcgc aggtatcggc  21600
gcggtgacac accctgggtt cctccagaca tggtcaaagc acctgtggga ctgcgggttc  21660
gcacaccgcg actaccttga gtcgctggcc gacgaagacg gcaacattca cgtcagcaag  21720
ctgccgaagc aacgcatccg gtggcaggca ccgttccgtg gtgcccgaag taactacaac  21780
aacgcagcgc gttgggtgtc gatggatacc ccggctccga gccgatgaa gctccccgac  21840 gttcggcaac tgacccagca ggagaacgag ttcatgctgc ggcagtaccg agagctgggt  21900
ctgatcaacg actacgtccc acagcgtgat atcgcacaag aattgaactg aggcaaggga  21960
aatggcagct ttggatgaca cccagccgct cgacctgagc gagctgttcg atgaagacga  22020
```

-continued

```
cgaactcggt ctgaacgatc tgatcggcgt ttcggacgaa gaggttgagg ccgcacggaa    22080
gaaggtcccc gagcccgcgc tggtgcgcgg cgggatcatg gccgtcgtcg gcctgatcgc    22140
cttcgtgctt ggcaagcaga tcgacaccgc atgggtcgaa ccgctgatgg acgtgtacgt    22200
cgtcggcgct cccctggcgc tcgcctggtg gattcgccgg aacgtcacac ccgttggaaa    22260
gcacgcaaag tgactccggg cttcgatccc accgactggg tcgacttggt cgcctacgcg    22320
atcctgacgg tccccgcaac catcggtgcg gtcgcagcat ggcgcagtca ccagaaggtg    22380
aagcagacgc actacgagat caccaacgat cacgactcca acatccggca tgacattgac    22440
gacctcgcca aagcagtccg cgacgggttc atcgacatcc gaagggacat cggtggcctg    22500
cgcgaggaac tgaggaccga gcgactcgaa cggatcgaag gagacaagct ccgggtcatc    22560
aactgccagt aaggaggtag tggatggata caccgaatcc taatccgaac aacggtcctg    22620
gtaccgagct tgagaagtgg ctcggcacag gcgcattcga gctaggtggt ggcgactaca    22680
actacggcca ggacttcacc gaagcagctg tgcggcagat gttcgagctg ccggccatca    22740
cgctactgaa cgccgtcgac ctgctcgaag agcagctcct gaagatgccc attgaggccc    22800
tccgggtgtt cgcaccgctg atcccggatg ccgtcgagga cgacttcgtg gatgtcgtca    22860
cggcggtcac caagatcatc gacaccctga ccgatgggcc tgcggccctc ctgcggggcg    22920
agttcgatga gtggctggag agcaccttcg gcaacctcgc taccgaggtc cagcagattc    22980
tggagattct ggccgagttc gtcgtgaccc cgatcaacgc cacggtccag gccgtcaagg    23040
actggtggaa cttgatcacc ggtcggacgc agcacctgaa ctcgtccggt cagctcgacg    23100
catccaagct gacgaatctc gtggacatgc cagagattcc gaatggcctg gacaagatgc    23160
ccgacctcca gaacctggtc gacgccgcca cgaacgcact gtcgggcgcg tcccaggtcg    23220
gtgaggagat catcggtgcg ggtctcgaca tcgcgaagaa cacgatggag aacctcttct    23280
ccatgctgtc gaaggtcacc cgcgacgtgc aggcgctgca gtcggagcag gaggccagcc    23340
aggtcggtgg tcgacggttc aacgtcgact tctcccagta cccgaacggc ccattcccct    23400
ctgggctgtt caacatcacc tactccgggc ctgggaccag caccctggct gtcagcaacg    23460
gcaaggcggt ctggaacacg gtcaacaacg gctaccgccg tgcgaccctg atctaccccg    23520
agccgacact gaccccgttc caggtcgtgc gtggcacgct gtcgtctccc ccggagcaag    23580
gcacgaacgt ccgaatctgg tcgattgctc gcgccaacga gacgggcacc gacttcgtgt    23640
tcgcacgcgg gtactgcaac ggcttcctga gctaccgagg cgacatcggc tgctacaagg    23700
acggtgtcga gtacgtctgg gcgtccaacg tcgcactgac gtggtctctg gacatgaaga    23760
tcgtctgcgg cgtcggtaac gatccgcgcc accacatcgt cctgtctggc gacaagatcg    23820
tcatcgacct ctatgagcca gccgacaagc agtctcgggt ggacgagaac cactgctact    23880
ggggctctat cgcggagacg gacggcgtca gggtccctgg caacgtggcc ggtgcgtcgg    23940
tggtcgacaa cgctccccg gccgtcgtcg gtacgacgct gcgggtctcg aagcgatcag    24000
ggggcgatgt caccatcgcc agtggtggct cgaaggtccc gaacaacttc tacgagacca    24060
tcgactacca gtcgcctgac ctgatctatg agcccagcaa gaactgccgg gtgactgcga    24120
cgaaggcagg cacctatctg gtcgagtacc gggcgtacca cggcgcgttc gccaccaaca    24180
ctggcgggca cgcgcagatt taccgcaacg gcaacgtgta cgccaagggc cagtggggct    24240
cctgcccgtt caacgtcggc ttcggcgtca tgtccgatcc gaccgacgcc acgcacggct    24300
cgttcctggt gccactgaac cccggcgact acatcgaacc gggcttctgg ttctcggcga    24360
```

-continued

```
acatgtccaa cacgggtgac gccggcctga tggccggtgg cgcacagtcc tacatgtccg   24420
tagcccgact gggcaccaac taacacaaaa gacccccctc ccaaggacat tcctcgggag   24480
gggggctttt ttgcgttcta cgggaggtcg acctgaccct tgtcgtcgta gtacatgcac   24540
atcggatcgt tggcctcacc ggtcctacgg tcctgtgcta cgacctggcc gtcgaccgtg   24600
atcttgcacc aggcttcgct atcgcggcct tccgaggtgt tggcccaggt gtacagaccc   24660
ttcggcggct gcggcacgtc ctcgccgtgc aactcgatcc gggtgacgcc aggcgggtac   24720
tcgatgccgt tctcgaagtt gtcgtcgtag gtcgcgtagc tgtagttgcc accgatctcg   24780
aagaccacgg ttccccgctt cgcctcttcc ttggcggctg gagcggttgg agctgccgag   24840
ggagcttcct ggctgcaccc ggccagcagg accgctgctg ccgtcagagt gagagcgagt   24900
ttgtgcattg ttctccttcc ttcaggacct ggccttgagc gccagttccg acatcctctt   24960
cgcgatctcg acatcgcggg cctcagaggc catctgatac ttcatcgcca tgcgtggcgt   25020
ggtgtgtccg agacggacca tcagctcctt ggtggtggcc ccggactggg ccgcgtaggt   25080
cgcgcccacg gcgcgcagat cgtggacccg gaggtccgtt cgaccgatct tgcggtagcc   25140
cttcttcagt gaccgggtga acgcagactt cgacagccgc tggccttggg tcgtggtgac   25200
cagcagggcc tcaggcccct tgttcatctt cgtgcggtca gccatgtgct cgcggaccat   25260
ctgtgcgacg tgcggcggca cggtcaccgg cctcttcgac cggacggtct tggtgtcgcc   25320
cacgacgatc ttctgaccga cgcgggccgc gccccggcgc acccggaaca gcatcgtatt   25380
cccgtcgtcc atgatgtcct tgcggcgtag ctcgatcagc tccccgaacc gcaggctcgt   25440
ccaggcgagg atgtagaccg cgacccggta gtgctcatgg acctcggcgg cgacgatctc   25500
cagctcctct ggagtgaggg cctcaacgtc gcgctcactc ggggccttct gctcgatccg   25560
gcacgggttc tcggagagca tcttgtcctc gacggcggtg ttcatcaccg cccgcaggac   25620
gttgtaggcg tgcctgcggg ctgtcgggta ctgcttgccc atcccggccc accacgtccg   25680
gacgagggcg ggcgtcagct cggacaccgg cacgtcgccc agcaccgggt agatgcgctt   25740
gcgggcgtgg gtcttgtaca gctcgcgggt gccctctgcg aggtccctct cttcgagcca   25800
cttccgcgtg tactcctcca ccgtgatgga cgaggctgcc ttcttcttga tccgctcttc   25860
gggcggcgtc caggtctcca tctcgatgag acggcgctcg ttgttgagcc aggcttcggc   25920
gtccatccgg ttgtcgtagg tctgcggcgc gtagtagcgc acgccgtcct gcgggtggac   25980
gtatgaggct tggattcgcc cgctgcgttg cgtcttcagc gatccccagg aacgtcgtga   26040
tggtgccaac taggtcccct ttctcccgac agagagggta ccgatttgca actctattgc   26100
aactcccgag actcaacacg ctgccgcgac ctgcaatttc tttcaacttc agcgttgcag   26160
tagggagggg gtaaaaatct agtctgacct gctggaacag ctccagacga caccctttct   26220
tccaaactag ctacgcgggt tcgattcccg tcgcccgctc cgcaggtcag gaggtgtttt   26280
cgcctcctgg ccttcttttt tgcagagggt ctgcaactct tctgcaactc ccctgacctg   26340
ggcatatgcg cttgcatcga ggggcacggc tcagtaactt cccctatgaa gttgtaagtg   26400
aaaagcccct gacctgcgcc aacagatcag gggcagcaca ccagatggga gctggtgcag   26460
tgacaattgt cgcacgtcgg agagttgcac tgggagttgc aacggccgga accgtcgcag   26520
tcggagggct cgcattcgcc ctttcgttca ccgccctgag agacctctca gcgtccaacg   26580
gagtcagcca ggcgtggatg gtccccctcg tagtcgacgg cggcatcatc gtcgcgacgg   26640
cggcgaccgt cgccctacgc cagcaccagt ggtacgcctg gacctgctg atcctgtcct   26700 cgatggtgtc ggtggcaggc aacgtggccc acgcccaggc ccacggtgcc atcgcgatgg   26760
```

-continued

```
tgatcgcggc gatcccgccg ctgtggctcc tggcggcgac ccacctgacg gtcatgctct   26820
cgcgttcgga gaaagagccc gttccggtgg cagcggaacc gctgcatatc gcgaacgccg   26880
cttgactgcg cccggtcggg acacatagcg attcgtgcat atttcgggta caaaaaaaga   26940 gcccccgag ccgacccgaa ggccgacccg aggggcgggg tagttcatgc ccagttgccg    27000
atgggccgca tcagggcctc gaccgaatcg cgctcgatgc ggatcagtcg ggggccgaga   27060
cggacggcct tcagcttgcc gtcagcgatg tagttgcgga cggtcctggt cgacacaccg   27120
aggtgatctg cgacctgctg gatggatgca cgttggggca gcaatcagtt ctccttgggg   27180
tagacgacgc gctcgatccc ggcggcgtcg atcagcttct ggcacccagg gcagggtgct   27240
cgggtgatgt agagggtggc tccgatgagg tcgtcccggt cggcatagag cagagcgttc   27300
gcctcggcat gaaccgatac gcaccgggtg ggtccgctgt cataatcaga cacaccagga   27360
accgccgctg ccagtcggcg agggcaggta tcacaccctg gtcttccaga cggcgcaccg   27420
ttgtatccag tgcctcgtac tcgtcggtcc ttgacgacga ctgcaccgac tttgctcctc   27480
tcacagtcgg atcgcgtggc gacagccttc gcgatgatca ggaagtactc gtcccagtca   27540
ggccggctca cgcggtgtca ccctcacgta ggactccccg aagatcagga agtcgagctg   27600
gattccgtcc tcgtcggtct gctcccggag cggacggtgg acgcggcagt agccggtccc   27660
ccagtagttg cattcggggc agtccatcag tccctccgca cggtcccgga ccacagcagg   27720
ttgaagtccg catcccacag cgcgatcttg gtgccgtcag gcaggccgtc gatggacagc   27780
caaccgggct ctccccggac ccccatcggc ccctgagggc cggggggacc aggaggaccc   27840
tgacggacgg tgaaggacga gacccaccac gcgagcgccg cgaggacgac gagcgtgacg   27900
agcatcgtga tggccgcacc cggccagctc atgaaccagt cagcgtccat tggctccctc   27960
agtagaagat cggggtgtag gtcccaccac gggtcatcgg cggcacgaag atgacgccgt   28020
tcgggtaggt gtccgagtcc gacgagccgc ccgtgtcgtc acacgcggtg acgctcagga   28080
cggctgcgat gacgagcagg atggcggcaa tggtcttcac aggtgttcct ctctggtggg   28140
tttcctgagt cccattgcgc gggaccaggt tcgcttcggt ttgggcttcg gcttgggccg   28200
gtggatcatc cggaagctga cctcacaggt ggtcgagcaa ccgtccatct cgaagttgaa   28260
ctggggctcc cacaggacgc cccagtcctc accgtggaag gtggcccaga gctggccgtc   28320
atcgcgcttc tcgacaacca agaccggctc agccacgccc cagttcccta cgcagctcgg   28380
cgttttcgag ttccagctcc gcgagccggc actcgcggga gtcccggtcg tagtcggccc   28440
tgtcggcttc atccagggcc atgtgcagtc gccgggtcag gtccggaacg cagccgtgga   28500
cggcggcgat gaagtcggcg tcttcttctc gctcgaatga agcgacgaac ttacgcccat   28560
cgacggcgtc ggggtccttg ctggcctccg cactgaccgc ccagatgttg aacgtccctg   28620
ggccagcggc atagtgctcg gtatcctctt cgacggccca gaaggtgttc tcggccccgg   28680
tggttttcgc ccactgctgg tgcagcaggt cgaagaagtc acgatcttcc attcacgatc   28740
tccttcatcg cgggtgtcag ttcgtcgtgc ggcatcagcg cccggatgac ctcgggcagc   28800
ttctcctgcg gcacccgtgt ggtgatccgc agcagcaccg agttggtcat gaacgaccgc   28860
gagtcgctgt cgctgacctc gacgtagtag tcagggaacc aagggaagtc gcctttcaca   28920
ggacgccctt ctccttgagt gcctgcttca tctggtcgac cgtcgcgtcg aacaggtact   28980
cgcgatagtc gggggcctcg atgaagtcga tgtactcgat gagcgccttc acgctcgcaa   29040
cctcgtcgcc cacaacgact ctgacttcga tctccactac ttctccctct cttgcagctc   29100
```

-continued

```
gatcaggtgc tccaagagct gatcgagttc tcggtccttc tgatcgagtt cgacctccag   29160
ctcccactcc ttgcggcggt ggaagtcgat gccgacacgg aggcggtcaa cctccgtgtt   29220
cagctccttg acgcgctgtg ccagcgtgtc gatgacgacg ttcgccatgt cctctccttg   29280
tgcgatgtct agtactcggc cccgtaaagc gagccccagg agcgaccacc aacctccggg   29340
tcggtgccga tgagcaccgg acccatctgt tcggccatca gctccccgat gcgcttggct   29400
ccccactcgg cgtggtcggc cggaacggac gccagaatct cgtcgtggat cggtagccgc   29460
agatacggcg tgaaaccggc gtcgtgcagc cgcaggagcg cccgagcggt cacgtcccga   29520
ctggaggact ggatgaggta gttcagcgcg ctgtaggccc gctgagggtc cactggcagc   29580
cgccggcctc ccagtccgtc gatgaacggg gtcgtgatgt agccgttccg gatcgcttcg   29640
cgctgcagcc gctggctgag cttctggacc tcggggtagg ccctgtcgaa gccggatacc   29700
acctgctggg cctgagccat gtccaggccg gtctgctcgg ccacggtctt ggcaccgccg   29760
ccgtagaccc ggccgaagtt caccgtcttg gcgtacttgc gctctgggct gtccttggtg   29820
atctcccgat ccggccacgc cgcccgtgcg gtcttcaggt gcaagtcctc gtcgttgagg   29880
aacgcctcga ccatcgcctt gtcccgagac agagcggcca gcacgcgcag ctcctgcgcc   29940
tggtagtcga cggaggccat cttgtggccc tcgtcggcca ggaagcagcg ccggatgatc   30000
cagtcaccag acggcagcgt ctgggccgga atgccggtga tcgacatacg cgccgtgcgg   30060
gcgcgcaggg ggttgatcga ggcgtggcaa cggttctggg agtccctggt cttcaggaac   30120
gtgtcaaccc aggtcttgcg ccacttcccg gccttcttcc cctcgatcac tgcctcagcg   30180
aactgagaga cctcggggct gccctccatg accaacttcg acagcaggtc gtcattgacc   30240
tgtcgcttgc cactcggcgt ccgaccgatg atccggacgc ccatcgactc cagaacgtcg   30300
gccacctgat cggtcgagtt gatcttctcg cagccgaagt tcagagcgac ctcgttgtag   30360
tggctctcct tcaccttcag gtccagcgac agtccctcgg tgtactcgac atcgagcagg   30420
aagccctgac gctccatgta cgagcagatt tcggcgagcc ggtgctcgtt gtcgatcagc   30480
tcgtcccgga ccttcaccag cggtgccagc ttctggatca gccgtgcggc caggatcggg   30540
tccatgcccg cgtagaggtt gtagacgggg tcgaacagct cgaccttctt ccagatggtg   30600
gccttcgtga cgcccttgcg ggcggcagcc agctcagcca tcagggtctt taccttgtcg   30660
gccacctcgg agtcgacgta gtgccgaacc gtctcctcca gcgagtgacc gatcccgcct   30720
tcgtccttgc ccctggggtc gaccaggtgg ctcaggatgc gggtgtcctt caccttcggc   30780
cacatggtct ccatcgggac gctgaacgtc cgctcgaaga cctggaggtc gaacgatgcg   30840
ttgtggagca cgaagccgtt cacagccttc agggcgtcga tgacggcccc ttcgtaggca   30900
ggacccagct ctaccgggac cacccaggct tcatgcggag tgccgaactg gacagtacgg   30960
caacggaagt cgtcgctgta gatgtccagc ccggtcgtct ccgagtcgag tccgaggaag   31020
cccagatgag cccggatgaa gtcacggaag ccctccaggt cgtcctcggt ctccactacg   31080
cgaatgacaa cctcgtcacc cgcgacctca tgccggtgct cgatcatgga tgctcctatc   31140
ggtgataaac cccccggacg atccgggaga tggttgatcg gttcacgtcg aaggaccacg   31200
cgatctcggc ctgcgagatg ccgctgcggg ccatctcgcg gatgtacttg gcctcttcgg   31260
cgctcagctt cttgcggttc ggacggccgg cccccttggc gtggagtgac tcggcccgga   31320
gcttctcgac ctcatggcgc aggtcttcgt tctccgcgag gatgtcctcg atctcgtcga   31380
ggaccctgag aagggttggg gtctcagcca attgaggtcc cctccttctc atcgttgggg   31440
acgatcacgt agtggctgac gtgccggaag ttgaagacgg tgtgggcacc gtcgtcaccg   31500
```

-continued

```
agcacgtaca gagcgccctc gtcgggctgg aagatgacct ccccctggcc gatggcgatc   31560
aagccgttct ccaggtggac gcggacagtg cagttctgca tgtgttcctc tctgtcggtt   31620
acaggtagag cccgtcgttg ctgccgatgg cctcgcggac tgcgtccttg ggcatggcac   31680
cgaggagctt ctggaagtac tcagcgacct cgtcctcagt cgggatgtcg gtctcacggc   31740
tgcgggtgta gaccacctcg tcggcgcgga cggtgaccgt ctcgccctcg gtggtggtga   31800
tgatgtggaa gccgttgtcg aagttcaccg gcagataggt gagcgcgacg acggtctgac   31860
cattccgcag gccgaagtac agcagacggc ctttcttgtt ctcttccaag ggatttcctc   31920
tcagtagctg taggggtgt cggggatgtc ctggtaggtg ttgggcgcga tctcccggag   31980
ctggcgcagc agttcgcctg ccaggtcacg gatttcggca tccgctgcct catgccagcg   32040
ggccttgatg acgtagcgcc atgcccggtg gttgccggtc acgaccatcg gtgagttggt   32100
catgttcggc aggaccgccc tggccgcttc gcgggccttc ttccggggca gaccggcgtc   32160
cttgtacagc tcgaccaggc ggtcgtagga cttgatcgac tcctcgacgg cgttccgcat   32220
gtgctggaat gccagccgct gcttgtcccc gtccagctcc tcgatggccg gtgggatgtg   32280
gaagcccagc gggaccggat cgacgtaccg ctgcgacacc accgagaacg acaggtgccg   32340
gtggcgctcc agctcggtca ggaccgaccg gctggcctcg atgtagaacg tggcgctggc   32400
gtgctccagg acgctctcat ggcccacgtc gaggatgtgg ttgaggtagg cctcgttctg   32460
ctccgtcatc gggttcggcc ggtggaagga ccggtagcag ttccggcccg cgaactccgc   32520
gagttcgtcg gcggcgtagt ccccgaagta gggctcgtcg tcgggctcga cgtagccgtg   32580
aggctcgtag ccgatctcct gcagagcgtc cacgtcgatg tccgtggctg cgatcagctt   32640
gaccttcatg tgttcctctc gtcaggggtg gaggggaggcc ccgaagggcc tccctccgtg   32700
tgcgatgtca aggacgaccc atgtcagaac cagacggggt cctcgttgct gccacgcggc   32760
ggcatccacg cctgccaggt gccgttgccg ttcttcttct tgccggactt gtaggtccag   32820
tccggacccg gcgcgggcgg ggcgtcggcg ggcggctcct gcgcctgacg cggcgcgttc   32880
gagcggcgct gaccgccacc gttgccacca ccgttaccgc caccgttgga cggcttcggg   32940
ccgaggccgg cgaagtgctg gcccgcgttc tggacgcgct cgaacagagc gcccaggggtg   33000 gccgcgttgt caccggtcac ctgatcgaga gcgtcgtcca ggtcggtggc gtggatgacg   33060
atccacggag catcgaagcc cgtgccgccc ttgaaggtca gcaccacctt gccctcctcc   33120
gaggcgacga cgttggtcac cttgggctcg gccttcttag gggctgcctt cttcgccggg   33180
gccttcttcg gggcttccgg cggcggggcg tcgaacaccg actcttcctg ggcctcgacc   33240
tcgggggcct cggtcgcgac gggagcgttg gcgaaggggt cctgcatgta tttcctttcc   33300
ttgtgggtca tcgaatcggg cacgccccgg aggcgcactc ttcatcgact gagtcggcaa   33360
cggcctgagc ggtcgctgcc tcgtattcct gcttggtgat ccgctcgtaa ggtgcttgcg   33420
gcatagacga ttcggggaag atcgtcgcgc ccttcaagag cccgccgaat gtacggagct   33480
gctgttgtac gtcagcagcg gtgtacgtcc ccggatcgac gttcgccgtg aagctcacgg   33540
cgttgtcagc ccacagcatc tggtagagcg cctggaatgc gagaagctga ttcagcgtca   33600
ggtcggcagc cgactcgaca atcgactcag catcgcggcc gtaccggtcc acgacctcct   33660
ggacgagaga gtccttggtc gggatcgtga cgacccaggt gttcgctgcg tacatgtccc   33720
gctcgacgtg gtaaccatcg gcggcgtact tcgagcaggt caggaactgg tcattgtcca   33780
gctccgagaa ccggattcgg cggttgaagt acttggcgaa gatcgggtgg ataccctcac   33840
```

-continued

```
tcacaccagg catcttcgcg atggtccccg tcggggccac cgtcctcttc ttcaccggca   33900
ccgggatgcg aagctcatgg gcgaacttcg ctgcggcctc atcgacctca gatgccagct   33960
cccgcagggt cttccggaac tgcttgtccg taggagcctg cgagtacttc cggccggtca   34020
tggcgaggaa cgaggccacg cccaggtgcc cgacgccgat gcgtcggttc cggtccagca   34080
cctccctgga cttcgggtct gccacgggcg agaacgtcgc ccggatcagg aaccgggtca   34140
tcagccggtg agcccggatc aggtcgatgt agtcgacctt cccgttgtcc ttgacgaacg   34200
cggccaggtt gatgtggccc aggttgcagg gctcccacgc ttcgagcgtg atctccccgc   34260
acgggttggt gcagatgacc tcgttgggct cgcccttgtt cgacaccgac gagtcccaga   34320
acccaggctc gccgttggcg accatcccct cggtcagctc acggaggatg cggttgttcg   34380
gaccagccca gccttcctcc acggccaccc agaactcgtc atcgacctcc agcgagatgt   34440
tggtcgtcca gtggctgccg gtgtcctgct tgagccgaat gaactcgtag acctgtgggt   34500
ccttccagtg catcatcgac atccgcgctg accggcgcac accaccagcg accacacact   34560
gcgcgatggc gtggtcgatc tccatcgcgt ccaggccggt gatccgacga cccttggccg   34620
tgctcaacac gttcgcggtg ttgtcgagca tgaccgccag cggcaggggg cctgaggccg   34680
tgccaccgaa ggtcttcagc ttcgccccag cgggccgcac ccgagacacg tcgtagacgc   34740
ggttcttgtg cagcacgatg gtcgcgtaga aggtgtcgat caggtcgacc agggcagccg   34800
cccagccctc acgcgagtcc tcgatgacga aggcaccagc ccagtcggcg tcgtactcgt   34860
cggacaggac gcctgcgtcc ttcatcgact ggtagtccgg atggtccggg tcgcagacga   34920
tgtggacctt cagcgcgtgg ttgacctccg ggtagtcggc caggaaccgg ttgctgtagt   34980
tggcaccgac accgccgccc tccatgaggc gcatgaacgt gaactcgaag tgatccgagg   35040
gcttctcggt ccaccccgac acccagcagt tgaacaggtg ctgggcgttc ttcacgcccg   35100
acgcccacag gtgacggccg gccgggatca tcttgaactc ggtgatgagc cggatcaggt   35160
cgtcccgctc gccgtcgagc tggtaccgct cgtcgaccag ggcgaggttg ccgtccacta   35220
cccgctggac cgtctcaggc cacgtctcac ggctgccgtc aggcttggtc cgtgagtagg   35280
tgcggttgta gaccagctcg ccgctcggtc cccacttgac ttcctctgtc acgcagcgtc   35340
cttcaccagt cgcaggtacc ccggcgtgta ctcgccgccg cagtacatct cccgatcctc   35400
tgcaggccag ttgtcgacca acatcggctt gacatcgggg aagctgtccg gggccagcag   35460
agcccggtag ttctccgagc cgcccatgcc gttgaatgtg ctgtcgaaga tgctgtgact   35520
gctcacaggt agttccttcc ttcgagccct gcctgggctg cttgctcgaa catgttcatt   35580
ccgtcgtagt agctgtcctg gaccagctcg gcctcaaagt cctcctgcgt caacatcatt   35640
cgtccacctc ctcccccgtc aggtcggagt agctggcgtt gatgagctgg aggttgcttc   35700
gcacctggcg cgtgccgggg ccgtcgtccc gctcggtgta gcccgtccgg tggatgcggt   35760
tcatctcctc ggtgagggcc gtggtcccac ggttcaggtc gttcttctcg acctgtagcg   35820
tcggcggttc atcgaagagg taccgcttga ccacggcgtc gtgataggcg acgttccggc   35880
cctccaaggc gctcatggcc tttcggaggt cgagcacgga atccttcacc gggggcttgg   35940
attcgccacc cgagccgcct cgcccgccac cgctctcgtc cgtgggacgc tggacatcgg   36000
ggtccagctc caggtgcttg agagcaccgg acttgagcag gcccttgacc tcagccactg   36060
agtaccggta gctgcccttg tagtgggcgt agtcagtccg ctcctgactg gcgatctgat   36120
ggcccatccg ggtgaggaac cggcgcagtg ccttgtcctc cagccctggc agcttcgcca   36180
cggtcccagg ggattcgagc agcttcaggt agatggtctg ctcgacatcc tcggcctcga   36240
```

-continued

```
tcactcccgg ccactgggcc gacaccgacc tagcagcctg ggtgatgacc ttctggacgc    36300
gacggaactg atcgtcggtc agattgagcg atgtcaagtt tcacacctcc cagactcgcc    36360
catcgaccgt gaagcgaccc ttgtggacgg gaaccggttc ggccttgacg tggctgttct    36420
cgaccgtcag caggccgaag ccctgctgcc agttgccggt gccgcccttg aggtactgcg    36480
ccagcttctg gttcatcagg ttgccgacct cgaacccggt cagaatccgc ttcatctcgc    36540
cgccgtagcc ctcggtgtgg ctgccgatgc ccagccggtg ggtgtggccc atcacgaccg    36600
aggtaccgaa cttgcgggcc gcgttgagcg cggtgttgcc cgcgatccgg ctgatgctga    36660
tctgcccacg gtggccgtgg gtggtgatcc agcccggagc caccttgtag aactcaggca    36720
gcagttcgat gccgaagccg tcgaagtcga gcaggttctc gaagttgaag aacccctcgt    36780
actcggccag ggccggggcg tacttggtca ggtactcacg cggacgcagg tcgtggttgc    36840
cttcgtggac accgaacggg ccgtcgtaga ccttccggat gtccccgagg aaccgcttgc    36900
ccttctcgtt gtgttccctc atccgcttgg cgaactcctc ggccgtgccc ttgctccagc    36960
gggccggcgt cgggtagtcc atcaggtcac cgatgtggat caactgatcc ggctggtagt    37020
caccgatgaa ctgggtgagg gccttgaccg acttgcggtc ctcgaaggga atctgcgtat    37080
cgctgatgac gacgatgcgc ttgctcacag gtcctccaga tcggtgggag cctgaaccgg    37140
ctcctcgtag atgcgctcga cgcatccggc gtagcccgcg atgtcggtga acgaatcacg    37200
gtggtagccg gtgcctttca ccctggcgat cttcacgagg atcatcaggt tggcaacgtc    37260
gatgtcgttg atcggctgtc ccaggtagcc cgagaacagc gcggcgatgt ccgagaagtt    37320
ctcacgcgga tggccgtagt tcttgttcct cggcccgtga atcagccgct gagcctcttc    37380
gagaatggac tcactcattg tcgtcgtctc cttcgtagac gtagtcgtgg acggcgtccc    37440
agtcgacctc gctgtgcgat gtcaagtttt tgggcagcgt cacgtcttca tcctttccag    37500
tagtgcttgc ttgcccttgc tgatgacgag gctgttcacg tcctcgcccg gtggcatcgg    37560
gatgacccgg ctgttcgcca gagtcgccgc caccgcgttg gcgaactgtg taccggcgtc    37620
gtcgccgtcc gcgaggatgt acaccgtccg gtagcccagg aacagctcac gcatgtacgg    37680
cttccacatc gaggcaccgg gcacacctac ggccggtagg ccgcacacct gggcggtgat    37740
cgcgtcgatc tcgccctcgg tgatggcgat gtccgggacc tctcgcatca gcgcgagcgt    37800
gttgtacagc cacggctggt caccaggcgc ggtcatgtac ttgccgtgtc cacggtgatc    37860
gtggtcctgg atgcaccggt accggatcga cacgacgatc cagccgtgct ccttcgacca    37920
tcgcagatac gggatcgcca tgaacccccg gtacatctca tgaccaggga gcgggtcgtc    37980
cacgtacccg agcatgaacc gatcgacctc ctcgcggacg ctgggggaacg tcagacccct    38040 tgtcgccaaa tactcttcgg ctggactgcc ggggaagctg cgacggtacc gctcggtcgc    38100
ttcccgaaga aagctcttct gcgattcgct gagcctttgc ataactcacc tcctcctgtt    38160
tcttgatcag cgtcacgaca tcaccccttga ccccacaggc caggcagttg aacgctccac    38220
gcctgaatga cacggcggca gacgggattt cctctgcgtg gaatgggcag aggcacctaa    38280
tccagtcctt cccagtgtct ttcggagctt cccagtctgg gtggtaacgg tgaatgaccc    38340
ggacgatcag tggctcaccg ctcatagaac gtgacctcgt agaccgagag gtccttcacg    38400
ttcgacttga actggccttc gaggaggccc tcgatgaaca tgcccatctc gtcttcagcg    38460
cggtcggact tgatgattgc gtcaatccgg tagtacatct gtctcctatc ggctcattcg    38520
ggcaccttcc ggataccgat cacctggacg gcaggcgggt tgtcgaggta gtcgatgaac    38580
```

-continued

```
cgctggaatg cctcggggtc atcacgcaga tggcccagga cgttccggtt gcacgcggtg   38640
cagagcagac ctcggacgat gcctgtttcg tggtcgtggt cgacgctgag gcgcttgcgc   38700
ttgccgttgg cgcggcggca gccgtagcac cggccaccct ggaactcgta gatggcccag   38760
tactcctcgg cggtgatgtt gtagacatcc atccaccgct gttcctgcgt caccgtcctg   38820
cgctgtgccc gcttggcccg gtggtgggtg gcgcaccgtg gccccggatg cggagccttg   38880
cggcggttca ccagcccctc ggcggtgcag tcgatgcacg gcttgcgctt gtgcgctcgg   38940
tcctggttgc ggtagttcgg cgtgtgctgg gtcatgcacc ctccagcagg aggtagatgt   39000
aggtccccac gccccaggcc gcgatcatgg ctgcgaacag ttgctggatg gtcaccgagc   39060 cagcacccccc gccagcgcga tgcagatcgc ctcggcaccg aactccggat cggccagcat   39120
ccatgagtgg aagccaccct ggaccgtgta gaagtcggcc ccggcgacgt ggccgcgct   39180 cctgccagcg gagtgcggga tgatctggtc caggtcgccg tggatcacgg cggtcggaac   39240
ctcgttcagc cgcatcttct ccagcagggg cactgtgtcg gcccgcatga gcgcgtaggc   39300
cgctcggacg aaccggaagc tggacaccga ctgccgtaag gtgtcaagca ggctcagacg   39360
atctgagccg tcccgaaccc gcatggcgtg gtaaccatcc ccgagcacgt ctacgaacgc   39420
gccagcgagg cgctgagcgg cccgcagcgg gatcgtggag ccgttgccca ccttgatgtt   39480
gtcgtggtgt tcctgacccg ccgcagcgtc cagcaggacg gtcgcgatgg tgcgctccgg   39540
ataggccgca gcgaactcca ccgccatgcc accacccatc gagtgtccga cgatcacggc   39600
gtgtgcgatg tccagtacgg aaacacgttcg ggcgaccaca tcggccatgt ctgccaccgt   39660
gtggccgcag ggcagcgagc cactgtcgcc gtggttggcg gcgtccgggg cgatgacgta   39720
gaagcctcgg gcagccagct cttcgagcag ctcggtgtag gccagggcgc ggacggtcag   39780
tccgtgcagg aacaccagcg gcaggccgtg gcggcggctg cccgccgtcg tcacagcgac   39840
ccggaacccg tcctcaagga cgagcgtcat gtgcttgagc gtcacgtctt ctccttcagg   39900
tatccgtggt tgaccacgcg gatgccggcg gcttcggccc gcccgatgca gtcccaggtc   39960
ccgatggacc caggcagggg gaacgcatgg cagacatcgg caccgaggtc gaccatcttc   40020
tggttccgga tcacgcctgc ggccttgccg aggccgtccc agtcggcggg gtgggcctcg   40080
acctggacct ggtatccggc ctgtgccatc ccccaggccc agcggtcagc gatgtcgtca   40140
gcaccgcgtg ccgcgccgtg gacgatgacc agcgagccga actgctccag ctcctgcttc   40200
agcgcgtacc agaccgtggt gcggtccttc cagtcacggc tgcccgtgac caggactcgt   40260
ctcacggaat ccatcgcttc gcggccagct cgacgttgaa ctcggagacg ttgcgggcca   40320
gcgggaaccg aagctccttg ccgatgacct tggtctcgat gatgtcgggc ttgcgcgggt   40380
ccgggctctt cggatcgacc gtcttgcggg tccacgacgt gggccgcgtc tcaatcaggc   40440
cggacaagag ctgctggtgc aggacgttcg ccttcttggt gggcttcggc atattcgatt   40500
cctttcgtgt gtgcgatgtc aagtaatcgg gcaagaagaa gggccagcag cgtcatgctg   40560
cgtccttgat ctgcatcgtg tctccgtcga acgcgagcga gacgaagtcg agcccggacg   40620
ggtccatgcg gcccgcacgg ttcttcaccg tcgagacgtt cagcgagtcc atgccgaact   40680
cctcggtgac tcggtgcagg gtgagcacca gctcgggcac gcgggtgatc tggcccttga   40740
cgcccgacag cgggatcggc ttgtcggcgt cgttgtagct accggtgacg tggtgcagac   40800
cgatgacgca ggcgctggtg cgccgtgcca tgtcgtggag gtagtccatc agcgactcca   40860
gccctgagaa cggatcgtcg tcgtccgtgc ccagccggat gttcgtgatg ttgtcgacca   40920
ccaccaggtc cggatagtcg ccgtagccct ggcagtacgc cttcatcgag tcctcgatct   40980
```

-continued

```
ggtcaaggct cggggaggcg ttgtagttga accggatcgg gatgtcctcg aactcggctg   41040
cgacctcatc gaggtcggag ttgcggacgg cccgagcgga tcgctccatg ctccacccgg   41100
tctggatcga gaccatgcgg gagagctggg tgaaggcgtc ggagtcggcg ctgaagtaca   41160
gcgtcggaac ctctgccttg agggcatacg tcagcacgaa cgctgacttg ccggtgccgg   41220
ggcctgcaca gaccagtgcg agctggccgc gcaggaacct ggtgcctttc agctccagcg   41280
tctggaacac aggcgggaga gggtcacccg ccgagccctt gacgcggagg ctctgtagcg   41340
gtgtgtacac ggtcctccta cgcggtgaag tacaggacga tgcctgagaa gagggccagg   41400
gccatgatga tgccgaagac gatgacctcg atcactcgcc acgcccttg cggcgctcct   41460 cgtccaggtt gcggacgggg atgatgcgct tggtggtctg gccgtcgtag atcggccggc   41520
cctgggtgtg agccttggtc tcgtcgtcca tctggctccg catcgccgcc atgatgcgg   41580 gcgggcgcat cccgaagttc ttcgcgatcc aggccccggc gaagccagcg cggtgagcgc   41640
gcaggacggc cccggtctca tgcggagcga gcgggctctt cagcgacgga tggttcgggt   41700
cccagtcccg agggttgttg ggtccgggtc gattggtcac ggtgtctcct atgtgcgatg   41760
tcaagttgaa gaccaacgaa aagagccagt ggatcatagg ccgaactctt cgtggtacat   41820
ggggatgaac tgggaggccg gtgtcggccg tccctcggcc acctcgcggt cgaacagggc   41880
caccagatgc tccaggtacc ccttgtgtcc cggcggtgcc tcagcgagga gctgggtcag   41940
cttgcggcgc tgcttggcga tgttcatccc tggttggatg ttcctcacac ccactccttt   42000
ccgttccagc gtcgtccgtc cgggtactcg atcacgatgt ctcgcttcgg gtcccgagcc   42060
ttgtgcgact gggcgaaccg ggtcgcggcc tcgaccgagg gaaacgagta cccctgcgag   42120
gcatacagct cctgatgcca gcgcggcctg tccgggatcg gacccatctg gacccgccag   42180
tactcagcct cggtcgaatg cacggtcatc tcttcggcct cttgaccttc gggtgagtgt   42240
tctgcggtgt cttggcaatc cggtggacgg tctcgacgcg ctccgggtag aagctccgga   42300
acgcctcgcg gccggggggtc ccgccgacga agtcgagcac ggtcagaccc ttcgatgtcc   42360
tggtggcctt gacgaaccgg aaccggccct gctcgcccct gaccgatacc tcggtaccgg   42420
gctccagggc gcgaccgttc accttgaccg gctcagtgat caactcggcc atatctcctc   42480
cttgtgcgat gtcaagtatc agcccacagc aaaaggacag gcgtagctca cgtcgcagaa   42540
ccggcacgta tcagggtcag gcttcggatc gaacctcccg gccctgatgt tctcgtccag   42600
ctccttgaac ttctcggtga cgcgctcgcg ggtccactcg gtgaggtcga acgggtaggt   42660
cggcttgccg gtcctgccca tccagtagtc accggacggg gcgaagactc cgtactcgtc   42720
ctccagtgcg accttgtaca cgccgagctg gaagtcgtca ccgggctggt tgcctgtctt   42780
gtggtcacgg acgtaaacct cgtcgccgca accggattgg agcacggcgt cgatgtagcc   42840
ccggaccagg actccgtcca ggtcgatgtc gaagctcagc tcgatgcctg gggtcccatc   42900
ctctgcgatc cagatgacct cgtcgcgatg gcttgcggcc cagttgatgt acttctcgac   42960
ctgctccagc ccgatgtcgt agcgacgtgc gatgtcaagt cttccgtcgt aacgaccgct   43020
ggcgaaccac cactcgaagt tcggcgtgat ctcgcacgcc gcgtcgatgt gcttcttgta   43080
ggactccctg aagacttcct gggcctcttc gagcgagagg gagcgccccg accgctccca   43140
cgcctcgatg gcttcgtgga ccgcactacc ctgcgccgtc caggccgccg gcctctgcca   43200
cgccttgtcg attctcgata gcttgtatgc gtatgggcac cgctcgtact gcttgagctg   43260
agatacgctg cggtgcttgc gttcttctgt caacccacct ccatttctcc tagtctcgcg   43320
```

-continued

```
tggatcaggt ccgggacgta tgccgggtgg ggcgcgaagt cccagttcct gatcaggtca   43380
atcgtccgca atacgcgagg atcggacggt tccttgatgt ctccgtcata gagcaactgc   43440
accttccagg tcgcttcccc gaacatcatc aggtcgtcgg gaatcgtctc ctcgacgatg   43500
gtcttgacgg agccagcccg tgccaatagg tgggccacgt cttggaatac cgggtcgtcg   43560
caccggcagt gcctgtctcc gcagtcgtcg gcctcggcgt ggtcctcgat ccagcggtcg   43620
gccgtgtcgc tgtggccgaa ggctcgaaac acatcggcca gggcttcgac ctcgacacag   43680
gtcatgtggg tggcgatgtc tccggacagg tatccgtcgc cccagacctc gatgaagtgc   43740
tcgatggcgc tcatgtcttg ttcctctcga ctcatccctc acctagccgc ccggacagga   43800
ggtgggtgtc cggacggcgt agtcagcgat gactcaggcg gtgccttcca agatcgccag   43860
gttgcggagc agggcctcag ccacggctcc gatgtgacca ccgtcggtgc ctccacgacg   43920
ggcgtactcg gcgttggccc gctgcatgaa ctcgaacgtc ggtccaccgt cgtcgtgtgc   43980
gaacgtcgcc ttgatctccg ctggggcgac gaggatttca acgctcatcg cgatgacgat   44040
ggggtcgcgc tgcaggcgct gccgggtctc ttcgtagtgc ggtgcctcga tggtcaatgt   44100
catccctctc gtttccagtt gttgcggttg cccttgcctg ggcgcttgaa ctctcgtttg   44160
cggttgcgat gcggctgtgc cgcgctgctg cgccgtagct ccagacgagc ccgaagctgt   44220
tcgggcgcgg cgcggccagc catccctctc tcctctctgt gcggtgtcaa gccttggtca   44280
gcggactgcg ccataggcgt atgccttgcc gtcgtcggca aggtggacca tcgtggcgta   44340
gctgacggat tcgtcgtcga ccgtgaacga cggagccttg taggggttgt acgacagctt   44400
gcgggcgtac tcgccctccc agtcatacgg ccggggatcg aagtctcgga cgatggtgcc   44460
gaccacgcca gcgtggacgt tcttcttctg ctcacggatc acccgctggc gtccggactc   44520
cgaaaccttg agctggcagt cgatcagggc gactgactcg gtgtgcccga tgaccttgcc   44580
cttgtgcggg ccggcctcgg cgcgaaggct ccacatcccg gagtgcaggt tgcggtaggc   44640
gaagaccggg gtgcggtcgc tgatcatgcg gcccttgtag ctgtggatga tgctcatgtc   44700
tcgatacctc tcagcggagc tggtcgatgt ggatgcagcc gacgcggtcg ggaccgaact   44760
ccggggcgta gcccaagact tcgtcctcag cgcaggggaa gttgcgctgg tcgaacgggt   44820
cataggcgtc ggcctcggcc atgcctccgt tgccgatgag gacggcctcg aacagggcga   44880
cggtgagcag tagtgccttc acgatgattc ctctctgagc gatgtcaagt ctcaggcgcg   44940
accgcgcgcc acgacccagg tgatggcttg catctgggca ggagcgatgc ctgcccgctt   45000
ggcggcgagc cggtagcagt gggcgatggc ttcgtacaca cccacccggc cgagctgctg   45060
ttcggtgatg cctgcgaccc gagcggccca gacatccacg gtgaccgcgt tgtcgtcgcc   45120
caggatgttg agcgcaaagc tccgagtctt cggtgccttg ccgaaggtgg accacgggtc   45180
ctcggcggtc atggcttgca gggcacggtc gaccgagcga ccgagcacac ccggagcctt   45240
gccggtcagg accagcgacc gagctgcctc gacgttcttg tcccagcgga gcctcgggga   45300
gagctgggcg atcatgacgg ccgactgctc caggtcatg cctccgtcga ccgcgcattc   45360
cacggccagg gccttggcct cctcgtacca caccttgccg tcgaggatgt cctgctccga   45420
tgccttggcg aagactcgga tgatgttgtc agtgaccttg cgagtgctca ggccgatctt   45480
gccgagcacg tcgttgtgcg atgccatgtc tccgttcccc tggtcgtcgt gagcgatgtc   45540
aagtcttggt cagtcgagat agatgtgccg gtacaggacg ccggcatcca acgcttcggc   45600
gatgagcagc tcagtgtcca gctcatcctc ggcgtggtca ggcagcgtgc tctccagctc   45660
gcggatgatc gaagcctggt cgaacttctc cccgtcgacg tggcgataca cgtagtcggt   45720
```

-continued

```
gatgtcgtcc atcgtgatct ctcgcatagc gatcccttca gtaggcccag ccatgacggc   45780
cggtcgaatc cttgacgagg tagcggtcga cgccatagct ctggcagtcg cgacggacca   45840
ccgtcagccg ctcaccccag ttgaagccgt ggctgtgctt gccgtcgact ccgttgcgga   45900
agctctgtcc tgcgctcatc gaaccctcac gatgttgttg cctcggatgg tgtagacctt   45960
gccgtcgagg tagacgcgct gttgcttgtt catgactcat ccctttgtgc gatgtcaagt   46020
ctgggagtga aaaaaaagcg gatcggaagg gcatcgaacc ctcggttgca ttcctcgtgt   46080
ccgatccgtg atggtctacc ctgctgcgtt acctggggcc gacgtgccgt tcgccgctag   46140
tcaccccgta ctgttcggtc cctcggatcg tggcgatggc tctcaatcca tcgctccccg   46200
aggacaaata tcctcacagg tccatctatg tctggcggtg tgggtgtgtc ggcgcttaga   46260
gcccctgcct cttgcccggg tcgtccggtg ttcaggtagc tgcattcccg tcatgctcac   46320
gcggtttctg caaccccgcc tttgtgaagt tgtggtgacc actctagcgg atcgtctgtg   46380
cgatgtcaag tccttcgatc ttggatcatc gggccggtct gctgttgtgg tgtgtctccg   46440
actctagcgt gtggactgtg cgatgtcaag tcccggatcg aatccggagc gggccgtttt   46500
gctattgcct gatgtgctcg taagggccgc tggctgaagg ccctacccgc tgtgctcgcg   46560
atgtccgctg tgctgttgtc gtgtcaccga ctgtagcagc ttggctgtgc gatgtcaagc   46620
cgtttggtct gacttgctgc gatccgctgt ggagttgtcg tggtgctgcg ttccgtggtg   46680
gaacgtctac gacggtacgc cagccgctgt gcgatgtcaa gcaattcgcc gaaattggtc   46740
cgaagtgcct ggtcggagcg ggtacaggac ccccctctgt ggaccccctg ggcactggca   46800
ggaccccctg tgcagggcac cccctgcagg gcctccctgg gacctgggca ccccctgggc   46860
accccctgcc ctgggtaccc cctggggtac ccccctgcctg cctccggggt ggggtaccc   46920 cctggggtac ccccggtgg caccccctt cgggggtgcc cccctcctgc ccccctgccc   46980
tgggcccggc cagtcccccc ttcgggggga ctggcacggc tggcctggcc tggcctgccg   47040 tccctgtcc cccttcgggg gacaggggac ccccctgggc ctggggtacc ccgtaggggt   47100
accccagggg ggtatgccct cccccgcctg ccctgaccg gccggtaa              47148
```

<210> SEQ ID NO 5
<211> LENGTH: 48228
<212> TYPE: DNA
<213> ORGANISM: Bacteriophage

<400> SEQUENCE: 5

```
tggcgctaaa cctggctacg gtctcgtcag agctttgacc tggggggtttg ctctctgacc     60 tggggcgatg acaggccccg gtgccgcacc tggcttgatc tgcggcgctg gggtttgttt    120
gctgggctag ccagattctt tgctgacggc gcccacccct cgcggcgcttg ggcaaggtcc    180 gatatactga tggcatgacg acgaacggat ggacccctga caacgtgccc gccggcaaca    240
cgctcttcga gctctacttt gctagccagg cggaggactc tgatcccgac ccctacgcct    300 tccccgggcga agcgcgttgc atcaagctct tcttgaccag ccccctcggg ctctcgatga    360
acgacttctc tctggtgccc gccgacgatc tcaaccctgg cgctgtcacc ggcgatcact    420
actaccgcat cgtgtggcat cgtgacggcg aagacgaaga aattggcgtt ctcgtcgccg    480
tcgcccaagg cccgctgccc gaggatcagg tgaactgatg aaggtcaagg cttgggacct    540
cgtgcccggc gactactacc gcgggcggaa gatcttcacg ctcacgcgac acccgaacgg    600
cactgtccgg atcgtcgtcg tctgtcctaa gcacctcccg gtgatcggcg aacccatggg    660
```

```
ctggaagggc aagacgtaca tcagcggcaa gttcaccttc gccggcaacg aagacgtgga    720
gatctaccga gacgaggtca atgatccgcg cttcacgccc gacatcatcg aaagtctctt    780
gacgtaacct gttgcgttcc tccccgagagt ctggtaagat ctaagcatga cgacgaacaa    840
atgctccgaa accttcaccc tcgccgacgg cactgccgtc acctgcaccc gcaaggctgc    900
gccgcgcaac caggttgccg gccacgagaa cgtctgcctc aattgcttcg aggcctggat    960
ggaggagaac ggccacaacg acggggaaca cgaagagggc gaaggcgtca actgccccgc   1020
ctgcgggacc tacgacccc gcccgaagcg caagggccat aagaacggga tctcgcatca    1080
ccgcacctcc cacaagcact gcggccaccc actcacgccc gctgcacgta aggaatgccg    1140
caaggcgcgt gccgcccgcg tggaggccaa gaaggagcag atcatcgagg agctgggcat    1200
cgaccgctcg aacctcctgc ctgctcccct gcctaagcag gccccgcgg cgattgctcg     1260 cctgcaggac ctgggtgtgg attacaccaa cgatcagatc attgccatcg ttgacctcgc    1320
ccgcaagcag aagacctcta tcgccaaact gtccgaggct tcgatccgta aggcaatcgc    1380
ctgacagcta catactcgtc cgcctgggtt tgtcgcaccg cgacacccgg gctgacgtgc    1440
agttatgccc gataggttgc cttcgaattt ttgacgtgtc acagtagtgt caggccaatc    1500
ggtcgtcgtc aatcgcgcag gaaggagcag ctcagtggta gcacggaaag acccagcggc    1560
acgtgcccgc aagaaccccg agcgagtccc cttcaaggtg atggagctcg aggctgttcc    1620
tcagcccccg ttgccggcgt acttcccgtg ggaaggcaag aagctcaagt ggcctcagca    1680
gactgttgac tggtgggagc actggaagga ctcagcgctc aacgagggct tcttgcagca    1740
cgattgggat tacctgctgg atacagcgat tctgcacgct aagcactggc tggggctgga    1800
tgcgaaggca gcaggagagc tccgtcagcg acaagcgaag ttcggtgtca cgccagaaga    1860
ccgggctcgc ctgcgcatca tcgttgtctc ggccgataac gccgaggaag cgaagcgagt    1920
tcgggaagag gcggatcgtc tcaaccagaa gatcgctatg cgcggtaatc gccgacgttt    1980
gaccggattg tcagcagacg tcgggtaatg ccctggaagc ctactgtacc cggtgagatt    2040
cccaccatgg ggtacatcgc cattgagtgg atgaaggagt atctggcagc tcccgattgc    2100
gctgagtatg agcctttcgt tccatacctc gagcaggaag acattctcct cgagtggtat    2160
gccctctggc ccgacggtac gcgacgattc aaccgcggtg tggtcggtcg atcacgcgga    2220 tgggcaagt cgcccttcct cgcggcgatc tcgtgcctgg aagctctcgg cccgatcaag    2280
ttcgacggct gggatgccaa cgggcagccc gtcggtcgtc cttggtcgac agtccggaca    2340
ccgctcgtgc agatcaccgc agtggatgag aaacagaccg ctaacacgtg gggtcccgtc    2400
ctcgagatgc tgcgtgagga agcgccgatc cactccgagt actccgtcaa cccgatggag    2460
accttcgtcg ccctgcccaa tcgcgggcgc atggagtgcc gtactgcctc gtctcgatcc    2520
atcaagggtg cccgcgctca cttcgccgtg ctcgatcaga cggaggagtg ggtgccgtcc    2580
aacggcggac cccgtctcgc caggaccatg cgagtcaacg ccgcgaaggt cggcgggacg    2640
acgctggagt cgccgaacgc atacactccc ggtgaggggt cggttgcaga ggcctcagcg    2700
aagttctggg acgacatcaa gcgcggccgg gcaaagtcgg aagggttgta ctacaaccat    2760
cgcgaggctc cgcctgagac ggactttgac tccgacgagt cactcatggc tgggctccgt    2820
gtggcatatg gcgacagctc gggtcacccg gacggctgtg tgatccacga tcctccttgc    2880
ccgcccggac acgtcgatct gccccgtatc ctcgagacga tccatgatcc cacacaggag    2940
gaagaggact cacgtactga cttcctgaac cagatcaccg agtcggcgga tgcctggatc    3000
tctcacttgg acatcaaggc tacccgcgac gacgaacacc ggacgctgga tcctcgagac    3060
```

-continued

```
gagatcgtcc tcggtttcga cgggtctcgc ggccgtgtga agggcaaacc tgacgccacg    3120
gcgctcgtgg gggtccgtgt ctccgacggt ttcacgtggg aatgcaaggt ctgggaggca    3180
aagctcaacg aaaaggactg gattccgcca gttctggaag ttgacgagga agtggacctc    3240
tggtttgagc gttgcaaggt catcggtttc tacgcagacc cgtccggatg gacggaatgg    3300
gtctcaaaat gggaagctcg ataccgccgc aagctcaagg tgaaggctac gaccaatcac    3360
ccgatctctt tgtggcctcg ggggaagacc cagtcggtgt atgacgcggt gaaagctgct    3420
cacgacgcca ttgccactcg agaaatggtg cacgacggaa gtccgaacct ctgccgccac    3480
ctgatcaatg ctcgaaagcg cgataccccg cgaggatatc tgctctacaa ggcctatccg    3540
atgtctccag acaagataga cgcggcatat gccttcgttc ttgcgtggaa agcgcgcatg    3600
gatgcactca gtcagggcta cgggaagacc cgggaagaga aagcccactc tggaaaggtt    3660
ctcatatcgt gaccattgcc ctcttggcag ggctgtccga cgacgaccgg gcactccttg    3720
ccgccttgga acggaaagtc gagagttacc gccagatcaa ccgccttctg cgtgcgtact    3780
acgagggcaa tatctggctg aacaagctcg gtttctcggt gcccccccaag atgaaggact    3840 tccagaacgt catcgggtgg ccggccatcg tggtcgacgt gatcgaggag cgcttgaagt    3900
ggcgcggctg gatcgacttc gatgacccgg cccccctcgag caaccaggta tcttcggtgc    3960
agaagttctt ggacctctgc tacgtggaga ataacctgga cgccgaggca cccctcgtcc    4020
acctcgatgc tctgatgttc gggtgtggct tcgtgtcagt cggtacccgg gacccggaac    4080
tggatgacga ggagagcact cctctcatca ccgccgagtc gacggaactc actaccggaa    4140
tctacgacac ccagcgtcgt cgtatgacct cgggcgtctc cttccgtaca gacgatgagg    4200
ggaacatcgt tcgggcgacc ctgtacaagc taggggagac gatcttcctc cgccgtactg    4260
gtgtccacgg atggtggcag gttgtcgacc gggatcagca cgacctcaag cgtctgccgc    4320
tgattccgtt catcaaccga cccaccgggt ctcgccggca aggtcgttcg gagatcaccc    4380
ggccgatccg gggctacacc gacatcggca tccgtaccct cctcggaatg gagaccaacc    4440
gtgagttctt ctcagctcct cagcgttacg cgcttggcgt cactgaggaa gacttcgtgg    4500
atgcagccgg aaacaagatc ccgggttggg cggctgtgct gggtcgtgtc tggggtgttg    4560
gtcgggatga caacggggat cttcctcagc ttggtcagtt tgatcctgct ccctcccgac    4620
cgtacctcga gcagatccaa ggcctggcac aactcattgc agcagatggg gcggttcctc    4680
aaacctacct cggcttcatg tcagacaacc cggcctcggc tgacagtatc cgcgccttgg    4740
agagtcgcct tattaagcga tctgagcgac gcatctccag cttcggatgg tcctgggctg    4800
aagtggggcg cgtaacctgg atgatccagg agaaccgcaa tactgcgcct cacctcgaca    4860
ccgactgggg caaccgggcg actccgacgc aacaggccga cgctgacgcg gcgatgaagc    4920
tggtctccgt ggatattctc gccaaggatt ccgtcatcac tcgcaatcgc ctcggcttca    4980
cgaagaccga gcagaagatc ctcgagcgcg aggaccgtca gcgggaagca aagcgacgac    5040
tcgaggagcg aaggaatgca aaccaaggaa tacaacagcc agctggaggc gctggaggag    5100
gaactccgcc taatgcttcc ggcgctcctg caggagcagg cgcaggacct aatcgaggag    5160
tacctgctgg gagtaacgga gctcgccgat gaagctaccg tcgtctccct gcagtactac    5220
gaggaactga agcctcgtag cctctacgtt cctgagcctt acgttgacga gtccttggaa    5280
ccgcggctcc ggcgaaccgt tcagtacgca gtcagtgaag catctccgga tgctgagtcg    5340
atactgaacg gcgccgggat ccgggcgatc cgcgaccagt cacgatccac cctgattacc    5400
```

-continued

```
aacgtggaag tcgagggcgg acgctgggga cgtatccccg ccgctgacgc ttgcggcttc    5460
tgccgtctgc tcggtgtgcg aggtcccgtc tacaagtctc aaaacgcggc gatggcatcg    5520
cacaacaact gccggtgcca ggtgggtgtg aacgtcctg gtatgtccta cacgcgcccg      5580
aagtacatgg ccgggtggaa tgatgagtac gaagccgcca agagccgtgt gagcgaacgt    5640
aggcagcggc aatcgctcaa gaatattgtc cgtgagtgga acaagatgat ccggcaccct    5700
gaggagttcg ccaaaggcct gaaccccgca gagcttgaca tcgtgaacct cgatgcggca    5760
taatggtggt gatgagttga tccgcgcccc cgccgatcct cgtcaccgaa ggcacacctg    5820
gacgtcgaga agggatttcg tcgtcgtctg ctccgtctgg gtgtgccttc tttaatggac    5880
gccccagctt accatcactg agctgggtga ggcgcaggtg gccgactgcg tggataagtt    5940
aacggcccta gtttacgccc acagagagcg gtaatctctg gtcctatcaa cagccgacgg    6000
gcttaaacgg aaggaagtac agtgagtggt aacaatggag gcggtaaggg tcccgacgct    6060
ggtgccggca acggcggtgg cggagaaggg aatggtggag gcggcgaagg cttcaagccc    6120
gttaccttca gcacccagga agaaatgaat gcagctttcg ctgaccgtgc ccagcgcgca    6180
gcagcgcagg cgaagcagga agttctgaag ggactgcccg agggagtttc gctggacgat    6240
gtcctggcgg ggttcaatgc ccacaagcag gcagaggacg ccaagaagga cgaagtcacc    6300
aaggagcgag aagcccgcga agcggctgag cgcaagctgc aggccatcga acaggcccag    6360
cagttgcgta ccaaggccgg agagatcgcc aaggagttca aggtgggcga cacgcctatc    6420
ccggcggaac tcctgcgtgg tggcaatgag gatgagctca aggctcacgc cgaagccatc    6480
aaggccttca ttgaaccact ggttggcccc cgtggcccga gacacaaccc ggaccaggga    6540
aacaacggcg gcggaaagga accggcaggc gattggctgc gggacacttt cttcggcggc    6600
gcagtttcca ccgggtagca gtaccccaac acatcaattc ctgaaaggaa gcccatcatg    6660
gcaggttttg ccaacatcca gggtcgcgca gacctgagtg atgttcatct gcccgaccag    6720
gtcatcaagg acgtgctcca gacggcaccg gaagcctccg tcctcctgaa tcgggcccgc    6780
aaggtgcgga tgtcttcgaa gaagacgaag cagcccgttc tggcctcgct gcccgacgcc    6840
tactgggtgg acggcgatac cggtctgaag cagacgacca agaacatctg gtccaacgtc    6900
tttatgaccg cggaagagct cgctgtcatc gtgcccatcc ccgatgccct gatcgcggac    6960
tccgacctgc ccctctggga cgaggtcaag ccgctgctgg tcgaggccat cggcaagaag    7020
gtggacgacg ccggcatctt cggcaacgac aagcccgcct cctggccggc tgcgctcatc    7080
ccgggcgcca tcgctgccgg caactcggtc accctcggca ccggtgatga catcggtgtg    7140
gacgtggcca ccctcggcga gcagctcgcg ctggacggct tcagcatcaa cggcttcatc    7200
tcgcgcccgg gcctgcactg gtcgctggtg ggtctgcgca acgcgcaggg tcagccgatc    7260 tacacccgc cgctcagcac cgggctcaac ggggctcctc ccacgccggc tctgtacggc      7320
ttcccgctga cgaggtcac ctcgggtgtg tgggacgcgg acgaggccat cctcctgggc      7380
gccgactgga gcaaggtagt gatcggcatc cgtcaggaca tcaccttcga cctcttctcc    7440
gaaggcgtca tctcggactc cgacggcaag gtcgtcctga acctgatgca gcaggactcg    7500
aaggcactcc gcgttgtctt ccgcgtcggc ttccaggtcg ccaacccgat gactcgcctc    7560
aaccccaacg aggccacccg ctaccggcg ggcgtcatca tcccggccgg tggtggctcg      7620
ggcgagggtg aaggggagag cgagtaacca tgaaggatct ccgcaagaag tccgcaaaga    7680
cggttgtctt cgtcggtgag gacgggacgg agctcaacgt ggttaccagc atctccaagg    7740
agtcgctggc gattctgaag cgcaaggggt acaagcgcaa gcgcgacgag accccggcgc    7800
```

-continued

```
cgaagaagac acctgcgaag aaggtcaccc cctcgactca gcctgagaag gatgagaacg      7860
aggatgagac gccttccgag gatgatgcac ccacgccgac ccgaccgcct gcaccgcgca      7920
agcgaccggc caagtagggg atagggtgg cagccaatgg aaaacccctt tgacggggat      7980
ggtcagaatg acatcgcccg gcggctgcca cacctgcccg ctgatactgt taaggacctg      8040
atcgaggacg catgggctcg agccatcgag gccgctcctt gcattgctca ggacgagttt      8100
ccggaagaaa aggcgccatt agtaaaggca ttgcttcgag cagtgatcct acgctgggcg      8160
gaccaaaata tgccaccgga ctcgggtaag ggcacgcata aggtcgctgg tccttatcag      8220
atgtcagtcg agcagccaca gagaaagggg tttcgcctcg atctcgggga gactgttgat      8280
ttccggaagc tgtgcctgaa gccaggtcgg cctttcacga ttgacaccct ccccgctgac      8340
ttcgaagtga agcctcctct ctatggtgtg gtagtcaacg gtgacgccca tctcaatggg      8400
cctgacggcg aatggtctga ggaggagctg tgagcgttcc ggacgtattt ctaccgctgc      8460
tgtattcggt agatcattcg gcctatgacg cgacagcgac gaacgacctc ggggacccaa      8520
ttcccgactg gcaagaaccg gtggaaagag atgtctacgg gtggggaccg cctcagcaag      8580
agactcccaa ggaagtcatc gttggtgacg accggatacg ggtagaactc gagctgatgg      8640
tcccacccgg atggcagtcg aaacaccggg acaagttcga cctgggctat ggcgatgatg      8700
tcgtctatta ccaggtcggg cctgttgagg attacgagca caaccccttc gggtggaatc      8760
ccggcagtgt agtcaacctg gtgtctatta aggggtgct atgagcaaga aaatgaagat      8820
caacagcaag aggctcacag cactccgcaa gggatcagga atcacggcgg tactgaggaa      8880
gtacggcgag cgacagacaa aggcagcgaa tgaggacttc tgggcgacag ctccggggaa      8940
tgagcgctac cgtcagcgga actcgtccaa atccaaagag ccgtatgaca tgactgtcaa      9000
gcagggtggt gatcgtactc gggtgttcgt tcagaccgcc tcgtatcccg cacgacgcca      9060
ggagaaacgg tcgtcctcgc tgttgaggtc gataatccag atcaagtccg ggggcgggtg      9120
atgaaaacac ttctttccc gcgtccaaaa ctgctagcca gaaccttctt gaaggagcag      9180
ttgccggcct tcggtgcaga tatgcccgtg gagcacagga accctgatcc gctgcccgag      9240
cgatgggtcc gcctcgatac tgagagcggt cctcagacct tgggcactct ggacgtgttc      9300
atcaccgctt acatctacaa caagcgggac tcgtcgcaag cagaggaaga ctcaggtctt      9360
gtgcgctcac tcatgcacga cgcaccgggt gtggccatcc cctacccagg cggacctgct      9420
gactttccgt gggttgtgag atcgcggcat atctcaggtc catctgacct cggcgacgag      9480
gacctccccg gtgcatccat gtatcgggtc atcactcagt ggaccctcca ctacctgaag      9540
gagatatcaa catgactgct cccgttctga ccagtgccgg tcgcgtgacg gaggtgtttg      9600
ccggttcgcc ggtgggcatc aacgtctacg gcggtatcta ctaccattcc ctcggtgaga      9660
cgattccgac cgacgcggtg accccgctgc cggcaacgtc tgtccatctg ggcttcgtgt      9720
ccgaggacgt tgtgaccatc accacggatc gctccggcga cccgacgatt gcgtggggcg      9780
gcgataagat cgcttacctg cagtcgtcct tcggtatcag ctggcagttc aagctgatgc      9840
agttcttcaa cccggacgtg gcccgtctgg cctatgggca cgcgaacgtg gcgactgtcg      9900
cggcgaccgc ccagcacggt aaccagatgg tcatcaagca gaactcgcag ctgctggatc      9960
tgggcatctt cgtgattgat gccttctacg gcaagaagaa ggttcgcgag gtcgctccgt     10020
acgcccggcc gacggaactg ggtgacaccc agctggtgca caccgagctg tcgggtgtgg     10080
aagccaccct ggagctgttc ccggacgact cgggcaactc cgcataccgc tacaccgacg     10140
```

-continued

```
acggcgagaa gaccgccggt ggaggcggag agggagaagg tgagggcgag tagccaacgg    10200
gcggacacgc tgctattgct gagcggagga attgactctg ctttctgcct ctggcagcgt    10260
gtccaagccg gcctcactac tcgtacccac catgtagacc tcgatgacca cgaaggtcgc    10320
tgtgctctcg agaagggcgc agtaacgcgg atcctgcact ggatggagaa tcacgggtcg    10380
ggtctcattg agcactcgtc ctcagcgatg accttccggg atatgtggat ccctaagaac    10440
tttcatgcct gggcgtactg ggcaggcgtc atcatggctt cgccatctgg tcaggacatc    10500
aacacggtga tactgccgcg tcatgcagac gctttcgatg acccagcagg cgctgaggcg    10560
tccgataacg cctacttggg tcatatcgaa ttgatcgcaa aacgcaggcc tcagctttcg    10620
tttccaatgc tccatctcac gaaggctgag gtcgtcaagg caatgccgaa ggatctcctg    10680
caactatgct ggtggtgccg tcgtccgaac ggtaagcagc cgtgccataa atgcaggact    10740
tgcaagcaag tagatcctgc gctctaggac cccggggggg tggcgctctt ctggcggcgt    10800
tgccctcccg gcctaagcca gaaacagcca gagaaaagag agaaggaatg tcgaacaccc    10860
ctgtcaagcg cgctccgcgc aaggcaagtc cgaagcccaa gaagtcgctg atcccgggag    10920
agcccggata cgactggcgc accatctacc cgacctcggt gaagctgttc aagttcacct    10980
cggacgacgg cttcgtggtg tgcttgccca agttccgtca gcccggcgaa ggtgaggtct    11040
ttggcctcat gctgatggac aagtcggatc aggaactgct cctgcacgtc ctgcgcgagt    11100
gcatcaccgc cgacgcgacc aatccgcaag acgcgctgat ggtgaccttc gaggccctgc    11160
gcaagatgaa ggcggacggt accgtcgaga agctccttga ggagtggccg gccgatgccg    11220
gcgtgaagct ggaaaaataa tcgcggtcat ccaccttgct aaaaagcatg aggatgcact    11280
gcggttggat ctcatgggta aggggtactg cctcgaatta cgcaccccgg gatggaatga    11340
tctctatgcg ttcttcgcgg cagccccgcc ctattctgca gtgcaccacg accttaacga    11400
gaagtggaat ctaacagacc atctgctggc tacactgctc gaccgggtga acgtgctgct    11460
gtggaccaag accaaggatg ctcacaagaa gcctccgagg aacatgccaa agcggatccc    11520
gcgcccgggt gtggatgacc gcaagaagct taatgacaag gtcaccgtca tggacatttc    11580
cgagttcatg cggcgacaga acgagtcggg ccggacggcc ctgatggcag ctggaggagg    11640
tggatagtga ccagtgctgg cgtggaactc gccgccgagt gggtaaccat cctgcccgag    11700
accgcagctt tggtgaagga gctcaagaac tttgagcccc caccgatcac tgttccagtg    11760
aagctggagt ctgcgagcgc tgtcaagggc gggaagcagg cgggtcgaga gatccggaca    11820
ggcattgtca ctgagaccaa gcaggcgggc aaggaagccg gcgacgccat cgtctcgggt    11880
gtggcatcga gtcgggggaa ggtatccacc gctgcgacga atgccggcga ggggatccga    11940
aagggtgtcg tcaccaaggc aaagcaagcg ggtcaagagg ccggtgatgc ggtcgccgac    12000
gaagtcaaga agaagagccc caaggcggaa gctgctggat ctacgttcgg cagcaagctg    12060
attggcggtc tgaagaagac agcccttgtt ggtgcggcga gtattgccac catcttcact    12120
ggtgctatcg ccaagggctt tactcgcctg aaggacattg acaacgctcg gtccacgctg    12180
caaggcttgg gccatgatgc cgagtcggtg accaagatca tggattctgc ccttgctgct    12240
gtgaagggca ctgcgttcgg tctcggtgat gctgccaccg tcgctgcctc agcagtcgct    12300
gcgggtgtca gccgggtga ggaattgact cgtacgctga ctctggtcgc cgatgcggct    12360
gccatcgcta agaccgatat gagcagcatg ggagccattt tcaacaaggc tgcgacgacc    12420
aacaaggtcc aaggtgagat cctgcagcag ctaggtgagc gcggtatccc catcgtgaag    12480
ctgttggctg atgagatcgg cgttacgact gccgagatcg ccaagatgtc tgccgacggc    12540
```

-continued

```
aagatcgact tcgccacctt ccagaatgcc atggaaaagg gcatgggtgg tgctgcgaag    12600
aacatgggga attcgttcac cggggccgtg tcgaacatcg gtgcagcact tgggcgtctg    12660
ggcgccacca tcctaactcc cttgttcaac aaggtaattg agtgggcgcc gaaggttatc    12720
gagtggctcg acaaggtgga agagcaagtc aagcccatgt tcgagcgatt gagcgcgggc    12780
ttcaagactt tcatggaagc attgtccacg tccgggcagt tcatcaaaga caatgccaca    12840
cagttcaaga tcgcggcagc ggtcatcacg acgctgttct tgcctggcat tgccgcagtg    12900
gctgcgcact acgcacgact ggctattgct aagactgtgc ttactgcgat cacggcggca    12960
accaagatcg ccaccgcggc tcaatggctt tggaacgctt cgcttttggc caaccccatc    13020
ggcctgatca ttgccgccat cgctgcggtc gtcgctgcct tggttctctt cttcacgaag    13080
acggaactcg ggcagaagat ctggcagact gtctggggggg cgatcaagac agctactcag    13140
gcagtcgtct cgtggttcac gacgacggca tggccggcga tgcagaaggc attccaggcc    13200
attggtcagg cgctgatgtg gttgtaccag aacgtctggc agccggcatg ggacgtgatc    13260
aagacggtgg cacaggtcgt ctgggccgcc cttgaggtca tcttcgctgc cttcggcgct    13320
gcgcttcgtg tactcggcgg cgtcatcgag tggtggtgga ataacgtcac tgtcccggcc    13380
tttaacgcgg tgaagaaggt catcggagtc gtctgggagt tcgtccgccc aatctgggat    13440
ctctggaaag cagctttcga caagctgatc gagggcatta ccaagttcaa ggacatcttc    13500
gtgaccggct tcgaagccat caagaaggtg ttcggttcgg tgtgggattg gatcaagccc    13560
aagctcgagt ggcttatcga caagttcaac agcgtccgcg acactctgaa caacttcaac    13620
cccttcggta actcgggagg cggcactgtg ccgtcggtgc ccggctttgc cggcggtcat    13680
ccggctggta ggacgtcctc aggtcgtctg tacgggcctg ggaccggcac ctccgacagt    13740
atcttcgggg tgaatgagtt cggtgtccca gttgtccgtg tgagcgctgg tgagggcatt    13800
gtcaaggagt cggcgatgaa gaacgggggc tctgccctcg tcgccatgct gaacgccggc    13860
tgggtgccct cggccaacta cctgcgcggt atgttgccag gcttcgccga aggcctgaat    13920
ccgggagcag attacctgcg ttcggtcgtg atgaagctgt ggcctcagat cacctcgatt    13980
ggtggtcgac gttcggaaga tggctatggc gagcacagct cgggcaatgc catcgacatt    14040
atgatcccga actggcagac gcctcagggt aaggcgctcg gtgactcagt gaaggccttc    14100
atcgtgaaga acgcggaagc gttgggcctc gatgggttga tctggcaaca gcgcagcttt    14160
ggttacggcg ggtcgctgac gggcgaaggc aagaagatga gtgatcgcgg gtcgccgacc    14220
cagaatcaca tggatcactt gcacgtcatg ctcggcaagg gccgtggtgc cggtgctcag    14280
gcagtgtctg cgccgtcggt gccgctcatc acgggcggtg tcaatggcag tattgccgca    14340
tcgggtgctc cctcgattct gaagggcagc acgtctggcg ctggtggtgg cggaagctac    14400
tacgaggttg acccgaagaa ggttcgggaa gctgaggaca aggtcaccga caaggaggcc    14460
gcactggctg tcgcagaaca gcgactgagc gaagtggaga gcaagagaa tgtcaagcag    14520 tccactctcc aagcggcgcg agatcgcgtt gaaaaactca gcgtgaaac cgaacaagct    14580 cgagcagatc tcgaagaggc ccggcaaggg aaatataaag aagggtctaa gaaagctgga    14640
caagccgccg gagagtcttc ggggctagac ggcaaggaac tcgggaagat gttcgtcggg    14700
ggcatcctcg agtcgttcgg cttcgacgga tcgctctttg acaacctctt cgagtcgccc    14760
aacgtcaagt cggccattgc cggcgtgaac gcctttgccc cggtgatctc caacctcctg    14820
ggcggaggca gcagcgatgg cttcatgggt gtgggatcgg gagatccgac gggcggcttg    14880
```

-continued

```
atcgcgggtg tcggtgatgc ctttggcgtc aatgcctttg accagcagtc gcttggcact    14940
gcacaaggtg atcagtctgc tcttggcggc gggtcgccgg tggtcgatat gcgtggcgct    15000
cagcttggct gggacccgca acagaccatg gacaaggttg aacagttctc ggcgtcgaag    15060
cggcgcttca ccaatctacc gggaccggga gcataggaat gacagatctc gtatctgatg    15120
aatatgtccc gcctcgggac gattggatgg gatccggcgg aaagccgatc tactggccgc    15180
agaatgcccg ctggccgggc tggcaaaaga acaccaactt caactggctg accaacggcc    15240
tcaaagggac ctccatgcgg atcgtgtggg tcgggcccaa tgggaagtgg tgggatcttg    15300
ccggcccgtt caggggggcgc caaggcgtcg gtatgaccaa cgagctgacc gggatagggga   15360 tgaccccctt tgagcacaag tactcagagg ggccctatct tcccggggct gagatcgacc    15420
gcaccgacga caagaagcgt ctgctgtcgt tcggcgcaat catcaacccc aataacaaca    15480
ttgtccggcc caaggcttat aacagcttgg cgtactacgg aattgagcgg gagtggtggc    15540
ggtcgttcag caagaccgag tacgggattcc tcggcttcta caccccgaccg actgggtggc   15600 gctggctgaa gtgcgtgctc gaggcttcac cgaatgacac catctcgctg gagcccacag    15660
cgttcgggaa caactcggcg aagtacgaca tgaagctggt ggcggttgat ccgtacttct    15720
acaagcgtcc cttcgtgaag acgtggaaga atccgatcac cggtcacaag gacgaagacg    15780
gatttggcac cgggtttatc acgttggcga atcgcggcac tatcgcatcg ccgcccatct    15840
acatcgtgac gtgcccggga caggccaaga tcggcgatgg tcctgaccgg ttgctcgaga    15900
tgcctgagac gtctgaagcg gacaagtggt acctgattga cactgccgag aacgcgatga    15960 cgatccaggat atcagaggat ccagtcgaca acgccttcta tcgtttcctg cgtcaggcag    16020
gcctgctgaa ttacttcctg catgacctga ctgctcaagg attgcccctg tggcggcggt    16080
gggaggatcc gcagctgttc gagtacgcaa tcgggcctga ggagtccgga acaacgaagg    16140
tccaacacaa ctacccgggc gggcaggtca ccatgattgt cccccagcgg ttcgactcgg    16200
cttgggggtg agatgtcaga cgcaggtggg tgggtaacac atgccgacct caccttcgag    16260
cgcctgaaag gcaacagcct ctttgcagca atggaggctg cgaaggaaga gagtgggccc    16320
ccagatcccc gcaacaatcc gctccgtgca ttgcgctacg cacgtacgcg acggaacgta    16380
atcgtcaagt cctacaaaca acgcccgctg atccgggtgt gggacaagaa ccacgattac    16440
atcgccgcca ttaccgccga gaaatcggtg gactggcaag agttgatgta ctcgcccggt    16500
tcagcgaaga ttctgctgcg ccggaacaac tggctgagtg acttcctgat caaggacgtt    16560
cgtgccgacg aggatctaca catcacgatt gatccgaggc ccacgaagcg gtcctgggag    16620
acacgatggg gcggcaaggt cactgctgcg catattcgac gtacgtccga tggtgcacat    16680
gaaattgagc tggagtgcat ctcgaactgg acgcactggc agcacctgat cttccaagcc    16740
aacccggtac tgccgcctga gattcagctg ccaaagatct tcatcttccc gatgaatatc    16800
cggacctcgg cgacatacac ggccatcctg aacctggcgc ggaactacgt gccgctgatg    16860
tccatcccga ccaacctgtt caatcctggg cactggttgg tgccgatcat tgatccggca    16920
ctaccaacgt ctcagaatcc gggcctgctg ggtaacttca gcatgctcga ttggccggta    16980
cagatggcgt tcgtcaatcc tgcgattgac cagtcccgct tctcctttgt caccgctcgg    17040
tggacaatgg cagatgtggc cacggacccg ttgttccgtg acgctggttg cttcttgcga    17100
gcgtacacat tccttaccga ggatgaaacg tcgccacaca gggagctggc agacctcatt    17160
ggcgaacgtc ggcccgacc gaaccgcaac tgtgtcgtac tcgcggtgct caacaaatcg    17220
ggtcacacag ggccgacagg cacccttgctg gacggcatca ttgacttggt tgcatccacc    17280
```

-continued

```
ctcgatgacg gaattaccga gatggtgttc cccatcgacc gggacagcga cgggattact   17340
gatcccttgt tccggaagtg gttgggggtg gcaccagcca aaccgaaggt cgtattccga   17400
gacggtgagt attcgggcat catcgaatcg gatcggatca attacaaggc taaggcccga   17460
acgatcgcca ctggcggtaa aagtcccggc tgggttaacc aggccatcac gttcggtatt   17520
cggtacgcac tatctcaact tgcccaggtc atcaactatg gcctcggtgc gtaccagcaa   17580
ccgggcacgg aaggtctgga taacctctat caaggccagc tggacgatac gttcttagcc   17640
ttccaaaagt acacagatcc caagcgtgtt ctcgacatgg gcgccatggc gttgctcgag   17700
cacatggagc agggatcggg cacagcgtgg acggtgtctg gcactgtcac gttacgcatg   17760
ggtcactgga agacccgccc gcgcaccgtc tgcaaggtct ccgtagtcaa cggctatccg   17820
tggctcgtct acgaggacta tgagctcggt gatcgggtcg gcttcgagct ggctcaggtg   17880
atcttcacag atcaagtaag cggtatcaag tggtcctact cggccagtca ggcgatgaag   17940
tgtgaacttg ccatcggcac tgatgatgac gaggaagacc cgtttgcaag ggccctccgc   18000
gctatccaga cagtctgggg cgtggttggc atggttctcg gtgatggcgg gagtacgttc   18060
taatgggtaa ggctgaggaa gagttcaatc ggcggcggga agaaattaag taccgccaaa   18120
cggagagcca ggagaagcgg gagaagctcg cgaaggatat ggcgaaagcc atgtatgacc   18180
tcgccaatga cttgacctat ccggtcgatg aagatggcaa cgtcatgcgc gttcacgagc   18240
tgatcccctt cctcagctat cacctagctc ggtgcggata ccggaagcac gaagacgaag   18300
ccgtgattaa gcaggtcccc gtcccgccca ctgcgggtgt ggtcgaggat gctgttaagt   18360
acgtgcccgt tgatgctccc gggtccgtcc cgagcgcgtt cgtcaagccc cccgagggaa   18420
cacccgaacg accgaacacg gacgggtgga agatcaagcc acacatcact cttgacggtg   18480
aaacgatccg aggaggcaac cggtgaccgt cgtcccgcct tacctggacc cggcagatgt   18540
gggggacctc gtcccgattg cacagatgct ggtcaatatg acctactacg gtcacgttat   18600
cgacctcgac actcctgccg gcacgtatgc ctccatggag caggtcggtg acgaagcagt   18660
agtcacaatg gacgtgatcc gcggacccaa gggtgataag ggcgaagatg cgcccatcat   18720
cacagtcctc tgggatccgg aaattgtgga gatcggtgac ctcccgaatg actggggtac   18780
tggtcctgag cacgtgaacc acggctactg gatcgaagac ctcgtctaca tctggacagg   18840
agatcaatgg atcccgaagc gacccgggtcc cgccggtcct cccggagtca cgccaacgct   18900
atccgtatcc gccgagctga tctcgctcga agatcaggat ctgggcgtcg agtcgtcggc   18960
agagatcacg ggtccggcaa ccaatcggca tatccacttc aaaattgccg cccctcaagg   19020
cccagtgggt cctgcgggac gcatccgtga gtcggacgac tacgacgagc cggacggaat   19080
caacgacggt gacgttccct cctggaacaa cagtaccggg aagtacgagc cccgggcact   19140
gaccaccgtc ctgcctcggt tctactcgat cccggaaggc gcgttcacga acttctcggg   19200
tgtggcacag agacagaaca tctgcgcatt ccccttgccg cccatgcctt ttccgtgggt   19260
gccgttcatc gttgggcaca tcaaggcagt cggcttggaa gtcgatagcg atccgctgac   19320
catcggctcg gagatccgca tcggtgatat gaacaccggt cagctcgtcg ctcgcggctt   19380
cggtaacagc actgggtggt cgacgttcac gcctcacttt tcgacggcca gcactgcttc   19440
catcggtgtt tctccggact ccgagatcgc ggtcgtgccg gcggatcaca cgggcaacga   19500
gggaaccatc tatgtgaacc tctacaacga tggtctcttc ggcatctaca acttcaacaa   19560
ggcaggagcc aggtgggtat cctcgtcatt ccagtggggt aggtaatgag cagagcctac   19620
```

-continued

```
gacgggcaga aacagccagt cgccgagtat gaccctcaga agcagctcca gttcgcgctg    19680
gacaaggcgg tcaaggagct gggcagcgga ctgttcgacc tcgtagatct ggtcttcgag    19740
gcggcgaagg aacgcatcaa ggaagtagtc gatactctca tcgggactat cactgatccc    19800
aatgagatga ttgatgagct tcgggactgg gtagagaatc tgcccaacct catggatcaa    19860
gcggtgcagc agctgaagga tcagctgacc ggtatcgtca attccacacc aacggatatc    19920
gacaactggt tgcttgacct cttgacgcag aactctccgc tgcctgctgc caatttgttc    19980
ggtcggatcc agcttcctca gttcggaggc ggcgtccccc tgaatgccct caccacgtcg    20040
gtggccaatg agctgggccc gttcaccgcg ctcactgttc ccaaccagga cggctggtcg    20100
tacaacgagg ctgaggatgc cgctcaagtc atctgcgacg gtgagcgaaa gactctgtgg    20160
gtacgaggta ctccgatcaa ggtggaggaa gaccaagcgg tcaactcgtc tatcagcgtc    20220
aagtattcgg acatcgttgc cggtgccggg gccaagctca ttaagtacgc cttcgagacg    20280
tacaccaccg aggatggctc gggcactgcg acgttggtcg acatcggcgg tatcgacaac    20340
ccttctggga cgctgagcac tcctgtggcg ctctcagtcg tcggttggga ggtaccgacc    20400
ggggtgcagt caatcaggcc tgtgctgatc gttgaggacc tagtaaccga gggcacagtg    20460
ttctggaaga acacgcccgc gctgacgaag ccgctccttg gtatcctcgc cggcgggttg    20520
ggtgcagccc tgcaggcacg gattgatgag ttcaatgggc ttgtccaagc tctactgact    20580
aacccaggat cggtgctcgg ggagatcccg aacatcatcg tggagggtat tgacaacgct    20640
cagaacctgg gcgaggcgct cgcgggcatc atcaataacg cggtgaatgg tgcgggtaac    20700
ctcgctggta gtggcttcgg tttcggcgac ctgttcgagg tgttccggga tcagcagcga    20760
cagatcaccg agcttaacga aggtctggca gcgctgcaag ctgacctcgg gggacagcag    20820
aacagcggta actcggtcgt cgtcaagttc aatgagtacg cggacgggcc agtcccggcc    20880
tcgtttgacc tcgttcagag tactggcgct ggtgatgtag tcgttgaggc tggcatgctg    20940
gagtggcaag acagcggaaa cgctgatgct acaaggtttt acatcttcca gcctgttgag    21000
ctgatgaccg actacttcga ggtgtccatg gtgatgcctc gtcgtccaga gaacgaactg    21060
ctcgggtctg atccttgctt cacttacctt ttcggtaggt cgaacgcggc gggagatacc    21120
aagtgcttcg cccgggtcgg ctactcgcgg atgcgtatgg gatgccacgt ctccggtaca    21180
gaaacacttt tcggcccggg tgatgtctca tacggtacgc cgccaggtgc ttatgtgacc    21240
ttccgcggcg gtactatcgg cggtgttcgt atcttccaaa tcttggtgaa caaccaggtc    21300
cgggcgacgg ctaccgacac cggcaacgtc agccagctcg gtgacctcta tcgccggtgc    21360
ggtgtgggat ccatgcacg agctcgcttc ggcggacagt caacaccagg taacgtgtcc    21420
atctggacga tgaacgacaa cgtgccggtt gaggtcaccg gtacgacgtt ccgcgcatac    21480
cgaagcctga ctgcaacggt cactgtgccg gttggcgaag ttcctttgcc ctccggcgta    21540
ttcgatgtgg tcgactacaa gtcccaggat ctggcttggg accctaccac caacgagatt    21600
accgtgaaca cggcgggcac ctatatggct actgcgcgca tcaagtataa caacgtagcg    21660
ggcatgggtc tgacgaactg gtaccacgtc tggtatgtca acggcgtgat taagggttac    21720
ggtaaaccgg tcaagtccgt gactgtgaat ggtgttggtg tgccggcgac ttcggcagac    21780
tcgggcatcg gcggtgatcc gttcatctac tacctcgctc cgggtgatgt catccgactg    21840
ggtatgggct cgaacggaag cacggcgatc aagggcgaga gcacgggagc ttacaccaac    21900
gtcacactga ccaagattag ctaggagacc aggatggagc aggggtggac cactacacca    21960
actgatccca ttatcaagcc agagtggtcg acctcgcgtc cgccggtcat tccgtcaggt    22020
```

-continued

```
gtcttgactg agtgggaagt tcgtatctcg cgaagactca gggatgaagg catcggtgaa   22080
gatgcagcca cgctgctgcc tctgctactt gcgtcagatg cggggcttgg gtcggatctt   22140
gcactagctc atcacctgat cggcacgagc gacacgggtg tgggtgaaga tctagcgcgt   22200
ctgggcctgc ttgcagcaga ctctggtgtc ggggctgacg acttgttgag cctcagcctg   22260
aggattgctg acagcggtat cggtacggac ctgctgagct cgttcaagcc ctcctatggg   22320
atcttcgact cagcggtcgg tactgatctt gctggcttca ctgcgaaggc gaacgtcgct   22380
gactcgggtg tgggacagga cgtagcaacg ggcggctttt cgccgatggc tgctgctacc   22440
acagtcatca ccgcttcggg tacctatcgg attcccgtgc agtgccgcta cattgacctc   22500
atcgttctcg gtggcggtgg tggcggtaag ggcatgcctc tgttcggtgt ttgggggcag   22560
ggcggcttcg caggttcttg gaactacgtt cgtctcgagc gaggtgtcga tattccgtgg   22620
actgcgatca ccattaccat tactatcggc aatggaggta atggcggtac aggtggtggc   22680
ggtggatctg ctggcggtgc aacaaccatc accatttctg gttggggcac attgactgga   22740
gctggaggtg cgggcggtac tcagagcaac ttggatactg ccggtaagtc tccaggaaac   22800
atcaccttcc aggggcagcc ttacaacggt ggtgctgagc aaggttcagc aggtgctgct   22860
ggcaacattc ctggcggtgg cggtgcagca gcgactgtga cgctggcagc aggtggtgca   22920
ggtgctcgag gtcaagcatg gatccgggcg agtcaatagg agaggtaaat ggcagtttat   22980
caagatgctc accggaatgc ctgcgctaac gccattgtgg cgctcggcaa ccggatcggg   23040
ctctacatgg atactacccg ggtgggaacg gtgtatgccg ataccacatg gggtggtgct   23100
gcgaaggtca cggaaggtgg aattgacaag gctgtctcta ccgggtccac agtgaccatc   23160
acagtgccgg gcggcacggt cagcaatggg gctgtcatca accgatacgg gatcttcaac   23220
gggtcaacgc tgttgcgtac cgaagcgctg ccggtgtcgc tcaccgtcaa cgacgggtcc   23280
caggagttca agatggacgt gacgccacag ttcaagtatc gcggagaata ggaaggacag   23340
ccagaatggc ctttattcag aagcaggggt attggatctc tgagaacggc tggcgaatgt   23400
gcaacaccgc cgagctggac tactcgccaa ttccggaac agacttcaag ctcggtgttc   23460
gcaagggcgc tccgtcggtc atcctcaagg cactcatctg gcgcctgcat cggatcgagc   23520
cgatgattac cacacagatc ggctgctaca ccgataccaa ctcgatggcg aacagcaatc   23580
acaactctgc tactgccatc gactacaact ggaacctgca tccctatcag aagtggggaa   23640
cgtggggtag caagcgcccc gcagtggatc aggtcatcaa ggactttcgc ggcattgtcg   23700
agttcggtgg cgactggacc tcaccgcgtg acgagatgca cttcgagctc cacttcgcgg   23760
aaggtcatgc tggcactgag cagctcgcta cggacctgcg caatggtctc tggggtatct   23820
acgcggccgc ctcggcgccg ccgcctgtcg tgatccctga gggctacttg cagcttggtt   23880
ccgaggggga tcaggtgcgt aagcttcagg tcggtatgaa caaggtcttc aagaactaca   23940
aggccatgcc cctcgatgag gatggcatct tcggcgcgtt caccgagtcg gcggtcaagg   24000
agttccaagc tcgctcactg atcggtgtgg acggtatcgt cgggcccgag acgaagcagc   24060
gcttggcgac atacggaatc gtcctcgatg gggcgactga gccgacctcg ccgcctcctc   24120
ccgtcgtgcc gtcgttcgtt tatccgtcga ccgacgagat ggtcaagcag gtttgggagc   24180
agcacttcgg cccgaaggca gaaggctggc cacagctcgg caagactccc gaaggaaaga   24240
atcgctacct cgttgacggg gtggcgtcac tcatcgccaa ggaggaagcg tgaccaagtt   24300
ctgggagttt gtcaagagcg acaagttccg cctctacttc tactcggtct gtgtggccgt   24360
```

-continued

```
catgggtctg ctcgtgtact acggcatcgt tgaggccgag gcagtcccgt actggctgac    24420
actgctgggg gctatcggga tggttggtaa cgctactgca gccgccaacc tcggcagcca    24480
gataaggcag aagggcgggg aggggtgaca tggtggtcag cagacttctg gaataacatt    24540
ggacctgttg gtctttcggt gctcgcttgc gtgttctttg ttgtcgctct tgtgagaggg    24600
tggctggtga ttggtcggta tcatcgagag acagttgagc gactggatgc gcgagcccag    24660
aaagatgctg agaccattga cgtccttagt cgggctgtca ccgagaaggt ggcggaggac    24720
caagcgacca cacggattct cagcgctatt cgggatctgt ggacgtcgtc taaagaggag    24780
gcgacgtgat gtggccgtgg aactgggggga agcgacaagt agagcgggca gaagcagctg    24840
agcgggaagc tgacgaacga cgcaggtcgg taaatcagct cctcgctcgg tcccgcgaag    24900
cctcgcgtgt ccttcgcgcc gaagtcgaca agaacagctg gtctgaactt ttcggcgagg    24960
cattccaagg tagaggagag gttcactaat gcgctggctg tacgtcgcgg gcattctcgg    25020
aatcatcggc actctcgcgg cagacccgtg gatggacacc gatgactaca agctcggggc    25080
cgatctcagc ctaacttacc tcgccatcct gtctgcttgc ttcaccgttc gatacgtcgg    25140
gtgggcaaac tggagagcca acaaaatcgg tcagatcttc gcccttttct cggtactact    25200
tacgcttacg ctgatccagg gagctgtgtc ggtgttgata aacccggatt acccggggcg    25260
tgagtatgtg cgcttcatca tctactcagg tggcgtgatc ggcatgctcg gcatgctcgt    25320
ctcgctatgg cagcaccaac gcagggacag gaagaacaag tgccagagtt cagagttgga    25380
tccaacggat ctgatgtaac acagtggcag gagtggttca accgctatgc caagtcatac    25440
gctccgcccg ttgacggcta ctacggggct cccgatgagg ccgccgtcaa gatcatgcag    25500
agccgattgg gcctgcccgt tacgggtcgg ttcgatgacg cgattgctgc ccgtgtggga    25560
tacaacaagg gtccttgggc gggcggtgtc gttgtcgagc gacgtaagat ctggatctac    25620
accgcaccgg gctcgggggc cgattggtgg gtgggaccgt cgttcgaggt tggcgagttc    25680
gccaagaacg tgttgaagat caaccaccag ccgctgtact tccagaaggg cggatacctt    25740
ggtctgctcg gcggtgatcc cgcgttctcg tatcaggacg tgatctggga tcagggcttg    25800
tcgctcgagt actgcctcga ccataacccg gacatcaacg acccggatct ggagctgtgg    25860
ttctcggggt attcccaatc agcagacggg atggaggacg ccgtccaacg gctgttcggc    25920
gacgagacgg gtaagtaccg agacatccga ggacggatta atgggctcat ccagttcggc    25980 aaccctcgc gtcagaagaa cagcggtcct gcgcccggtt ggggcatcgc tcgcaagaca    26040
cgccctgtgt ggcttcgaga gctcgtgacg gacatcgtgg cgacgagccc cggtgctcct    26100
gacttctacg ccgcctgtga cgacgagatc cgcccgttgt tctatgagtg gttcgtggaa    26160
gccgagacag agcttccctt cgtcatctac accgcgcaga tcatcattcc ggcgctgctg    26220
aaccttgtgg cgcccttcct gtcgggactg ggcggtatca ccaacccgtt ggcggctggc    26280
gtgttagcag gagccacagg gctgcctatg tcgctgattg gatcgctgat cagcggtgtt    26340
gctggcacta acaagaagcc caacccgaag ctcatcgagc tgctatctat caaagggggtg    26400 ctcaccaacc tgcccagct gatccacttg ctcactcaga tctcgggcgt gcagacacat    26460
ggggagtacc acctgcccaa gcccgagttc ggcgggcgaa ccggcatcca ggttggttgt    26520
gacatcatgg cggctttccg gcgctgacct gcggatctcc ccaggcgctc aggggtgaac    26580
gtagacctgt gatacactga ctgggcaagg caaccaggac ttcccctgtt acctacaccc    26640
cgccagaaag gttctacatc atggctactg ccacccgtac ccgcaaggcc cctgccaaga    26700
aggctgctcc caaggcggcc gagaagccgg cgaaggaagc cgccgaggtc aagggctctg    26760
```

-continued

```
catggctgcg cgatcacgtc aacgagacgc tgggaacgac tcacgagtcg acccggatcc    26820
gcgccgtgct gcggaagctc gtcgccgacg gcgagatcga ggcccgcgag ggaggtcgct    26880
acgacttctc cggcccgcgt gatcccatcg tgaaggctgt catcgccgcg ctgaaggccg    26940
aggccaagac ccccaccaag cggggccgca agccgaaggc cgcgaaggcc gaggtcgaaa    27000
ccatcgaaga ggtggaggaa gaggtcgaag acctggacct cgactgatcc ggtgcgaaag    27060
aaggtgccct cctccgggag ggcccttttt ttgtagcttc ttgagcttga cgcgccgggt    27120
tgacacgacg acgaccatct cttagactag tacttgcacg acgacgaaac cctctcgaaa    27180
ggacgacgac taatgaacac caccgaagcc gctcgcgtta tcggcatcaa gcccaaggcc    27240
ctgcgcacct tcctccgcaa gtcgaagtcg ggtgtgggat cgggttcccg ttacgacttc    27300
tctcacgacg aagtcatggc gatgaaggat gcctactggg aagcactcgc gaagccgaac    27360
gcgaaggatg acggcgacgg gttgggggag ggctcgaagg gcttgcccct gcagtggctg    27420
aacgatccga gcaagaaggc cttgttcgcc gccgaacaac gcgcccgcct cgagcgtctg    27480
aacgcccgtc tgcgtgaggt gaagctggac gtgccacaca tgactgataa ggagctcaag    27540
gtcaacgggc gcgccatgcg cgtcgaggag atcaacgcct gatcccaaaa acctctgagt    27600
cccgggttgc aaagctcggg gctctttggt aagatctacg tatgacgacg aacacgaacg    27660
acctcaccaa cgccaccgtt ctcgaccggc atgggcggga atgcactgtc ctccaggaca    27720
cgggcaacgt caacgtccgg atccgcatca acggcaccaa ctacggcggc tgggtccccc    27780
gcgcctcgct gactgtcaag gaggcctgat catgtctctc atcttctgca acggcgtgaa    27840
tcactctgac gaggcgaagg aacaggcctg caagcgttgc gggcgcaagg ttgcacgacg    27900
cgctgacggc aaggtgttcg acacccgcga ctactacacc gaggcaggca atccccgcca    27960
tgtgtactcc tgctggttcc cccagcatca ctgcgatgac aaggacatcg agctgtacca    28020
ggaggccaag gctcgaagca ttgctgccgg cgagctgatc gtggggcaga aggtcatcgt    28080
tgcgcgaggc cgcaagatcc cgaagggtat caccggcgag atcacctggc tgggcgcgtc    28140
tgacttcggg atgcgtgctc gcgtgcaacc cgatgagggt gaagccttct tcatcgcgct    28200
gaagaatctt gacgtgaacc cttgacatca ctggcgcggg ggtggtacac tctaagcaca    28260
acgacgacga aaggcactcc ccatgtctac ttacaccatc tccgaccaca ccgccgctga    28320
gtacaccgcg atggctgagg attgcatccg ccgcgagcag gagtcctggg agcgctccga    28380
taccgacggc ttcctctcgc agtgggcctc caactcgatg gctcgcacgt accgcactct    28440
cgcccgcctt gccgccaacg gaggcgacgt gcaggagatt acctggctct tcaccaccga    28500
cggaacgcct gttgacgaat ggcgctgggt tgaaggcaag tacggcgcct ccatccgggt    28560
gtggcacaac aagcaggtta cttggttccg cccgtcacag gcgaagaaag gtgaacgccg    28620
cgaagctgca gatcgtgcga aagggtttgt gttcggcact gttgctgcca aggtcattgt    28680
caagaccgtg ggtaacggct acgcactctc cgacgtttgc gttgctgcga acgacaacgc    28740
cagcgacatc gtccgcgtga tcgaggttgg caactacacc gatcacaagc actaacccac    28800
caaaaagggg cactcaggat gaactgggcg ccccttcttg gtggacgtgc tagaccggat    28860
cgtagatcac gctcgagacg tcctcgacgc acgtagcgac gattacgctc ccgccggcgc    28920
gcttgatcat tgagtgcacc cactcctgcc tctgtgtggg acgttgaccc ggttgcttga    28980
cctcgatgcc ccagaacgtc ccgcgataac acgcgatcag gtcggggagg ccggccatca    29040
tctgagggcc gccatgcacc ttgaagacga acgcgccgag gtcgtcctcg aggtacttcc    29100
```

-continued

```
tgatcttctg tcctatccgg gcctcaggtt gcatctgaga cctcgtcggt gctcatcagg    29160
gtatgtgtac cggcagcgct gtcttcggcg acgaggcgat caatgagggc ctgttccggg    29220
acgttcacga gcggctgccc tgttcgcgga tcgtgcgttg acatcggtac cgactgcggc    29280
gagaagtcga ggaacggggt gggcccaata cctcggatcc gtgccaggtg caggacgagt    29340
gcctggaacg actgcagcca ggcccgctca ctggtgccgg tgaactcagc cttccggagc    29400
aactcgtcca cctgctcgag ctgtccttgg aggtggtagt tcgctgcctg aaggtgagcc    29460
ttctgggcct tgagctcgag gatcttggcc tccttcttgg agacctgctt cttacccatc    29520
gaccgggagc cccaccagct tgcggatgtc cttcacgacg ttactcagcc ggtagtgatc    29580
ctgctgcaga gtcgagttcg gggccggctg cgtcttcacc aagtcccgga tcttctggat    29640
ctgaatctcc agatccctga tcctcgtctg gcgcgtcttc gccacgtcct gcaggtcgtt    29700
cagctccgct gacaccgctg ccaccgtctt ccgcggcttc ttctccgcgt ccttcttctg    29760
ctccgccatg atcgaacaat cccttctcga agtgatccat tgcagcccga agagtgggga    29820
gcccggaagc tcccacctcc ccggaatcca gccgatagcc gaagccctcc gcgttggaga    29880
aatacctcga ctggttccca ttcatcgtgt actactcctt acagctcgtc gatgtcgagg    29940
tcttcgaggt tctcctcttc ctcgtcctcg acagccgcct tcttggcagc acgcttggca    30000
ggagccttct ttgccggtgc cttcttggcg ggacgacgtt tcgggggctc gggctcctct    30060
tcctcttcct cctcggcgtc ttcctccggt tcctcctcgg gctcctcttc ttcctcgtcg    30120
tcggcgtcgg gctcgaggtc ttcgtcctct tcctcgtctt cctccggcgc atcgccgacc    30180
tcgctggccg ggaacacctc aacgatgacg gacttcatcc gaccctcgta ctcgtcgtct    30240
tcgagcgcga agccgatctc cttgccgatc aggcgattgg ggtcgacctt caccttgcgc    30300
ttgcccaccg acgtgccggc ggcctcgaac aaggacttca gcttgaagaa ctggttctcg    30360
gcgagcttgc agtagtacgg ataggttgca cgaggaatct ccggggactc gatggtgaac    30420
gtccacatct tcgtgccgtc cttggccggg tcatccacca ccttggtgat cttccccggg    30480
taatcgccgg ccgccacgtg cttgggctgg tagttcccgc gctccttgac gttggagaag    30540
tcgatgatct cggcttttgc cttacttgtt gccacttact ttctttcctt ccattagtcc    30600
caccagtcgg ggaacggttg ggctctccag gtaatcgggg agtttgtatt ctgatcgggc    30660
gccggtgtca taggacacgg acggggccag ccacaggcgg cgtcggacta catcggttcc    30720
ttcctctccg ggtactttca cggtgtacag acggcctaca acgtccacaa taccgttgac    30780
ggccgcacgg atgcccttgg gcaagtccgg gacatactgg atggacccgc cctcgaactc    30840
ctcgtcttct tcgtcatcga agttcgcttc gacctgtcgc tcctgcgcgg tgtagatgat    30900
gcccatgtcc agcgtgtgga atttgtcgag catcgtcttg accagctcgc cggcgttgcc    30960
tcgatcttgc agcttaacga gccctgggcg gcgtgtgagg tcggcttctt cagcgttccg    31020
agtgatgtat cgcagcgcca tcgttgagat cttcgtgagg ccgtcaagcg ctacccactc    31080
gtagttgtgc ttgcccgagc gcaggaactg atagatgtcc tccatttctt cccacgcttc    31140
aaaatgccac acagcgggat cggctttgat gaagcgatca gtcccgcgtt ctgggtcaac    31200
gatcaggatc ttgcccttgc cggcggacat cgtgaagcgc gtcttgccct tcttattacg    31260
ggcgtagacg aggatccgag gcggtctcat ctgaccgttc ttctcagcga gcttggacgg    31320
ggacgtgatc ttgctggccg caatcgcggc ataatccttc cccggtgtcg tctgtgctcg    31380
cacattgcgc cgaatgggtc gggtcacttc cggtccttct cctcgtagta ggccaaggga    31440
tttgctttct tgtacatctg tcgtcgtacg ttatcggaat tgactccgac gagctcggca    31500
```

-continued

```
atgcacaagt acttgtactc acaccagtca caagaccgat cattcagcct ctcgactgcg   31560
tccttattct cccaagcgta ttccacgaac ctgtcggcgg tgtacgtcgc ttctgcgagt   31620
gtgcgagcga tcatgtcatc gtgcttttcg agcacgtcac ggcgaaacac agggctgttc   31680
tgggtagccc cgtactcgta ccgaatcgtc ttgagctgct tcaggatctc agcgtactcg   31740
ggctcattct cgaggccttc agctttcagg cctttgagcg cggtcgggta atcggtgatc   31800
ggctgacgcg catacagccc gccgcggacc ttgatcctca agggctcggg tgcagtcggg   31860
acgacgtagt tccagatgaa gcctttgacg gggataccgc actcgcgcag cgcccagatg   31920
tagaggactg actgagtgtc gcggtaacga tagtcgagcg agggcagtcg cttgtgggtc   31980
ttgtggtcga cagcccaaag tccgtactcg tcctcgatga gcatgtcgat cttgccttgg   32040
tactggaggc cattcggcag ttctgcttcg accttcatct ctacctcgtg cacttcccac   32100
gacttgtcgc cgcggtaata ccagttgtag gagttgtata ggcgaggcat ctcacgcggc   32160
aggtcgccga gcgtgtcctt ctcctcgtct gtcaggtcgt gatacttctc gcacagcgcg   32220
gtgtggaccg ctttcacgtc ttcacccttg taccgggcct cgagcagttc atggaaccag   32280
gatccacgct caagaggctg tgagtacttc tgcctcggtg tcaccaactc gatgtacttg   32340
tagagtgctt ttcgaggaca gctccggaat gacttcagga ggctgttggt aatgatcagg   32400
ttatcggtgt caagcggcat ctaggagtcc tctctcgtta agccaagctt cgagcgcgtc   32460
cggttcgtgt accaggtgtc caggaatctc atcagctcca ccccaggagt cacccacctt   32520
gatgtcagca acgatgggta ttccgggaac gaagtcgaaa agtggaccga gtggcggatt   32580
ctccataact cgtttgatgg ttggtaagac catcgggagg tggtcgttcc ggacctcaaa   32640
gttgattgcg tcgtggacag tcccaatagg agtggctgcg agcttatctc ggcggaaacg   32700
tcggtcgagg agaacgaggc tgagaaggca caagtcgctc gcgaacgcct ggaccgggga   32760
attaatagat tggcgctcag cttcagcgac gacaccggac tcgggagatt tgatatccgg   32820
caagtggcgg atgcgaccca ggggggattg cactcgggag ttgcggtggg cgagtcgtcg   32880
ttggcgggca tgccacttga gcagctcagg aaactgtccg aagaaggcgg ctcgagcagc   32940
ttgagcttcc tcaggagaga cacgtagtcc gtaattattc caggcagtct caatgaactt   33000
cttccatccc attccgtaca agaatccgaa gttcactgcc ttcgctttct tgcgttcttc   33060
cttggtcacc cgagaagcgg gcttcccagt cattctcatg gccatagcca tgtgaacgtc   33120
ttccccgttt atgtagagct gcttgagggt cggttcgccc gagatctcag ctgccacccg   33180
taactcgatc tgcgagtagt cagcctccac aaaagaccaa ccccggggag caccgaatat   33240
gctgcgtaca agtggatccc gaggaacctg ttgtagattg atacctcgca cagatgacgc   33300
tttagaacca gtaactttat ctgagtctgc cttcccagaa gacaatcgac ccgtaactgt   33360
cccggccagc ttgaacgtcg tatggagacg ggaatcatcg gtaatcagct cccggtaagg   33420
gttgaagaag gacgactgga acttctgcca cttgacccgc tcgaccagta gatcgacagc   33480
tgggtgtgga tttgtcgcgg cgagttgagt gaggaccgtc tcagcgacgc tagggcctgt   33540
tttgccttcc ttgagcacag gtagatcgag gtgatcgtag aggaaccagc ggaggaagtt   33600
ggaagggttg aagttgacat cggtcactcc ttccggcaca tactccataa ggccatcgtg   33660
aatctcctgg agcttttcct cgaccagctt agcaccttca tcaagtttct ctcgatgaac   33720
ataaacgcct cttcgctcaa tgtgtacgag actctgagaa gccggcatga tgagcttttc   33780
aaagagtcgt tccaggcgag gatcagagtg aagctcagaa ctgaatatgc gatataggcg   33840
```

-continued

```
aagagtatgc caggtgtcca gtgcattgta ctgaagaatc tcccggagag tatgctgcat   33900
gtaccagggc tcggcattct tgccgccctt gatgtcaatg tcccatgccg gcgcgttcag   33960
cagcatctgt gctagaggtt taagaccctt aaatcggttc tcgtcaagga tatgagctgc   34020
cagcatagta tcaaagttgc aaggtagagg tgctccaaac tgaaccagcc agcgacaatc   34080
aaactttgca ttgtgagcaa cccgcacagg tacccgctta caagcgtcgg tagcacggcg   34140
aagaatgctg tcccaattgg atcggcatgg agaccgggga tgggagagtg gaagagccca   34200
gcaggacatc gtgccatcct catcgaggag agagaatgct gcagagacga tgaacgcgcc   34260
atcttcgagc tcattaaatc cagaagtttc cagatcatat gcaaccgcct tcgctgtctt   34320
cgttgccaca ccgaactgct cgagcgactt ctcgtccttg atgatgcgga ccttgctcgg   34380
cttgacttgc ttgtcctcgc tgccgtagag ctcggtgtgg agcgctcgaa tgtcagcgta   34440
cagcagttga atctgtgacg ggttgcggtc gatagcaccg agggcaatgg tcggcatgac   34500
gaggaggtcg ggatggagcg ggatcacccg gtcctgtgct cgaccgcgcc acttcataat   34560
gccgctgtgc ccggtagtga tgaagagagc ctcgttaccg agggcgagaa tagcgtctgc   34620
attatgctgc aggacattct cttggaacgt agcgcgtagt tccttcaggt ctgccttgga   34680
gaactcaccg tcgtattgcg acggcgcgca gcccatgaag actagctcat catcccggaa   34740
cccctggctc ttcacgcggc ggatcatttc ttcccgtaaa gaaccgcgga ggacgaactt   34800
cgtaagaatc actattttca tcggctagag cgctccagta gttgtctgcc ggcgtctcgt   34860
cattatgcag acgatacaca ttaatgccga catcgttgag tagccggacc ccggcggggt   34920
ctcggtattc ccgattgaag aacagcgtct tgatcccgac attcaccagg aggcaggcgc   34980
aggtgtagca aggggagtcg gtgcagtaga agtctgagtt caacagcgag accccgtgac   35040
gggctgcaaa ggcaacggcg ttcgcctcgg cgtgtactga gcgtgtgcag ggctccccag   35100
gaggatgcgt gcagtgctgc ataccgattg gcgcgccgtt gtaccgggtc gacaagatgc   35160
ggccgtctat ggacgccaca gcacctacac ggagccgcgt acaggtcgct cgttgtgcga   35220
cgaggaacgc catgctcagc agcatgtcat ggcgtgtggg acgttcagtc atcgagctcc   35280
tccatcgtta cgaggtcctc ccccaccaaa acgccattca tcagcggtga ataggtgaag   35340
gttagaaatg aataccgtga gtgacccggt aaagggaaaa tcttcctttc gagtctggtc   35400
caccatccac tggagcaagc gaccggcaag atataggtcg ttgtgcagat gacgggtgaa   35460
gtcgcaacta cgtaggaagt aattacaatc cagcttgagt ccgttgcgaa tgaagtggta   35520
cccgagggta cacgggactc tctgcccaag agtcgtgcca gtatcttccg gaaaccagac   35580
ggggaggtat gcttgtcggg tccatggatc ttttcgtagg agctccacta cgtctcgtag   35640
atctccccag ccactctggt cttgtcccgc ccaccatcct tcttgcggcc aaaaccgttc   35700
ggggtaggta tggtcaaatc tctgattccc tccactcgtc aagaaagtat ctctggattt   35760
ctggctgtgc catggccatc gcgcatacga gggggggagga ttgtgcggaa tacccgatac   35820
cctctcgagg aagtgttcct cggcccatgg aaggtcgggc tgagtcaggt ctatcaggtg   35880
ctgtactgaa ctcgagatat cgggtagttc cagaatcacg ttcgggatct cgcggacagg   35940 agaggggcg gacgtgctct gccaggactc tctgcacgtg atactccgtg atagcaattg   36000
ctcggccaaa acgtcgcgag tgggattgac cagatgaagc acggttaagc ctccagaccc   36060
agtttatcaa gtgtaaggga tttgacgtca acgagggaa gtacagagaa tggtttgtcg   36120
ccagggtctg taaactgact cgcgtagtca acacctcgta cttgactatg gaatctcttc   36180
cgcggacgtt gagacgaacg gtaagtagaa agctcatcat atgtcaggcc ttccttgtcc   36240
```

```
gcctgcagcc acttcgtgta ctgcttccag tttctatgca gggcggggta gtcctcgagg   36300
ttgccttcct tcacgagctc acggcatcgc gaggtgaata gcttacgctc actttccaga   36360
ccaagggggt aggcaattgt gcggaagcag tggtactgga tcgactcagc gaaccacacg   36420
aagcggaagg cagcgatatc caggcccaga cgctccgcag cgagccggcc gacgtgatac   36480
gcgactgacc agtcgagcac actgaggtag cccatgtagc ccgtcctcga gtgcagcagg   36540
atctgcgggt gtggctcgag agcaaacgac agggacagca tgcaactgcc gagtgctctt   36600
gttgtcactc gtcctccgcg tcgaggctgg acggtgttgg tgcgcaagat cattcggttg   36660
gcgttcttct tgctggtgcg gccctcgatg agatcgagcc attcccgtac agcatcaggg   36720
tcgaggtact ggttaatcat ctttgtccat cgcgtgccgg cgagccagaa gcgggagaga   36780
tcacactccc actccatggt ctcggcctca gcgaacacgt tggtcttgat gacatcggta   36840
ccgctgatcc agtcatactc cttggcatgg ctgtacagca tatccgcaca gagctcctcg   36900
tggagctccg tcatcgttcc ccgtgtgaag tggtgcatca gtacccgttg atctgccgct   36960
gttcgttgac gagcgacttc ctgaagtagt gcttgaacac atcggtcgga ttgatgccgg   37020
cgagaatatg gaactcgatg aagaagtgcc aggcatcagc gagctcctcg aagaacttgt   37080
cccggtcggt ctcccgcatg gtctgcttcc agggcttgtt cttcagatta ttgattgctt   37140
cgtacagttc ctccacggtg tacgaggcga actctcgcag cgaggcctgc gtccgccgag   37200
aatcaaggtc gccccatttt tctggcggca gctgagcgtc ctcgttgatc tgggcgtagg   37260
cctgcatgtg cttgagctgt tgagcgaaca tcgtgctcaa gatatccggg acgttgtccg   37320
gctgtgtgga atcccacaag ccgtcgaact cgtcatctga tggggtccag ggaatttggg   37380
attccaccgt cgtcatgctg ctgccgattc cttccatagt tttccgtgtg agtccgtgag   37440
agcgtagcga aggccttccc acgaagcgtc gtgctgctgg tagttgaaca ccaccgagcg   37500
cccaggccag aatacgcgat gctgttggta caggttgtag atcttggtga tgttctccct   37560 taccccggc atctggtcgt cgtccatgat gttcgtcatc accgcggtga gtgatggcaa   37620
gcaccagatc atcagggagt gccgagcgat gcgttgccgg atacgcatca tcgagtcact   37680
caggaaggct cctgatgggc cctcagcggg cggtacgcac gtccgataca cgtactccga   37740
cacaaccggg tggcggtcgt agatgaagtg cgtagggcgc gcctggacgt ctttgaagac   37800
tgcctctgac aggttggcga ttggtcctcc tgtcgaggta cagaatcgag gatgcacctc   37860
gagtcccggg aagagatact gcagctcctg gatcagcgtc gttttgccgg cgccgtcggg   37920
accttctacg atgattgaca tctacttccg caataccttt ctcggattct tcataatagc   37980
ctcagcgacg ttaccgtcat gggcaagtgt atcgaagagg aactcgtcta cagtgtgccg   38040
ggccaggaga tatgtgtagg tgatcgactt cttggagagg gcaattcgat ccttggcctg   38100
cttgaagttt acccacgaga ctggtaagga ataccagacc atgtgagatg cagtgctcag   38160
gtcaattcct tctccacctg cttgcggatt gatgatagcc actgcagcgc cttcagcgtc   38220
tcggaagtct cgtacgttct gagcagactc ctgacgagta agtccgccac gaactgagaa   38280
atgaggaagc cccttccgag tagccatagc ctcaatcgca tccagttcgg ggcggaatcg   38340
agcacagacc acaagcttat cttcgttgtc caaggcctca tcaaagatct cgtcgaggat   38400
ggcaagtttc tccccgccca gctcaacctg ctctccttcg gctgacttgg taaacccacc   38460
tgtaatttgt gtaaggcgga gagtaagtac aagcggtatt gatgcttcga gtagatgctt   38520
gacatctccc ctttccagct cgaccaccat ctcctcagcg agcttgtcgt agacatgagc   38580
```

-continued

```
tgtctcctgt tccaggtcga tatgtctgat aaccggcggc atttccggcg ggaggtcgaa    38640
gcactcgctg cgcttgacta tgaaggcgtc ctgatccatc aactccttga gctgtgtggt    38700
attcttggcc ctcaggaatt gagggaagcc attccgatga gtccatctgc caaagtggtt    38760
cttgaactca tcgactgtcg gccattcctc gaatcgttcg ggattgagga acttccactg    38820
catatagaca tcgaagaccc gctttgcctt ggtgactggc gtacctgtca ggatcaagcg    38880
atagtcgaac agcggacgca tggacacaac catgctggac gcccgcccgg acggtgactt    38940
gatcttgtgc gactcatcga gcacgccggc agcaggcttc ccgtcgagcc atttgatgat    39000
ggccgtacga ttggcgaagc gtccggttgt cttcgagcgt cgtcccgatg caagcttctt    39060
tcctggcgtc ccaaaggcct cgtagttgac caacaggacg gtcagctggt gaaccttctg    39120
gacaggaggt aaagcgctct tacgggcctg cttgtcccag atgatggtgt gatacctcag    39180
cgggcaatgc tcgtggaatt gttccaccca gacatcgaga atccgagcag gcgcgatgat    39240
gaccgcccgg tcgatcttgc cggcagtagc gagcacagac aggtagtcga tggcgacctt    39300
ggtcttacct gtccgaggct ccatcaagag agcccctccc cagcctgagg agaggacttt    39360
cttgagagcg tgaacttgat ggacgtacgg cttagtccgg tatttgtact tggtcaaggg    39420
gatccaattc tccagtttgg acgtgaggtt caccggctgc tctattgccg tcccagaagt    39480
atgaccgggt cacactgact cttatccatc tattggccac gaagcaatac gacttaaaga    39540
ccagtcgctg tcggtgccaa ggaagaggac ttaccgttgt cggaagaagt cggtagacat    39600
ggtcacaccc ggaatggtca cccctcgctt gcgtcggccg cggcatcggt gtcctcgccc    39660
aggtgatccg tccagttgcc gtcttcgtcc tgcttctgca gcacgtagcc actctcggtg    39720
tggtatcgga tcaggtccgg gtattggagc atgatcttgt ccccggattt gtagttgtag    39780
gcccgccaga tgagtttgcg gtcgggctga tcctgttcgg tcatagtgtg atcgggtgtc    39840
ccttcaagta gttgaggcca agcgaagtgg aggtgagtac agcgaatgac actcgtacgg    39900
tctcagcatc attgctacta ctggcgagtt cgtgtagtgc ctgaagtagc aactccgtat    39960
cctccagttc ttgtaatcgc tgagattcca tcatatcgtc cataactcat cccttcccgt    40020
aagtattgag ggcagcctcc cggctgatcc cgcaatagta acaacgcatc aacccgggaa    40080
cgatcacggg ggcgtgcttg agggcatgat gagtcttcag gtatagacgg aactccgtcg    40140
ggcgacgaca acgaccgcac cattcttggc ccggggcaca gagctcttca gcgagggcat    40200
gaggagtact gaagacccgg ttgcgagcaa tgatggcgat gtccgcatac tcacccgagt    40260
gccacaactt cttggtggct tcccacgatg tccggaagtc cggacggaag ccgtttcgcc    40320
atttcccttc atgcgtgaca gcaacgatct gccacttatt ggggtcagtc gaacggaagc    40380
agcggatgtt ccgcttgaag tattcagcgt agccctcgtg gcgcaacaag ctaggtaaca    40440
cgggtaatgt tagtgcggtt gtcatgcagt aatcataccg aaggggtctc caagatttat    40500
ggacgtcgat aaacaacttc gcattctcag ggctatctgg cgcaaggctg acgggtatgt    40560
cttcttgccc tacatcgaaa agaaatgggc ccggacagac gagcggaaac accactggcg    40620
ggagggtccg gctttccgta tcccggcgga ctacgacaag atgcgtgacc acctcgagaa    40680
gcactgggag gacgatctct acttctcccc gatggtattc actgggccca agcgcatctc    40740
agagtgggcg gcaatcggga ataggctttg ggccgacctc gatgaagcca accctgatga    40800
catcaaggaa gaacttaagc ctactctcgc ctgggaaacc tcgcccggtc gcttcgctgc    40860
aatctggttc atgcactcgt cgcggcctga gacaaccgaa cgaggcggag agaatcatcg    40920
cctgtccatt gcgctcggtg cagatcccag tggatgggat accacacagc tactacgagt    40980
```

-continued

```
accgggagt gctaacaaca agcccggata tgtagaaggt attcggggac gcctcgtgtg    41040
gcgcggaggc tcccgcctcg cgtgggacga gatcgaccgt ctgccagaaa ttccccaggc    41100
ggacgtggtc gggggagacc tcgtaactga gcagcttctt gagagtatcg acccgtatga    41160
gtcctacgcc cgcgtcaagc gcaagcttcg aggcgttatc aggcagtaca tgcgactcaa    41220
agatgactcg ggtctggaca ggtcggagat cgcttggcaa gtcgagcggg aactcgcgga    41280
cgctggctgc acgctgctgg agatggtagc gatcattcga ccaactccat ggaacaagtt    41340
cgagggacgc gccgacgagc tcaagcgatt gacgctggag tgcggcaaag cgctcgctct    41400
caagaagccc aaagagactg ctgctcttga tcaggatact gaggttaaac acaagctagt    41460
ccctttctgg cggaatgagg aatatcttaa tgcgccagag ccggaatggc tttatgacca    41520
gtttatccca aaaggagggt gcggcttcat ctcggggatt ccgaagtcga tgaagacgtg    41580
gctggcgatg gatctggcca tctcatcggc gctcggcaag gagtacctga gctacgagtg    41640
cgagcagccc attaacgtcc tctacgtgca gcgagaggat ccgacgacca tggtcaggtc    41700
acgtcataac gtgatcgcca gcacgaagca tccaaagtac tccctagatc gcccacagcg    41760
tgagctcgag cagtacccgg gggcgttgta cgtcgaaaca atgttggcgg ttgatttgag    41820
cgatgagggc tggcagacgt ggctgtctga tgtcatccaa gagtcacagc tgtcgctggt    41880
gatcgttgac accctcactc gcgctgcgcc gggtgtggat ttggacagcg cctcgacggt    41940
gacaggtgac ctgctgaatc cgatgaagga gattgcccgt caggagaact gtgcgctggt    42000
gttcgtgcat cacaacacga aggcacaggc gaatgggcgt gctgctcaga acatggctgg    42060
atcgggacag attcacgcct gggctgactt cggcatctac gtgactgaga agcgtgagaa    42120
cggcccgacg atagagctcg acttcacgca tgagacgaag tacacggggga cgaacgaact    42180 cacgttccgt gtggcaggtc tgcctgatcg ctgggacccc gaggaatacg tcaaatccac    42240
acccagcaag ggccgaaagt acaccgatga cgacgagctg acagaggacg atctcgccgg    42300
acataaggca ccggcggctg tccgggtaca gcaatatgtc cggtcatgtc cggacgcgac    42360
aacggcggaa atagccgctg cttgtggggt caccgaacgc actgtccgac gagtccggaa    42420 atagggaaa agggcggcgg cggacacgtt gtgcgttcga ggtgtgtata tacacacttc    42480
ctcgatgtcc gccctaaatg accgggcaca agcagcaccg agaacgcgca acagggaaaa    42540
gagaaattgg ataccccgac cacgtacacc tcggacacgg acatccattc ccctgccgg    42600 gggatgtccg cggtccgggt gtccgggtcg aacgaagaga cagacaaggt aaagtactga    42660
ccatgccgac tgacgactac gactctctca tgtctgacat cgactcgctc atctccgagg    42720
acctcgagcg aggcgagagg gacgaggccc atcaagcgaa tccggatccg tgcccccact    42780
gcaaccagat gtggcatggg cttccgatca cccgccgaat ggtggagatg cgcgaggagt    42840
acctcgagca ccagcaggat ctcctggacg gttatcgaga gggagagccc ggtgaggtag    42900
attatgctca ctgggtgatg ccggaggatt actcctatgc cactgacgac tctcacgtct    42960
tctgcccggg gtccgacgtt cttgggccta accctcccga tcagatctgg gacaagcgcc    43020
accgtctgca gtactacggc aacgagggac gctatcgcca gaagcactac aagacctacc    43080
gcttccaacc accgaattgg gatgagtggg acatcgccgt tgacgtgact cacgagttcg    43140
cggagtcgag gtaccccctc agcaggatcc ccgtccatac tcgtcagacg atgacggtgg    43200
agcatcgcga ggctttctca atgcgtgagc tccgtgagcg gggtgtggat taccggcaac    43260
tcactgacgg gcaatggctg ctgcaggatc agtcctactg gattccaccg aagacctcat    43320
```

-continued

```
tcgactacac agagatggtg gtgcaatcga cagatccaaa ggaaccgccg acttacttcg   43380
agatcgtcac cagccagaga atcctcgagc gctactactg gctgactttc atcgctcgag   43440
aaatgccgac aagcccggtc tcgtatactg ctactgaata ccaaaagacc tggacgctga   43500
aaggacttgc ccagaaatga gccagaatcg gaactccacc cgtgactccc gccggaggaa   43560
gcgactcgct aagcgcaacg gggatcggca gttcttcaag caggtcgagc tgatccgacg   43620
acgcaagctc caggaatggc agaaggagca cgacccccag cgtctcgctc gccgtatcgc   43680
acagcaagcg ctgttcgcgg cgaagcgcga tgccaagcag ctgctgcgtg acgcagcccg   43740
caagaaggag acccaggatg cctgagaagc agccgaactg cgctgggtgt ggcaagaagc   43800
tcaccaagtc gaccaagtcc aacaatggct gggctcacaa gaagcgtgag cactggacct   43860
cgaagcccca caaggcggtg ccggtatggc cccagtaatc caaggaccga tccgtgaggg   43920
cgtctatgcg cccctcggct tcccgcccgc acatcaaccg tcgtcgggag cgactcagtc   43980
gctcatagac gatctgaggg cccattacgg accccttgga aacgtcgtgc ccgtcatcac   44040
ttggcgtatg cacccccttgg tgatgcgtct gtacgggggga ttaccgagac acctcgatca   44100
cagctacctg ttcgtgacgc cgcttgtcgg gcccctgctc gacctggtgt ggtacgtgca   44160
aggggtagtg ccggggggtc acccggactg ggagctttcc aacggctcct actacatcta   44220
ccacaaggca ttggagcgtt tccggtgagg cgcaagaatg cttctcacat cgccgaggaa   44280
ctcgaggctt tgggttttat gcccgagcgc ttcatcaccg catacctcga gatcgttcgc   44340
acgggtatgg ctgtcagctc tcaagcggcg aagtatgacg agcacgtagc agcacaggtg   44400
aagaagcgct tccacgagca cgcgggcgga ctcaaggatg agaacaccct cagattcaag   44460
gcctggatcg accgccgtct ccgtgagatc gggcgagaca tgcaggtgta cctgaacgcg   44520
aagcacggga ccttcgagac gccgagtcag aagcgggctg cgcgtagagt tgccaaggag   44580
atggaaaaag gagttgagct gaagtgcaag tactgcgaga agtacgtctc ctggcaatgg   44640
ctctactgtt cctggtgtgg aaaggagctg gacaatggcg gtgagcaggc gacagcggcg   44700
cttagcgcga cacatggaac tggtgcagag caacagcttc cccgggaaac gcggaaagac   44760
gctcatcgag aagatgcaag atgccctgga tgcggaattg ttagcacgtg ggaacatcac   44820
cgatgcgaag gagcgactga agaacgaggg caagatcttg gggatgataa agatgctgtc   44880
aatcatgcgg acaccatcat ccccaaagca tgaactggaa ctggcaaaag ccaggatcct   44940
actcaccgat gaagaggagt aagaaatgca aatgtggttt gaaggcgaaa ctcgcgcagg   45000
agaaacggtt cttgtcaatc tctgcactgt gacttcagtg gtcagcggta cggactcatt   45060
cttcgtgtcc actgccgtca acgacaagat cgagatcatc ggcgactacc aggtcttccg   45120
agctcgattg ctggatctct tggattcaca atgaagttct catggaagca gccagtctgc   45180
aatcactgct gggatggctt gaagctcaag gtcggtcatc ccgcccaaac ccccaacgct   45240
cggtgctgct actgtggccg tcagatcccc tcggggaag cccagtatat agtccaagtg   45300
aacccgggca ccgtgcccta ccctctctc gaaaggacca agaaatgatc cgcatcccca   45360
cctaccacaa gcgccaggtg cgccgtaccc tcggagtgat ggccgcaggt gcggtgctcg   45420
ctgggacagg cctagcgttc tccgatcatg ccaatgccag tcctggcatc agcaagtcgg   45480
agctcatctg caacatgatg gacgccgggg agatgtccta cctggagatc ggcattgaca   45540
tcgtgggacg gtacaacgtc acgcctgagg atgccggcgc agcgatgtac acggcggtca   45600
ccacgacgtg cccagagcac aagcaggacc tgcaggactg ggcggatcag ttctgatgtc   45660
ccaacctctc gcggatttga ttctccccgt caagacggag aaatgggaag cgtcagtcgt   45720
```

```
tgacccgagc tctgatgact acaacgcagt gaaggccttg actgatcgca tccagtacaa   45780
ggtggactgg tggttcaacg tcgaactgaa ctacatgctc ggttacacag cgctcaagat   45840
catcagtgct cccgtcatcg actcctacca tccagaacgc ggcgtgcagg cccgtgtgga   45900
aatgttgcac ccggtgcccg ttggtttcgc cacatggtcc gagaagcgac aggtctgctg   45960
gttcaaggag tgcatccgct cgatggagca ccatgagatg gacgagtggt tgaagatcga   46020
cggggtgatg atccacgatc cgcactcagg gaagaactac gatgacgcca attgatcgcg   46080
cactgctgag catcaccaag acattcttgg cggtgcatca gctgatgccc acacgtggag   46140
aggcactgta cgcagccctg aacaagccgt gggagaagca gaactggctg gcgctacgta   46200
cgttctgggg caacacgaaa agggctcagc gggagctaca gaggcagatt gacgaccttg   46260
agcacatcgc ttgggcgagg gagcttcgac gtggctaagc atagacgtga ggacatcatg   46320
cgggcctttg gcagttaccc tgtccgagag aagatcgcgg tagcgccgaa tgaccagggc   46380
gacttcaagc ggttcttcta catctaccaa gatggggccg gatatctagt gcaagcagtt   46440
ccattgcgtc ccacaccgat cacatgtggc aggcacagca aggagcacat cgagcgagga   46500
ggttacaaga agatcagcct cacgctgcac ctatcgcctg ggcctcccgt aatcaccctc   46560
gaccagtgag aaccaacgaa tcgaacagct gggtgtgggc tcggatccag aagcgatacc   46620
tgcgcactca tccccgctgt gagatgggcg cctggggctg tctgggacgt gccacggttg   46680
tcgaccacat cattgatcgt gtggacggcg gtggagacgc tgacgacaac ctcagggccc   46740
tctgtcatcc ctgccatgag aggcatacgc aggagactaa ggcacgacgt gcgaagatga   46800
gaaaggaagc ggccgaagag gccaaaagga aaaaccatcc cggtcggaag accgctgggg   46860
aatgagaaag gtaaggaaga tggcatattc gtatgagggc atttactgcg ataccctcga   46920
ggaactgatc agtctcaaga cagcgttgga caccggggtg attcctcgac ctgtgatggg   46980
ggccgaggaa gtggaagacg aagagcagca agtcgtggag acgacgggct ggcaggttgc   47040
cttcgtgctg aactggtgga agaagtcgaa gcaccgcaac aagacggtga cgacaaatct   47100
gctctctgaa ctgctgctcg agaaataccc ggacgtttct tcgtccactg cgcacaatgc   47160
gctgtacaag ggtcaggaat acggcctgat cgagcgggtg gatcacaatc actaccgctt   47220
gacctcattg gcgaaagagg cggcaattgt cggaactcag cggaaggtca tcgagtgaat   47280
tgcccttctg atcccatgcg cgagtggtat aacactcccc ctgctgtagg aagcaaattc   47340
tgggacctgc taggtctcgg ctccgtacca caccaaggaa gggctctcat ggccgaaggc   47400
acgtgctcga cgttcacgct cacaccgaac gggggtggta tgcgaggtgg ggctaagatc   47460
gtcattgacg gggacctcac gctggagctg gatcacgttg atgtagggcg ccttcgtgac   47520
gcgctctcgg tgtgtggtga tatggcgcct gggcaggtga ccttttccct gatcttcccc   47580
cgtgagaaga aggaatgaaa taccacacca atcgcaatgt gcatccgcgt gatatgaccc   47640
agccacatag ggtgtcgtat atacggcgtt ctatacgggt acgttatgca ggcctggtat   47700
atatccactc atggtcccct gtgtatgggt gggtagagca tagcgtgcac ctatgggcat   47760
ccgtgccaca catcagaaca aggggtatca cattcaaggt ggttgtgcca tgacaggtaa   47820
caatcgtgtg tatgtgacgg ggtcattatt gcggcgcctt aagcgtgatc gtgacgccct   47880
cggtgacatc atccgtgtgg ttgatgatgg cacgcatagg catacgccta gtgatgtggt   47940
gctgggaaac atcaaagcaa tactccgacg acgacgggag acgaggtagt ggaggaggca   48000
gagcgggtgg tggatcagat gcggcgatgc ccacacgaca tggtgcatta cttggatggg   48060
```

-continued

```
gtagggaaca gaaagtgcgg ggactgcaat gccttcgtcc gccccgttcc gggtgccgca  48120
ctcgtgccgc gatggatgga cccgtcgttt gctgagaagt ttgctggccg gggcacccca  48180
cccccagggg gagcacccca tcccgagcca tcctccacgt agcggctt              48228
```

BACTERIOPHAGES FOR THE TREATMENT OF TUBERCULOSIS

CROSS-REFERENCE TO RELATED APPLICATIONS

This patent application is the U.S. National Phase of International Patent Application No. PCT/US2020/033985, filed May 21, 2020, which claims the benefit of U.S. Provisional Patent Application No. 62/850,942, filed May 21, 2019, each of which is incorporated by reference in its entirety herein.

STATEMENT REGARDING FEDERALLY SPONSORED RESEARCH OR DEVELOPMENT

This invention was made with Government support under Grant Number GM116884 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 339,462 Byte ASCII (Text) file named "757041_ ST25," created on Nov. 15, 2021.

BACKGROUND OF THE INVENTION

Tuberculosis (TB) is a disease that kills over one million people per year, and it is estimated that the causative agent, *Mycobacterium tuberculosis*, infects about one-third of the world's population. TB can be treated with antibiotics, but the treatment regimen requires a minimum of three drugs taken for six months. Non-compliance to drug therapy has fueled the emergence of antibiotic resistance, including multidrug and extensively drug resistant strains of TB (MDR-TB and XDR-TB).

Bacteriophages, viruses that infect bacteria, present an alternative potential therapy for TB. However, identification of phages that efficiently infect and kill clinical isolates of *M. tuberculosis* that could be combined into a broadly used phage composition (or "cocktail") has remained elusive. Thus, there is a global need for new strategies for TB treatment, for shorter therapy regimens, reduced resistance, and treatment of drug resistant strains. A phage cocktail suitable for use as an anti-tuberculosis therapeutic agent is presented herein.

BRIEF SUMMARY OF THE INVENTION

An embodiment of the invention provides a composition comprising a combination of two or more (e.g., three, four, or five) phages, wherein the phages are two or more of: (a) phage D29; (b) phage AdephagiaΔ41Δ43; (c) phage FionnbharthΔ47; (d) phage Fred313cpm-1; and (e) phage Muddy$^{HRMN0052-1}$; and a pharmaceutically acceptable carrier. Another embodiment of the invention provides a composition comprising (a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier.

Another embodiment of the invention provides a method for treating, reducing, or preventing a disease caused by *Mycobacterium tuberculosis* in a mammal comprising administering a pharmaceutical composition comprising a combination of two or more phages wherein the phages are two or more of: (a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier, thereby treating, reducing, or preventing the disease in the mammal.

Additional embodiments of the invention provide methods for treating, reducing, or preventing tuberculosis, tubercular meningitis and disseminated infections, bone and joint tuberculosis, and antibiotic resistant infections in a mammal, comprising administering a composition comprising a combination of two more phages, wherein the phages are two or more of: (a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier, either alone or in combination with an antibiotic. The inventive compositions and methods described herein are suitable for mammals including, but not limited to, humans.

BRIEF DESCRIPTION OF THE SEVERAL VIEWS OF THE DRAWINGS

FIG. 1A is a picture of a culture plate showing spots of bacterial cultures placed onto solid media without the addition of any phage.

FIG. 1B is a picture of a plate showing spots of bacterial cultures as shown in FIG. 1A, after seeding with $10^9$ pfu phage D29 and incubating at 37° C. for six weeks.

FIG. 2A is a picture of a culture plate showing spots of bacterial cultures placed onto solid media without the addition of any phage.

FIG. 2B is a picture of a plate showing spots of bacterial cultures as shown in FIG. 2A, after seeding with $10^9$ pfu phage AdephagiaΔ41Δ43 and incubating at 37° C. for six weeks.

FIG. 4A is a picture of a culture plate showing spots of bacterial cultures placed onto solid media without the addition of any phage.

FIG. 4B is a picture of a culture plate showing spots of bacterial cultures as shown in FIG. 4A, after seeding with $10^9$ pfu phage FionnbharthΔ47 and incubating at 37° C. for six weeks.

FIG. 6A is a picture of a culture plate showing spots of bacterial cultures placed onto solid media without the addition of any phage.

FIG. 6B is a picture of a culture plate showing spots of bacterial cultures as shown in FIG. 6A, after seeding with $10^9$ pfu phage Fred313cpm-1 and incubating at 37° C. for six weeks.

FIG. 7A is a picture of a plate showing infection of *M. tuberculosis* strains N1283 (clinical isolate) and H37Rv (lab strain) by Muddy HRM derivatives HRM-1-6 after spotting with each derivative and incubating at 37° C. for six weeks.

FIG. 7B is a picture of a plate showing infection of *M. tuberculosis* clinical isolate strains N1274 and N0155 by Muddy HRM derivatives HRM-1-6 after spotting with each derivative and incubating at 37° C. for six weeks.

FIG. 7C is a picture of a plate showing infection of *M. tuberculosis* clinical isolate strains N0145 and N0157 by Muddy HRM derivatives HRM-1-6 after spotting with each derivative and incubating at 37° C. for six weeks.

FIG. 7D is a picture of a plate showing infection of *M. tuberculosis* clinical isolate strains N0052 and N0072 by Muddy HRM derivatives HRM-1-6 after spotting with each derivative and incubating at 37° C. for six weeks.

FIG. 7E is a picture of a plate showing infection of *M. tuberculosis* clinical isolate strains N0053 and N0054 by Muddy HRM derivatives HRM-1-6 after spotting with each derivative and incubating at 37° C. for six weeks.

FIG. 7F is a picture of a plate showing infection of *M. tuberculosis* clinical isolate strains N0004 and N0136 by Muddy HRM derivatives HRM-1-6 after spotting with each derivative and incubating at 37° C. for six weeks.

FIG. 7G is a picture of a plate showing infection of *M. tuberculosis* clinical isolate strains N1216 and N0031 by Muddy HRM derivatives HRM-1-6 after spotting with each derivative and incubating at 37° C. for six weeks.

DETAILED DESCRIPTION OF THE INVENTION

An embodiment of the invention provides a composition comprising a combination of two more phages, wherein the phages are two or more of:

(a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier.

The pharmaceutically acceptable carrier for use in the inventive pharmaceutical composition can be any of those conventionally used and is limited only by chemico-physical considerations, such as solubility and lack of reactivity with the active compound(s), and by the route of administration. The pharmaceutically acceptable carriers for use in the present invention—for example, vehicles, excipients, and diluents—are well-known to those skilled in the art and are readily available to the public. It is preferred that the pharmaceutically acceptable carrier be one which is chemically inert to the active agent(s) (i.e., the two or more phages) and one which has no detrimental side effects or toxicity under the conditions of use. The choice of carrier will be determined in part by the particular phages used in the pharmaceutical composition, as well as by the particular method used to administer the two or more phages.

The two or more phages for use in the inventive pharmaceutical composition can be any phages which infect a bacterial host, i.e., bacteriophages, which infect *Mycobac-*

*terium tuberculosis* (*M. tuberculosis*) bacteria. *M. tuberculosis* is the causative agent of tuberculosis (TB), and other diseases including, but not limited to tubercular meningitis and disseminated infections and bone and joint tuberculosis. Infection of *M. tuberculosis* by the two or more phages causes the biological activity of *M. tuberculosis* to be inhibited, as compared to activity which is observed in the absence of infection by the two or more phages. An embodiment of the invention provides a composition comprising (a) phage D29; (b) phage AdephagiaΔ41Δ43; (c) phage FionnbharthΔ47; (d) phage Fred313cpm-1; and (e) phage MuddyHRM$^{N0052-1}$; and a pharmaceutically acceptable carrier.

Figure 8:
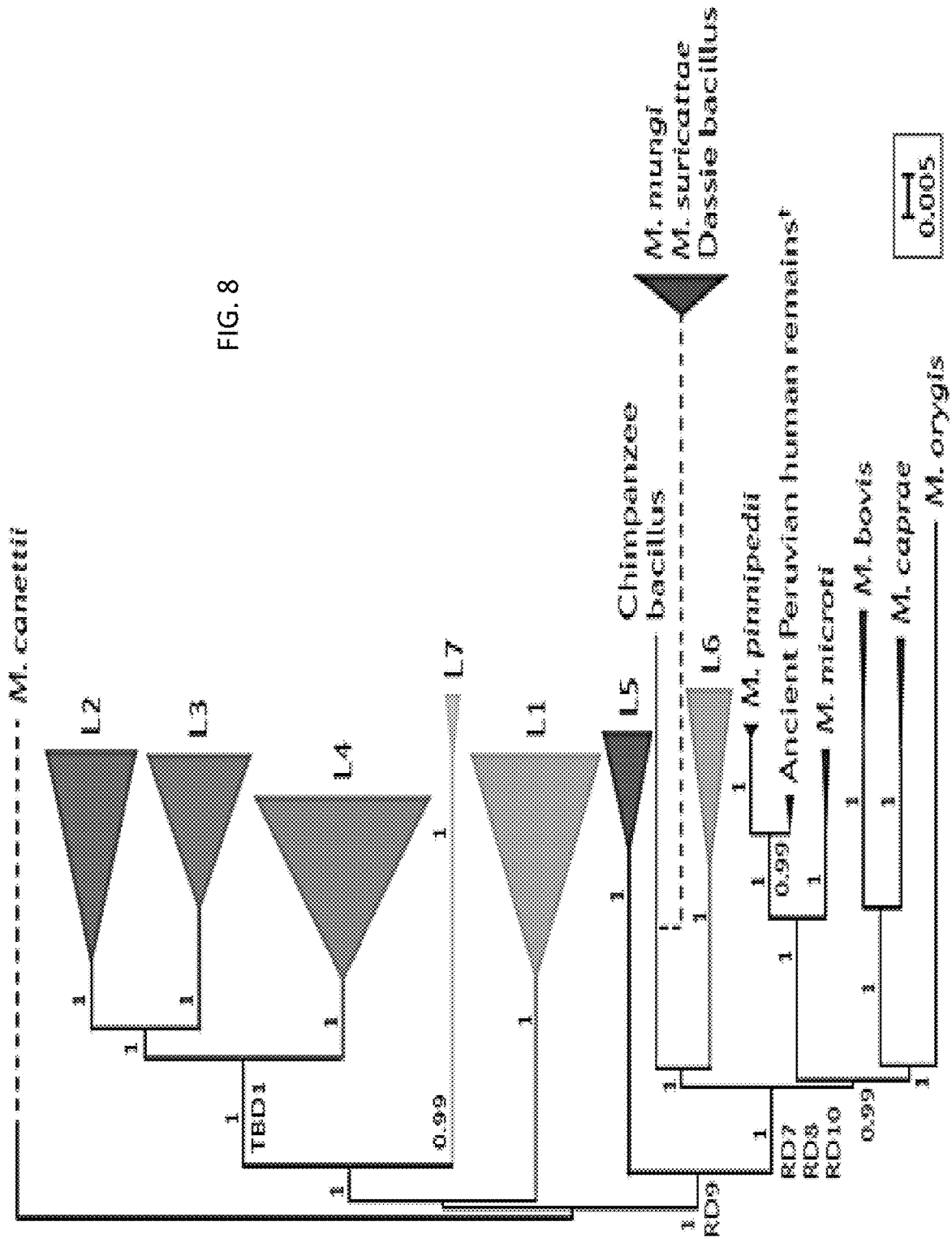
FIG. 8 is a schematic showing the geographical distribution of *M. tuberculosis* strains.

TB is the cause of death of over a million people per year worldwide, and it is estimated that about one-third of the world's population are infected by *M. tuberculosis*. *M. tuberculosis* encompasses limited genetic diversity, and genomic comparisons identify seven major lineages (L1-L7), of which lineages L1-L4 predominate, and span much of the diversity, represent a vast majority of the isolates, and are most geographically widespread (FIG. 8, Gagneaux et al., *Nature Reviews Microbiology*, Vol. 16, 202-213 (2018), which is herein incorporated by reference in its entirety).

In an embodiment, the invention provides a method of treating, reducing, or preventing a disease caused by *M. tuberculosis* in a mammal comprising administering a pharmaceutical composition comprising a combination of two or more phages and (2) a pharmaceutically acceptable carrier, thereby treating, reducing, or preventing the disease in the mammal. In an embodiment, the invention provides a method of treating, reducing, or preventing tuberculosis in a mammal comprising administering the inventive pharmaceutical composition, thereby treating, reducing, or preventing tuberculosis in the mammal. In an additional embodiment, the invention provides a method of treating, reducing, or preventing tubercular meningitis and disseminated infections, and bone and joint tuberculosis in a mammal comprising administering the inventive composition, thereby treating, reducing, or preventing tubercular meningitis and disseminated infections, and bone and joint tuberculosis, in the mammal.

Bacteriophages (which may be referred to as "phages") are viruses that infect bacterial hosts. As used herein, the term bacteriophage may refer to any bacteriophage or product thereof, including, for example, polypeptides, fragments, variants, or derivatives thereof, including those with genomic insertions, deletions, or any other modifications, isolated from a bacteriophage of the invention, or related to a bacteriophage of the invention, or which has similar properties as a bacteriophage of the invention. The bacteriophages, polypeptide, fragments, variants, and derivatives of the invention exhibit a biological function or activity associated with the bacteriophage from which it was isolated or derived (e.g., antimicrobial or antibacterial activity (e.g., lytic cell killing)).

Bacteriophages may serve as therapeutic agents. Phage therapy may include (1) a personalized system in which phages are identified that infect an infectious strain in one specific patient, and (2) a broad-based therapy that can be used to generally treat infections by a particular pathogen. Both approaches suffer from obstacles, including, for example, that clinical isolates of any particular bacterial pathogen can be extremely varied, especially in their phage susceptibility profiles. Phages are often highly specific for their hosts, and often to do not infect all clinical variants. Additionally, phages in laboratory stocks may become unstable over time.

Tuberculosis is an attractive target for the therapeutic use of phages. There is a strong clinical need for TB treatment because of widespread infections worldwide and the prevalence of antibiotic resistant strains. Additionally, *M. tuberculosis* clinical isolates are more genetically homogenous than most other bacterial pathogens (Gagneaux et al., *Nature Reviews Microbiology*, Vol. 16, 202-213 (2018), which is herein incorporated by reference in its entirety), increasing the prospects of identifying phages whose infectibility spans most clinical strains. Further, mycobacteria do not contain lipopolysaccharide (LPS), which is highly toxic, and therefore a contaminant of certain phage preparations.

Phages for use in the present invention can be obtained in the field, or from any collection of individual bacteriophage isolates. Bacteriophages which are suitable for the inventive composition and methods comprise any bacteriophage, polypeptide, or fragment, variant, or derivative thereof, including those with genomic insertions, deletions, or any other modification, collected from the field, or from any accessible collection of individual bacteriophage isolates, such as those provided herein. An exemplary collection of bacteriophage isolates was collected in the large multi-institutional Science Education Alliance Phage Hunters Advancing Research and Education (SEA-PHAGES) program. The SEA-PHAGES program collection includes 10,000 bacteriophage isolates which were isolated using *Mycobacterium smegmatis* mc2155 as a host. The genomes of a portion of the isolates have been sequenced. The sequences may be accessed at the website for the Actinobacteriophage Database, phagesdb.org. Additional bacteriophage sequences and strains which are suitable for use in the inventive compounds and methods are available from the American Type Culture Collection (ATCC), which may be accessed at the website for ATCC, atcc.org. Additional bacteriophage sequences and strains which are suitable for use in the inventive compounds and methods are archived at the University of Pittsburgh, Department of Biological Sciences (Pittsburgh, Pa.).

Previously, a subset of the isolates collected in the SEA-PHAGES program were tested to determine which will efficiently infect *M. tuberculosis* mc27000 (an avirulent derivative of the lab strain *M. tuberculosis* H37Rv), and it was shown that many representative phages of clusters/subclusters A2, A3, and K infect this strain (Jacobs-Sera et al., *Virology*, 20; 434(2): 187-201 (December 2012), which is herein incorporated by reference in its entirety). It was also previously shown that although some phages do not efficiently infect *M. tuberculosis*, that some infect at a reduced plating efficiency, and that mutants can be readily isolated that plate with similar efficiencies on *M. tuberculosis* mc27000 and *M. smegmatis* mc$^2$155.

Phages infecting actinobacterial hosts can be grouped into clusters according to their sequence relationships, and some clusters can be further divided into subclusters. The largest cluster is Cluster A, which is divided into 20 subclusters (A1, A2, A3, etc). Because the overall sequence diversity is large, phages within either clusters or subclusters may differ in a substantial number of their genes. Phages that are genomically different from each other are more likely to differ in their overall biology than phages grouped in the same cluster, and those that differ genomically are the least likely to share resistance mechanisms. Accordingly, when selecting phages for therapeutic use, more than one phage is used in combination (i.e., a therapeutic phage "cocktail"), and the phages should be selected such that resistance to one phage does not confer resistance to other phages in the cocktail. Therefore, it is advisable to use phages that span considerable genomic diversity.

Exemplary phages include, but are not limited to: phage D29, phage AdephagiaΔ41Δ43, phage FionnbharthΔ47, phage Fred313cpm-1, and phage MuddyHRM$^{N0052-1}$ and any product thereof, including, for example, polypeptides, or fragments, variants, or derivatives thereof, including those with genomic insertions, deletions, or any other modification. Further exemplary phages are those isolated from, related to, or similar to phage D29, phage AdephagiaΔ41Δ43, phage FionnbharthΔ47, phage Fred313cpm-1, and phage MuddyHRM$^{N0052-1}$. Such phages replicate lytically, either naturally or though engineering, have broad host ranges among *M. tuberculosis* clinical isolates, and diversity which suggests that they are unlikely to share common resistance mechanisms. Additional descriptive information is provided below.

Phage D29 (SEQ ID NO: 1). Phage D29 is known to infect *M. tuberculosis*. (Jacobs-Sera et al., *Virology*, 20; 434(2): 187-201 (December 2012), which is herein incorporated by reference in its entirety). D29 is grouped through genomic comparisons into Subcluster A2 (Hatfull et al., *J. Mol. Biol.*, 397(1): 119-143, (Mar. 19, 2010), which is herein incorporated by reference in its entirety). D29 is a lytic phage and does not form lysogens, although genomic analysis shows that it is a derivative of a temperate parent (Ford et al., *J. Mol. Biol.*, 279: 143-164 (1998); Dedrick et al., *BMC Microbiology* 17:225 (2017), which are herein incorporated by reference in their entirety).

Phage AdephagiaΔ41Δ43 (SEQ ID NO: 2). Mycobacteriophage Adephagia was isolated as part of the SEA-PHAGES program and is archived at the University of Pittsburgh, Department of Biological Sciences (Pittsburgh, Pa.). Genomic characterization showed that Adephagia can be grouped into Subcluster K1 (Pope et al., *PLoS ONE* 6(10): e26750 (2011), which is herein incorporated by reference in its entirety). Adephagia is a temperate phage, but its repressor gene has been identified and a deletion derivative was constructed (Adephagia Δ43) in which the repressor gene is deleted (Petrova et al., *Microbiology*, 161(Pt 8): 1539-1551 (August 2015), which is herein incorporated by reference in its entirety). A second derivative was constructed (Adephagia Δ41Δ43) in which the integrase gene was also deleted (Petrova et al., 2015). Adephagia was shown to infect *M. tuberculosis* mc$^2$7000, a property shared by many other Cluster K phages.

Phage FionnbharthΔ47(SEQ ID NO: 3). Phage Fionnbharth was isolated as part of the SEA-PHAGES program. The genome was sequenced and the phage is grouped in Subcluster K4 (Pope et al., *PLoS ONE* 6(10): e26750 (2011), which is herein incorporated by reference in its entirety). Fionnbharth efficiently infects *M. tuberculosis* mc$^2$7000 (Jacobs-Sera et al., *Virology*, 20; 434(2): 187-201 (December 2012), which is herein incorporated by reference in its entirety). Although Adephagia and Fionnbharth are in the same cluster (Cluster K), they differ in many parts of their genomes (FIGS. 3A-3H). Without wishing to be bound by theory, it is plausible that resistance to one may not necessarily confer resistance to the other. Preliminary experiments with *Mycobacterium smegmatis* mc$^2$155 as a model system suggest that resistance to one of these phages may not confer resistance to the other.

Phage Fred313cpm-1 (SEQ ID NO: 4). Phage Fred313 was isolated as part of the SEA-PHAGES program. The genome was sequenced and the phage is grouped in Subcluster A3 (Butela et al., *Genome Announcements*, 5(43) e01182-17 (October 2017) DOI: 10.1128/genomeA.01182-

17 2017, which is herein incorporated by reference in its entirety). Fred313 is a different genomic subcluster to D29 (which is in subcluster A2). Without wishing to be bound by theory, Fred313 and D29 have sufficient differences (including different tail genes) such that they may have distinct resistance profiles (FIGS. 5A-5G).

Phage MuddyHRM$^{N0052-1}$ (SEQ ID NO: 5). Phage Muddy was isolated is archived at the University of Pittsburgh, Department of Biological Sciences (Pittsburgh, Pa.), and is one of only two members of Cluster AB; its genome sequence is known (Pope et al., *PLoS ONE* 6(10): e26750 (2011), which is herein incorporated by reference in its entirety). Muddy infects *M. tuberculosis* mc$^2$7000.

All of the phages that infect mycobacterial hosts are morphologically siphoviral, and over 50% are temperate, forming stable lysogens that are immune to superinfection (Hatfull, *Microbiol Spectr.*, 6(5): 10.1128/microbiolspec.GPP3-0026-(October 2018), which is herein incorporated by reference in its entirety). Temperate phages are not suitable for therapeutic use because temperate phages have the ability to integrate their DNA into the bacterial host genome (i.e., they are lysogens). Lysogens is not useful for phage therapy because once the genome is integrated, the bacterial cell becomes immune to other similar phages. Lytic derivatives in which the repressor gene has been altered or deleted are suitable for phage therapy, and can be isolated or engineered using BRED technology (Marinelli et al., *FEMS Microbiology Letters*, 344(2), 166-172 (July 2013), which is herein incorporated by reference in its entirety).

All of the phages known to infect *M. tuberculosis* have genomes with defined termini and thus use a cos-type DNA packaging system. Such phages usually do not mediate generalized transduction at any readily detectable frequency. Avoiding generalized transduction is a desirable property for a therapeutic phage. Additionally, genomic characterization of the phages that infect *M. tuberculosis* has not yet identified toxic genes such as Shiga-like toxins.

TB can be treated with antibiotics, however, current therapeutic regimens require a minimum of three drugs taken for six months. Non-compliance with therapy has fueled the emergence of antibiotic resistance, including multidrug and extensively drug resistant strains (e.g., MDR-TB and XDR-TB). Accordingly, antibiotic resistance is a global concern for the treatment of *M. tuberculosis* infections. Antibiotic drugs typically used for TB therapy include, e.g., isoniazid, ethambutol, pyrazinamide, rifampicin, streptomycin, amikacin, kanamycin, ciprofloxacin, delamanid, and bedaquiline or any combination thereof. Resistance occurs independently within *M. tuberculosis* lineages, and typically involves mutations within target genes for the antibiotics used. For example, resistance to rifampicin is solely due to rpoB mutations. Therefore, without wishing to be bound by theory, there is not anticipated to be systematic differences in phage susceptibility related to drug resistance profiles. Further without wishing to be bound, it is believed that using the inventive composition in combination with antibiotics such as those listed above, as a treatment for diseases caused by *M. tuberculosis* and related antibiotic resistant infections, may reduce the current treatment time of six months, and may also reduce the incidence of antibiotic resistance.

In an embodiment, the invention provides a method of treating, reducing, or preventing a disease caused by *M. tuberculosis*, tuberculosis, tubercular meningitis and disseminated infections, and bone and joint tuberculosis, and antibiotic resistant infections such as pulmonary tuberculosis, comprising administering a pharmaceutical composition comprising a combination of two or more (e.g., three, four, or five) phages comprising two or more of: (a) phage D29; (b) phage AdephagiaΔ41Δ43; (c) phage FionnbharthΔ47; (d) phage Fred313cpm-1; and (e) phage MuddyHRM$^{N0052-1}$, in combination with an antibiotic. Suitable antibiotics for use in combination with the inventive composition include, but are not limited to: isoniazid, ethambutol, pyrazinamide, rifampicin, streptomycin, amikacin, kanamycin, ciprofloxacin, delamanid, and bedaquiline, or any combination thereof. Without wishing to be bound, it is believed that treatment of the diseases listed herein, with the inventive composition in combination with one or more antibiotics, would reduce the total length of treatment, as compared to treatment with antibiotics in the absence of the inventive composition.

In this respect, the length of time for a typical therapeutic regimen for the treatment of TB with one or more antibiotics, in the absence of the inventive composition, is about six months, as noted above. In an embodiment, the invention provides a method of treating, reducing, or preventing a disease caused by *M. tuberculosis*, tuberculosis, tubercular meningitis and disseminated infections, bone and joint tuberculosis, and antibiotic resistant infections such as pulmonary tuberculosis, comprising administering a pharmaceutical composition comprising a combination of two or more phages comprising two more of: (a) phage D29; (b) phage AdephagiaΔ41Δ43; (c) phage FionnbharthΔ47; (d) phage Fred313cpm-1; and (e) phage MuddyHRM$^{N0052-1}$, in combination with an antibiotic, wherein the length of treatment is reduced as compared to the length of treatment with an antibiotic alone. In embodiments, the length of the inventive therapeutic method may comprise, 6 months, 5 months, 4 months, 3 months, 2 months, or one month.

As noted above, about one-third of the world is infected with *M. tuberculosis*, although a large percentage of carriers have latent (asymptomatic), not active, TB. In latent TB, the bacterium establishes itself in the body at relatively small numbers, but are never cleared from the carrier's body. There is a 10% chance of activation of latent TB infection into an active TB infection over the course of a TB carrier's lifetime. Patients suffering from immunocompromising conditions such as e.g., AIDS or HIV, or who take immunocompromising drugs, have an increased chance that such latent infections will activate into TB disease. Without wishing to be bound by theory, it is plausible that the inventive bacteriophage composition described herein could be used to treat latent *M. tuberculosis* infections by eliminating the bacteria from latent infections and thus eliminating the risks arising from the potential for activation.

In an embodiment, the invention provides a method of treating, reducing, or preventing activation of a latent disease caused by *M. tuberculosis*, comprising administering a pharmaceutical composition comprising a combination of two or more phages comprising two more of: (a) phage D29; (b) phage AdephagiaΔ41Δ43; (c) phage FionnbharthΔ47; (d) phage Fred313cpm-1; and (e) phage MuddyHRM$^{N0052-1}$, The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive compositions and methods can provide any amount of any level of treatment or prevention of disease caused by *M. tuberculosis* in a mammal. Furthermore, the treatment or prevention provided by the inventive method can include treatment or prevention of one or more conditions or symptoms of the disease caused by *M. tuberculosis*, e.g., tuberculosis, being treated or prevented. Also, for purposes herein, "prevention" can encompass delaying the onset of a disease caused by *M. tuberculosis*, or a symptom or condition thereof. With respect to the inventive methods, the disease may be any disease caused by *M. tuberculosis*, including any of the types of diseases caused by or associated with *M. tuberculosis* and any of the conditions or treatments discussed herein.

For purposes of the invention, the amount or dose of the inventive composition administered should be sufficient to effect the desired biological response, e.g., a therapeutic or prophylactic response, in the mammal over a clinically reasonable time frame. The dose will be determined by the efficacy of the particular composition and the condition of the mammal (e.g., human), as well as the body weight of the mammal (e.g., human) to be treated. The dose of the inventive composition also will be determined by the existence, nature and extent of any adverse side effects that might accompany the administration of a particular phage or combination thereof.

Typically, the attending physician will decide the dosage of the inventive composition with which to treat each individual patient, taking into consideration a variety of factors, such as age, body weight, general health, diet, sex, composition to be administered, route of administration, and the severity of the condition being treated. The dose, or dosage, of a pharmaceutical composition of the present invention may be appropriately determined by considering the dosage form, method of administration, patient age and body weight, symptoms of the patient, or severity of the condition.

Generally, the daily dose for an adult can be, e.g., between 0.1 ml to 10,000 ml at once or in several portions. In embodiments, the dose comprises between $1 \times 10^1$ and $1 \times 10^9$ plaque forming units (pfu) per dose (e.g., $1 \times 10^1$ pfu, $1 \times 10^2$ pfu, $1 \times 10^3$ pfu, $1 \times 10^4$ pfu, $1 \times 10^5$ pfu, $1 \times 10^6$ pfu, $1 \times 10^7$ pfu, $1 \times 10^8$ pfu, $1 \times 10^9$ pfu, $1 \times 10^{10}$ pfu, or any ranges therebetween) of bacteriophage. These examples are not limiting. These doses, or dosages, may vary, depending on the patient body weight and age, and the method of administration; however, selection of suitable dose, or dosage, is well within the purview of those skilled in the art.

Similarly, the dosing period may be appropriately determined depending on the therapeutic progress. In embodiments, the dosing period may comprise less than one year, less than 9 months, less than 8 months, less than 7 months, less than 6 months, less than 5 months, less than 4 months, less than 3 months, less than 2 months, or one month. In embodiments, the dosing period may comprise three doses per day, two doses per day, or one dose per day for the length of the dosing period.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. The mammal can be non-diseased, a mammal afflicted with a disease caused by *M. tuberculosis*, or a mammal predisposed to having a disease caused by *M. tuberculosis*.

In an embodiment, the invention provides administering the inventive composition comprising a combination of two more phages, wherein the phages are two or more of: (a) phage D29; (b) phage Adephagia$\Delta$41$\Delta$43; (c) phage Fionnbharth$\Delta$47; (d) phage Fred313cpm-1; and (e) phage MuddyHRM$^{N0052-1}$ to the mammal intravenously, intramuscularly, subcutaneously, or intraperitoneally, or as an aerosol, using an inhalation device. The following formulations for administration are exemplary and are in no way limiting. More than one route can be used to administer the inventive composition, and in certain instances, a particular route can provide a more immediate and more effective response than another route.

Intravenous, intramuscular, subcutaneous, or intraperitoneal formulations may include any suitable carrier. For example, formulations suitable for intravenous e.g., as a bolus or by continuous infusion over a period of time, intramuscular, subcutaneous, or intraperitoneal administration may comprise sterile aqueous solutions of the inventive composition with solutions which are preferably isotonic with the blood of the recipient. Such formulations may be prepared by dissolving the inventive composition in water or other suitable physiologically acceptable solvent containing physiologically compatible substances such as sodium chloride (e.g. 0.1-2.0M), glycine, and the like, and having a buffered pH compatible with physiological conditions to produce solution (e.g., an aqueous solution or solution of the inventive composition (i.e., bacteriophages) in a suitable physiologically acceptable solvent), and rendering said solution sterile.

Alternatively and additionally, an effective amount of the pharmaceutical composition described herein, via an inhalation route. Commercially available nebulizers for liquid formulations, including jet nebulizers and ultrasonic nebulizers are useful for administration. Liquid formulations can be directly nebulized and lyophilized powder can be nebulized after reconstitution. Alternatively, the inventive compositions described herein can be aerosolized using a fluorocarbon formulation and a metered dose inhaler, or inhaled as a lyophilized and milled powder.

The following example further illustrates the invention but, of course, should not be construed as in any way limiting its scope.

EXAMPLE 1

This example demonstrates the process for identifying the genomically distinct phages that infect and kill all of the tested *M. tuberculosis* isolates tested.

A set of clinical isolates of *M. tuberculosis* for testing phage susceptibility profiles was obtained (Table 1) from the Department of Immunology and Infectious Diseases, School of Public Health TB Research Program, Harvard University (Boston, Mass.). The set of strains provided in Table 1 contains 2-4 isolates of each of the six lineages (L1-L6). All of the strains were cultured for testing, although several strains (N1176, N1063, N1272, N0091, N1202, and N1177) representing lineages L6 and L7 have not yet been propagated. Identification of phages that broadly infect the L1-L4 lineages provides a resource for evaluating the clinical utility of phage interventions for TB. Lab strain H37Rv, a member of L4, was also tested.

TABLE 1

| Strain | Lineage | Country of Isolation | Place of birth of patient |
|---|---|---|---|
| N0157 | L1 | USA | Philippines |
| N0072 | L1 | USA | India |
| N0153 | L1 | USA | Vietnam |
| N0145 | L2 | USA | China |
| N0052 | L2 | USA | China |
| N0031 | L2 | USA | China |
| N0155 | L2 | USA | China |
| N0004 | L3 | USA | India |
| N1274 | L3 | Germany | Afghanistan |
| N0054 | L3 | USA | Ethiopia |
| N1216 | L4 | Ghana | Ghana |
| N0136 | L4 | USA | USA |
| N1283 | L4 | Germany | Germany |
| N1176 | L5 | Ghana | Ghana |
| N1063 | L5 | Switzerland | Liberia |
| N1272 | L5 | Ghana | Ghana |
| N0091 | L6 | The Gambia | Gambia |
| N1202 | L6 | Ghana | Ghana |

To identify phages that infect these strains, the focus of testing was on the types of phages that were previously shown to infect *M. tuberculosis* mc²7000 (Jacobs-Sera et al., *Virology*, 20; 434(2): 187-201 (December 2012), which is herein incorporated by reference in its entirety), together with a screen for additional phages. These phages were examined in further detail to identify those that infect the clinical isolates. The resulting phages were then further manipulated as appropriate, either to convert from temperate to lytic phages, or to mutationally expand their host range. The goal was to identify 4-5 genomically distinct phages that infect and kill all of the isolates tested. The methods and resulting phages are described below.

Methods

The following methods were used for each phage described below.

A lab strain of *M. tuberculosis* H37Rv, as well as the isolates listed in Table 1, were grown in Middlebrook 7H9 media with OADC (oleic acid, dextrose, catalase), and 0.05% Tween80 for 3-6 weeks at 37° C., with shaking. These *M. tuberculosis* strains grow with a doubling time of approximately 24 hours, with isolated colonies visible on solid medium in 4-6 weeks. For plaque assays, *M. tuberculosis* cultures were sonicated briefly in a cup-horn sonicator (Q-sonica 700, Qsonica, Newtown, Conn.) at 30% amplitude with 15 sec on and 10 sec off until visibly dispersed.

These studies confirmed several general features among these phages: (1) some of the phages infect only some of the clinical isolates, (2) some phages infect all or most of the clinical isolates; (3) some of the phages do not efficiently infect the isolates, but host range mutants can be isolated that do (e.g. Muddy, described below), (4) some of the host range mutants infect all of the clinical isolates, but some do not (e.g. different mutants of phage Muddy, described below), and (5) many of the phages that infect *M. tuberculosis* are temperate, but lytic derivatives can be identified or constructed (e.g. Fionnbharth and Fred313cpm-1, described below). The five bacteriophages described herein were identified as candidates for components of a therapeutic cocktail.

Phage D29

Figures 1A, 1B:
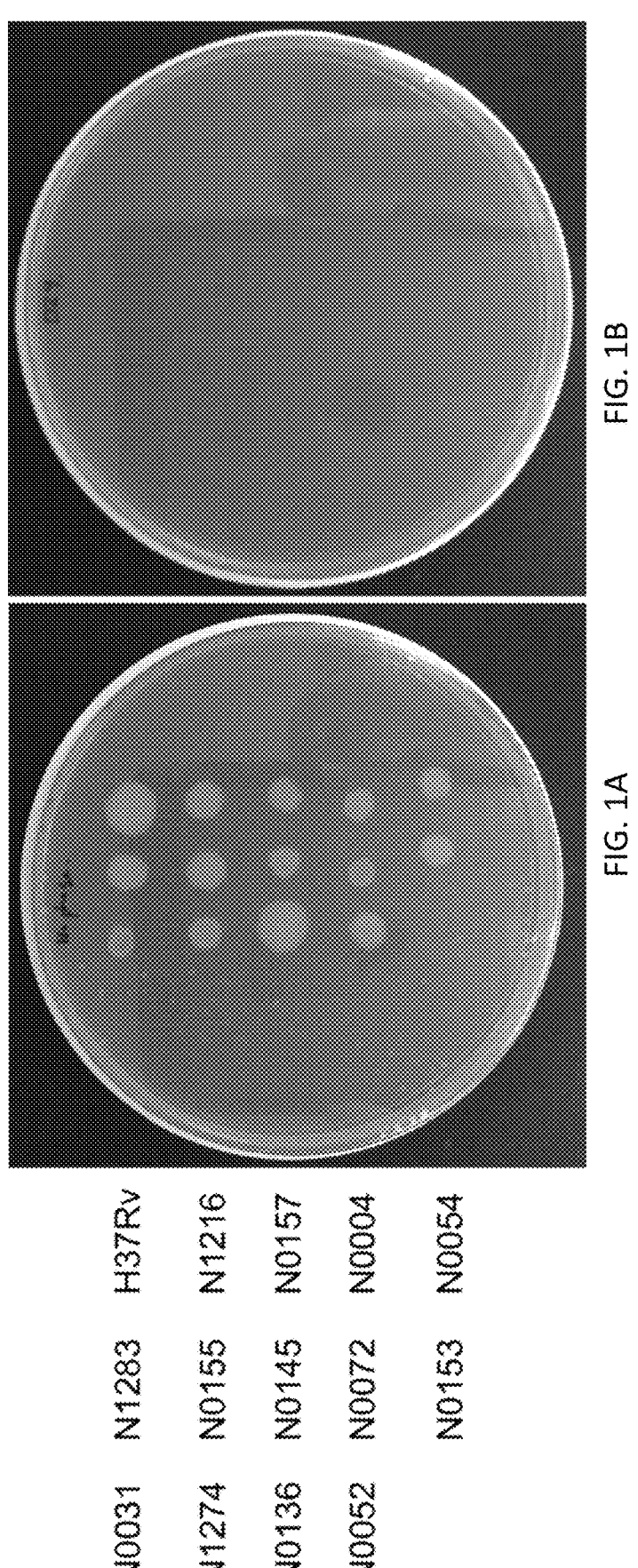
FIGS. 1A and 1B are pictures of culture plates spotted with bacterial culture with and without the addition of phage. The key to the bacterial strains is shown to the left of FIGS. 1A and 1B. H37Rv is the lab strain of *M. tuberculosis* tested; all other strains are clinical isolates.

Thirteen *M. tuberculosis* clinical isolates (Table 1) as well as the lab strain *M. tuberculosis* H37Rv were grown and spotted onto solid media seeded with 10⁹ plaque forming units of phage D29 (SEQ ID NO: 1) (FIG. 1B), or without phage (FIG. 1A), and grown at 37° C. for three weeks. As shown, Phage D29 prevented growth of all of the *M. tuberculosis* strains.

Phage AdephagiaΔ41Δ43

Figure 2B:
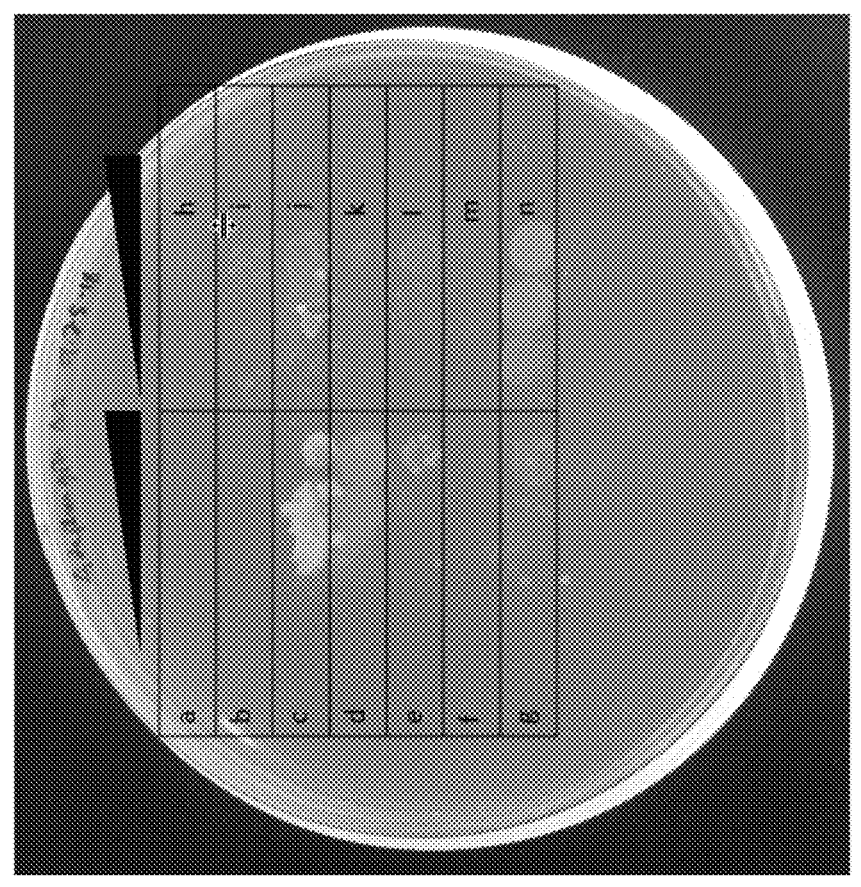
FIGS. 2A and 2B are pictures of culture plates spotted with bacterial culture with and without the addition of phage. The key to the bacterial strains is overlayed on the culture plates shown in FIGS. 2A and 2B. H37Rv is the lab strain of *M. tuberculosis* tested; all other strains are clinical isolates. a=N0145, b=N0136, c=N0004, d=N0072, e=N0052, f=N0054, g=N0153, h=H37Rv, i=N1283, j=N0031, k=N1216, l=N0155, m=N1275, and n=N0157.
Figure 2A:
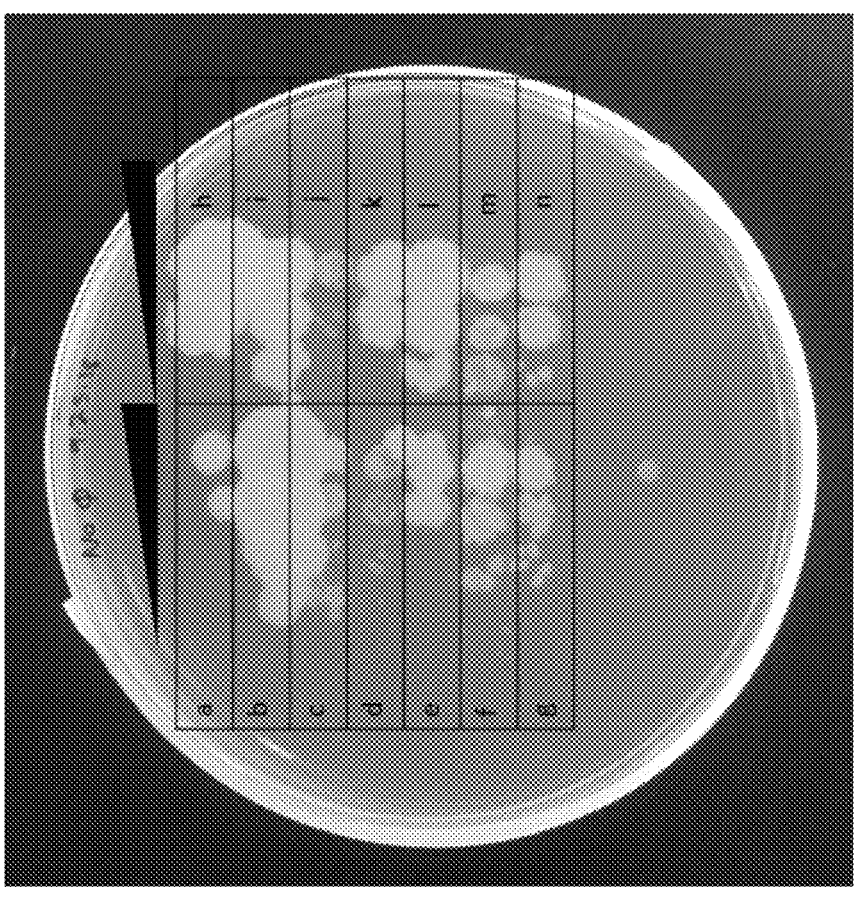
Figure 3A:
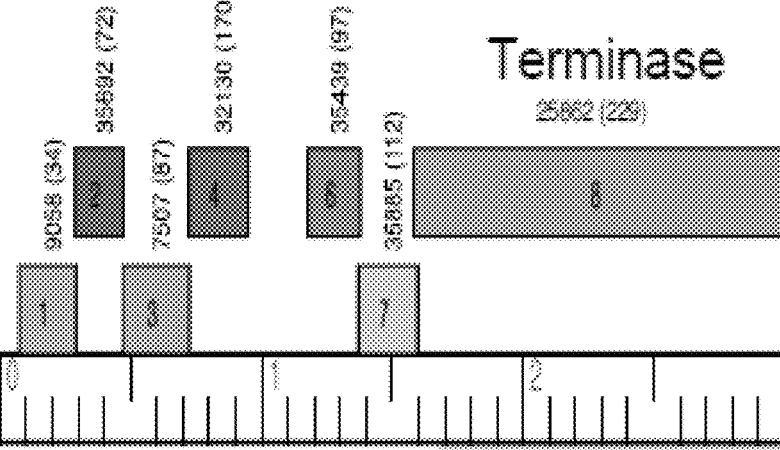
FIG. 3A shows a comparison of the genome maps of phage Adephagia (top) and phage Fionnbharth (bottom). The ruler shows the length of the genome from about 0 Kilobase pairs (kb) to about 7 kb of the genome map of phage Adephagia (top). The shading between the genomes indicates nucleotide sequence similarity with darker shading reflecting closest similarity and the lightest being the least similar above a threshold E value of $10^{-4}$.
Figure 3A:
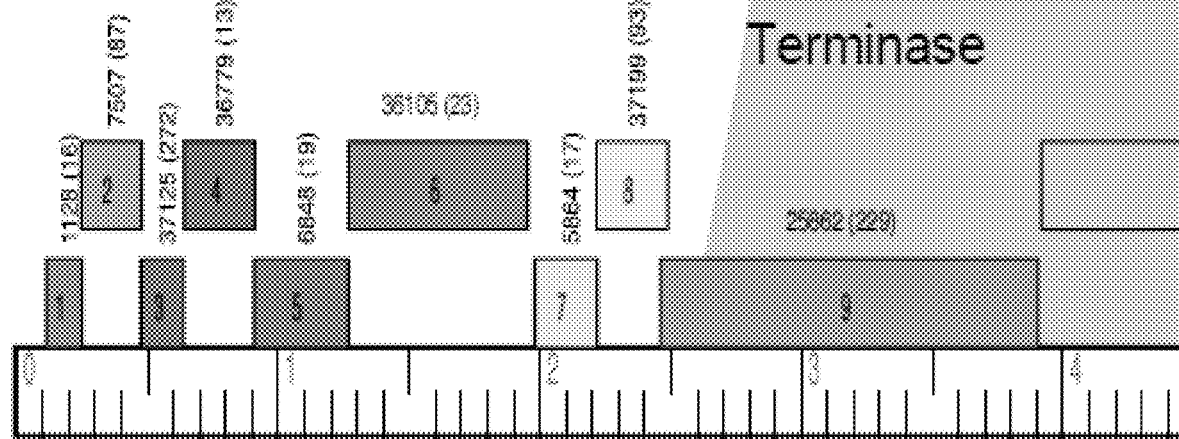
Figure 3A:
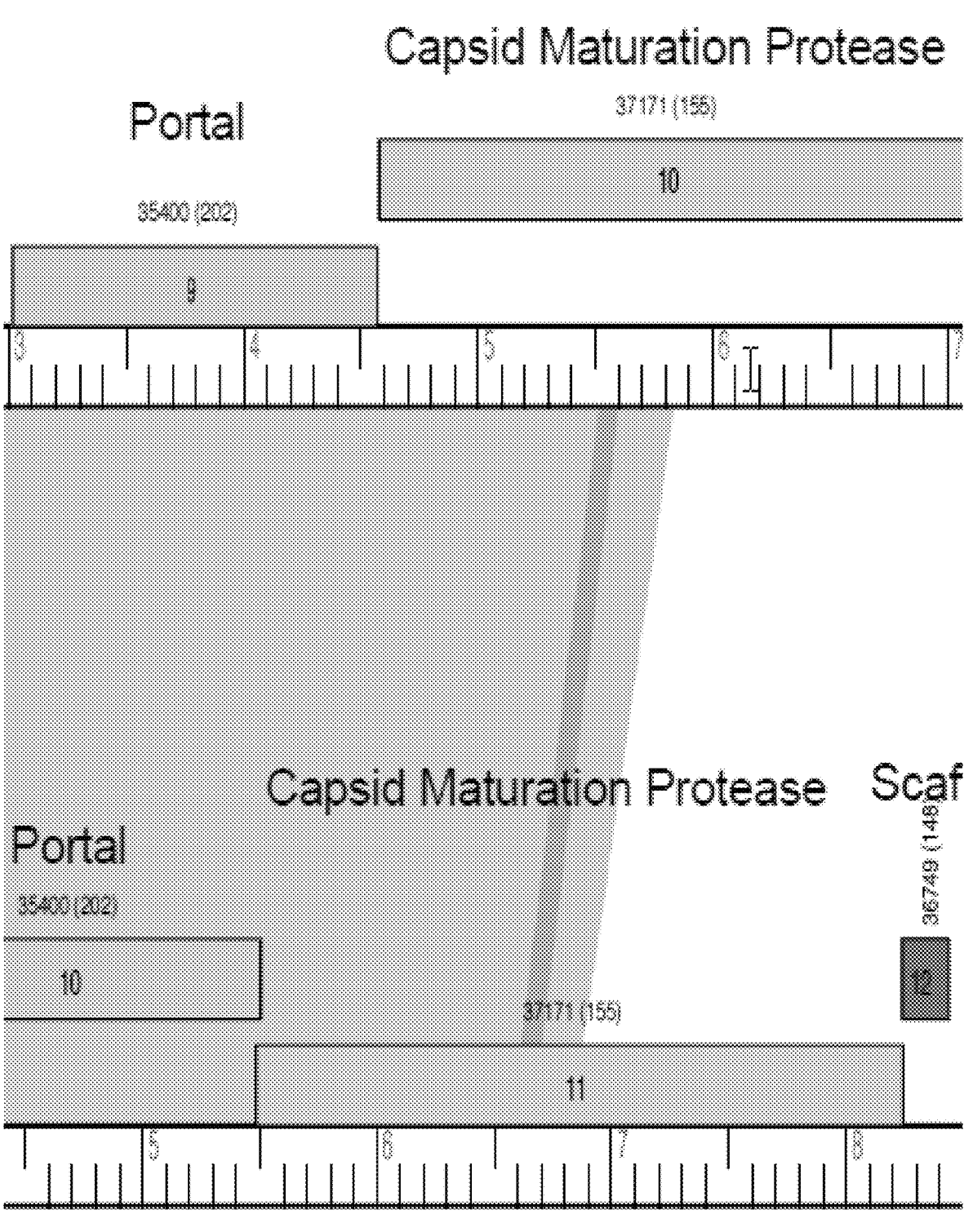
Figure 3B:
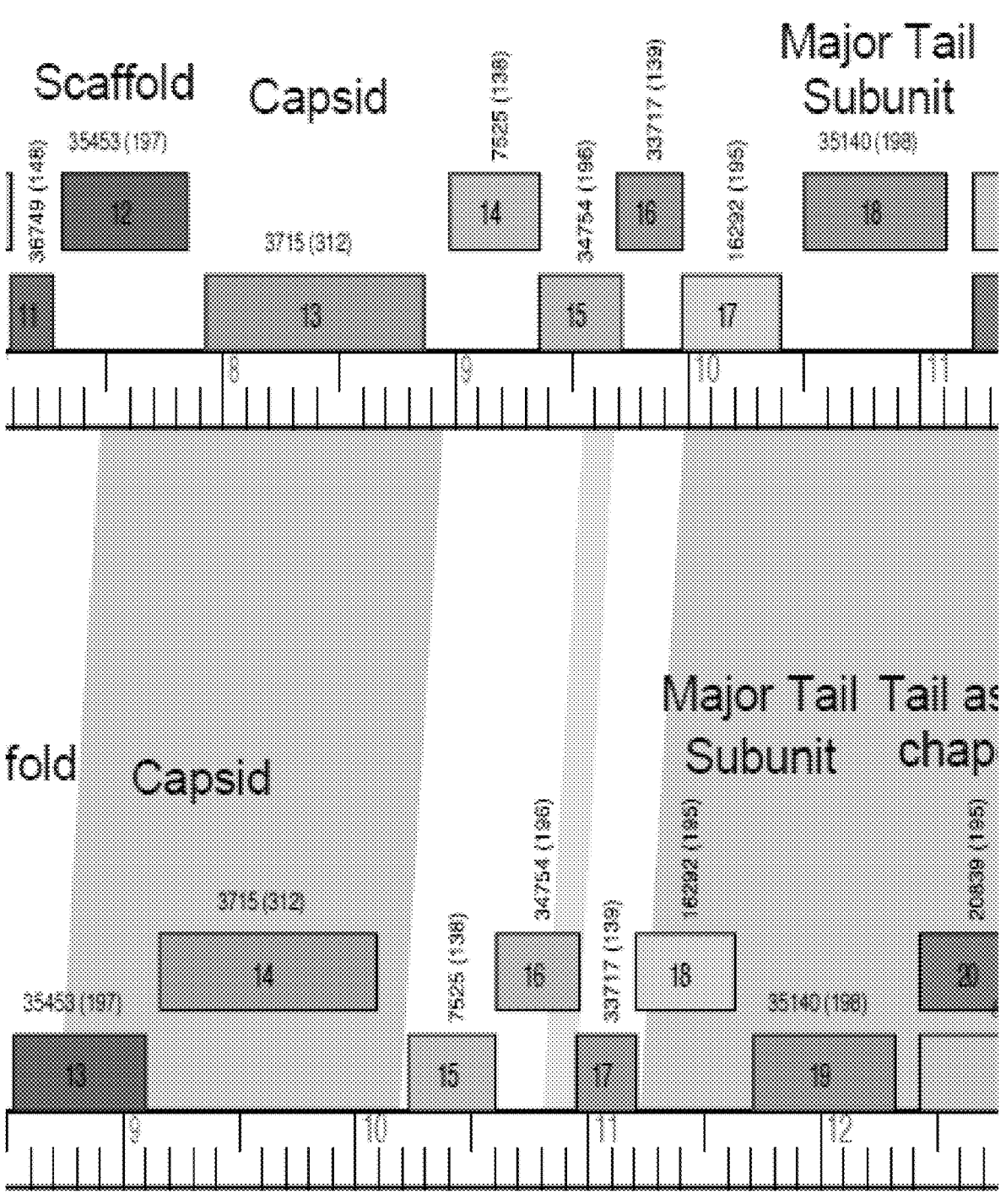
FIG. 3B shows a continuation of the genome maps of phage Adephagia (top) and phage Fionnbharth (bottom) shown in FIG. 3A. The ruler shows the length of the genome from about 7 kb to about 15 kb of the genome map of phage Adephagia (top). The shading between the genomes indicates nucleotide sequence similarity with darker shading reflecting closest similarity and the lightest being the least similar above a threshold E value of $10^{-4}$.
Figure 3B:
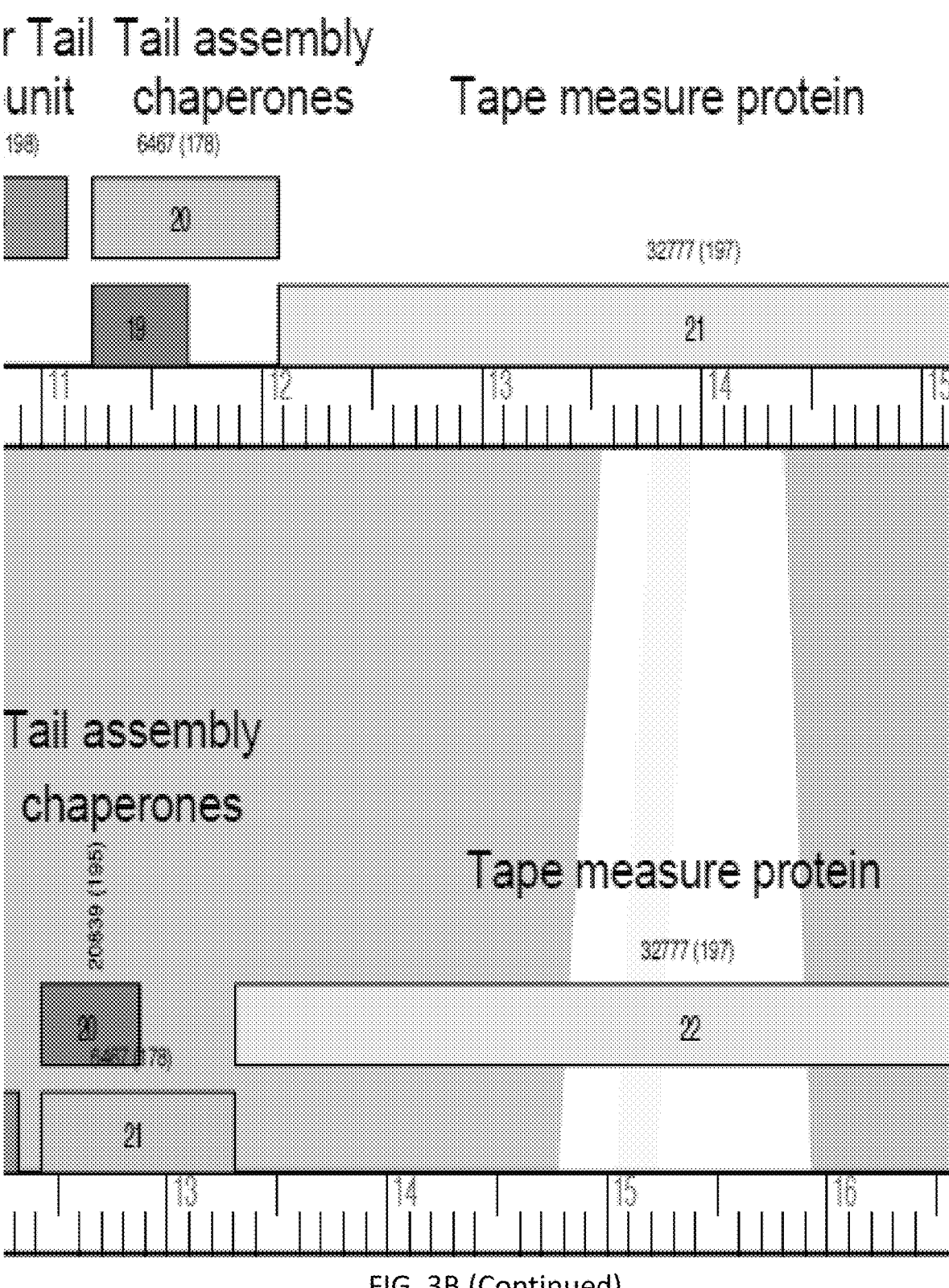
Figure 3C:
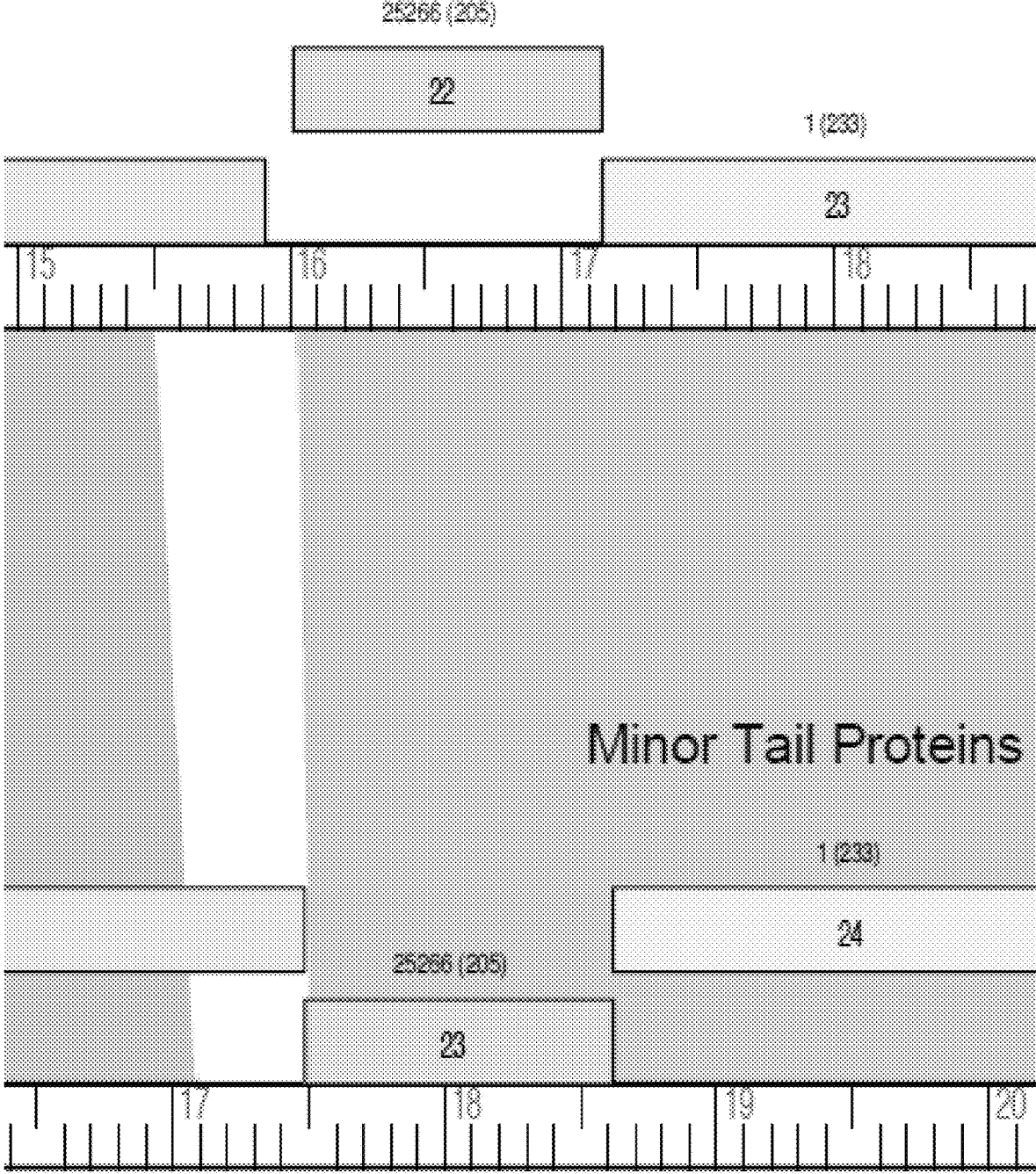
FIG. 3C shows a continuation of the genome maps of phage Adephagia (top) and phage Fionnbharth (bottom) shown in FIG. 3B. The ruler shows the length of the genome from about 15 kb to about 21 kb of the genome map of phage Adephagia (top). The shading between the genomes indicates nucleotide sequence similarity with darker shading reflecting closest similarity and the lightest being the least similar above a threshold E value of $10^{-4}$.
Figure 3D:
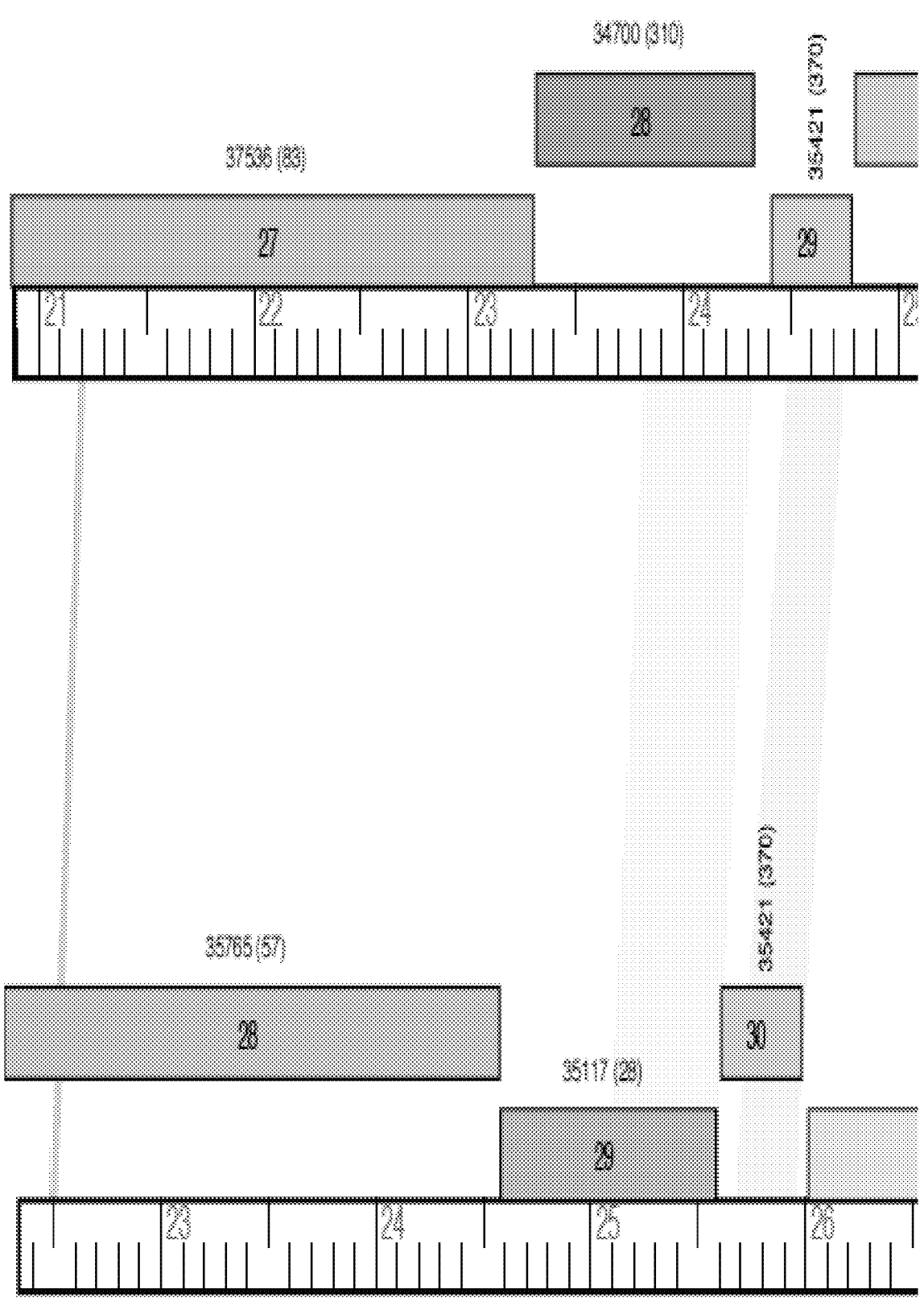
FIG. 3D shows a continuation of the genome maps of phage Adephagia (top) and phage Fionnbharth (bottom) shown in FIG. 3C. The ruler shows the length of the genome from about 21 kb to about 29 kb. The shading between the genomes indicates nucleotide sequence similarity with darker shading reflecting closest similarity and the lightest being the least similar above a threshold E value of $10^{-4}$.
Figure 3D:
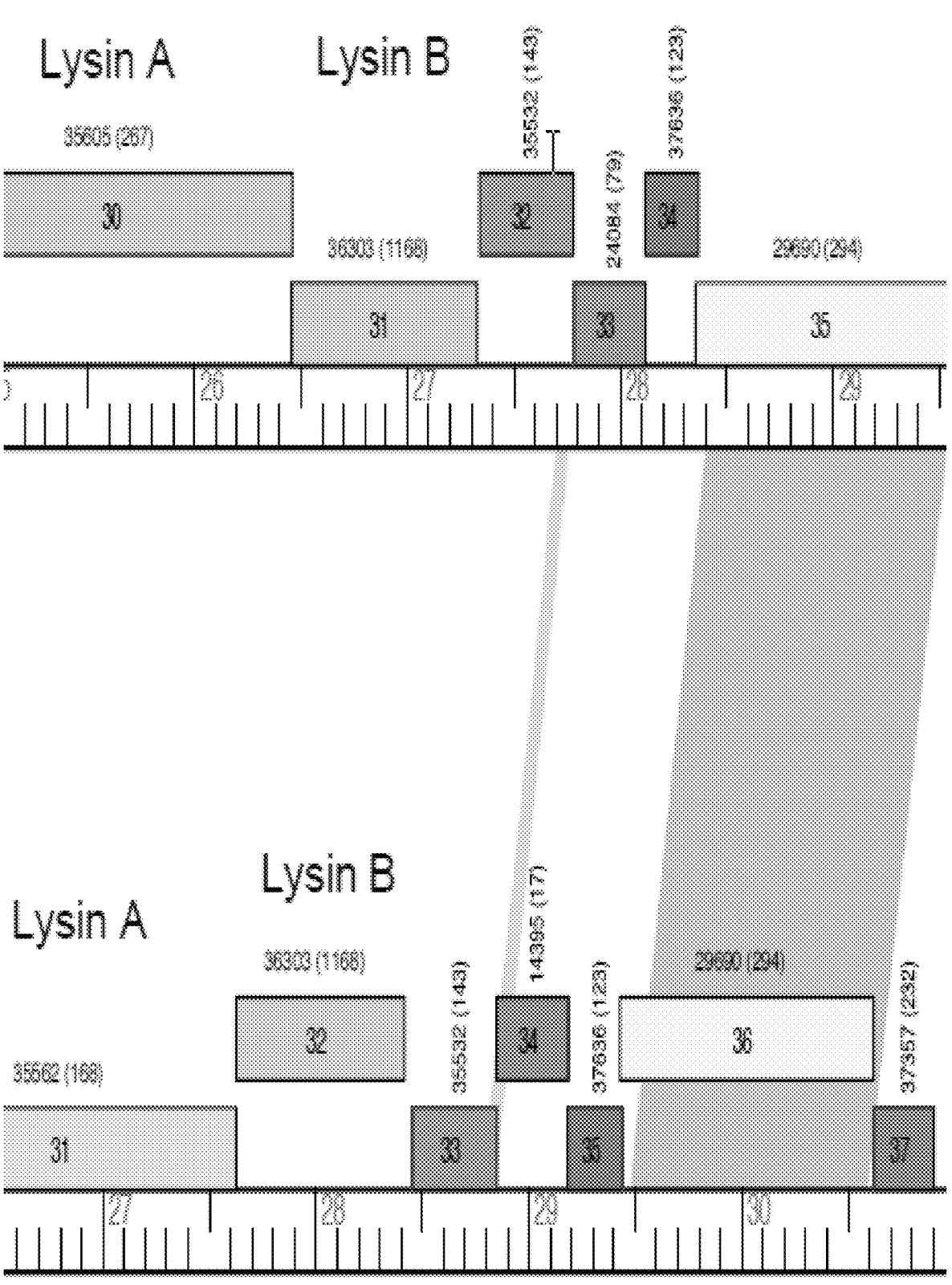
Figure 3E:
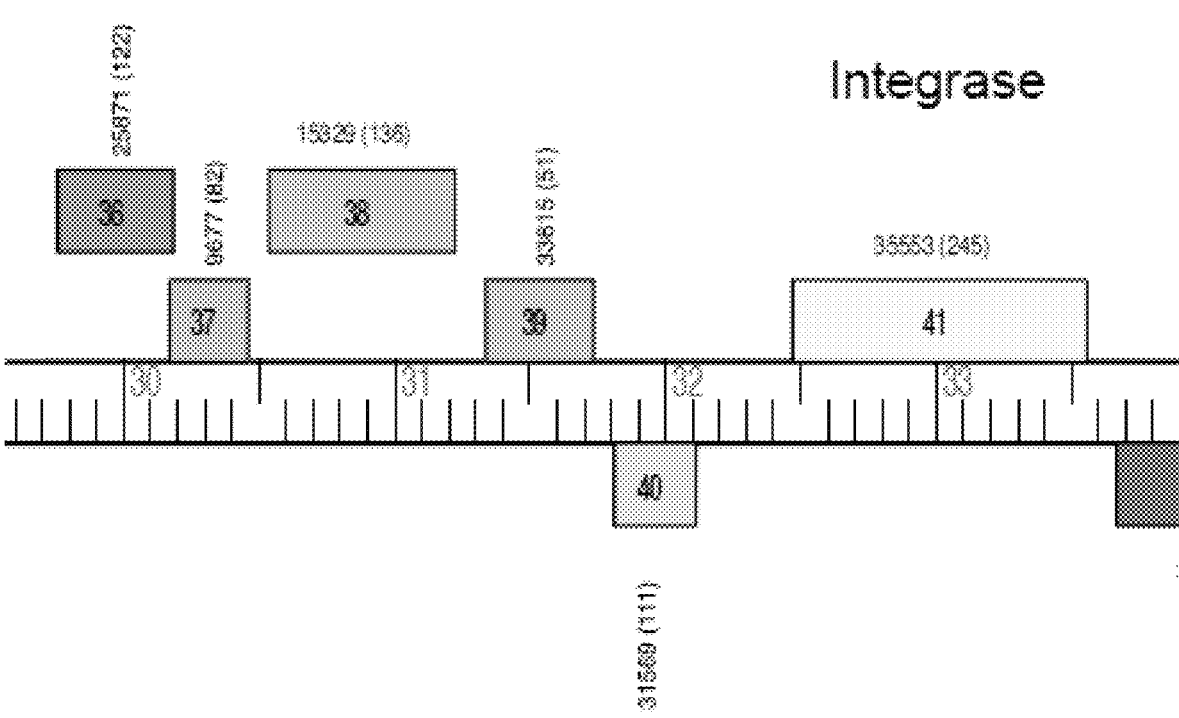
FIG. 3E shows a continuation of the genome maps of phage Adephagia (top) and phage Fionnbharth (bottom) shown in FIG. 3D. The ruler shows the length of the genome from about 29 kb to about 38 kb of the genome map of phage Adephagia (top). The shading between the genomes indicates nucleotide sequence similarity with darker shading reflecting closest similarity and the lightest being the least similar above a threshold E value of $10^{-4}$.
Figure 3E:
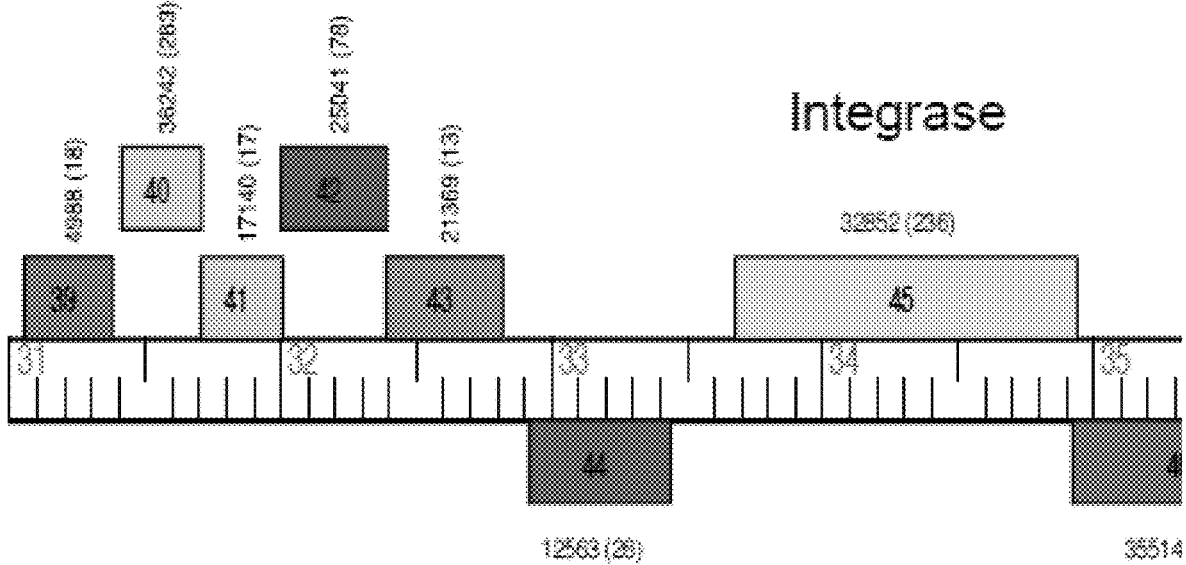
Figure 3E:
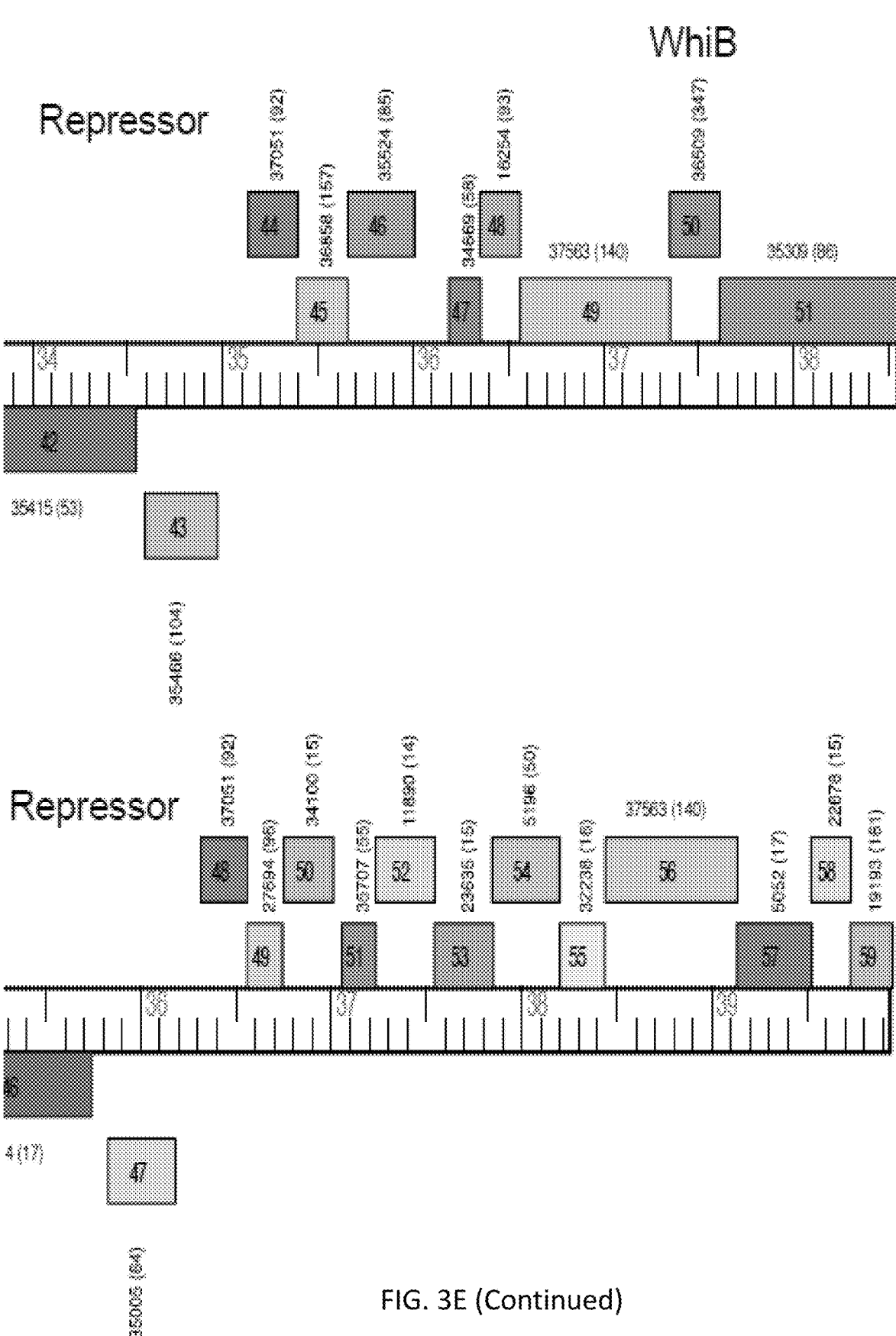
Figure 3F:
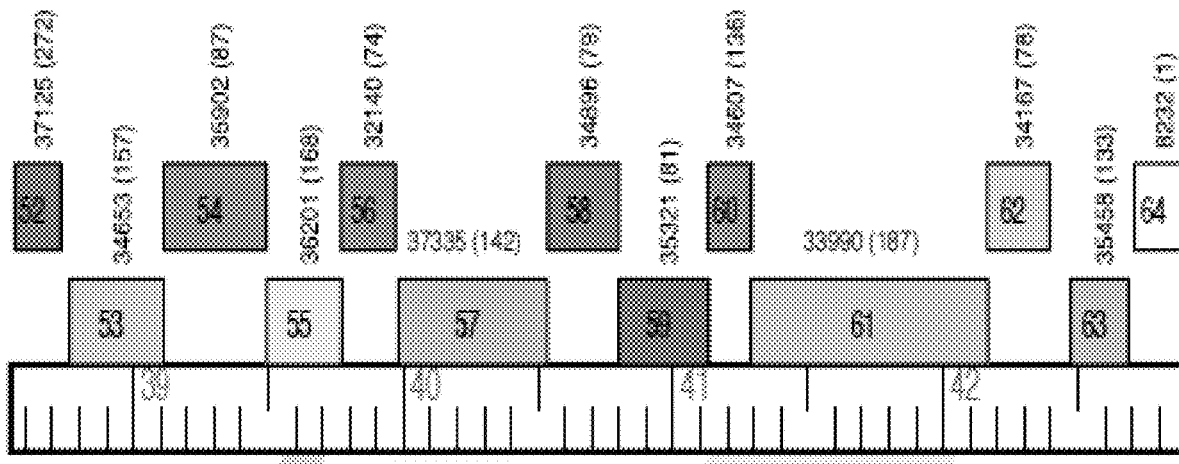
FIG. 3F shows a continuation of the genome maps of phage Adephagia (top) and phage Fionnbharth (bottom) shown in FIG. 3E. The ruler shows the length of the genome from about 38 kb to about 46 kb of the genome map of phage Adephagia (top). The shading between the genomes indicates nucleotide sequence similarity with darker shading reflecting closest similarity and the lightest being the least similar above a threshold E value of $10^{-4}$.
Figure 3F:
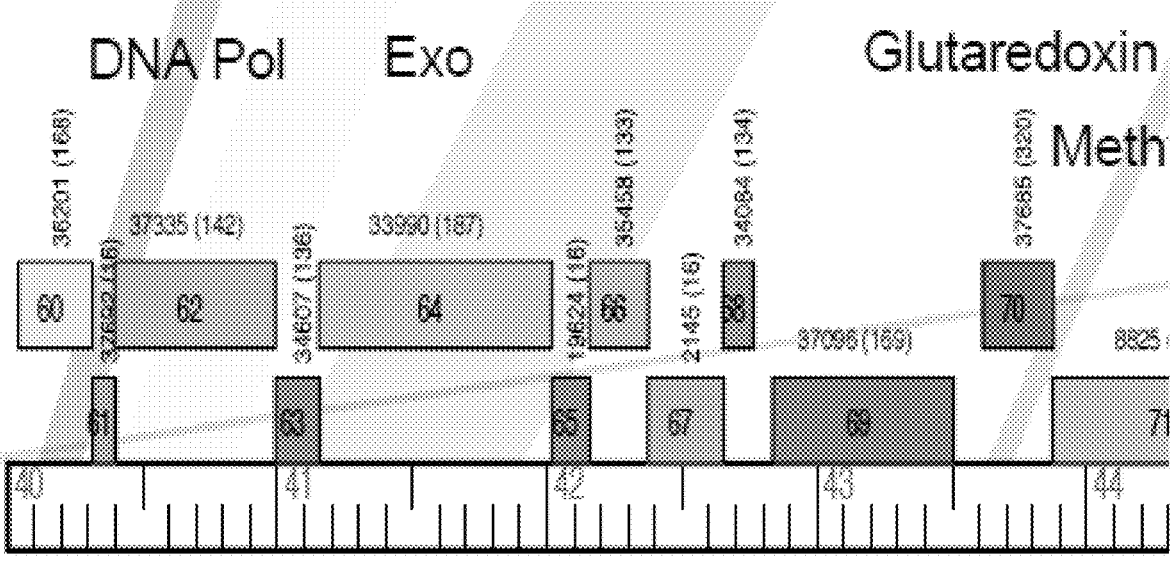
Figure 3F:
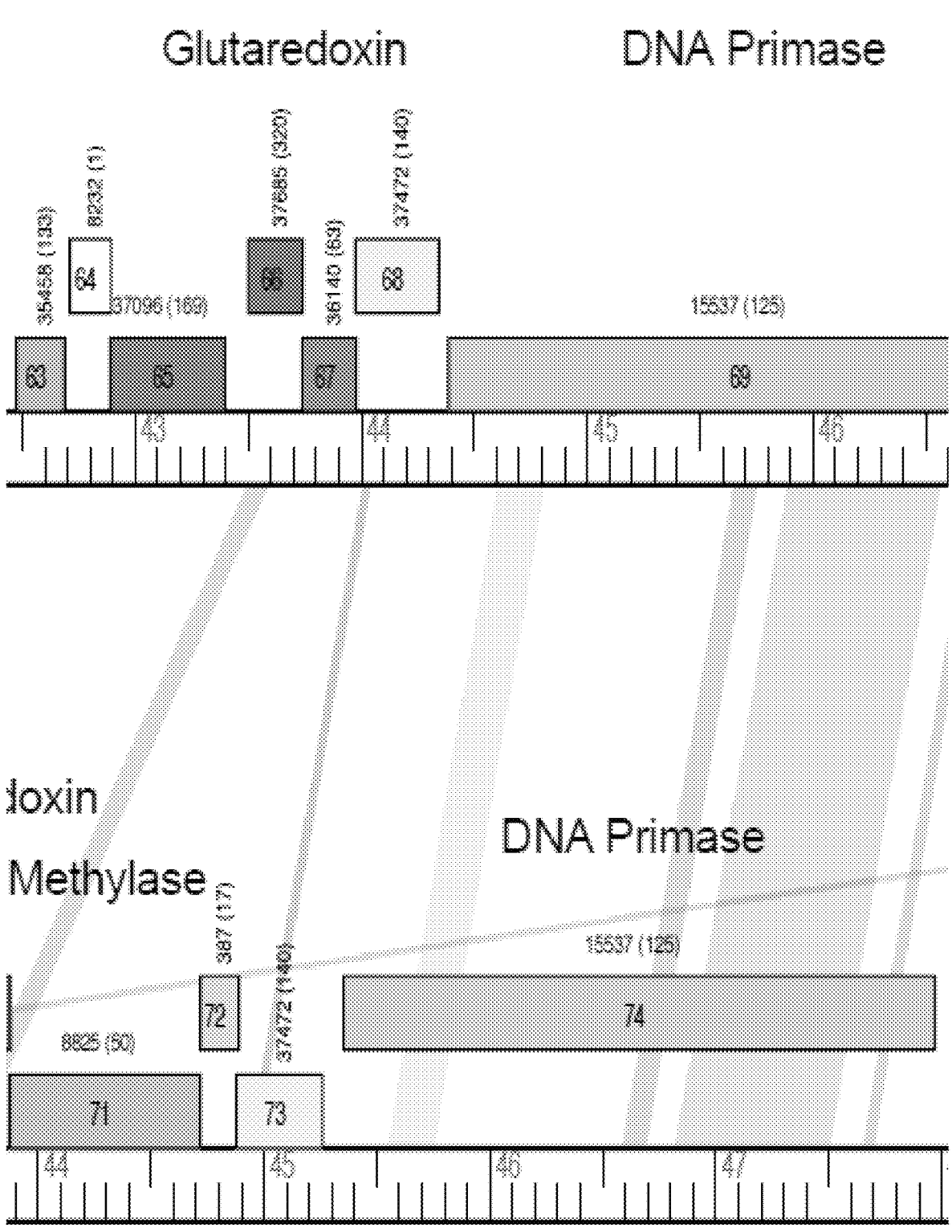
Figure 3G:
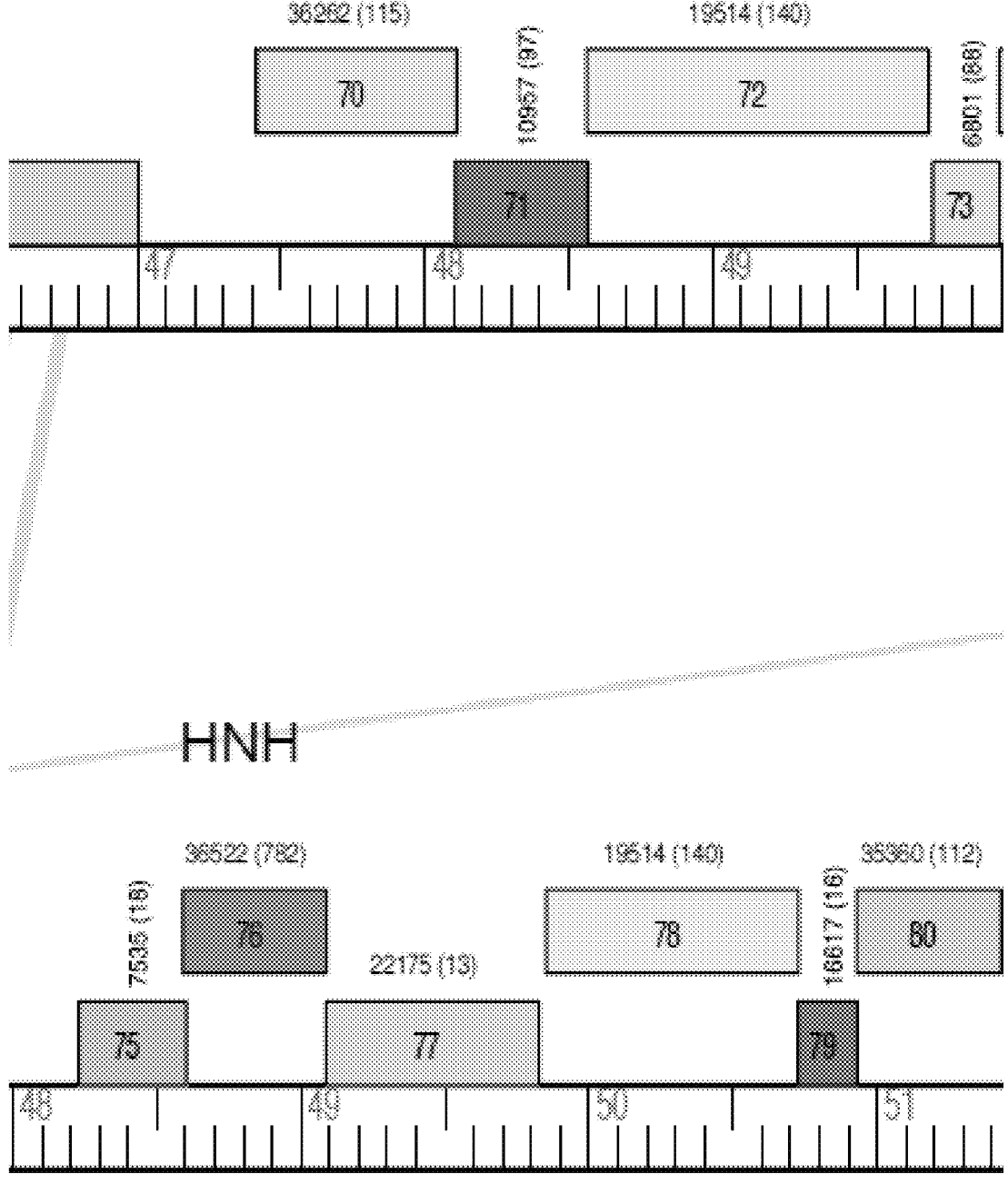
FIG. 3G shows a continuation of the genome maps of phage Adephagia (top) and phage Fionnbharth (bottom) shown in FIG. 3F. The ruler shows the length of the genome from about 46 kb to about 53 kb of the genome map of phage Adephagia (top). The shading between the genomes indicates nucleotide sequence similarity with darker shading reflecting closest similarity and the lightest being the least similar above a threshold E value of $10^{-4}$.
Figure 3G:
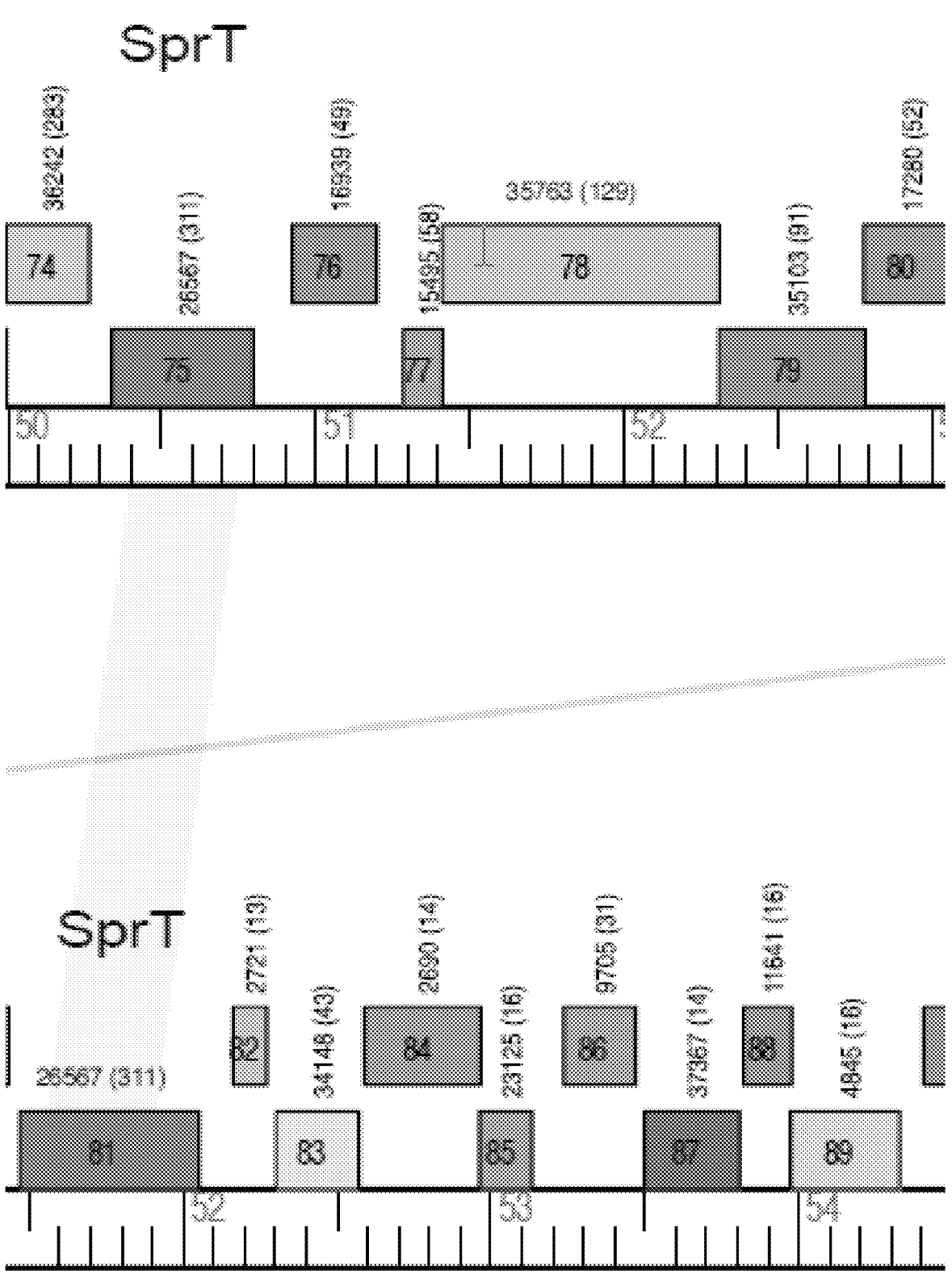
Figure 3H:
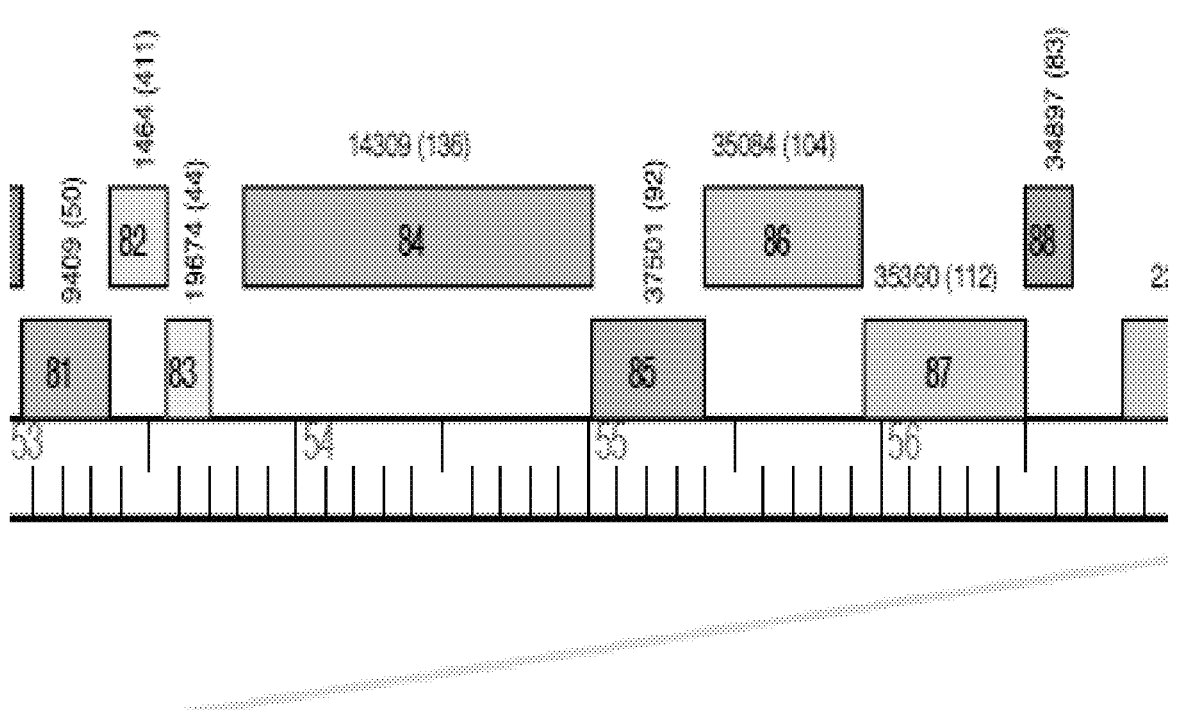
FIG. 3H shows a continuation of the genome maps of phage Adephagia (top) and phage Fionnbharth (bottom) shown in FIG. 3G. The ruler shows the length of the genome from about 53 kb to about 60 kb of the genome map of phage Adephagia (top). The shading between the genomes indicates nucleotide sequence similarity with darker shading reflecting closest similarity and the lightest being the least similar above a threshold E value of $10^{-4}$.
Figure 3H:
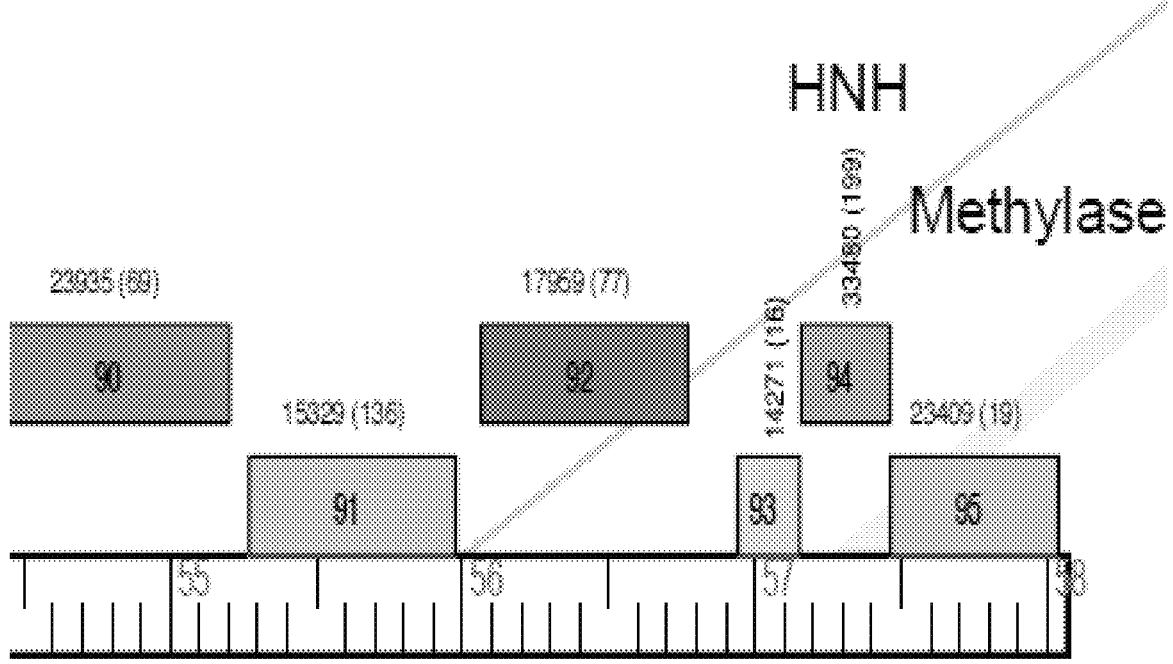
Figure 3H:
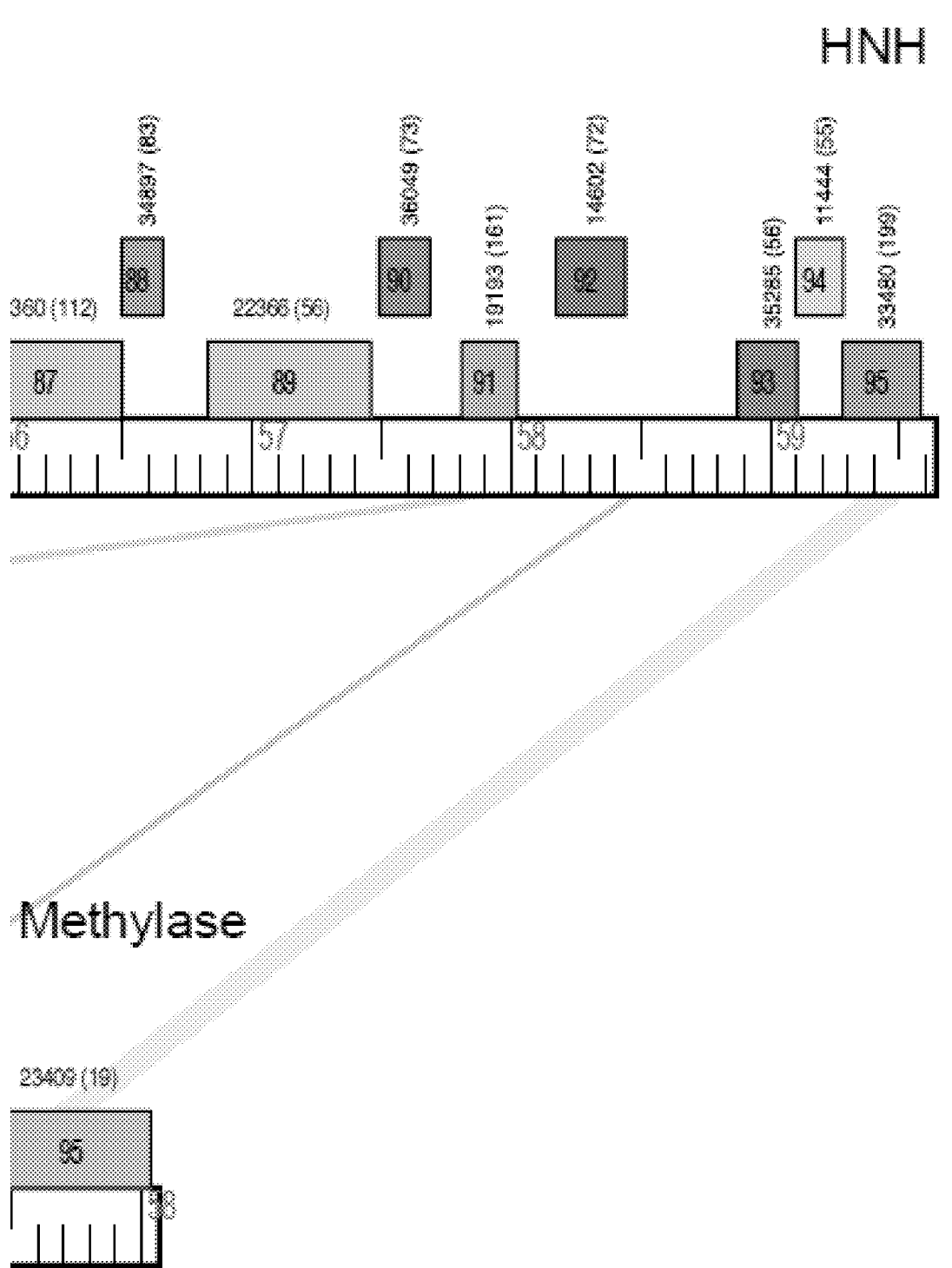

*M. tuberculosis* strains were plated on solid media. One plate was grown without phage (FIG. 2B), and the other was seeded with 10⁹ pfu phage AdephagiaΔ41Δ43 (SEQ ID NO: 2), and efficient killing was observed (FIG. 2B). Specifically, four 100-fold serial dilutions of bacterial cultures were spotted (right to left) and the plates incubated at 37° C. for six weeks. For some strains (e.g. N1274, FIG. 2B) some residual spots were observed, although they did not appear to continue to grow after prolonged incubation. Some colonies of strain N0136 were observed that may correspond to resistant mutants (FIG. 2B).

Phage FionnbharthΔ47

Figure 4B:
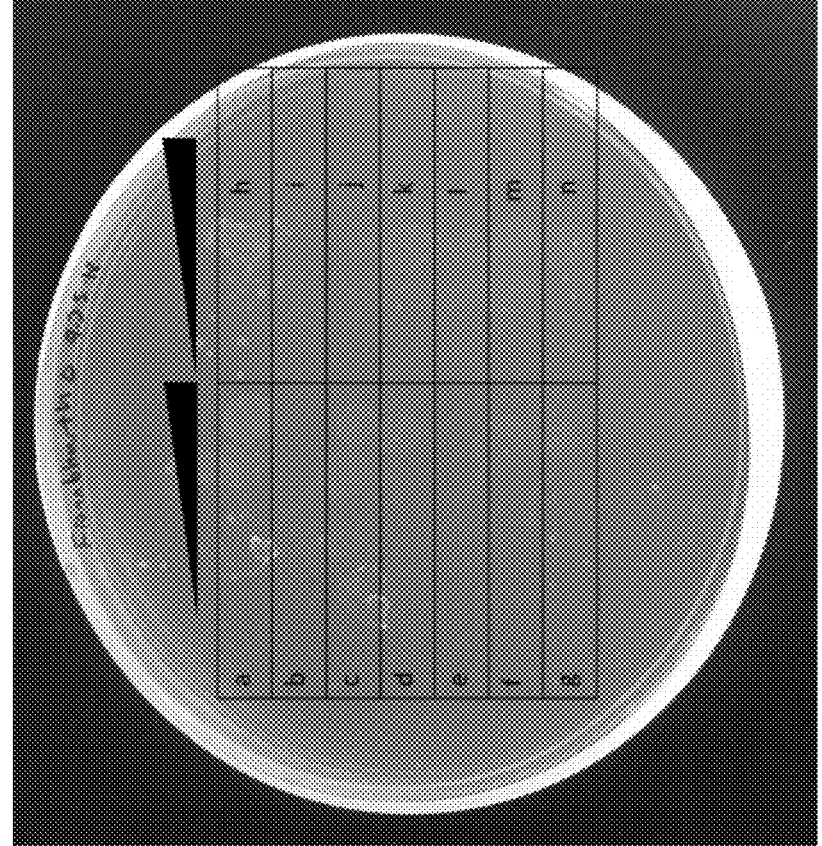
FIGS. 4A and 4B are pictures of culture plates spotted with bacterial culture with and without the addition of phage. The key to the bacterial strains is noted on the culture plates of FIGS. 4A and 4B. H37Rv is the lab strain of *M. tuberculosis* tested; all other strains are clinical isolates. a=N0145, b=N0136, c=N0004, d=N0072, e=N0052, f=N0054, g=N0153, h=H37Rv, i=N1283, j=N0031, k=N1216, l=N0155, m=N1275, and n=N0157.
Figure 4A:
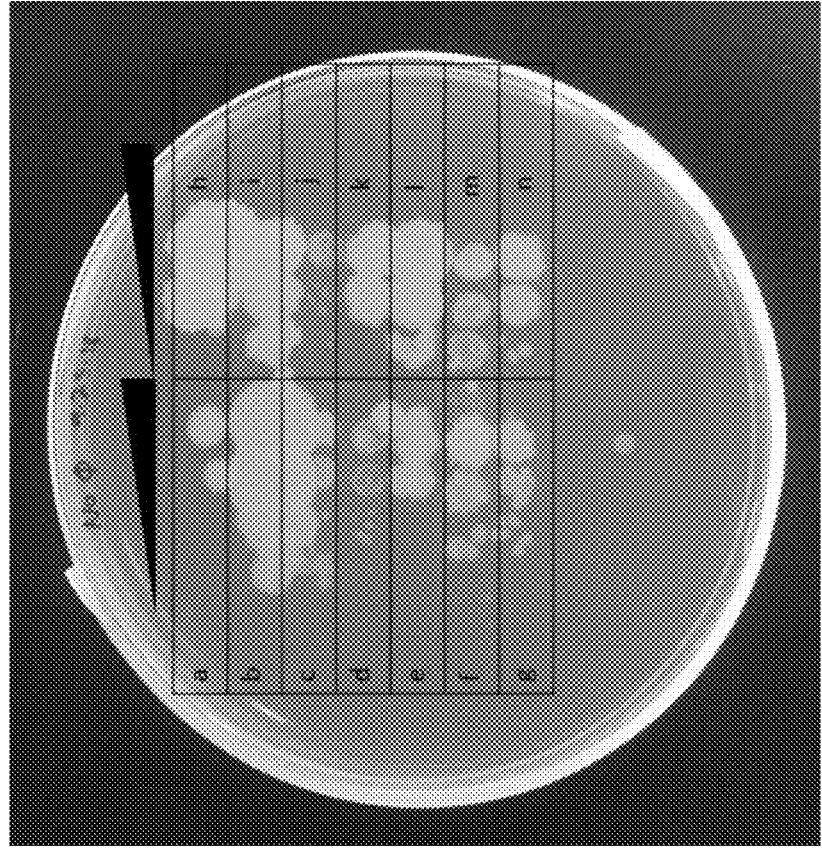
Figure 5A:
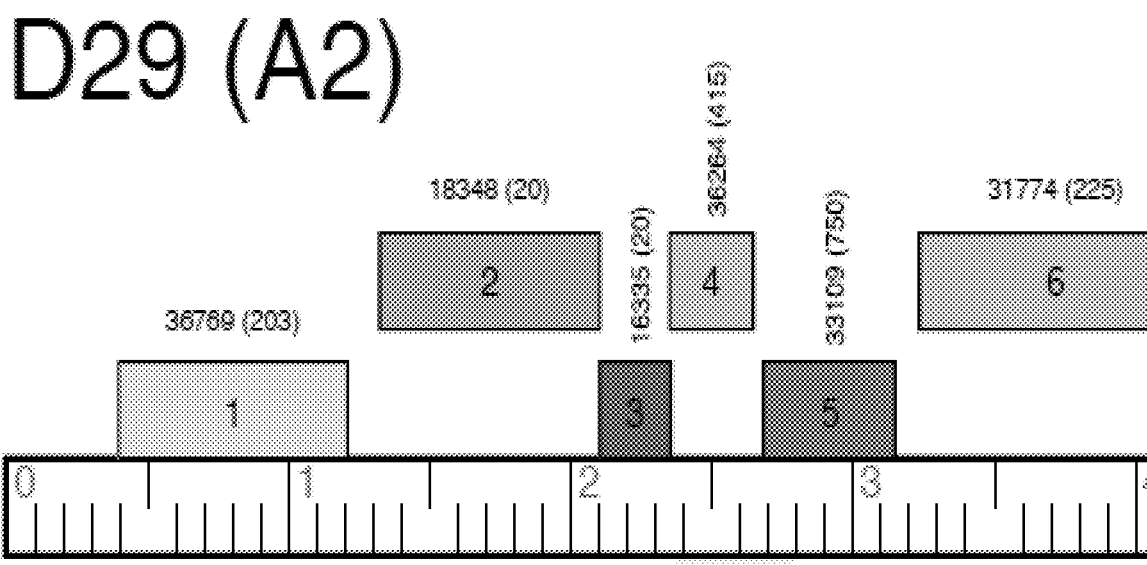
FIG. 5A shows a comparison of the genome maps of phage D29 (top) and phage Fred313cpm-1 (bottom). The ruler shows the length of the genome from about 0 kb to about 7 kb of the genome map of phage D29 (top). The shading between the genomes indicates nucleotide sequence similarity with darker shading reflecting closest similarity and the lightest being the least similar above a threshold E value of $10^{-4}$.
Figure 5A:
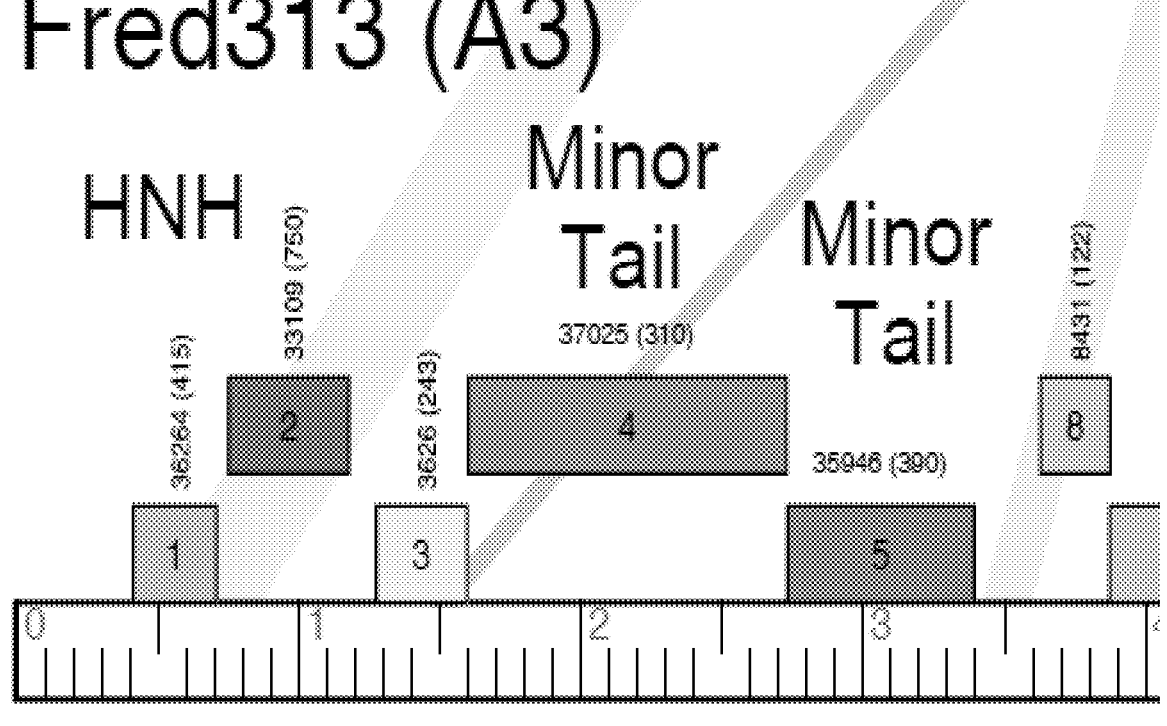
Figure 5A:
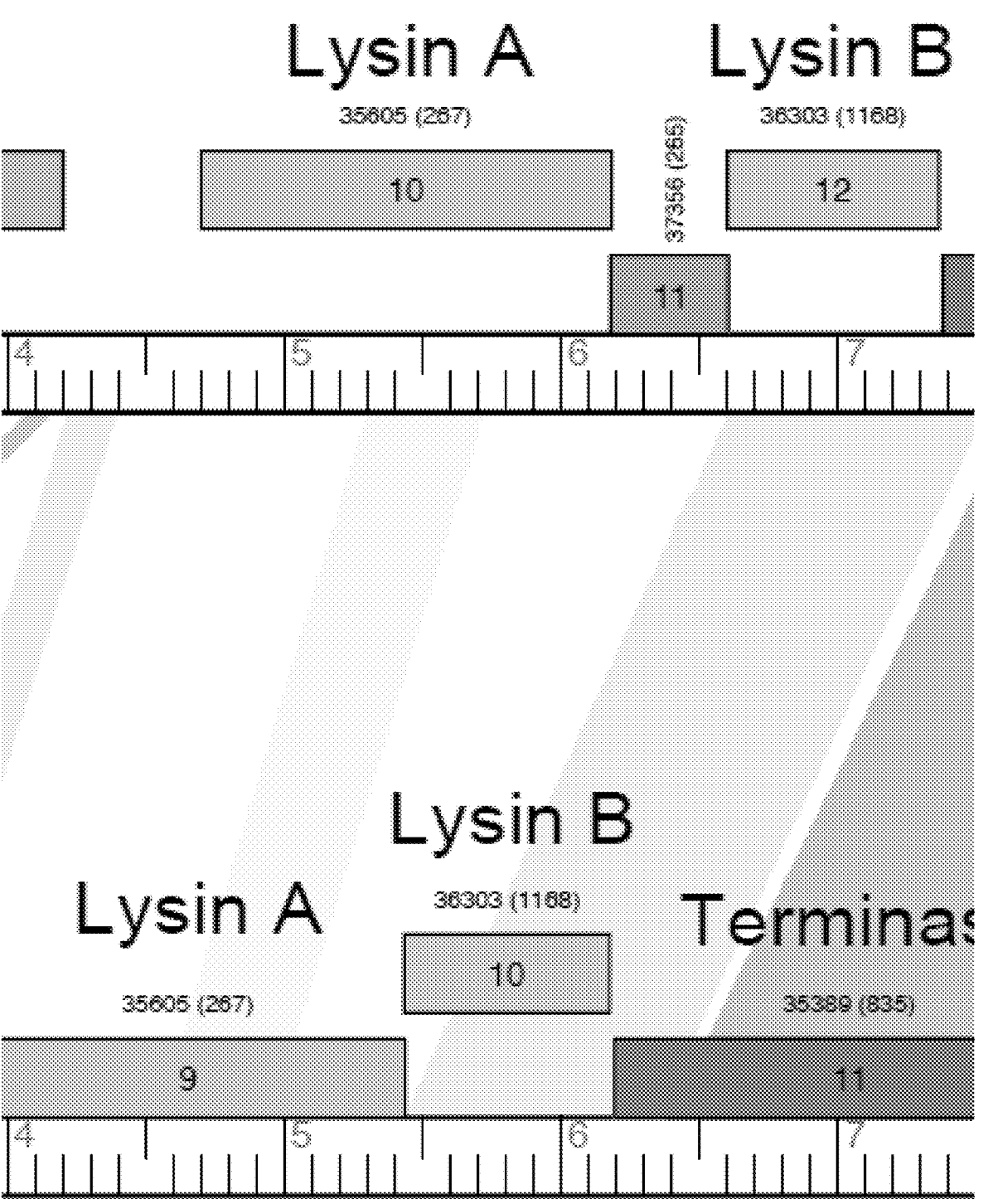
Figure 5B:
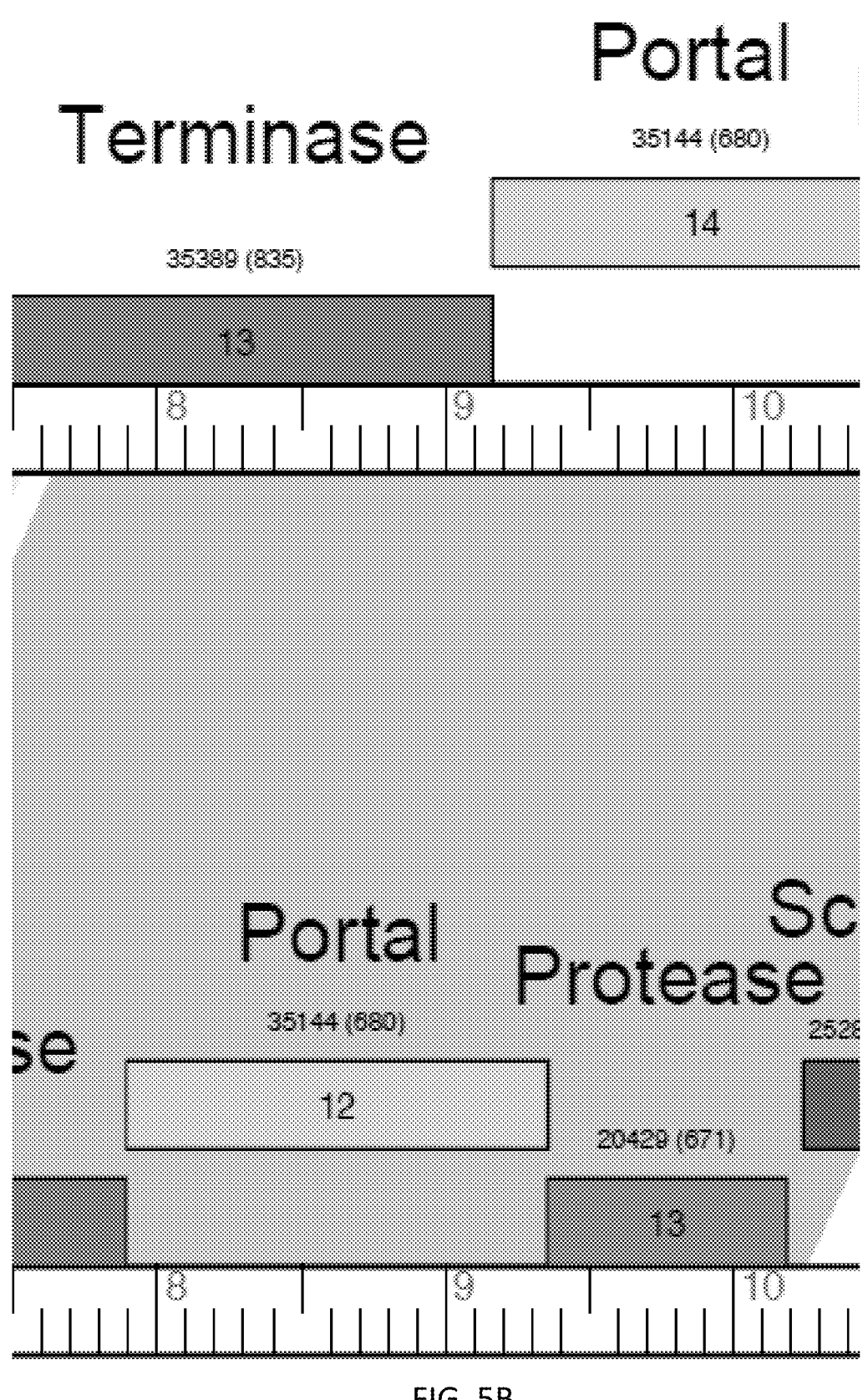
FIG. 5B shows a continuation of the genome maps of phage D29 (top) and phage Fred313cpm-1 (bottom). The ruler shows the length of the genome from about 7 kb to about 13 kb of the genome map of phage D29 (top) shown in FIG. 5A. The shading between the genomes indicates nucleotide sequence similarity with darker shading reflecting closest similarity and the lightest being the least similar above a threshold E value of $10^{-4}$.
Figure 5B:
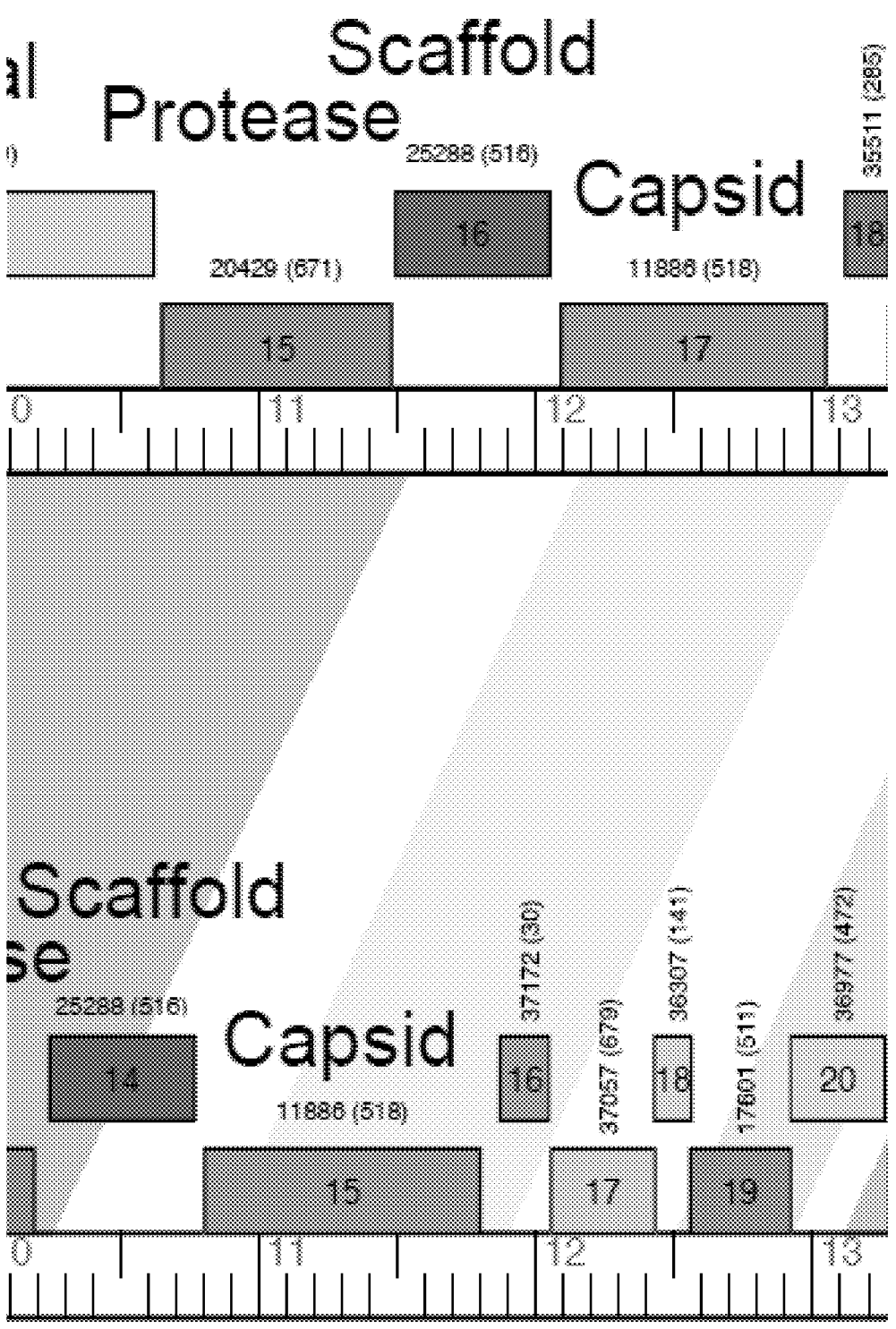
Figure 5C:
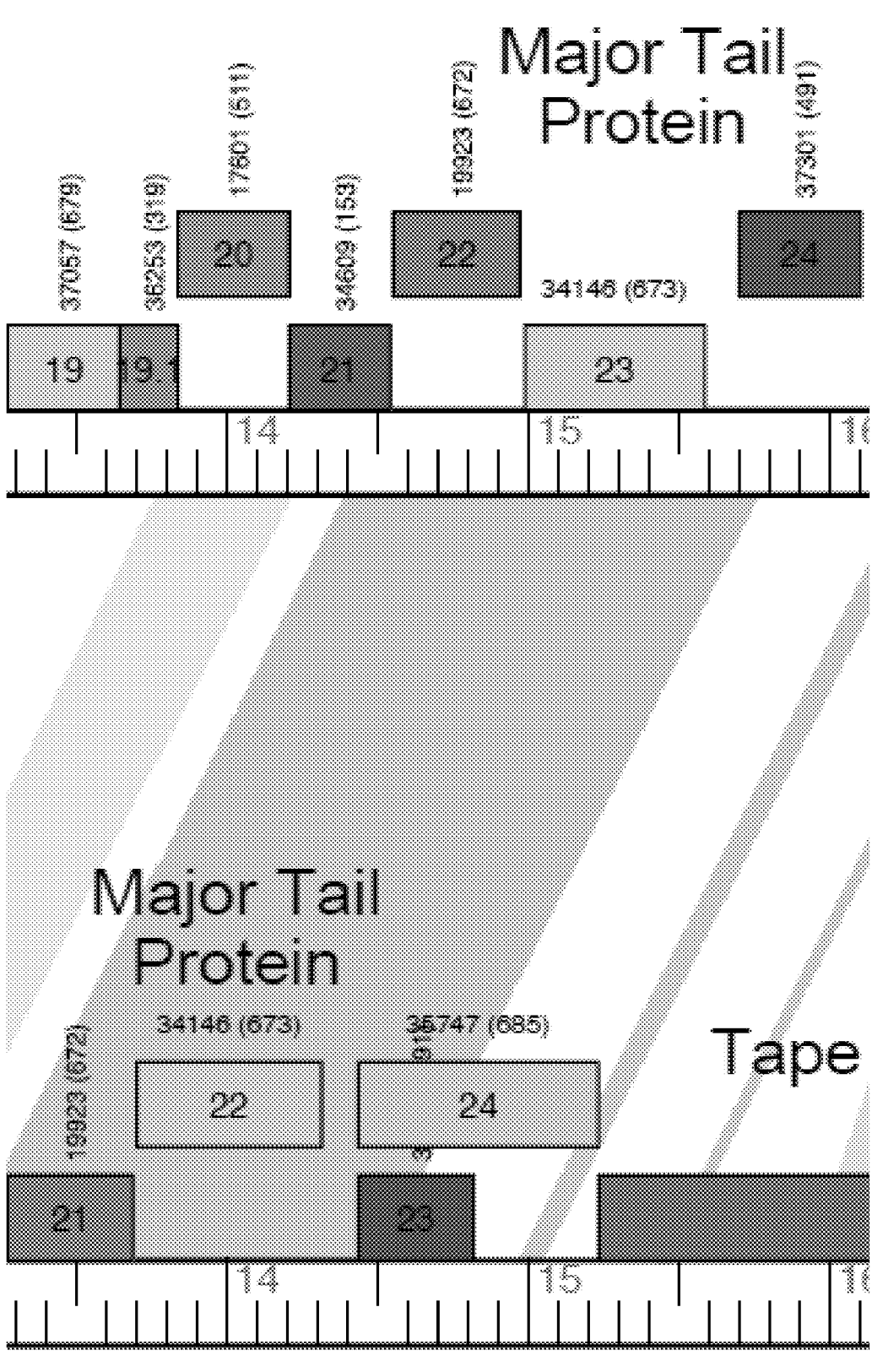
FIG. 5C shows a continuation of the genome maps of phage D29 (top) and phage Fred313cpm-1 (bottom) shown in FIG. 5B. The ruler shows the length of the genome from about 13 kb to about 19 kb of the genome map of phage D29 (top). The shading between the genomes indicates nucleotide sequence similarity with darker shading reflecting closest similarity and the lightest being the least similar above a threshold E value of $10^{-4}$.
Figure 5C:
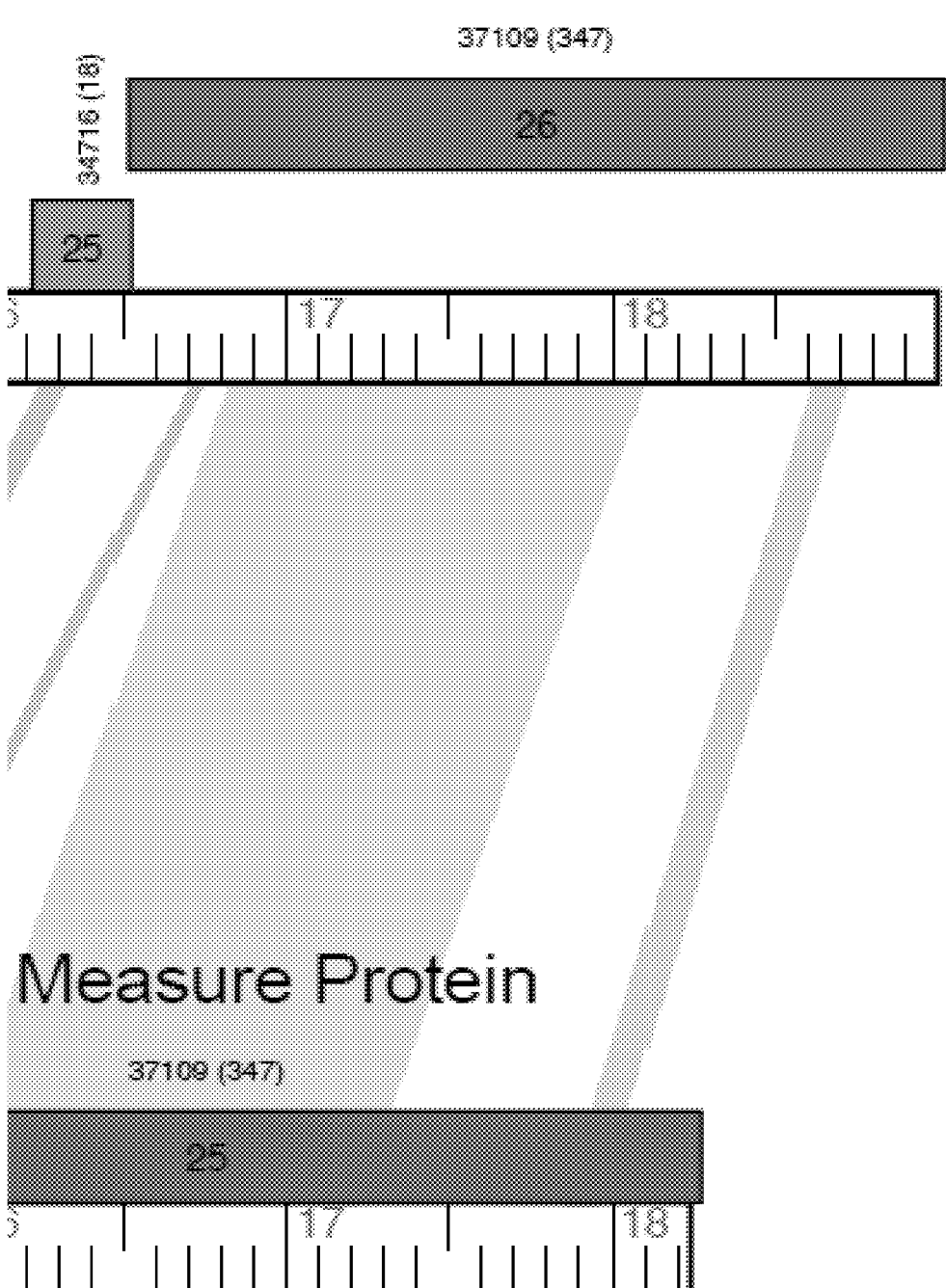
Figure 5D:
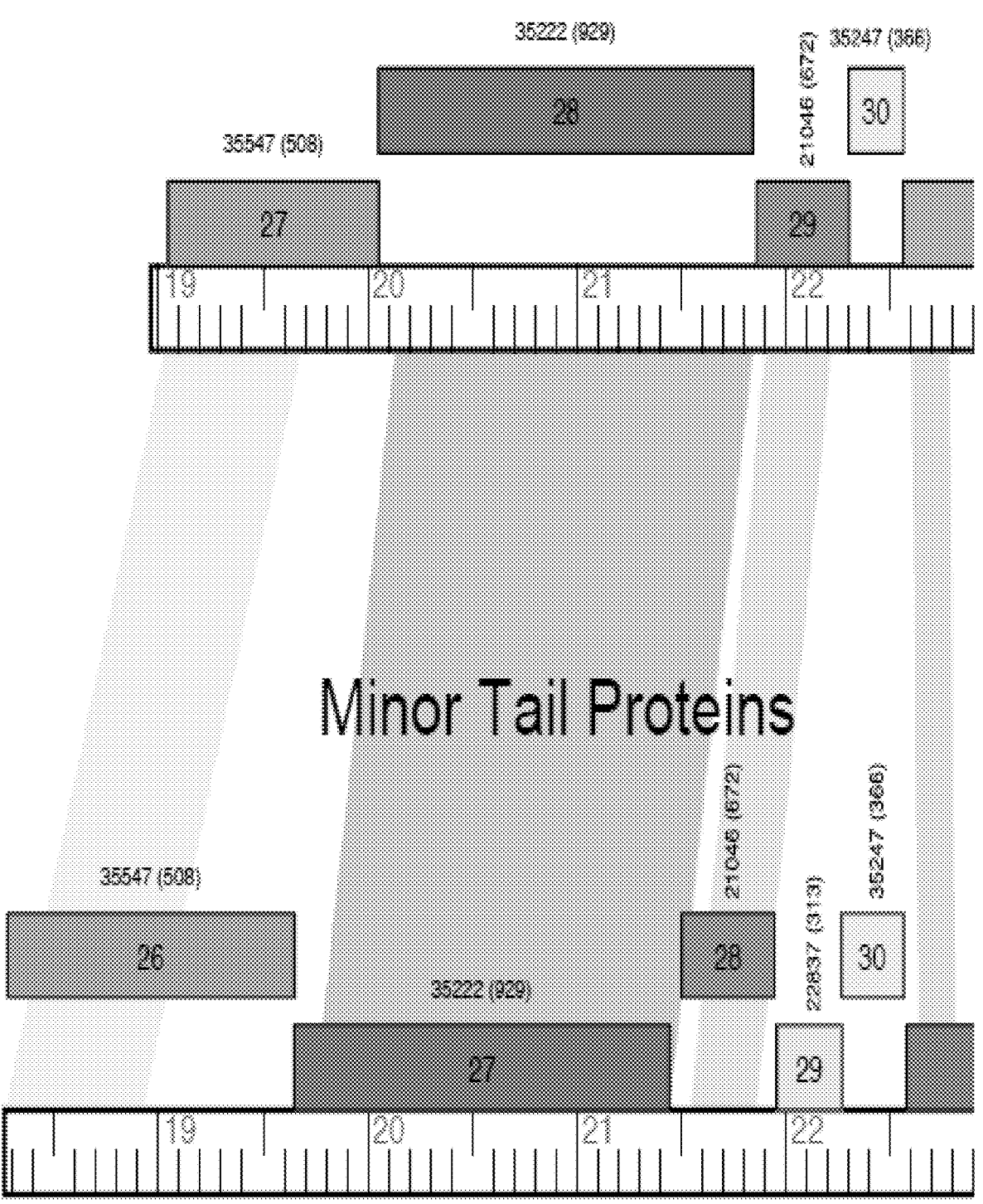
FIG. 5D shows a continuation of the genome maps of phage D29 (top) and phage Fred313cpm-1 (bottom) shown in FIG. 5C. The ruler shows the length of the genome from about 19 kb to about 27 kb of the genome map of phage D29 (top). The shading between the genomes indicates nucleotide sequence similarity with darker shading reflecting closest similarity and the lightest being the least similar above a threshold E value of $10^{-4}$.
Figure 5D:
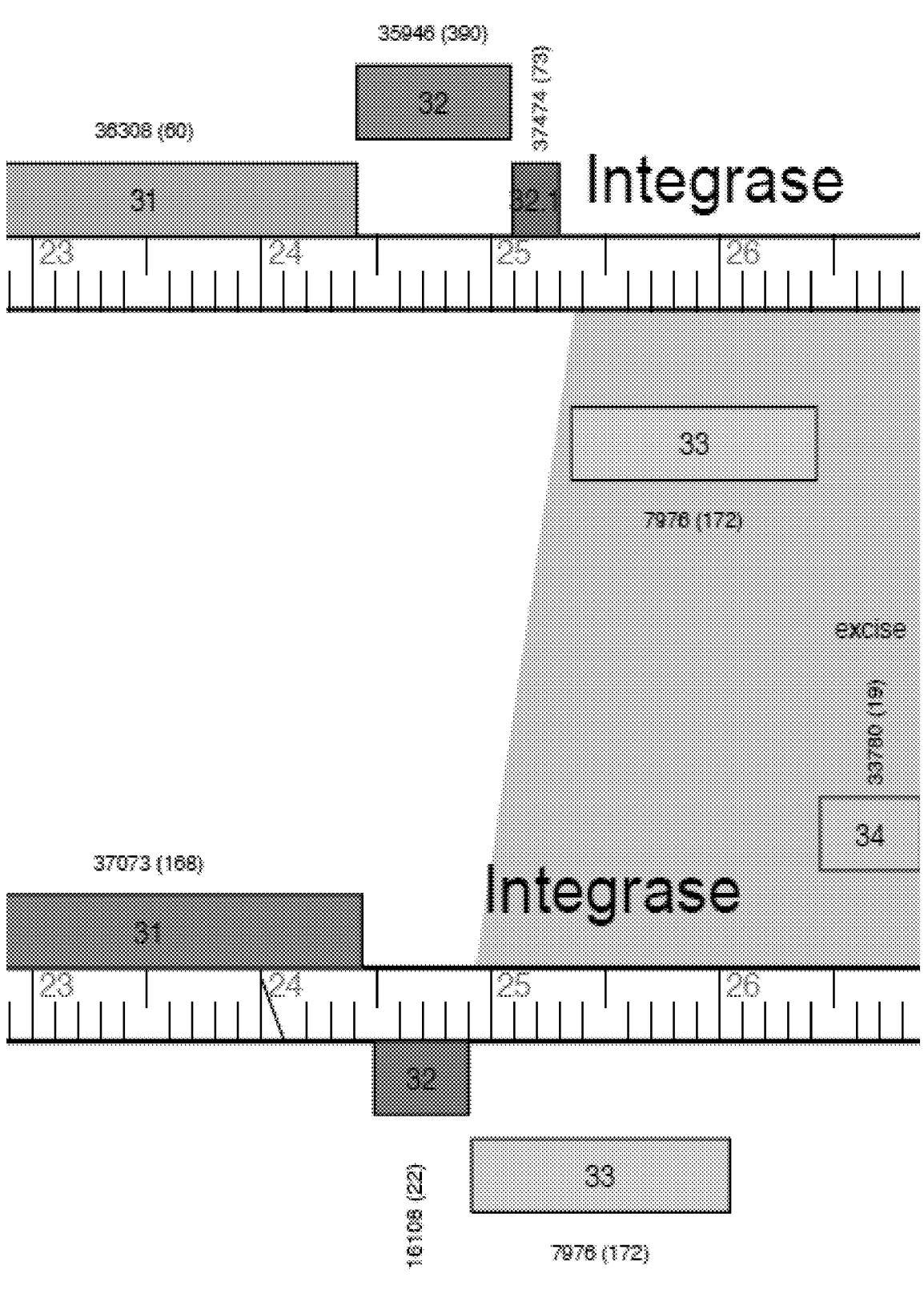
Figure 5E:
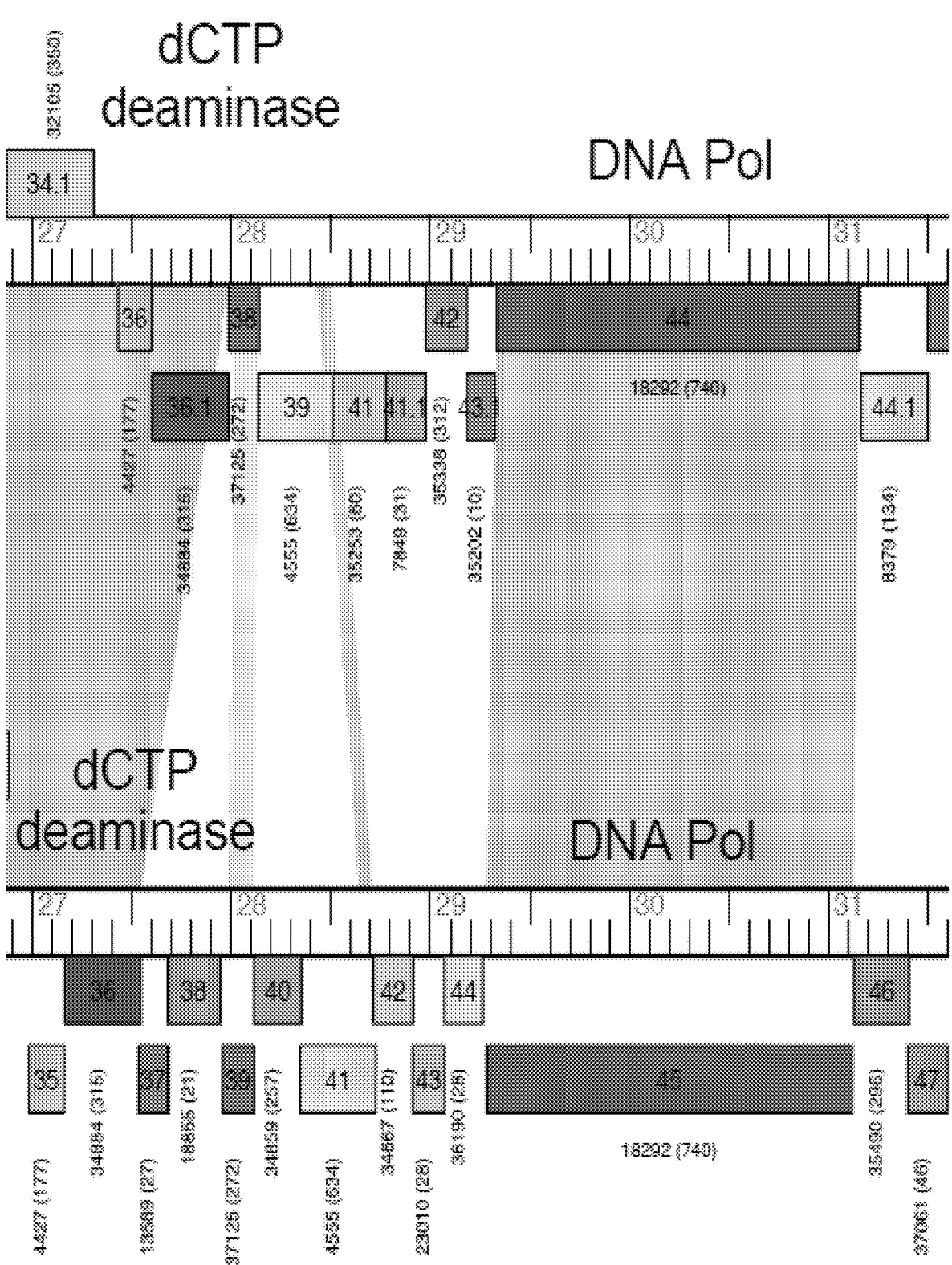
FIG. 5E shows a continuation of the genome maps of phage D29 (top) and phage Fred313cpm-1 (bottom) shown in FIG. 5D. The ruler shows the length of the genome from about 27 kb to about 35 kb of the genome map of phage D29 (top). The shading between the genomes indicates nucleotide sequence similarity with darker shading reflecting closest similarity and the lightest being the least similar above a threshold E value of $10^{-4}$.
Figure 5E:
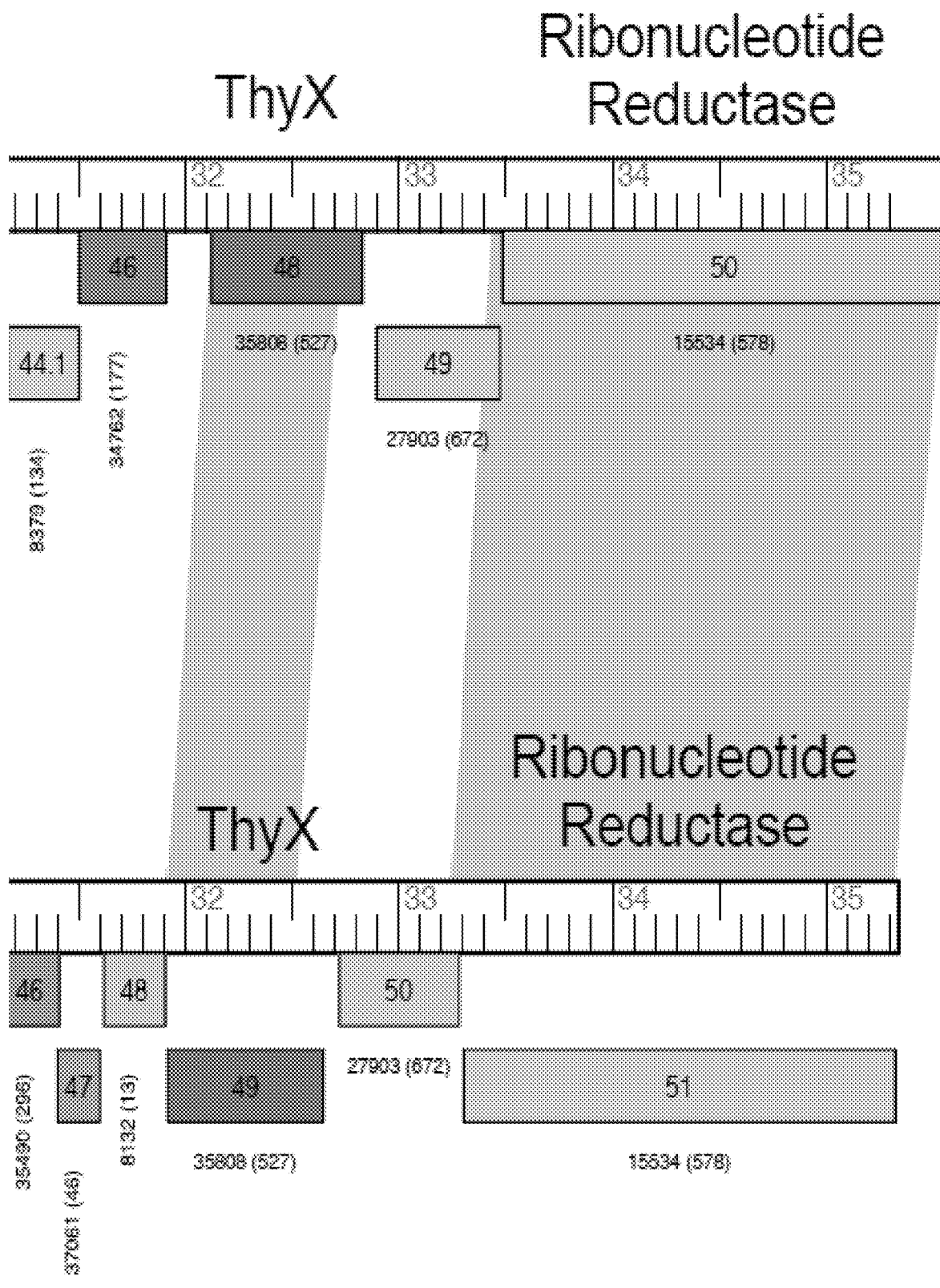
Figure 5F:
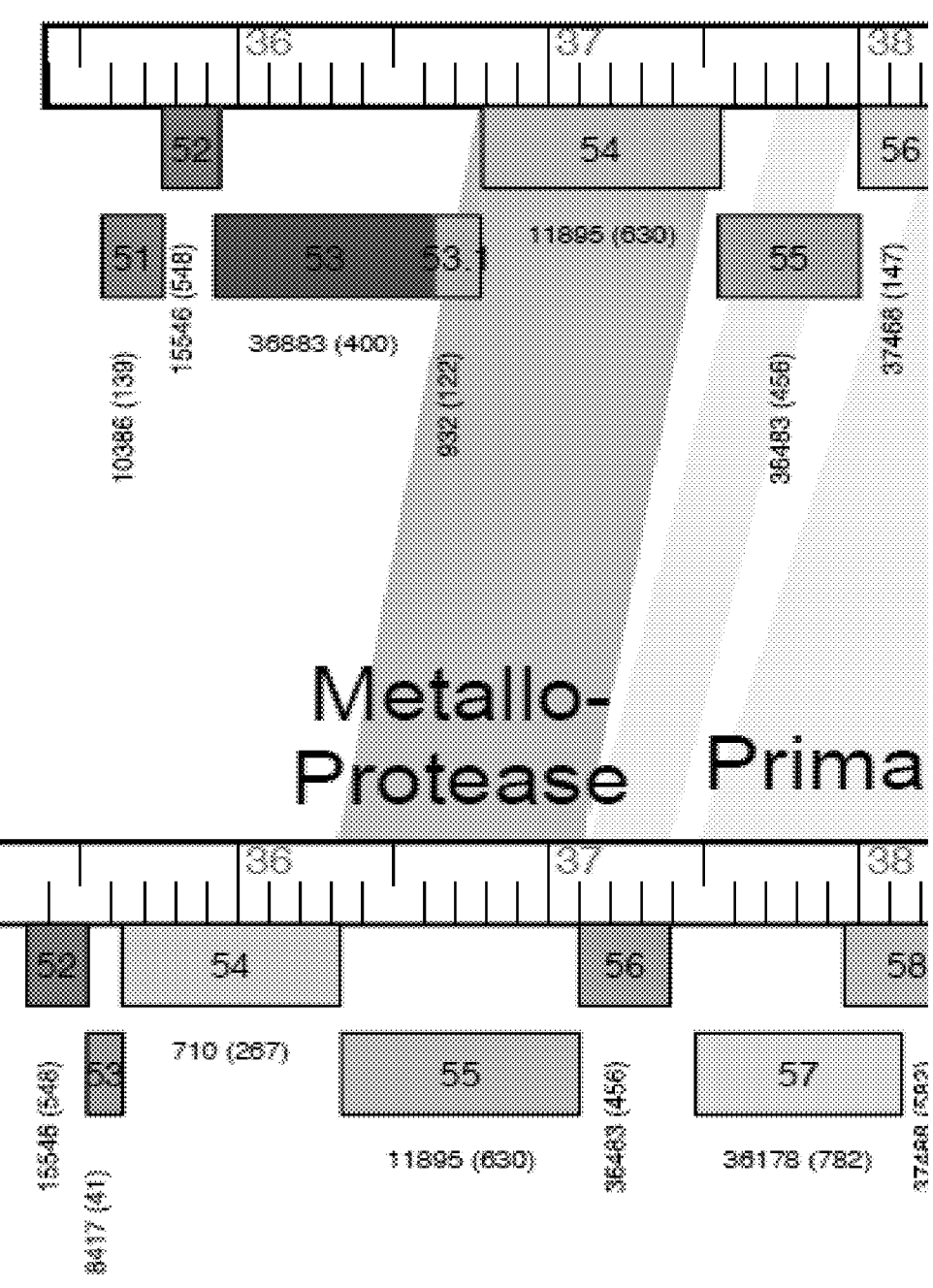
FIG. 5F shows a continuation of the genome maps of phage D29 (top) and phage Fred313cpm-1 (bottom) shown in FIG. 5E. The ruler shows the length of the genome from about 35 kb to about 41 kb of the genome map of phage D29 (top). The shading between the genomes indicates nucleotide sequence similarity with darker shading reflecting closest similarity and the lightest being the least similar above a threshold E value of $10^{-4}$.
Figure 5F:
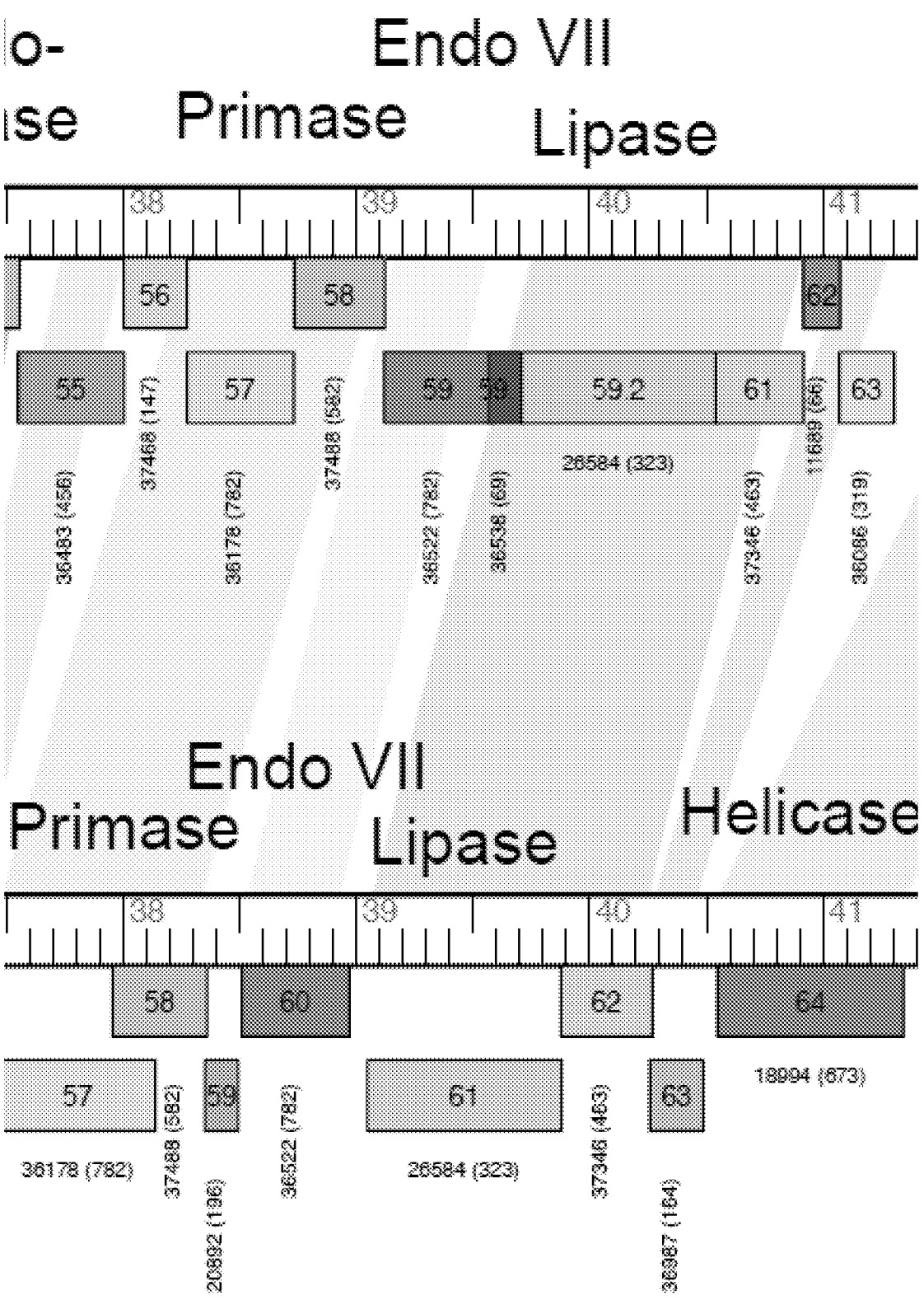
Figure 5G:
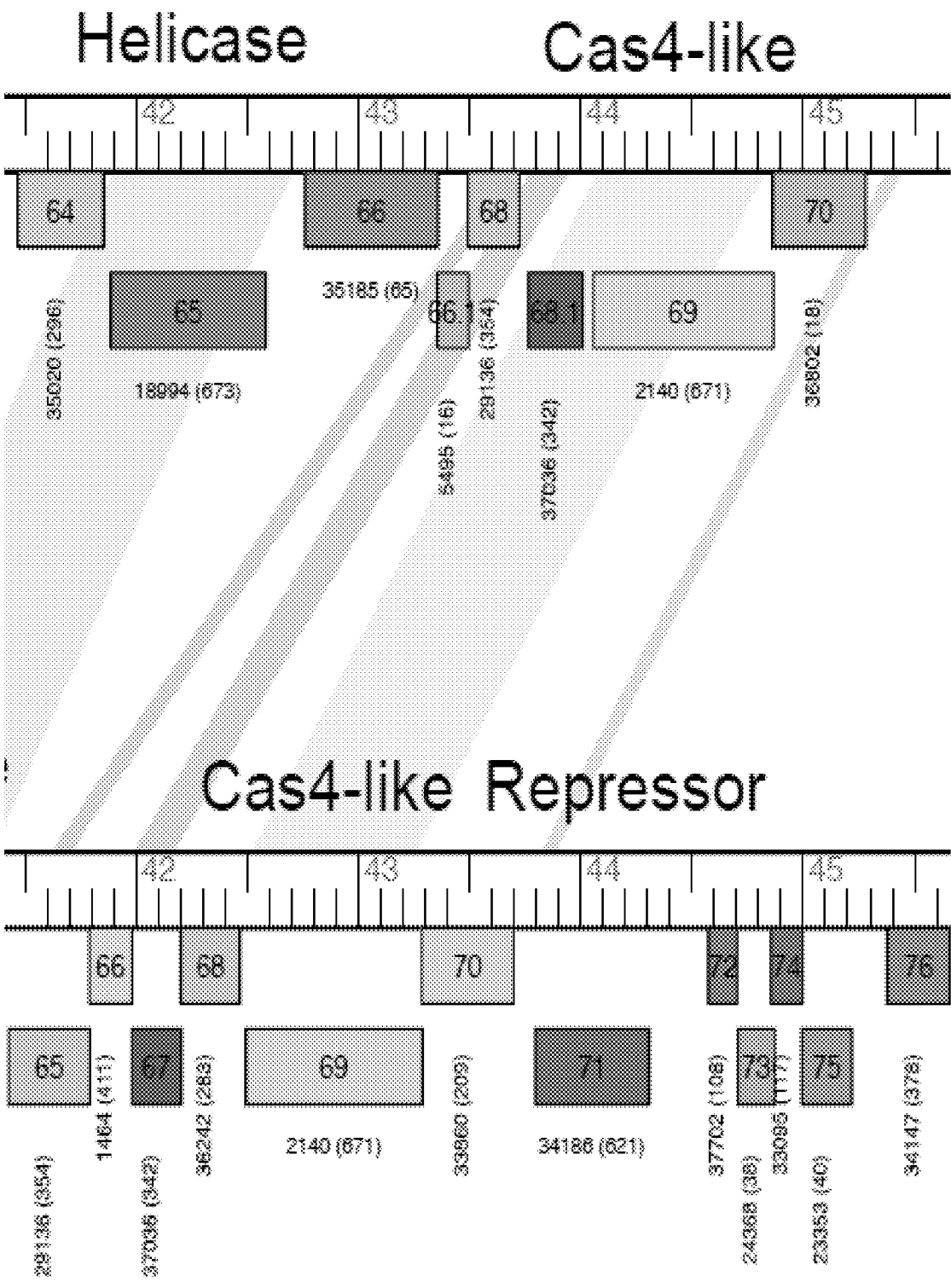
FIG. 5G shows a continuation of the genome maps of phage D29 (top) and phage Fred313cpm-1 (bottom) shown in FIG. 5F. The ruler shows the length of the genome from about 41 kb to about 49 kb of the genome map of phage D29 (top). The shading between the genomes indicates nucleotide sequence similarity with darker shading reflecting closest similarity and the lightest being the least similar above a threshold E value of $10^{-4}$.
Figure 5G:
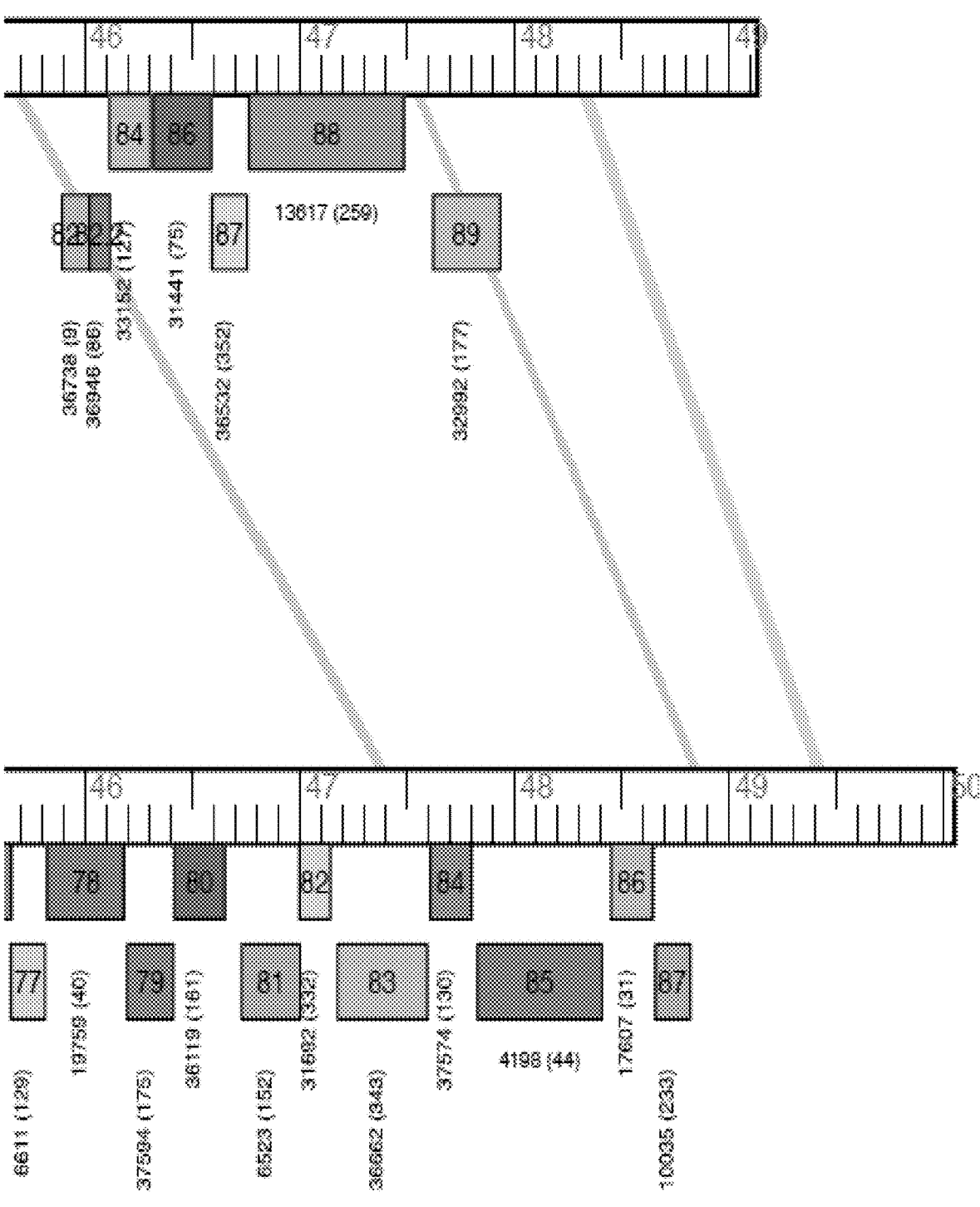

As noted above, Fionnbharth is a temperate phage and thus not suitable for therapeutic use as-is. Thus, BRED engineering technology was used (Marinelli et al., *FEMS Microbiology Letters*, 344(2), 166-172 (July 2013), which is herein incorporated by reference in its entirety) to construct a derivative in which the repressor gene (47) is deleted (SEQ ID NO: 3). Four 100-fold serial dilutions of bacterial cultures were spotted (right to left, FIGS. 4A and 4B) and the plates were incubated at 37° C. for six weeks. As shown in FIGS. 4A (no phage) and 4B, this lytic derivative (FionnbharthΔ47) efficiently kills *M. tuberculosis* clinical isolates.

Phage Fred313cpm-1

Fred313 is a temperate phage and forms turbid plaques on lawns of *M. smegmatis* mc²155. To develop a lytic derivative, a clear plaque variant (Fred313cpm-1), was isolated, purified, and sequenced (SEQ ID NO: 4). Fred313cpm-1 contains a 2,904 bp deletion (coordinates 43,561-46,464) that removes all of the repressor gene (71). Fred313cpm-1 also contains single nucleotide polymorphisms at G2278A, G22996A and 48934ΔA that are likely not related to the clear plaque phenotype.

Figure 6B:
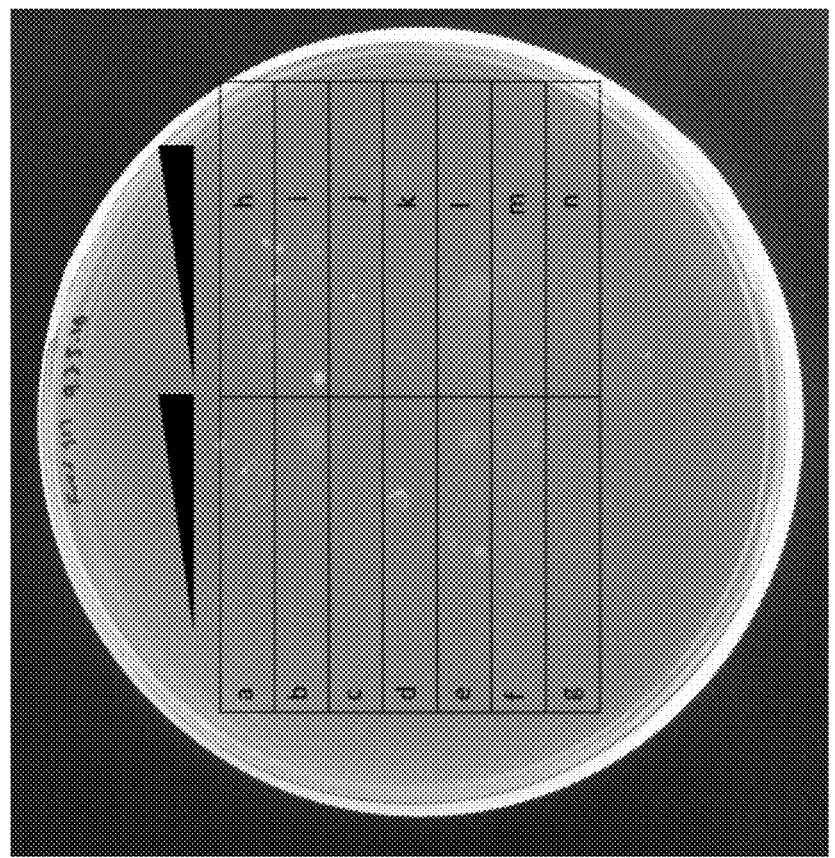
FIGS. 6A-6B are pictures of culture plates spotted with bacterial culture with and without the addition of phage. The key to the bacterial strains is noted on the culture plates of FIGS. 6A and 6B. H37Rv is the lab strain of *M. tuberculosis* tested; all other strains are clinical isolates. a=N0145, b=N0136, c=N0004, d=N0072, e=N0052, f=N0054, g=N0153, h=H37Rv, i=N1283, j=N0031, k=N1216, l=N0155, m=N1275, and n=N0157.
Figure 6A:
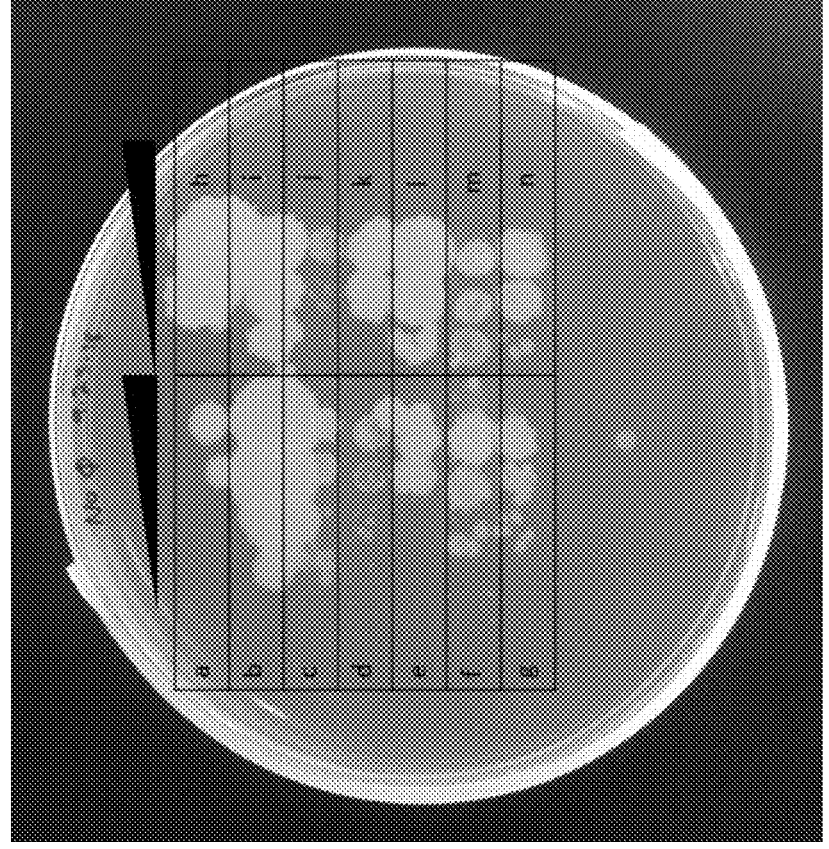

Survival of *M. tuberculosis* on solid media seeded with 10⁹ pfu phage Fred313cpm-1 is shown in FIG. 6B (*M. tuberculosis* without phage is shown in FIG. 6A). Four 100-fold serial dilutions of bacterial cultures were spotted (right to left) and the plates were incubated at 37° C. for six weeks. FIG. 6B, as compared to FIG. 6A, show that phage Fred313cpm-1 kills all tested strains efficiently.

Phage #5: MuddyHRM^(N0052)-1

Muddy is known to infect *M. tuberculosis* mc²7000 and therefore it was tested on the *M. tuberculosis* clinical isolates listed in Table 1. Reduced efficiencies of plating on all or most of the strains tested was observed. To recover derivatives with clinical utility, phage particles were recovered from plaques observed at low frequency on each of the other strains (designated HRM-1-HRM-6).

HRM-1 contains a DNA substitution of a G to an A at coordinate 21643 (i.e. G21643A). The mutation lies within Muddy gene 24, and confers a substitution of a glutamic acid residue with a lysine residue as position 680 of the protein (i.e. E680K).

HRM-6 likely is a mixture of two mutants. The first mutant has a DNA substitution of a G to a T at coordinate 21064 (i.e. G21064T). The mutation lies within Muddy gene 24, and confers a substitution of a glycine residue with a tryptophan residue as position 487 of the protein (i.e. G487W). The second mutant has a DNA substitution of an A to an G at coordinate 21427 (i.e. A21427G). The mutation lies within Muddy gene 24, and confers a substitution of an alanine residue with a glycine residue as position 608 of the protein (i.e. T608A).

While not wishing to be bound by any particular theory, the mutations in gene 24 are believed to expand the host range of Muddy to include other clinical isolates of *M. tuberculosis*.

Figures 7A, 7B:
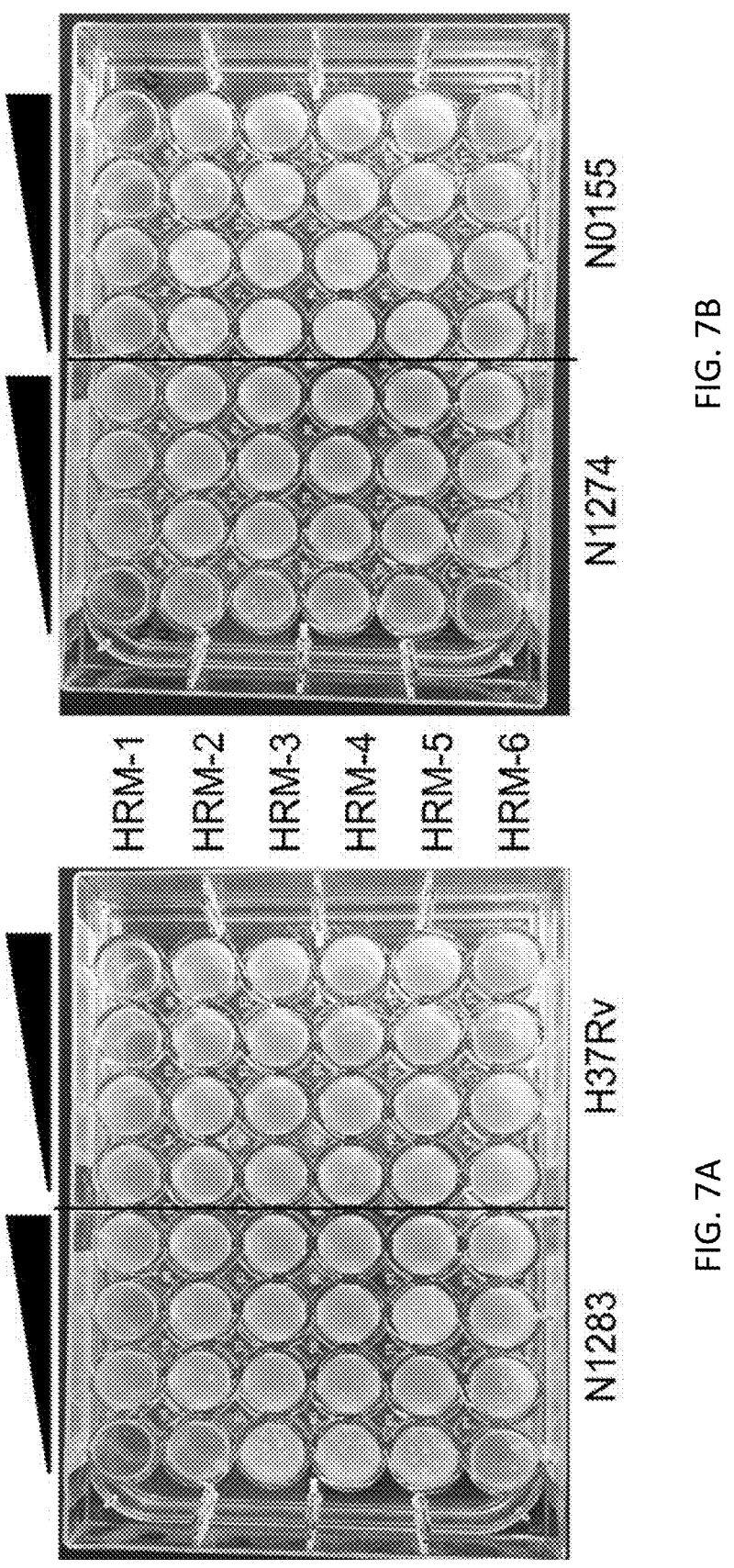
FIGS. 7A-7G are pictures of culture plates taken of a plaque assay performed to test phage MuddyHRMN0052$^{-1}$. Host Range Mutants (HRM) of Muddy are designated HRM-1 to HRM-6. Each plate contains two set of strains, as shown. The key to the bacterial strains is noted below each culture plate. H37Rv is the lab strain of *M. tuberculosis* tested; all other strains are clinical isolates.
Figures 7C, 7D:
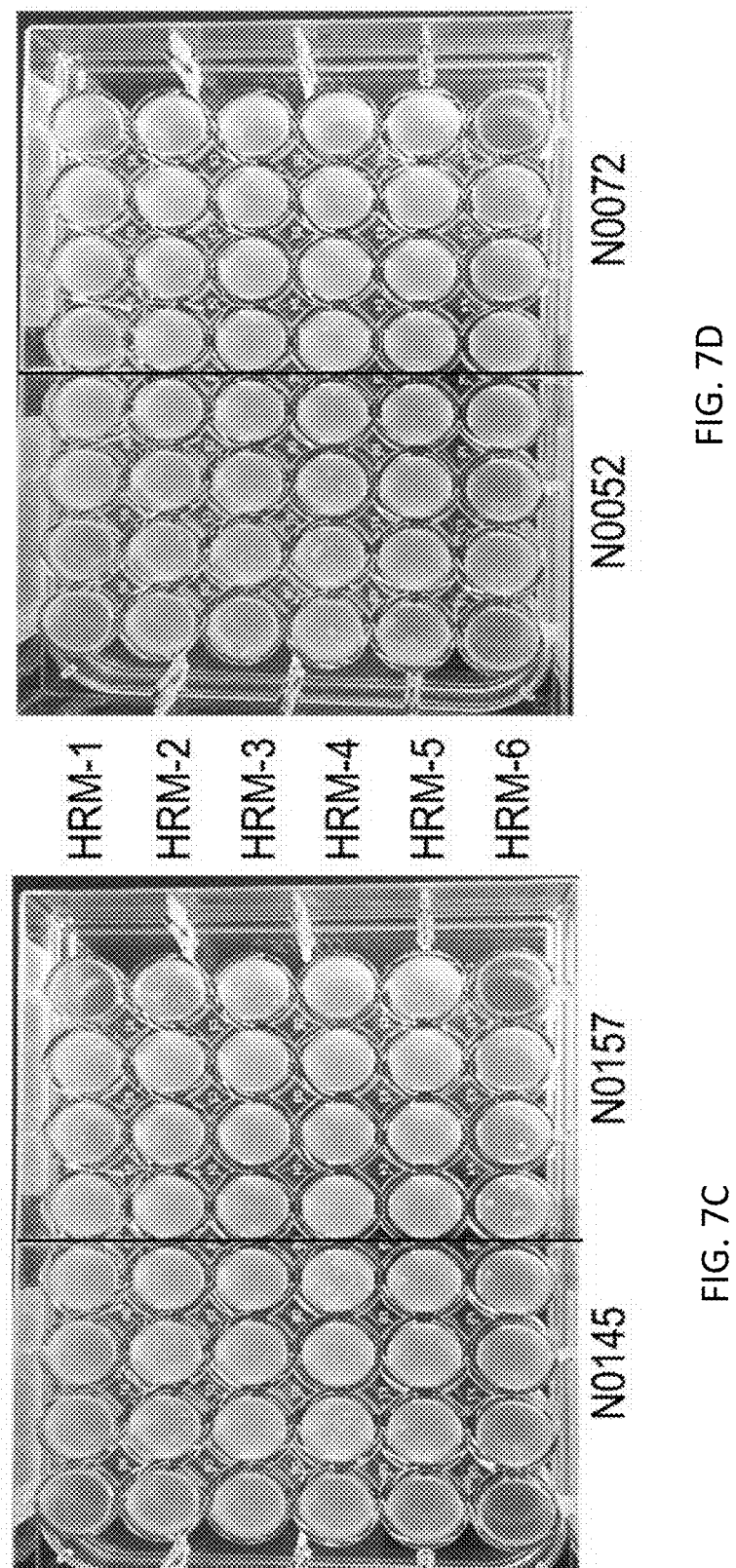
Figures 7E, 7F:
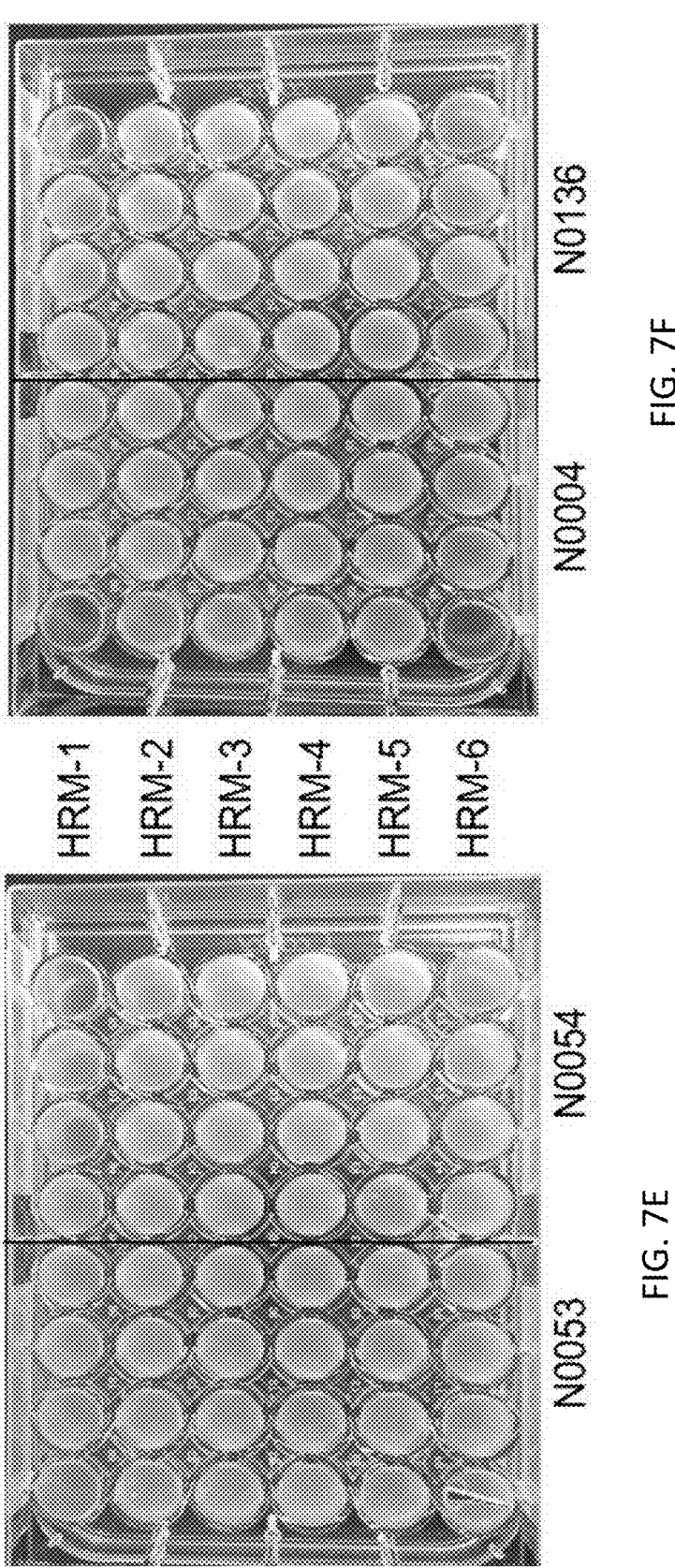
Figure 7G:
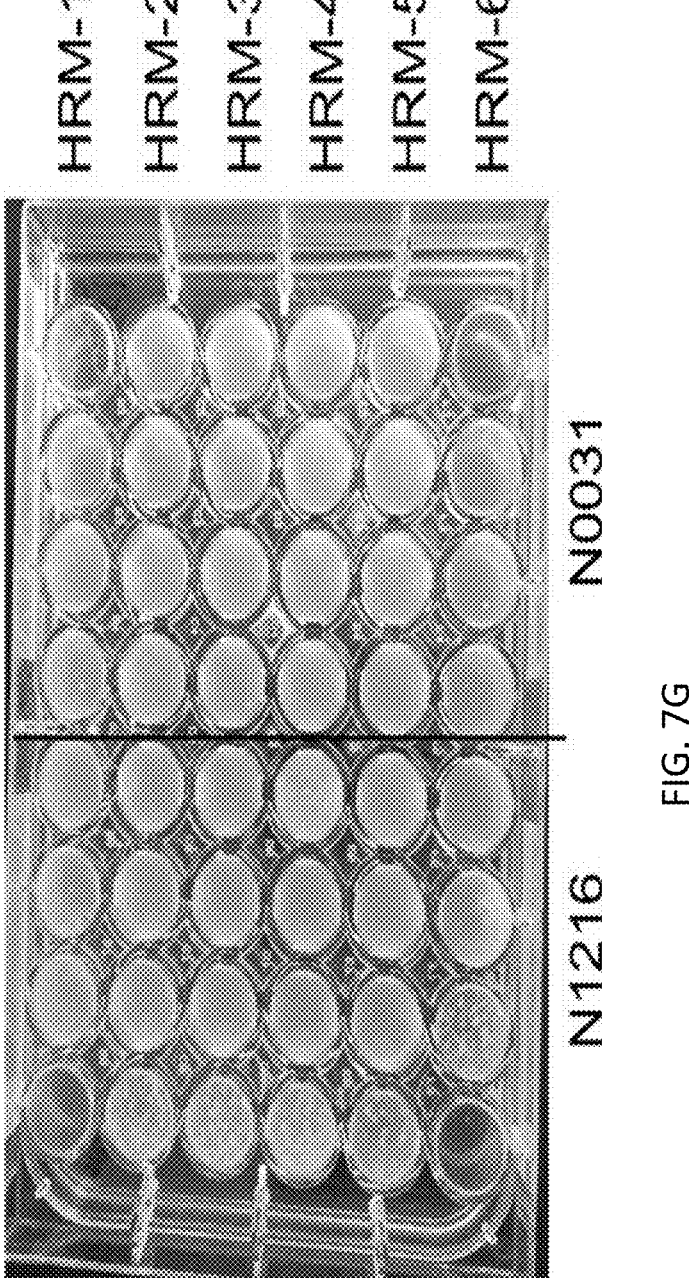

These were propagated on *M. smegmatis* mc²155, and tested in a plaque assay on the other strains. The results are shown in FIGS. 7A-7G. Each plate contained two set of strains. Muddy HRM recovered from different *M. tuberculosis* hosts were serially diluted 10²-fold and added to cells as an overlay on solid media. Muddy HRM-1 and HRM-6 infect all strains; HRM-5 does not infect strain N0155 (FIG. 7B). It was found that some of the HRM derivatives of Muddy infect some but not all of the strains. For example, HRM-5, which was recovered by its ability to form a plaque on strain N0072 (lineage-1) does not infect strain N0155 (FIG. 7B). In contrast, HRM-1 and HRM-6, which were recovered from strains N0157 (FIG. 7C) and N0052 (FIG. 7D), respectively, infect all of the strains tested. These derivatives represent good candidates for therapeutic evaluation.

This example demonstrates the process for identifying the genomically distinct phages that infect and kill all of the *M. tuberculosis* isolates tested. These phages are good candidates for inclusion in a phage cocktail for the treatment of diseases caused by *M. tuberculosis*.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition comprising a combination of two or more phages, wherein the phages are two or more of:
(a) phage D29;
(b) phage AdephagiaΔ41Δ43;
(c) phage FionnbharthΔ47;
(d) phage Fred313cpm-1; and
(e) phage MuddyHRM$^{NO052-1}$; and
a pharmaceutically acceptable carrier.

2. A pharmaceutical composition comprising:
(1) (a) phage D29;
(b) phage AdephagiaΔ41Δ43;
(c) phage FionnbharthΔ47;
(d) phage Fred313cpm-1; and
(e) phage MuddyHRM$^{NO052-1}$; and
(2) a pharmaceutically acceptable carrier.

3. A method of treating or reducing a disease caused by *Mycobacterium tuberculosis* in a mammal comprising administering the pharmaceutical composition of claim 1, thereby treating reducing the disease in the mammal.

4. The method of claim 3, wherein the disease caused by *Mycobacterium tuberculosis* is one or more of: tuberculosis, tubercular meningitis and disseminated infections, and bone and joint tuberculosis.

5. A method of treating an antibiotic resistant infection in a mammal comprising administering the pharmaceutical composition of claim 1 to the mammal.

6. The method of claim 5, wherein the antibiotic resistant infection comprises pulmonary tuberculosis.

7. A method of treating or reducing activation of a latent disease in a mammal caused by *M. tuberculosis*, comprising administering a pharmaceutical composition of claim 1 comprising a combination of two or more of: (a) phage D29; (b) phage AdephagiaΔ41Δ43; (c) phage FionnbharthΔ47; (d) phage Fred313cpm-1; and (e) phage MuddyHRM$^{NO052-1}$, thereby treating or reducing the activation of the latent disease in the mammal.

8. The method of claim 7, wherein the composition is administered in combination with one or more antibiotics.

9. The method of claim 8, wherein the antibiotic comprises: isoniazid, ethambutol, pyrazinamide, rifampicin, streptomycin, amikacin, kanamycin, ciprofloxacin, delamanid, and bedaquiline, or any combination thereof.

10. The method of claim 7, wherein the composition is administered intravenously.

11. The method of claim 7, wherein the composition is administered as an aerosol.

12. The method of claim 9, wherein the length of treatment is reduced as compared to the length of treatment with one or more antibiotics alone.

13. The method of claim 12, wherein the length of treatment comprises 1 month, 2 months, 3 months, 4 months, or 5 months.

14. The method of claim 7, wherein the mammal is a human.

*     *     *     *     *